United States Patent
L'Heureux et al.

(10) Patent No.: US 9,540,323 B2
(45) Date of Patent: *Jan. 10, 2017

(54) 7-HYDROXY-INDOLINYL ANTAGONISTS OF P2Y₁ RECEPTOR

(71) Applicant: BRISTOL-MYERS SQUIBB COMPANY, Princeton, NJ (US)

(72) Inventors: Alexandre L'Heureux, Ste-Julie (CA); Sheldon Hiebert, Landmark (CA); Carol Hu, New Hope, PA (US); Patrick Y. S. Lam, Chadds Ford, PA (US); John Lloyd, Yardley, PA (US); Zulan Pi, Pennington, NJ (US); Jennifer X. Qiao, Princeton, NJ (US); Carl Thibeault, Mascouche (CA); George O. Tora, Langhorne, PA (US); Wu Yang, Princeton Junction, NJ (US); Yufeng Wang, North Brunswick, NJ (US); Tammy C. Wang, Lawrenceville, NJ (US); Michael S. Bowsher, Prospect, CT (US); Ruel Rejean, Saint-Lambert (CA)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/418,023

(22) PCT Filed: Jul. 30, 2013

(86) PCT No.: PCT/US2013/052628
§ 371 (c)(1),
(2) Date: Jan. 28, 2015

(87) PCT Pub. No.: WO2014/022343
PCT Pub. Date: Feb. 6, 2014

(65) Prior Publication Data
US 2015/0259286 A1   Sep. 17, 2015

Related U.S. Application Data

(60) Provisional application No. 61/678,151, filed on Aug. 1, 2012.

(51) Int. Cl.
| | | |
|---|---|---|
| C07D 209/26 | (2006.01) |
| C07D 401/04 | (2006.01) |
| C07D 401/12 | (2006.01) |
| C07D 403/04 | (2006.01) |
| C07D 403/14 | (2006.01) |
| C07D 409/04 | (2006.01) |
| C07D 413/04 | (2006.01) |

(Continued)

(52) U.S. Cl.
CPC .......... *C07D 209/26* (2013.01); *C07D 209/14* (2013.01); *C07D 401/04* (2013.01); *C07D 401/12* (2013.01); *C07D 403/04* (2013.01); *C07D 403/12* (2013.01); *C07D 403/14* (2013.01); *C07D 409/04* (2013.01); *C07D 413/04* (2013.01); *C07D 413/14* (2013.01); *C07D 417/04* (2013.01); *C07D 417/12* (2013.01); *C07D 417/14* (2013.01); *C07D 471/04* (2013.01); *C07D 498/04* (2013.01); *C07D 513/04* (2013.01)

(58) Field of Classification Search
None
See application file for complete search history.

(56) References Cited

U.S. PATENT DOCUMENTS 7,388,021 B2 * 6/2008 Chao ..................... C07C 275/30
                                                       514/332
7,550,499 B2   6/2009 Tuerdi et al.
(Continued)

FOREIGN PATENT DOCUMENTS

WO   WO 2007/002637   1/2007
WO   WO 2008/048981   4/2008

OTHER PUBLICATIONS

Hechler, B. et al., "MRS2500 [2-Iodo-$N^6$-methyl-($N$)-methanocarba-2'-deoxyadenosine-3',5'-bisphosphate], a Potent, Selective, and Stable Antagonist of the Platelet P2Y₁ Receptor with Strong Antithrombotic Activity in Mice", The Journal of Pharmacology and Experimental Therapeutics, vol. 316, No. 2, pp. 556-563 (2006).

(Continued)

*Primary Examiner* — David K O'Dell
(74) *Attorney, Agent, or Firm* — Barry Jacobsen

(57) ABSTRACT

The present invention provides compounds of Formula (I): Formula (I) as defined in the specification and compositions comprising any of such novel compounds. These compounds are antagonists of P2Y₁ receptor which may be used medicaments.

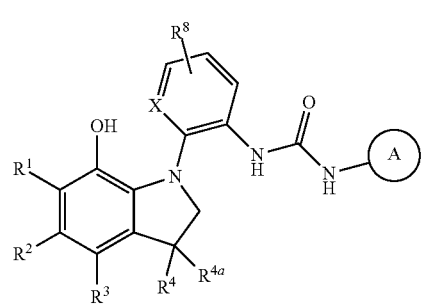

(I)

9 Claims, No Drawings

(51) Int. Cl.
*C07D 417/12* (2006.01)
*C07D 417/14* (2006.01)
*C07D 471/04* (2006.01)
*C07D 498/04* (2006.01)
*C07D 209/14* (2006.01)
*C07D 513/04* (2006.01)
*C07D 403/12* (2006.01)
*C07D 413/14* (2006.01)
*C07D 417/04* (2006.01)

(56) References Cited

U.S. PATENT DOCUMENTS 7,728,008 B2 6/2010 Qiao et al.
2005/0261244 A1* 11/2005 Tuerdi ................ C07D 209/08
514/63

OTHER PUBLICATIONS

Hechler, B. et al., "The $P2Y_1$ receptor, necessary but not sufficient to support full ADP-induced platelet aggregation, is not the target of the drug clopidogrel", British Journal of Haematology, vol. 103, pp. 858-866 (1998).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors: II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

Wong, P.C. et al., "Nonpeptide Factor Xa Inhibitors: III: Effects of DPC423, an Orally-Active Pyrazole Antithrombotic Agent, on Arterial Thrombosis in Rabbits", The Journal of Pharmacology and Experimental Therapeutics, vol. 303, No. 3, pp. 993-1000 (2002).

Yamada, Y. et al., "Preparation of 7-Halo-indoles by Thallation of N-Formylindoline and Their Attempted Use for Synthesis of the Right-Hand Segment of Chloropeptin", Chem. Pharm. Bull., vol. 54, No. 6, pp. 788-794 (2006).

Anbazhagan, M. et al., "Direct Conversion of Amidoximes to Amidines via Transfer Hydrogenation", Synthesis, No. 16, pp. 2467-2469 (2003).

Kihara, Y. et al., "Oxidative Heterocyclization Using Diethyl Azodicarboxylate", Synthesis, pp. 1020-1023 (1990).

Qiao, J.X. et al., "Transformation of Anionically Activated Trifluoromethyl Groups to Heterocycles under Mild Aqueous Conditions", Organic Letters, vol. 13, No. 7, pp. 1804-1807 (2011).

* cited by examiner

7-HYDROXY-INDOLINYL ANTAGONISTS OF P2Y$_1$ RECEPTOR

The present application is a 371 application of International Application No. PCT/US2013/052628 filed on Jul. 30, 2013, which claims priority benefit of U.S. provisional application Ser. No. 61/678,151, filed Aug. 1, 2012; each of which is fully incorporated by reference herein.

FIELD OF THE INVENTION

The present invention provides novel 7-hydroxy-indolinyl compounds, and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b, and A3), which bind to and are activated by the nucleoside adenosine, and the P2 receptors, which comprise a second, more diverse class of receptors which are activated by a wide variety of nucleotides including ATP, ADP, UTP, and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al., *Drug Development Research*, 52:187-189 (2001)). In addition, an eighth receptor, P2Y$_{14}$, has been considered by some to be a member of this class although it does not respond to ribosylated nucleotides and is activated by UDP-glucose (Abbracchio, M. P. et al., *Trends Pharmacol. Sci.*, 24:52-55 (2003)).

Several studies have suggested that modulators of specific members of the P2Y family of receptors could have therapeutic potential for the treatment of a variety of disorders (for review see Burnstock, G. et al., *J. Pharm. Exp. Ther.*, 295:862-869 (2000)), including diabetes, cancer, CF, and treatment of ischemia-reperfusion injury (Abbracchio M. P. et al., *Pharmacol. Ther.*, 64:445-475 (1994)). P2Y$_1$ receptors, almost ubiquitous among human organs (Janssens, R. et. al., *Biochem, Biophys, Res. Comm.*, 221:588-593 (1996) have been identified on microglia (Norenberg, W. et al., *Br. J. Pharmacol.*, 111:942-950 (1994)) and on astrocytes (Salter, M. W. et al., *J. Neurosc.*, 15:2961-2971 (1995)). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, J. et al., *Proc. Natl. Acad. Sci.*, 95:8070-8074 (1998)). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation (Jin, J. et al., *J. Biol. Chem.*, 273:2030-2034 (1998)). The first signal arises from ADP driven activation of the P2Y$_1$ receptor and can most easily be tracked by measuring the transitory increase in intracellular free Ca$^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS, and A2P5P), Daniel, J. L. et al. (*J. Biol. Chem.*, 273:2024-2029 (1998)), Savi, P. et al. (*FEBS Letters*, 422:291-295 (1998)), and Hechler, B. et al. (*Br. J. Haematol.*, 103:858-866 (1998)) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al., *Circulation*, 103:718-723 (2001), in a model of thromboplastin induced thromboembolism using both a P2Y$_1$ knock-out mouse and the P2Y$_1$ antagonist MRS-2179 (Baurand, A. et al., *Cardiovascular Drug Reviews*, 21:67-76 (2003)). These results were subsequently extended to include the inhibition of both venous and arterial thrombosis in the rat (Lenain, N. et al., *J. Thromb. Haemost.*, 1:1144-1149 (2003)) and the confirmation of the phenotype of the P2Y$_1$ knock-out mouse in a second laboratory using an independently derived animal (Fabre, J-E. et al., *Nature Medicine*, 5:1199-1202 (1999)). These studies highlighted the need for more potent and selective P2Y$_1$ antagonists and recently, using the P2Y$_1$ antagonist MRS-2500 (Hechler, B. et al., *J. Pharmacol Exp. Ther.*, 316:556-563 (2006)) succeeded in demonstrating strong antithrombotic activity for a selective P2Y$_1$ antagonist in the mouse. Taken together, these data suggest that the discovery of novel P2Y$_1$ antagonists with improved pharmaceutical characteristics could have significant utility in the treatment of a variety of thrombotic or thromboembolic disorders (see Gachet, C. et al., *Blood Cell, Molecules and Disease*, 36:223-227 (2006) for a recent review).

U.S. Patent Publication No. 2005/0261244 A1 published Nov. 24, 2005 discloses a series of P2Y$_1$ antagonists including spiropiperidine indolinyl of the following formula:

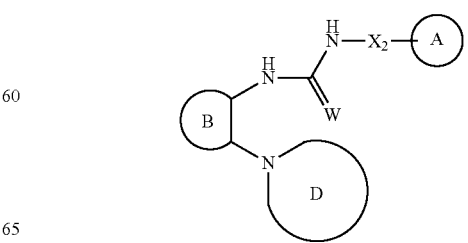

wherein ring A is $C_{6-10}$ aryl substituted with 0-5 $R^1$, or a 5- to 10-membered heterocycle comprising carbon atoms and 1-4 heteroatoms selected from N, $NR^{11}$, O, and $S(O)_p$, wherein said heterocycle is substituted with 0-5 $R^1$;

ring B is phenyl or naphthyl substituted with 0-4 $R^7$, or a 5- to 10-membered heteroaryl comprising carbon atoms and 1-4 ring heteroatoms selected from N, $NR^{11}$, $S(O)_p$, and O, wherein said heteroaryl is substituted with 0-4 $R^7$;

one of the ring D groups is substituted with 0-5 $R^{6a}$; wherein $D_1$ is a 5- to 7-membered carbocycle or a 5- to 6-membered heterocycle comprising carbon atoms and 0-3 ring heteroatoms selected from N, $NR^{11}$, O, and $S(O)_p$, and 0-2 carbonyl groups, and 0-3 double bonds;

W is O or S;

$X_2$ is $-(CR^{16}R^{17})_s-$, or $-(CR^{16}R^{17})_tC(O)(CR^{16}R^{17})_r-$;

$R^{6a}$ is a variable defined therein;

alternatively, when two $R^{6a}$ groups are attached to the same carbon atom or silicon atom, together with the carbon atom or silicon atom to which they are attached, they form a 3- to 7-membered carbocyclic or heterocyclic ring comprising carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$; and other variables are defined therein.

It is desirable to find new compounds with improved pharmacological characteristics compared with known $P2Y_1$ antagonists. For example, it is desirable to find new compounds with improved antiplatelet activity in the platelet aggregation functional assay and good binding affinity in the $P2Y_1$ binding assay.

SUMMARY OF THE INVENTION

The present disclosure provides novel 7-hydroxy-indolinyl compounds and their analogues, including stereoisomers, tautomers, pharmaceutically acceptable salts, or solvates thereof, which are useful as selective inhibitors of the $P2Y_1$ receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof The compounds of the invention may be used in the treatment and/or prophylaxis of thromboembolic disorders.

The compounds of the invention may be used in therapy.

The compounds of the invention may be used for the manufacture of a medicament for the treatment and/or prophylaxis of thromboembolic disorders.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

(I)

or a stereoisomer, a tautomer, a pharmaceutically acceptable salt, a solvate, or a prodrug thereof, wherein:

X is independently CH or N;

ring A is independently selected from $C_{3-6}$ carbocycle substituted with 0-3 $R^5$ and a heterocycle substituted with 0-2 $R^5$; wherein said heterocycle is selected from thienyl, thiazolyl, thiadiazolyl, pyridyl, $R^1$ is independently selected from H, halogen and OH;

$R^2$ is independently H or halogen;

$R^3$ is independently selected from H, halogen, $C_{1-6}$ haloalkyl, $C_{1-4}$ haloalkoxy, CN, $C_{1-4}$ alkoxy, $C_{1-4}$ alkylthio, CHO, $CO_2(C_{1-4}$ alkyl), $SO_2N(C_{1-4}$ alkyl)$_2$, and a ring moiety substituted with 0-3 $R^6$ and selected from the group consisting of $C_{3-6}$ cycloalkyl, phenyl, thienyl, oxazolyl, isoxazolyl, thiazolyl, pyrazolyl, 1-($C_{1-4}$ alkyl)-pyrazolyl, 1-Ph-pyrazolyl, oxadiazolyl, pyridyl, pyrimidinyl, pyrazinyl, benzoxazolyl, benzothiazolyl, 1-($C_{1-4}$ alkyl)-benzimidazolyl,

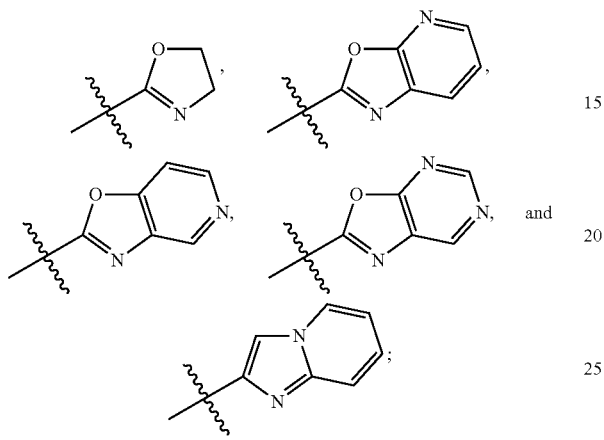

and $R^4$ and $R^{4a}$ are, independently at each occurrence, selected from $C_{1-6}$ alkyl, $CO_2(C_{1-4}$ alkyl) and $C_{1-6}$ haloalkyl;

$R^5$ is, independently at each occurrence, selected from halogen, $C_{1-6}$ alkyl, $C_{1-6}$ alkoxy, $C_{1-6}$ alkylthio, $C_{1-6}$ haloalkyl, $C_{1-6}$ haloalkoxy, $CO_2(C_{1-4}$ alkyl), $NO_2$, and

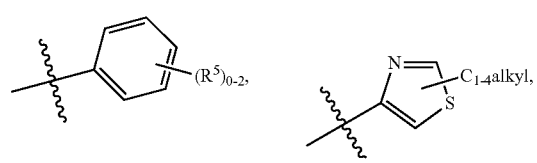

$R^6$ is, independently at each occurrence, selected from halogen, $C_{1-6}$ alkyl, $C_{2-6}$ alkenyl, $C_{1-6}$ haloalkyl, $C_{1-4}$ alkoxy, $C_{1-4}$ haloalkoxy, $C_{1-4}$ alkylthio, $CH_2OH$, CN, $CO_2(C_{1-4}$ alkyl), $NH(C_{1-4}$ alkyl), $CH_2N(C_{1-4}$ alkyl)$_2$, and morpholinylmethyl;

$R^7$ is independently selected from $C_{1-6}$ alkyl, $C_{1-6}$ haloalkyl, $CO(C_{1-4}$ alkyl), —$(CH_2)_{1-2}$—$C_{3-6}$ cycloalkyl, and $COCF_3$; and $R^8$ is independently selected from H, halogen and CN.

In a second aspect, the present invention includes a compound of Formula (I) or a stereoisomer, a tautomer, a pharmaceutically acceptable salt, or a solvate thereof, within the scope of the first aspect, wherein:

ring A is independently selected from

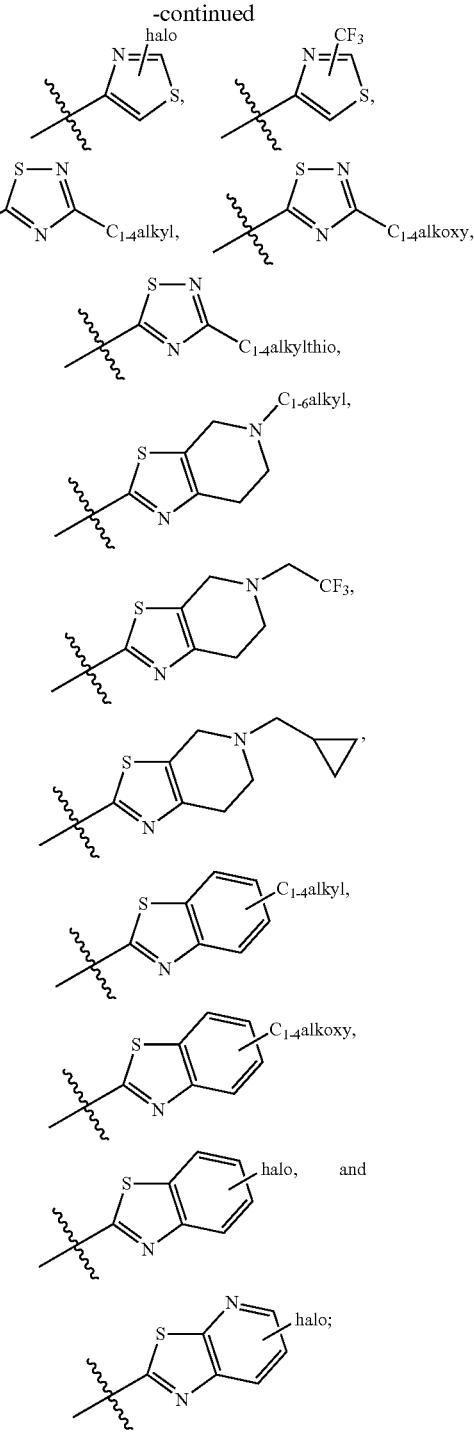

$R^1$ is independently H or halogen;

$R^2$ is independently H or halogen;

$R^3$ is independently selected from halogen, $C_{1-6}$ alkyl, $C_{1-6}$ haloalkyl, $C_{1-4}$ haloalkoxy, CN, $C_{1-4}$ alkoxy, $C_{1-4}$ alkylthio, CHO, $CO_2(C_{1-4}$ alkyl), $C_{3-6}$ cycloalkyl, and a ring moiety substituted with 0-2 $R^6$ and selected from the group consisting of phenyl, thienyl, oxazolyl, isoxazolyl, thiazolyl, pyrazolyl, 1-($C_{1-4}$ alkyl)-pyrazolyl, 1-Ph-pyrazolyl, oxadiazolyl, pyridyl, pyrimidinyl, pyrazinyl, benzoxazolyl, benzothiazolyl, 1-($C_{1-4}$ alkyl)-benzimidazolyl,

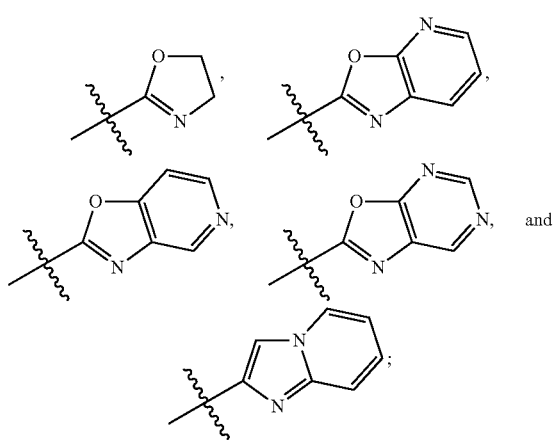

$R^4$ is independently $C_{1-6}$ alkyl;

$R^{4a}$ is independently selected from $C_{1-6}$ alkyl, $CO_2(C_{1-4}$ alkyl) and $C_{1-6}$ haloalkyl;

$R^5$ is, independently at each occurrence, selected from halogen, $C_{1-6}$ alkyl, $C_{1-6}$ alkoxy, $C_{1-6}$ haloalkyl, $C_{1-6}$ haloalkoxy, and

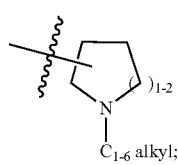

and $R^8$ is independently selected from H or halogen.

In a third aspect, the present invention includes a compound of Formula (I), or a stereoisomer, a tautomer, a pharmaceutically acceptable salt, or a solvate thereof, within the scope of the first or second aspect, wherein:

ring A is independently selected from

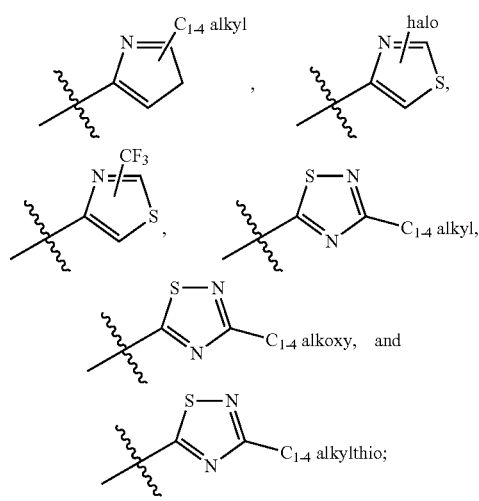

$R^1$ is independently H or halogen;
$R^2$ is independently H or halogen;
$R^3$ is independently selected from halogen, $C_{1-6}$ haloalkyl, and a ring moiety substituted with 0-2 $R^6$ and selected from the group consisting of phenyl, isoxazolyl, 1-($C_{1-4}$ alkyl)-pyrazolyl, pyridyl, and benzothiazolyl;

$R^4$ is independently $C_{1-6}$ alkyl;

$R^{4a}$ is independently $C_{1-6}$ alkyl or $CO_2(C_{1-4}$ alkyl);

$R^6$ is, independently at each occurrence, selected from H, halogen, $C_{1-6}$ alkyl, $C_{1-6}$ haloalkyl, $C_{1-4}$ alkoxy, and $C_{1-4}$ haloalkoxy; and $R^8$ is independently H or halogen.

In a fourth aspect, the present invention includes a compound of Formula (I), or a stereoisomer, a tautomer, a pharmaceutically acceptable salt, or a solvate thereof, within the scope of the first, second or third aspect, wherein:

ring A is independently selected from

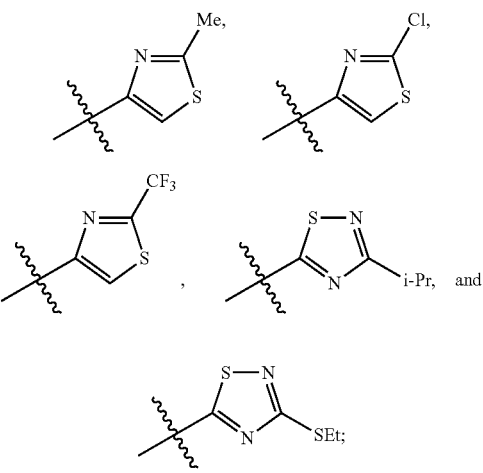

$R^1$ is independently H or F;
$R^2$ is independently H or F;
$R^3$ is independently selected from F, Cl, Br, $CF_3$, 4-(t-Bu)-Ph, 4-F-Ph, 4-Cl-Ph, 4-$CF_3$-Ph, 3-$CF_3$-isoxazol-5-yl, 1-(i-Pr)-5-$CF_3$-pyrazol-3-yl, 5-$CF_3$-pyrid-2-yl,

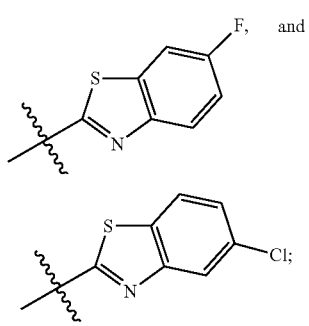

$R^4$ is independently Me or Et;
$R^{4a}$ is independently selected from Me, Et and $CO_2Et$; and
$R^8$ is H.

In a fifth aspect, the present invention includes a compound of Formula (I), or a stereoisomer, a tautomer, a pharmaceutically acceptable salt, or a solvate thereof, within the scope of the first or second aspect, wherein:

ring A is independently selected from

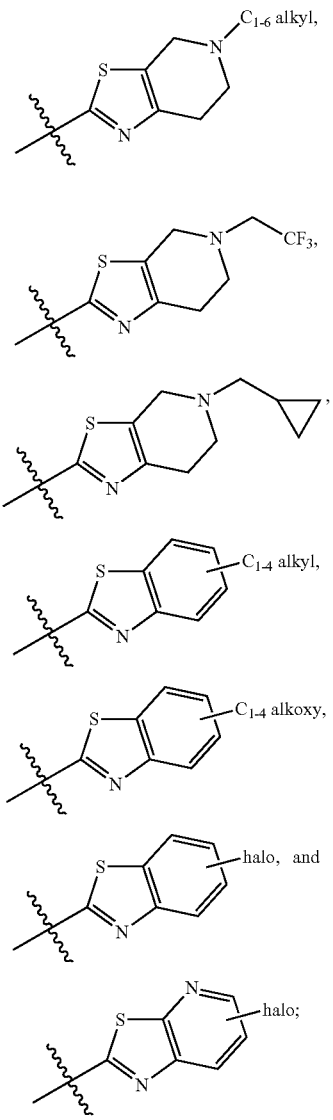

ring A is independently selected from

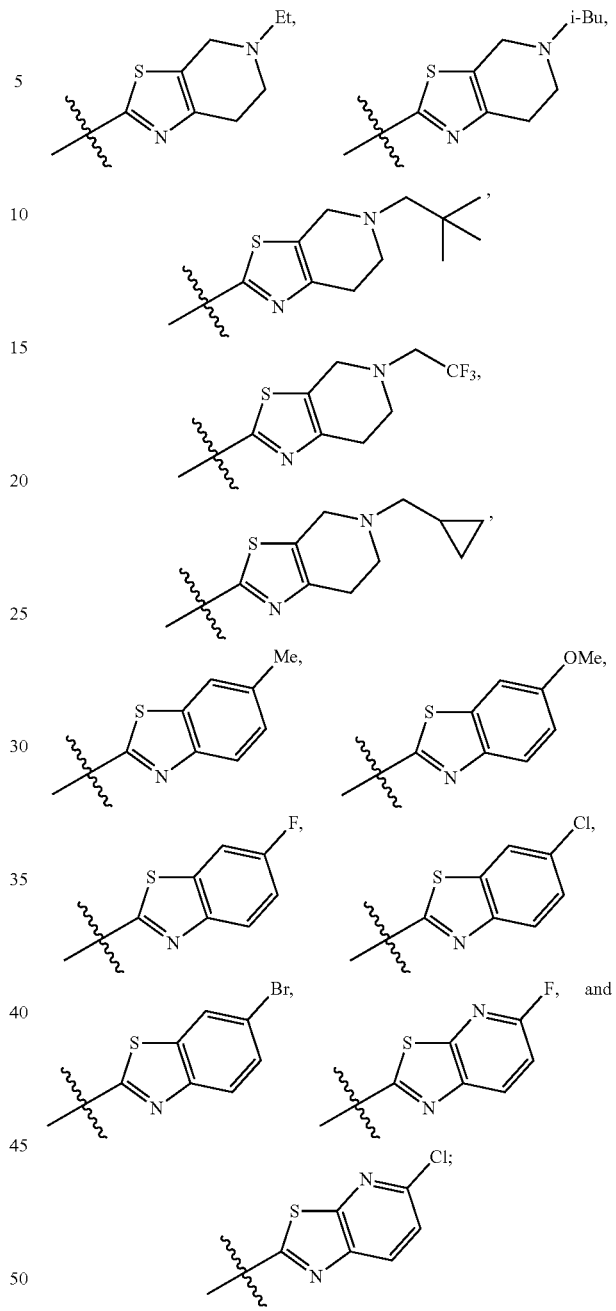

R¹ is independently H or halogen;
R² is independently H or halogen;
R³ is independently selected from halogen, $C_{1-6}$ haloalkyl, and a ring moiety substituted with 0-2 R⁶ and selected from the group consisting of phenyl, thienyl, oxazolyl, isoxazolyl, 1-($C_{1-4}$ alkyl)-pyrazolyl, oxadiazolyl, pyridyl, benzoxazolyl, and benzothiazolyl;
R⁴ is independently $C_{1-6}$ alkyl;
R⁴ᵃ is independently $C_{1-6}$ alkyl or $CO_2(C_{1-4}$ alkyl);
R⁶ is, independently at each occurrence, selected from H, halogen, $C_{1-6}$ alkyl, $C_{1-6}$ haloalkyl, $C_{1-4}$ alkoxy, and $C_{1-4}$ haloalkoxy; and
R⁸ is independently H or halogen.

In a sixth aspect, the present invention includes a compound of Formula (I), or a stereoisomer, a tautomer, a pharmaceutically acceptable salt, or a solvate thereof, within the scope of the first, second or fifth aspect, wherein:

R¹ is independently H or F;
R² is independently H or F;
R³ is independently selected from F, Cl, Br, $CF_3$, 4-F-Ph, 4-Cl-Ph, 5-Cl-thien-2-yl, 2-(t-Bu)-oxazol-4-yl, 3-$CF_3$-isoxazol-5-yl, 1-(i-Pr)-5-$CF_3$-pyrazol-3-yl, 1-(i-Pr)-3-$CF_3$-pyrazol-5-yl, 4-$CF_3$-pyrid-2-yl, 4-$CF_3$-pyrid-3-yl,

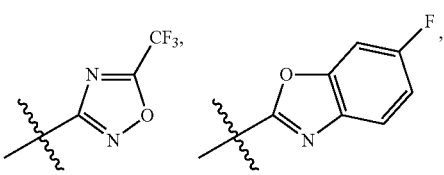

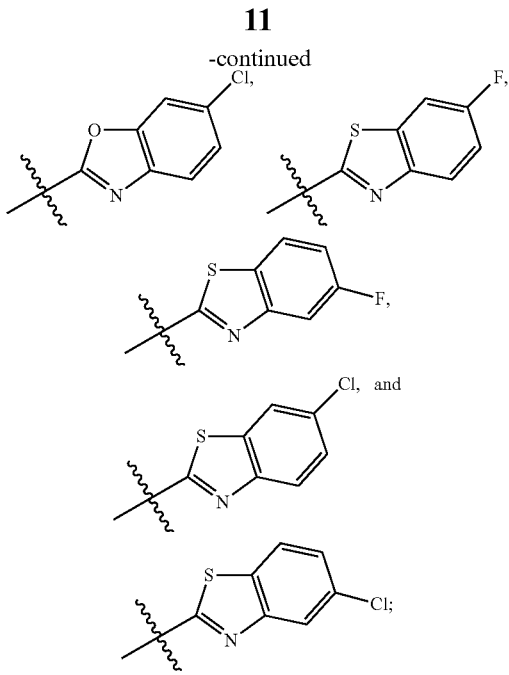

R⁴ is independently Me or Et;
R⁴ᵃ is independently selected from Me, Et and CO₂Et; and
R⁸ is independently H or F.

In a seventh aspect, the present invention includes a compound of Formula (II):

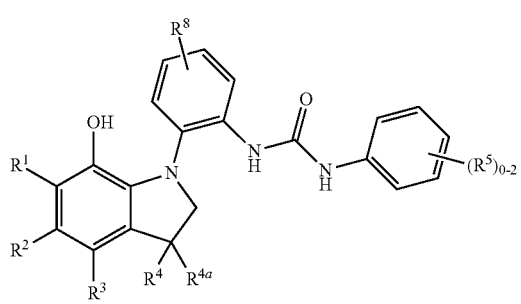

or a stereoisomer, a tautomer, a pharmaceutically acceptable salt, or a solvate thereof, within the scope of the first or second aspect, wherein:

$R^1$ is independently H or halogen;
$R^2$ is independently H or halogen;
$R^3$ is independently selected from halogen, $C_{1-6}$ alkyl, $C_{1-6}$ haloalkyl, $C_{1-4}$ haloalkoxy, CN, $C_{1-4}$ alkoxy, $C_{1-4}$ alkylthio, CHO, $CO_2(C_{1-4}$ alkyl), $C_{3-6}$ cycloalkyl, and a ring moiety substituted with 0-2 $R^6$ and selected from the group consisting of phenyl, thienyl, oxazolyl, isoxazolyl, thiazolyl, pyrazolyl, 1-($C_{1-4}$ alkyl)-pyrazolyl, 1-Ph-pyrazolyl, oxadiazolyl, pyridyl, pyrimidinyl, pyrazinyl, benzoxazolyl, benzothiazolyl, 1-($C_{1-4}$ alkyl)-benzimidazolyl,

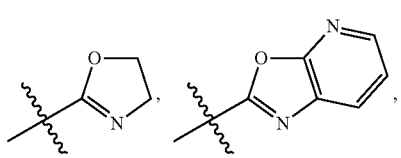

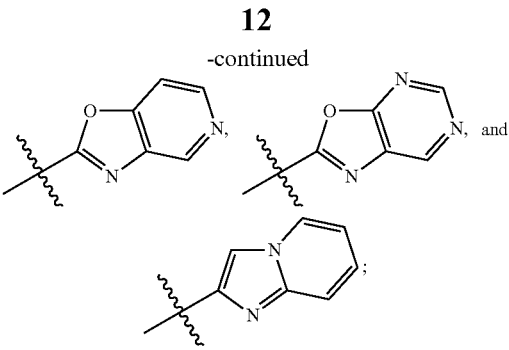

$R^4$ is independently $C_{1-6}$ alkyl;
$R^{4a}$ is independently selected from $C_{1-6}$ alkyl, $CO_2(C_{1-4}$ alkyl) and $C_{1-6}$ haloalkyl;
$R^5$ is, independently at each occurrence, selected from halogen, $C_{1-6}$ alkyl, $C_{1-6}$ alkoxy, $C_{1-6}$ haloalkyl, $C_{1-6}$ haloalkoxy, and

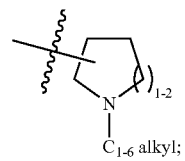

$R^6$ is, independently at each occurrence, selected from halogen, $C_{1-6}$ alkyl, $C_{2-6}$ alkenyl, $C_{1-6}$ haloalkyl, $C_{1-4}$ alkoxy, $C_{1-4}$ haloalkoxy, $C_{1-4}$ alkylthio, $CH_2OH$, CN, $CO_2(C_{1-4}$ alkyl), $NH(C_{1-4}$ alkyl), $CH_2N(C_{1-4}$ alkyl)$_2$, and morpholinylmethyl; and
$R^8$ is independently H or halogen.

In an eighth aspect, the present invention includes a compound of Formula (II), or a stereoisomer, a tautomer, a pharmaceutically acceptable salt, or a solvate thereof, within the scope of the first, second or seventh aspect, wherein:

$R^1$ is independently H or F;
$R^2$ is independently H or F;
$R^3$ is independently selected from H, F, Cl, Br, CF₃, CH₂CF₃, CN, S(t-Bu), CHO, CO₂Me, CO₂Et, cyclopropyl, Ph, 4-(t-Bu)-Ph, 2-F-Ph, 3-F-Ph, 4-F-Ph, 3-Cl-Ph, 4-Cl-Ph, 4-CF₃-Ph, 4-CO₂Me-Ph, 3-CN-Ph, 4-CN-Ph, 3-CH₂N(Me)₂-Ph, 3-Me-4-F-Ph, 2,4-diF-Ph, 3,4-diF-Ph, 3,5-diF-Ph, 2-F-4-Cl-Ph, 3-F-4-Cl-Ph, 3-Cl-4-F-Ph, 5-Cl-thien-2-yl, 2-Me-oxazol-4-yl, 2-(i-Pr)-oxazol-4-yl, 2-(i-Bu)-oxazol-4-yl, 2-(t-Bu)-oxazol-4-yl, 3-CF₃-isoxazol-5-yl, thiazol-2-yl, 2-(i-Pr)-thiazol-4-yl, 1H-3-CF₃-pyrazol-5-yl, 1-(i-Bu)-pyrazol-4-yl, 1-Me-3-CF₃-pyrazol-5-yl, 1-(i-Pr)-5-CF₃-pyrazol-3-yl, 1-Ph-5-Me-pyrazol-4-yl, 1,3,5-trimethyl-pyrazol-4-yl, pyrid-4-yl, 4-pyrid-4-yl, 6-(t-Bu)-pyrid-3-yl, 5-OMe-pyrid-3-yl, 4-F-pyrid-2-yl, 4-F-pyrid-3-yl, 5-F-pyrid-3-yl, 3-F-pyrid-4-yl, 2,6-diF-pyrid-4-yl, 4-Cl-pyrid-2-yl, 5-Cl-pyrid-3-yl, 2-Cl-pyrid-4-yl, 4-CF₃-pyrid-2-yl, 4-CF₃-pyrid-3-yl, 4-F-5-Me-pyrid-3-yl, 5-Me-6-F-pyrid-3-yl, 5-(i-Pr)-pyrimidin-2-yl, 2-(t-Bu)-pyrimidin-5-yl, 2-(SMe)-pyrimidin-4-yl, 5-F-pyrimidin-2-yl, 5-Br-pyrimidin-2-yl, pyrazin-2-yl, 5-Cl-pyrazin-2-yl,

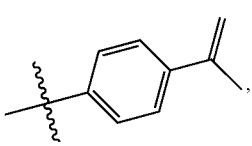

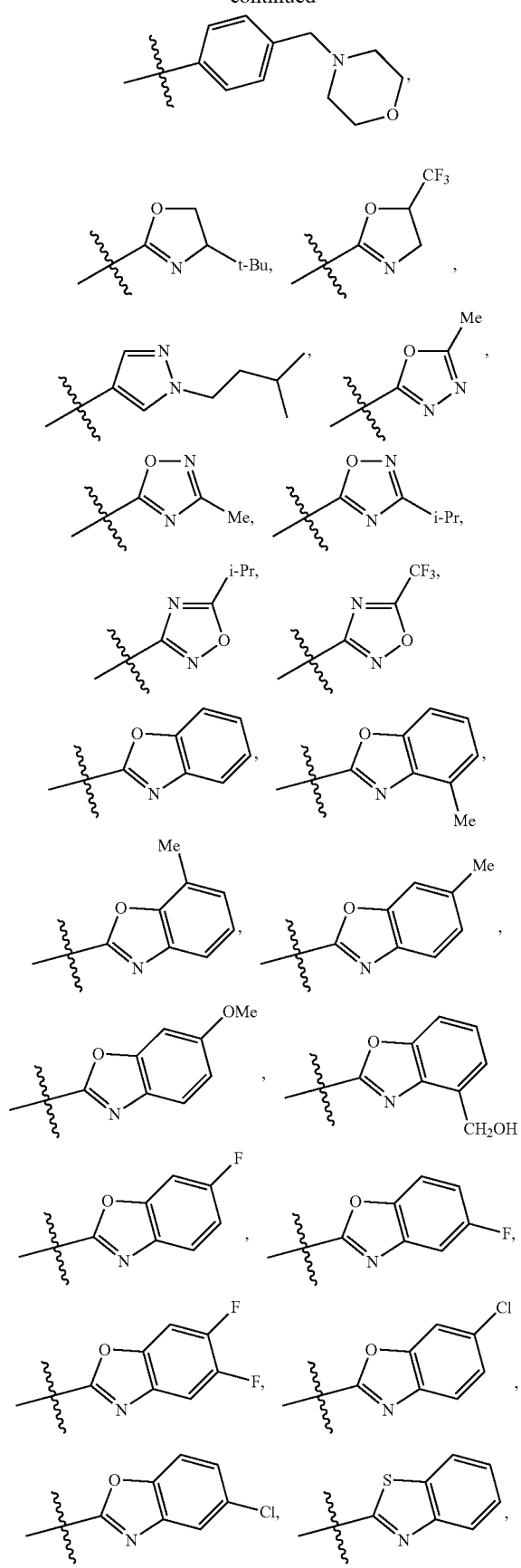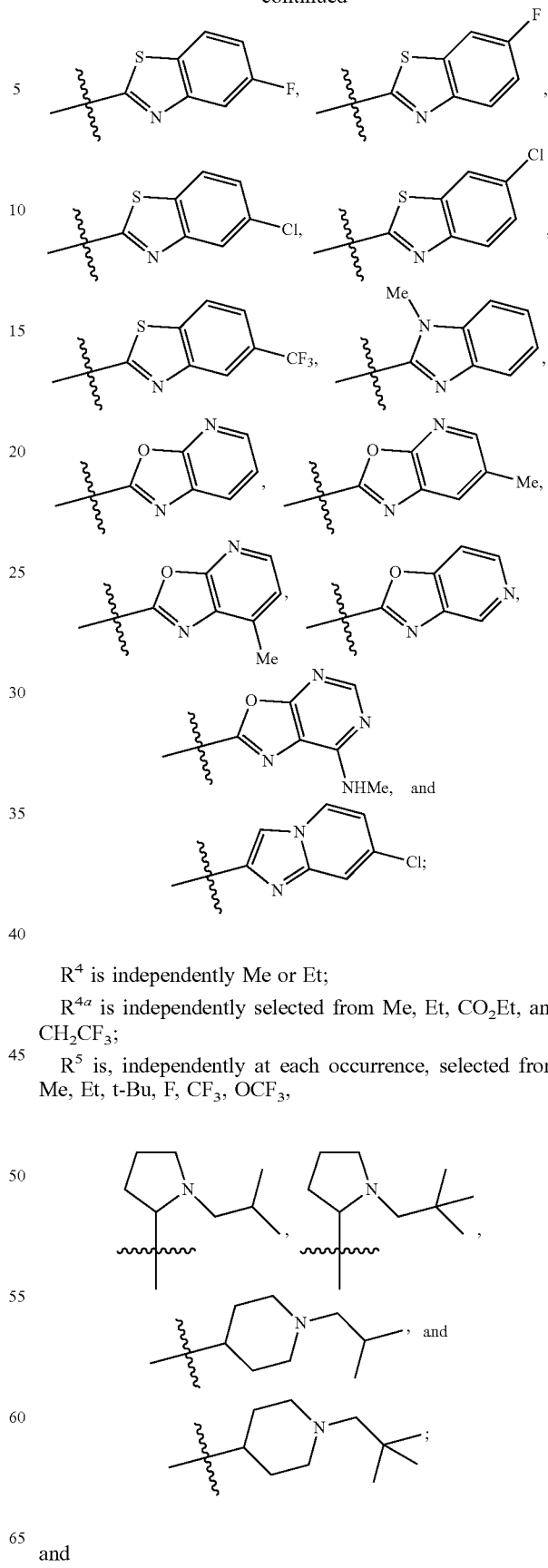
R[4] is independently Me or Et;
R[4a] is independently selected from Me, Et, $CO_2Et$, and $CH_2CF_3$;
R[5] is, independently at each occurrence, selected from Me, Et, t-Bu, F, $CF_3$, $OCF_3$,
and
R[8] is independently H or F.

In a ninth aspect, the present invention provides a compound selected from the exemplified examples or a stereoisomer, a tautomer, a pharmaceutically acceptable salt, or a solvate thereof In another aspect, the present invention provides a compound selected from any subset list of compounds within the scope of the ninth aspect.

In another embodiment, the compounds of the present invention have in vitro human antiplatelet activity in the platelet aggregation assay: PA $IC_{50}$ values ≤40 μM with 10 μM ADP.

In another embodiment, the compounds of the present invention have in vitro human antiplatelet activity in the platelet aggregation assay: PA $IC_{50}$ values ≤5 μM with 10 μM ADP.

In another embodiment, the compounds of the present invention have in vitro human antiplatelet activity in the platelet aggregation assay: PA $IC_{50}$ values ≤1 μM with 10 μM ADP.

In another embodiment, the compounds of the present invention have in vitro human antiplatelet activity in the platelet aggregation assay: PA $IC_{50}$ values ≤0.2 μM with 10 μM ADP.

II. Other Embodiments of the Invention

In another embodiment, the present invention provides a composition comprising at least one of the compounds of the present invention or a stereoisomer, a tautomer, a pharmaceutically acceptable salt, or a solvate thereof In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the modulation of platelet reactivity comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In one embodiment, the present invention provides a method for the treatment and/or prophylaxis of thromboembolic disorders, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a compound of the present invention for use in therapy.

In another embodiment, the present invention provides a compound of the present invention for use in therapy for the treatment and/or prophylaxis of thromboembolic disorders.

In another embodiment, the present invention also provides the use of a compound of the present invention for the manufacture of a medicament for the treatment and/or prophylaxis of thromboembolic disorders.

In another embodiment, the present invention provides a method for the treatment and/or prophylaxis of thromboembolic disorders, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of thromboembolic disorders.

The compounds of the present invention may be employed in combination with additional therapeutic agent(s) selected from one or more, preferably one to three, of the following therapeutic agents: potassium channel openers, calcium channel blockers, sodium hydrogen exchanger inhibitors, antiarrhythmic agents, antiatherosclerotic agents, anticoagulants, antithrombotic agents, pro-thrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning In another embodiment, additional therapeutic agent(s) used in combined pharmaceutical compositions or combined methods or combined uses, are selected from one or more, preferably one to three, of the following therapeutic agents in treating a thromboembolic disorder: an anti-arrhythmic agent, an anti-hypertensive agent, an anticoagulant agent, an anti-platelet agent, a thrombin inhibiting agent, a thrombolytic agent, a fibrinolytic agent, a calcium channel blocker, a cholesterol/lipid lowering agent.

In another embodiment, additional therapeutic agent(s) used in combined pharmaceutical compositions or combined methods or combined uses, are selected from one or more, preferably one to three, of the following therapeutic agents in treating a thromboembolic disorder: warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, apixaban, rivaroxaban, edoxaban, dabigatran, disulfatohirudin, tissue plasminogen activator, modified tissue plasminogen activator, anistreplase, urokinase, and streptokinase.

In another embodiment, additional therapeutic agent(s) used in combined pharmaceutical compositions or combined methods or combined uses, are selected from one or more, preferably one to three, of the following therapeutic agents in treating a thromboembolic disorder: an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_{12}$ antagonists, thromboxane receptor antagonists, and aspirin.

In another embodiment, the additional therapeutic agent(s) are an anti-platelet agent or a combination thereof The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" (or alkylene), is intended to include $C_1$, $C_2$, $C_3$, $C_4$, $C_5$, and $C_6$ alkyl groups. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "counter ion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Nielsen, N. M. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
4-$NO_2$Ph 4-nitrophenyl
Bn benzyl
MeOH methanol
EtOH ethanol
i-PrOH or IPA isopropanol
AcOH or HOAc acetic acid
2MeS-ADP 2 methylthio adenosine diphosphate
cDNA complimentary DNA
DMEM Dulbecco's modified Eagle media
EDTA ethylenediaminetetraacetic acid
FBS Fetal Bovine Serum
SCX Strong Cation Exchanger
EDC (or EDC.HCl) or 3-ethyl-3'-(dimethylamino)propyl-carbodiimide EDCI (or EDCI.HCl) hydrochloride (or 1-(3-dimethylaminopropyl)-3- or EDAC ethylcarbodiimide hydrochloride)
EtOAc ethyl acetate
$Et_2O$ diethyl ether
AIBN azobisisobutyronitrile
$AlCl_3$ aluminum chloride
BOP reagent benzotriazol-1-yloxytris(dimethylamino)phosphonium hexafluorophosphate
$BBr_3$ boron tribromide
$BCl_3$ boron trichloride
$BH_3 \cdot SMe_2$ borane dimethyl sulfide complex
$B(OMe)_3$ trimethoxyborane
BINAP 2,2'-bis(diphenylphosphino)-1,1'-binaphthyl
BnBr benzylbromide
nBuLi n-butyllithium
t-BuOH tert-butyl alcohol
$Bu_3SnCl$ tributyltin chloride
$Bu_3SnH$ tributyltin hydride
Boc tert-butyloxycarbonyl
$(Boc)_2O$ di-tert-butyl dicarbonate
$CaH_2$ calcium hydride
$CH_2Cl_2$ dichloromethane
$CH_3CN$ or ACN acetonitrile
$Cs_2CO_3$ cesium carbonate
$Cu(OAc)_2$ copper (II) acetate
$Cu(PPh_3)Br$ copper triphenylphosphinebromide
$Cy_2NMe$ N-methyldicyclohexylamine
DCE 1,2 dichloroethane
DCM dichloromethane
DIC or DIPCDI diisopropylcarbodiimide
DIEA or DIPEA N,N,-diisopropylethylamine
DME 1,2-dimethoxyethane
DMF dimethyl formamide
DMSO dimethyl sulfoxide
DPPA diphenylphosphoryl azide
EDTA ethylenediaminetetraacetic acid
Fe iron
HCl hydrochloric acid
$H_2SO_4$ sulfuric acid
HEPES 4-(2-hydroxyethyl)piperaxine-1-ethanesulfonic acid
Hex hexane
$K_2CO_3$ potassium carbonate
LAH or $LiAlH_4$ lithium aluminum hydride
$LiBH_4$ lithium borohydride
LDA lithium diisopropylamide
MeLi methyllithium
NBS N-bromosuccinimide
$NH_2NH_2$ hydrazine
D-PBS Dulbecco's Phosphate Buffered Saline
$PCy_3$ tricyclohexylphosphine
$P\text{-}(t\text{-}Bu)_3$ tri-tert-butylphosphine
Pd/C palladium on carbon
PS polystyrene
Py pyridine
$Pd_2(dba)_3$ tris(dibenzylideneacetone)dipalladium(O)

Pd(OAc)$_2$ palladium acetate
Pd(PPh$_3$)$_4$ tetrakis(triphenylphosphine)palladium
RED-AL® sodium bis(2-methoxyethoxy)aluminumhydride
SiO$_2$ silica oxide
SnCl$_2$ tin(II) chloride
TBAF tetrabutylammonium fluoride
TBAI tetra-n-butylammonium iodide
TMSCN trimethylsilyl cyanide
TEA triethylamine
TFA trifluoroacetic acid
TFAA trifluoroacetic anhydride
THF tetrahydrofuran
TRIS tris(hydroxymethyl)aminomethane
KOAc potassium acetate
t-BuOK or K-t-OBu potassium tert-butoxide
MgSO$_4$ magnesium sulfate
MsOH or MSA methylsulfonic acid
NaCl sodium chloride
NaH sodium hydride
NaHCO$_3$ sodium bicarbonate
NaNO$_2$ sodium nitrite
NaOH sodium hydroxide
Na$_2$SO$_4$ sodium sulfate
Na$_2$S$_2$O$_4$ sodium dithionite
NaBH$_4$ sodium borohydride
NaCNBH$_3$ sodium cyanoborohydride
NaO-t-Bu sodium tert-butoxide
NH$_3$ ammonia
NH$_4$Cl ammonium chloride
NH$_4$OH ammonium hydroxide
NH$_2$OH.HCl hydroxylamine hydrochloride
OTf triflate or trifluoromethanesulfonate
OTs tosylate, para-toluenesulfonate
Xantphos 4,5-bis(diphenylphosphino)-9,9-dimethylxanthene
Zn zinc
ZnCl$_2$ zinc chloride
ZnI$_2$ zinc iodide The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition, Wiley-Interscience (1999)).

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons, (1991)).

All references cited herein are hereby incorporated in their entirety herein by reference.

Schemes 1-17 describe synthetic routes of making compounds of the invention. Schemes 1-4 describe preparations of compounds of the invention from a key amine intermediate 1 or 4. Scheme 5 exemplifies some of the carbocyclic or heterocyclic A ring intermediates in NH$_2$-A (compound 7) or COOH-A (compound 9) that can be used to prepare compounds of the present invention. Schemes 6-13 describe several preparations of the amine intermediate 1 or 4 or the substituted indoline derivative 11 via a variety of methods from commercially available starting materials or can readily be prepared from commercially available materials by methods known to one skilled in the art of organic synthesis. Schemes 14-17 exemplify preparations of compounds in the present invention wherein R$^4$ is a trifluoromethyl group or a bromo group as well as elaborate further functionalization of R$^4$ of the molecule, such as preparation of compounds of the present invention wherein R$^4$ is a heteroaryl or an aryl group.

Scheme 1 describes a preparation of compounds of the present invention, Formula (I), the substituted urea 3, from the amine intermediate 1 or 2. Substituted isocyanates 2 are commercially available or can readily be prepared from commercially available materials by methods known to one skilled in the art of organic synthesis. Reaction of the isocyanate 2 with the amine 1 typically occurs at temperatures between 20° C. and 80° C. in a variety of solvents such as tetrahydrofuran, dichloroethane or dioxane. This reaction can also proceed in the presence of organic or inorganic bases, such as Et$_3$N, DMAP, or K$_2$CO$_3$, etc. Alternatively, the phenolic group in amine 1 can be protected as shown in intermediate 4, wherein the protecting group can be methyl, benzyl, allyl, or silyl-based group. Urea formation between the amine 4 and the isocyanate 2, followed by deprotection to free the phenolic group of the intermediate 5 can afford the urea 3. When the protecting group on the phenol is methyl, demethylation can occur with BBr$_3$, BCl$_3$, BBr$_3$—SMe, BCl$_3$.SMe AlCl$_3$, or BCl$_3$/TBAI (tetra-n-butylammonium iodide) at temperatures between −78° C. and refluxing in a solvent such as CH$_2$Cl$_2$. When heating is needed, the reaction can also occur under microwave irradiation to shorten the reaction time. When the protecting group on the phenol is a benzyl group, debenzylation can occur by using hydrogenation (such as Pd/C, H$_2$) in a variety of solvent such as methanol, EtOAc.

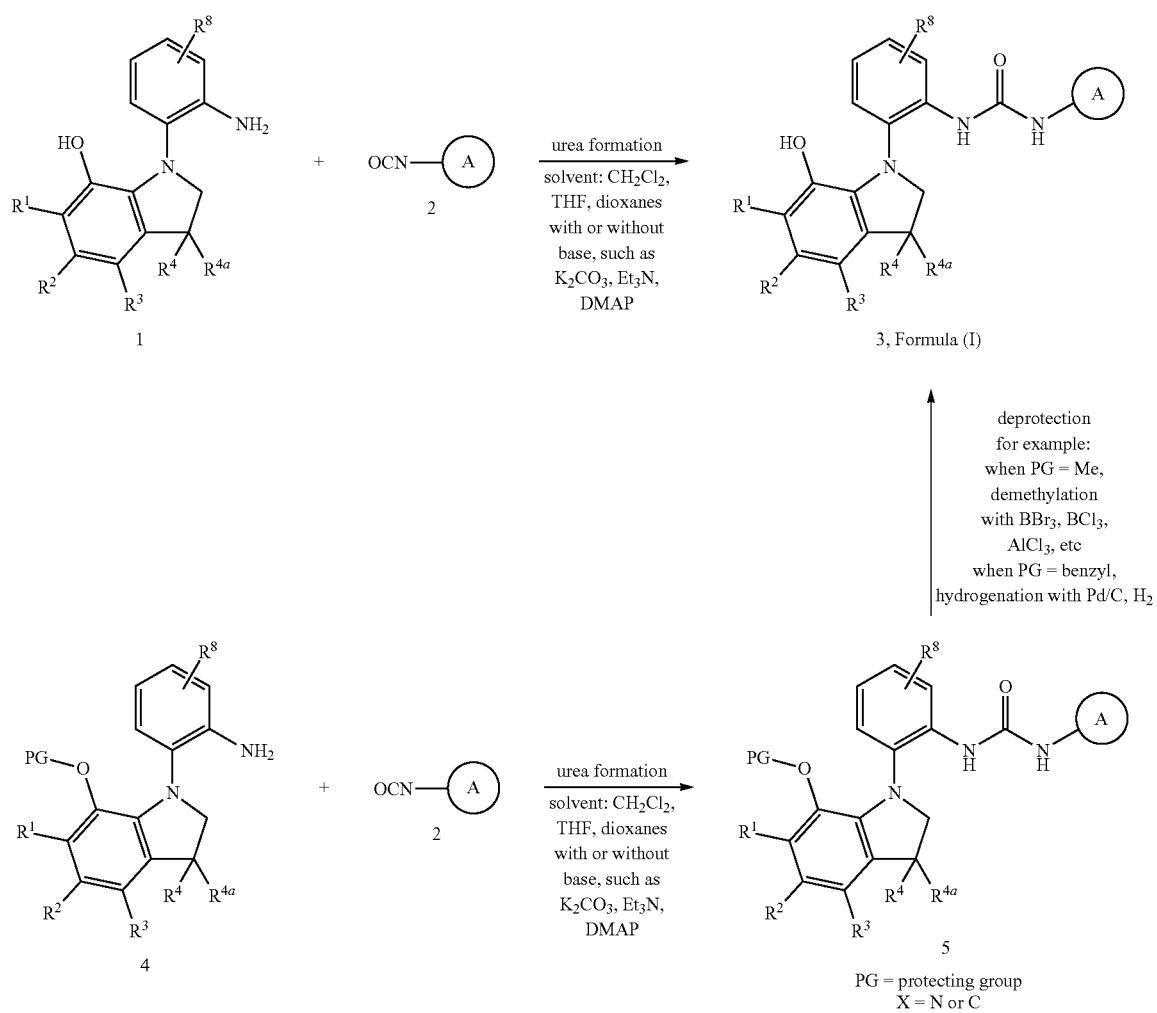

Scheme 1

Scheme 2 describes a step-wise preparation of compounds of the present invention, Formula (I), the substituted urea 3, from the amine intermediate 1 or 4. Substituted anilines and amino-substituted heteroaromatics 7 are commercially available or can readily be prepared from commercially available materials by methods known to one skilled in the art of organic synthesis. Reaction of intermediate 1 or 4 with chloroformate (e.g., p-nitrophenyl chloroformate, phenyl chloroformate or isopropenyl chloroformate) affords the carbonate intermediate 6 in the presence of an inorganic or an organic base, such as $Et_3N$, DMAP, or $K_2CO_3$. The carbonate 6 can be further replaced with a variety of aniline or amine 7 to afford the desired urea 3 or 5 by heating in THF, $CH_2Cl_2$, DMSO, etc at elevated temperatures or under microwave irradiation in the presence of an organic or an inorganic base, such as DMAP, $Et_3N$, N-methylpyrrolidine, $K_2CO_3$.

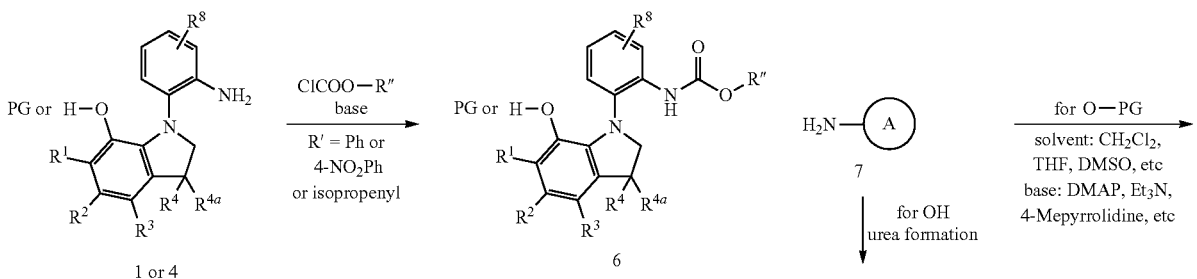

Scheme 2

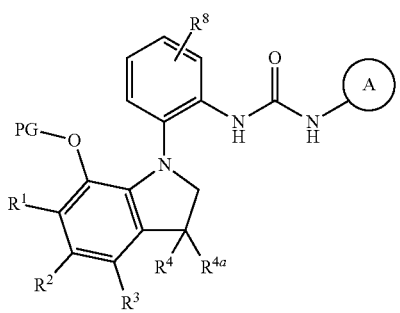

deprotection
for example:
when PG = Me,
demethylation
with BBr₃, BCl₃,
AlCl₃, etc
―――――→
when PG = benzyl,
using hydrogenation
with Pd/C, H₂

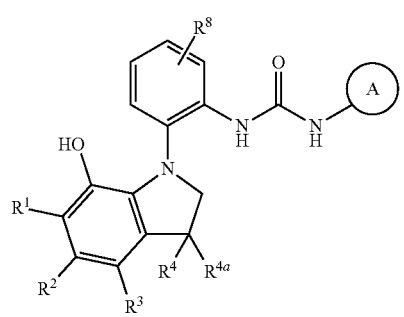

5

3, Formula (I)

Scheme 3 describes a preparation of compounds of the present invention, Formula (I), the substituted urea 3 from the key isocyanate intermediate 8. Substituted anilines and amino-substituted heteroaromatics 7 are commercially available or can readily be prepared from commercially available materials by methods known to one skilled in the art of organic synthesis. Reaction of the isocyanate 8 with aniline 7 typically occurs at temperatures between 20° C. and 80° C. in a variety of solvents such as tetrahydrofuran, dichloromethane, dichloroethane or dioxane. The key isocyanate intermediate 8 can be prepared via treatment of the aniline 4, prepared according to Schemes 6-12, with a phosgene equivalent in an organic solvent such as dichloromethane, dichloroethane or toluene, to produce the corresponding isocyanate. Phosgene equivalents include diphosgene, triphosgene, carbonyl diimidazole, trichloromethyl chloroformate and disuccinimidyl carbonate.

-continued

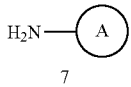
urea formation
―――――→
solvent: CH₂Cl₂,
THF, dioxanes
with or without
base, such as
K₂CO₃, Et₃N,
DMAP

5

7

Alternatively, Scheme 4 depicts a preparation of the compound of the present invention, Formula (I), the substituted urea 3 via the Curtius rearrangement of the carboxylic acid 9 using diphenylphosphoryl azide (DPPA) in the presence of aniline intermediate 1 or 4 while heating in toluene. Aryl/heteroaryl/alkyl carboxylic acids 9 are commercially available or can readily be prepared from commercially available materials by methods known to one skilled in the art of organic synthesis.

Scheme 3

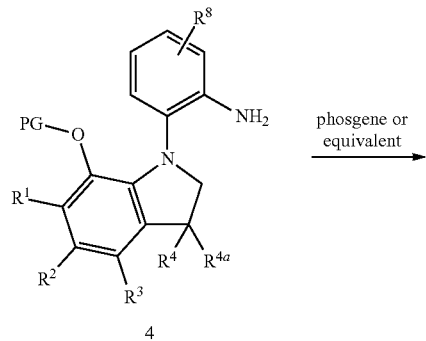

phosgene or equivalent
―――――→

4

Scheme 4

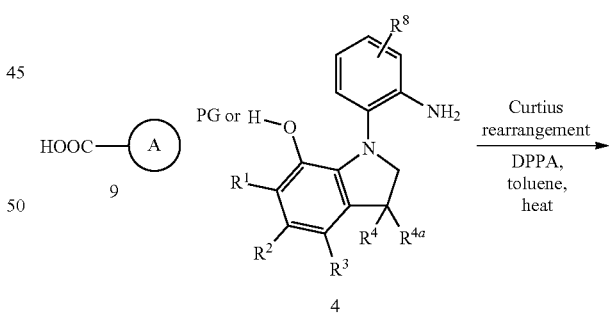

Curtius
rearrangement
―――――→
DPPA,
toluene,
heat

9

4

5 or 3

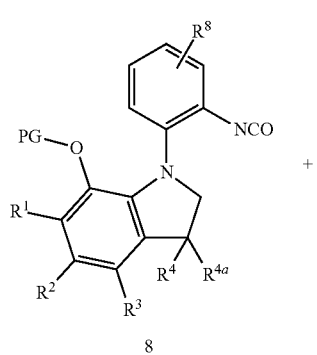

8

Scheme 5 exemplifies some of the carbocyclic or heterocyclic A ring intermediates in NH₂-A (compound 7) or COOH-A (compound 9) that can be used to prepare compounds of the present invention. Ring A is optionally substituted. These intermediates are either commercially available or can be prepared using methods known to those skilled in the art of organic synthesis.

Scheme 5

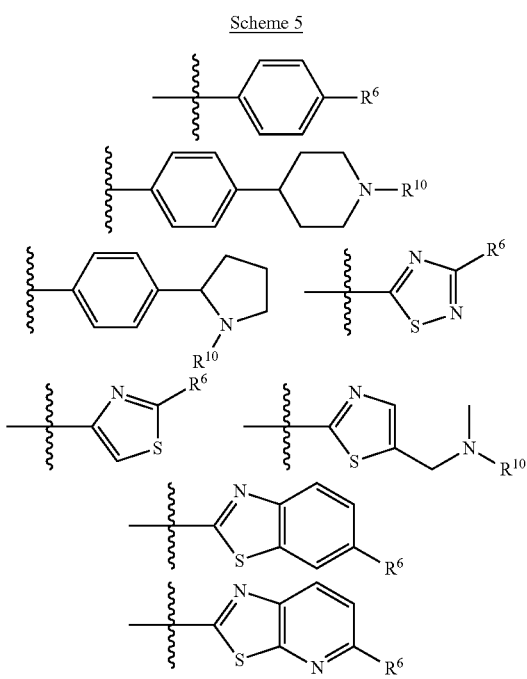

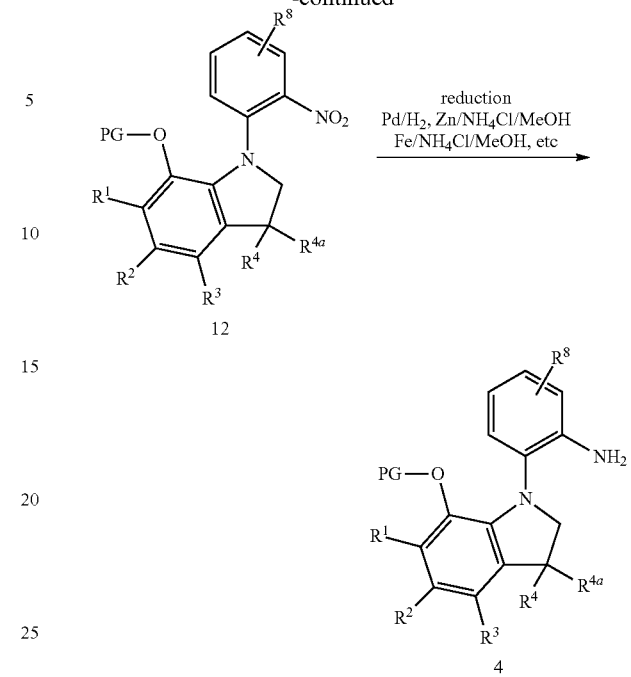

Scheme 6 outlines one possible preparation of the aniline intermediate 4, which proceeds by aromatic nucleophilic substitution followed by reduction. Nitro phenyl derivatives or nitro pyridinyl derivatives 10, substituted in the ortho position with a halogen (such as chlorine, or fluorine), are commercially available or can readily be prepared by one skilled in the art of organic synthesis. They can be reacted with NH-containing cyclics 11 as nucleophiles to provide the corresponding compounds 12. Typical reaction conditions involve the reaction of a nucleophile and a halonitro aryl/heteroaryl derivative either in an organic solvent such as THF, DMF, toluene, dioxane or n-butanol, or under neat condition, in the presence of a base such as potassium carbonate, cesium carbonate, triethylamine, sodium or potassium tert-butoxide, or DIEA. The reaction temperature is usually between room temperature and reflux condition. Reaction conditions can be chosen based on the nucleophilicity of 11 and/or halogen difference. Microwave irradiation and/or heating at higher temperature can also be used to accelerate the rate of reaction. Following aromatic nucleophilic substitution, the resulting nitro derivative 12 can be reduced to the corresponding aniline. Typical conditions include hydrogenation in the presence of a metal catalyst such as palladium or platinum. Other conditions include treatment with reducing agents such as $SnCl_2$ or Zinc or iron powder with ammonium chloride.

On the other hand, the aniline intermediate 4 can be synthesized via Cu or Pd chemistry (for a review paper, see, Ley, S. V. et al., *Angew. Chem. Int. Ed.*, 42:5400-5449 (2003) between a 1,2-substituted aryl/heteroaryl halide 13 and a NH-containing cyclic 11 followed by deprotection or functional transformation of intermediate 14 as exemplified in Scheme 7.

Microwave irradiation can also be used to accelerate the rate of reaction in the coupling step when using the Pd or Cu chemistry. For example, the ester 15 can coupled with the amine 11 via the Chan-Lam chemistry in the presence of Cu catalyst $(Cu(OAc)_2, Et_3N$ or Py, $CH_2Cl_2$, boronic acids. For a recent review, see Qiao, J. X. et al., *Synthesis*, 829-856 (2011), to form the intermediate 16, which can be hydrolyzed, followed by the Curtius rearrangement to afford the protect amine 17. Removal of the amine protecting group in 17 can give the desired aniline intermediate 4. On the other hand, coupling of the bromo nitro compound 18 with the amine 11 via Buchwald-Hartwig amination in the presence of a palladium (O) catalyst such as tris(dibenzylideneacetone)dipalladium(O) $(Pd_2(dba)_3)$ or a palladium (II) catalyst such as palladium acetate $(Pd(OAc)_2)$ with a phosphine ligand such as BINAP or Xantphos and a base such as $Cs_2CO_3$ or t-BuONa, can afford the nitro intermediate 19. Reduction of the nitro group in 19 with a variety of reducing reagent such as Zn, Fe, Pd/C—$H_2$, $SnCl_2$, $Na_2S_2O_4$, can afford the desired aniline intermediate 4.

Scheme 6

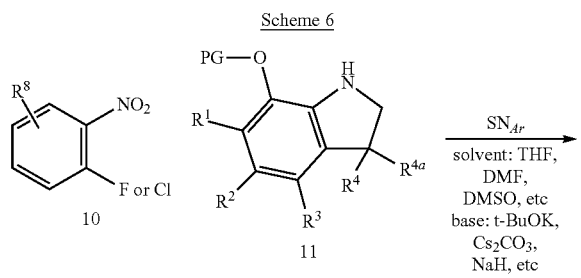

Scheme 7

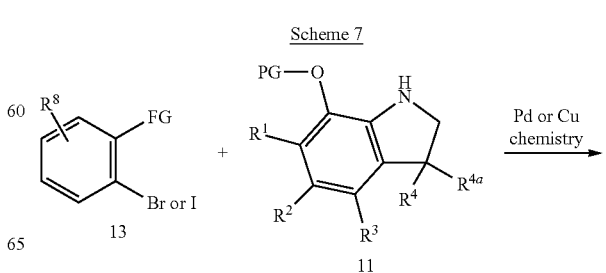

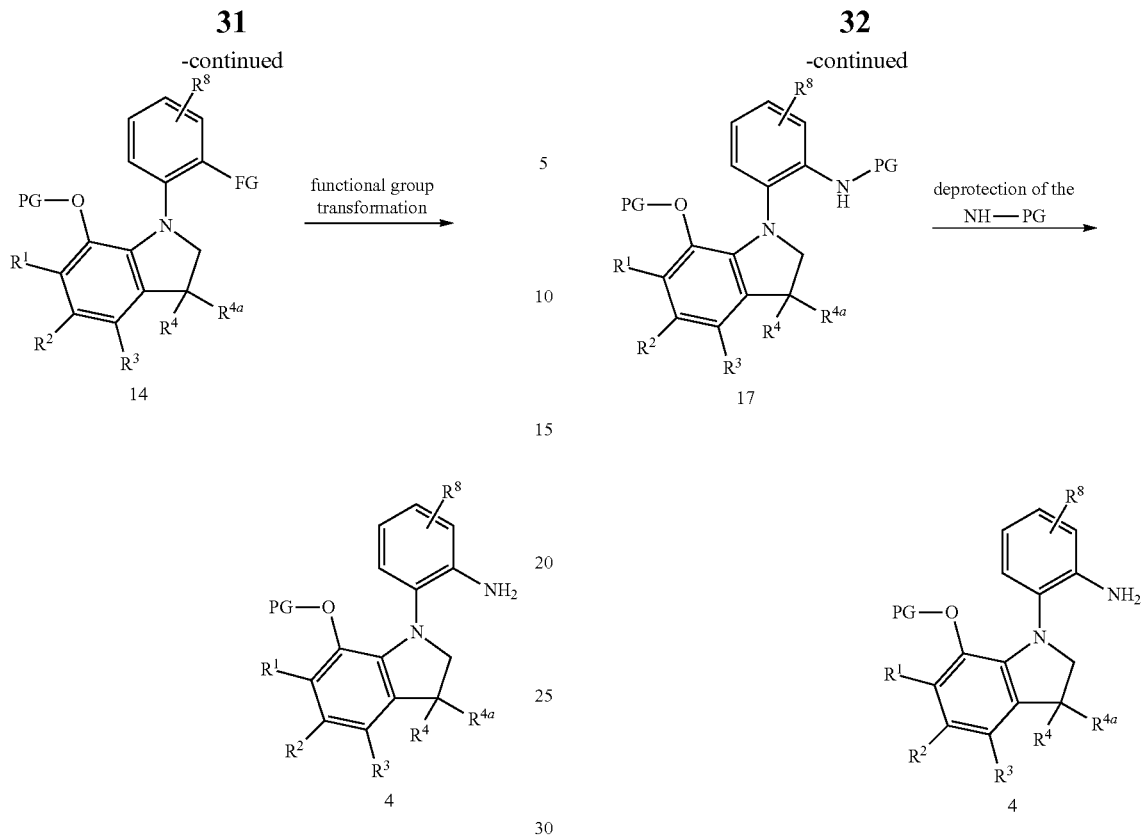
For Example:
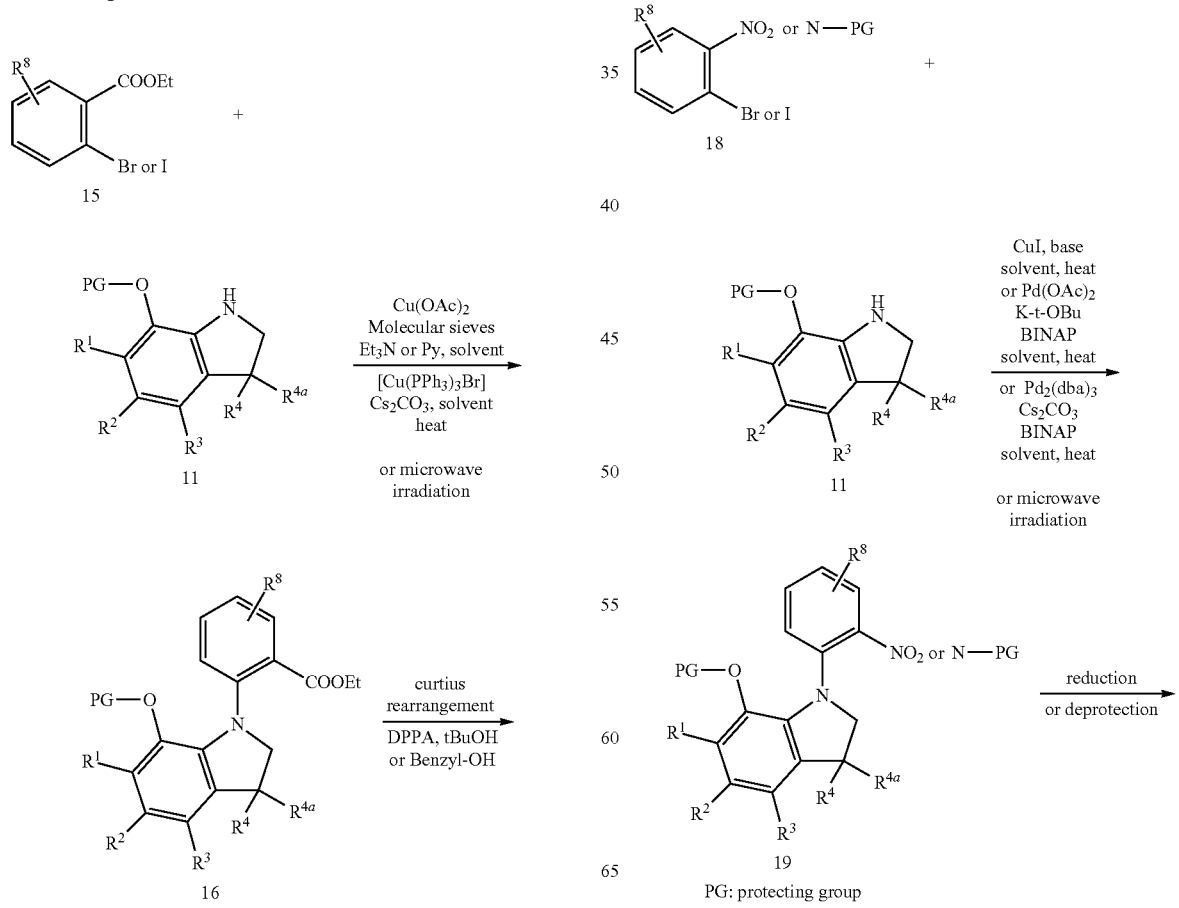
PG: protecting group

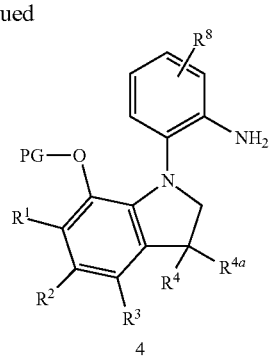

Compounds of the present invention wherein the amine intermediate 11 is a substituted indoline derivative, can be prepared by using the methods shown in Schemes 8-13 and by using methods known to those skilled in the art of organic synthesis.

Scheme 8 illustrates the preparation of the indoline derivative 11 via Fischer indole synthesis followed by reduction of the indolenine intermediate. Substituted phenyl hydrazines 20 are commercially available or can readily be prepared from commercially available materials by methods known to one skilled in the art of organic synthesis. Thus, Fischer indole reaction of the substituted phenyl hydrazine 21 and the aldehyde 21 under acidic conditions (e.g., $H_2SO_4$, HCl, HOAc, TFA, MsOH, $ZnCl_2$) at reaction temperature from 0° C. to refluxing in solvent such as $CH_2Cl_2$, toluene, EtOH, HOAc, 1,4-dioxane, can yield the indolenine intermediate 23, followed by reduction of 23 with reducing agent such as $NaBH_4$, $NaCNBH_3$, or $LiBH_4$ in MeOH at −78° C. to room temperature or refluxing can afford the desired indoline 11.

Scheme 8

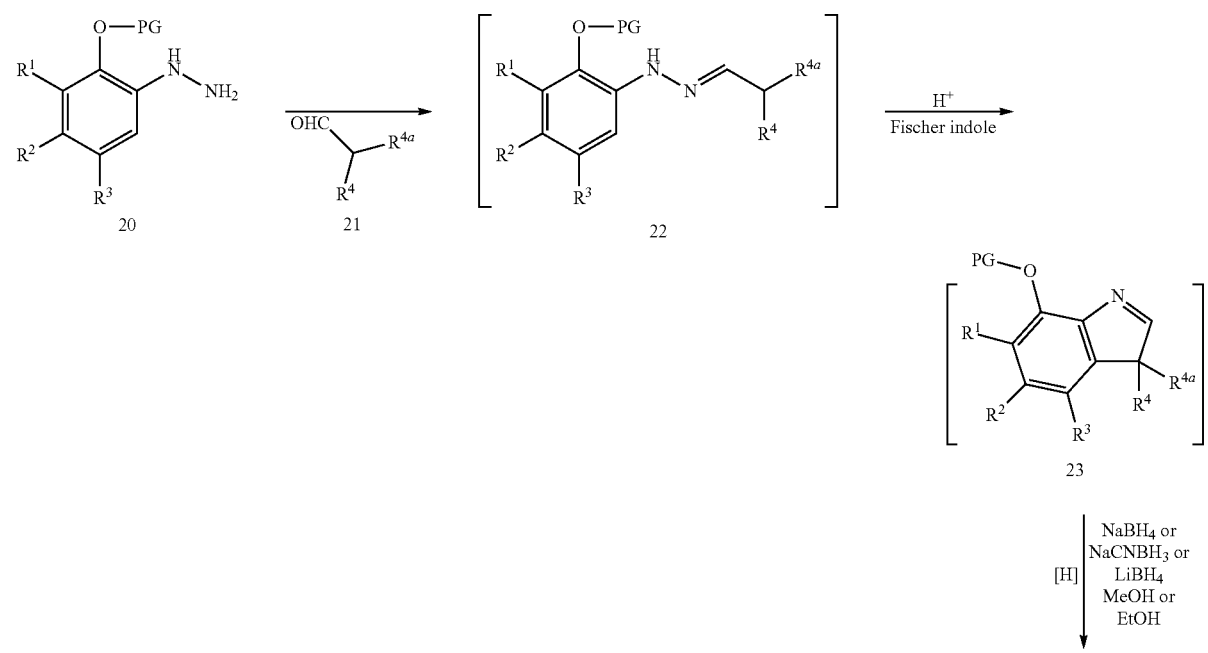

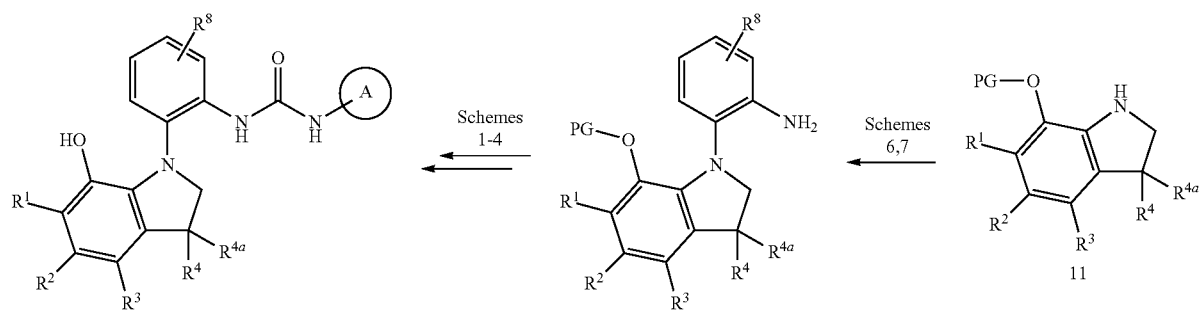

Alternatively, the indolinyl derivative 11 in the present invention can be synthesized via the reduction of indol-2-ones 24 using reducing agents such as LiAlH$_4$, BH$_3$ (Scheme 9). The indol-2-one intermediates 24 are either commercially available or can be prepared using methods known to those skilled in the art of organic synthesis. For example, sequential alkylation of intermediate 25 followed by reduction of the nitro group in 26 and subsequent intermolecular cyclization can afford the desired indol-2-one 24. On the other hand, the indol-2-one can be prepared via cyclocondensation of the appropriate hydrazide 27 with calcium hydride under heating.

Alternatively, in Scheme 10, the indol-2-one intermediate 24 can be prepared from the reduction of the indol-2,3-dione 28 followed by sequential alkylation. On the other hand, the indol-2-one 24 can be prepared from the Cl, Br, or I intermediate 28 via either intramolecular Heck reaction of in the presence of a palladium catalyst (such as Pd$_2$(dba)$_3$, Pd(OAc)$_2$), a phosphine ligand (such as BINAP, PCy$_3$, P(t-Bu)$_3$, etc), a base (such as NaO-t-Bu), in solvent (such as 1,4-dioxane, toluene) or a radical cyclization process with Bu$_3$SnH, AIBN in DMF or toluene under normal heating or microwave irradiation.

Scheme 9

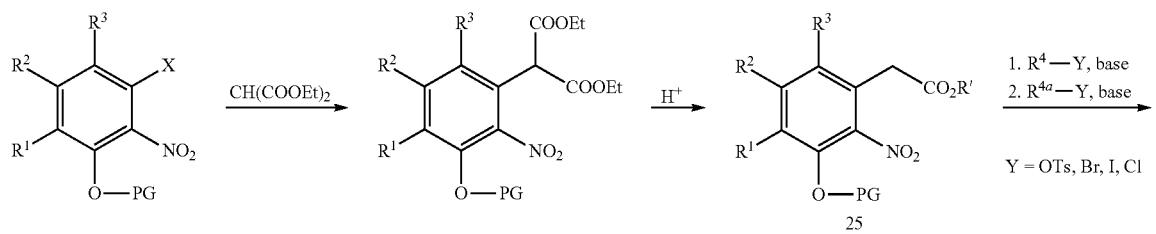

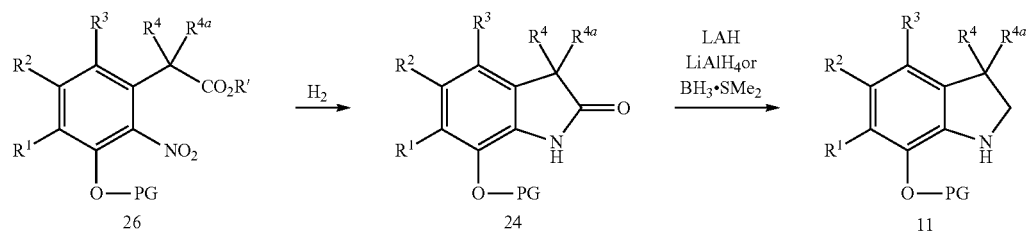

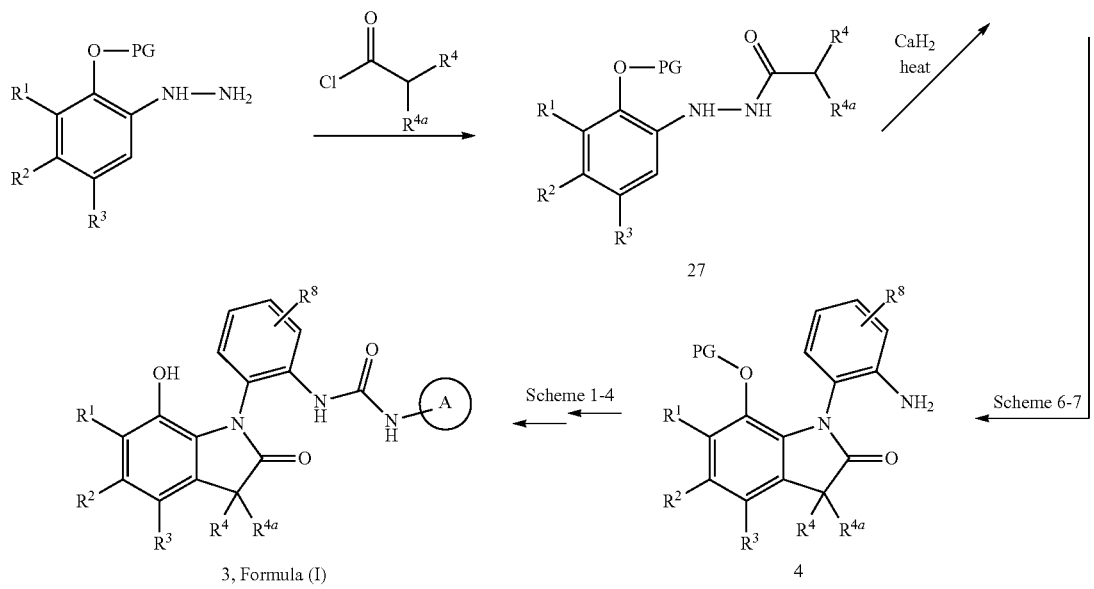

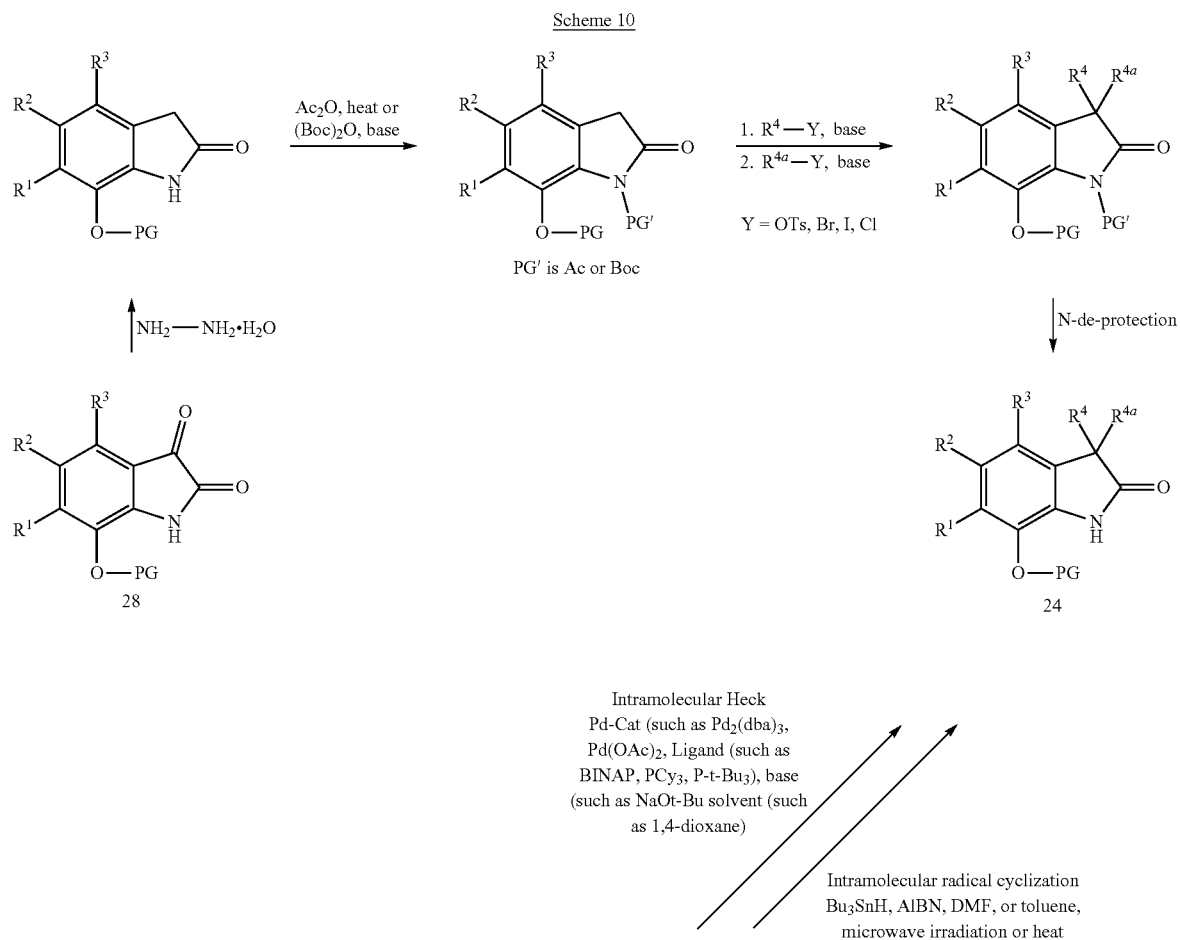
Scheme 11 illustrates the preparation of the indoline derivative 11 (in particular, for $R^4$=Me) via intramolecular Heck cyclization of the appropriately-substituted allyl aniline 30. Cyclization of 30 in the presence of sodium formate can also afford indoline 11 under reactive Heck reaction condition (Liu, P. et al., *Tetrahedron Letters*, 2307 (2007) and reference therein).
Scheme 11
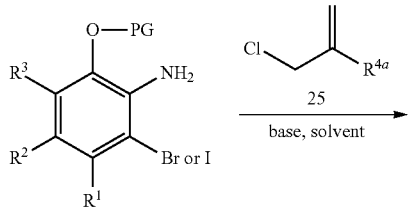
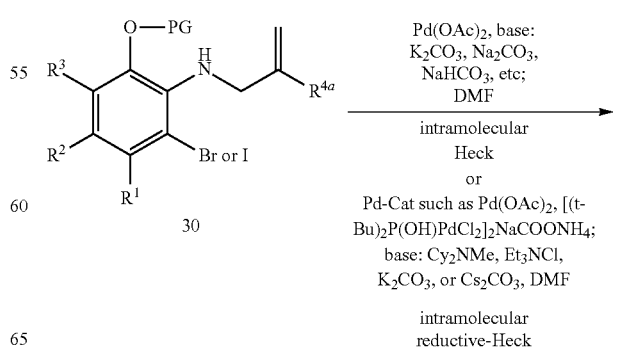

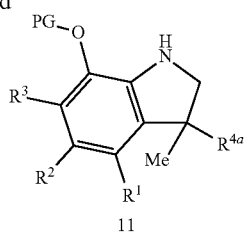

Scheme 12 indicates that the indoline intermediate 11 can also be prepared via alkylation of the nitrile intermediate 31 followed by reductive cyclization of the resulting piperidinyl derivative 32. The nitrile intermediate 31 can be prepared from displacement either the bromide, or tosylate 33 with nitrile anion. Intermediate 32 can also be obtained by reaction of a tertiary alcohol 34 in the presence of a Lewis acid (such as $ZnI_2$) and TMSCN (Schwartz, O., *Tetrahedron Letters*, 1009 (2002)). The alcohol 34 can be prepared via ortho lithiation of the fluoride 35, then trapping with the ketone 36.

Scheme 13 illustrates the 7-OH indoline intermediate 37 in the present invention can be prepared via a variety of methods known to the skill of art of organic synthesis. For example, 7-OH indolines can be prepared via thallation of N-formylindolines 38 or N-acetylindolines (Yamada, Chemical & Pharmaceutical Bulletin, 788 (2006)) or via acid hydrolysis of the amide lactone 39 (Shiyama, K. et al., Tetrahedron Letters, 1021 (2005)), or via benzylic hydroperoxide rearrangement of intermediate 40 (Boger, J. Org. Chem., 5436 (1986)).

coupling of 45 with 46 under Buchwald-Hartwig condition or $SN_{Ar}$ displacement of 47 with 44 yielded the N-aryl derivative 48. When the phenolic protecting group is OBn, Pd—C catalyzed hydrogenation of 48 led to the aniline intermediate 49. When the phenolic protecting group is OMe, reduction of the $NO_2$ group followed by demethylation with $BCl_3$/TBAI at −78° C. to room temperature resulted in the aniline intermediate 49. Urea formation of 49 with either the isocyanate 50 or the acid 51 using methods

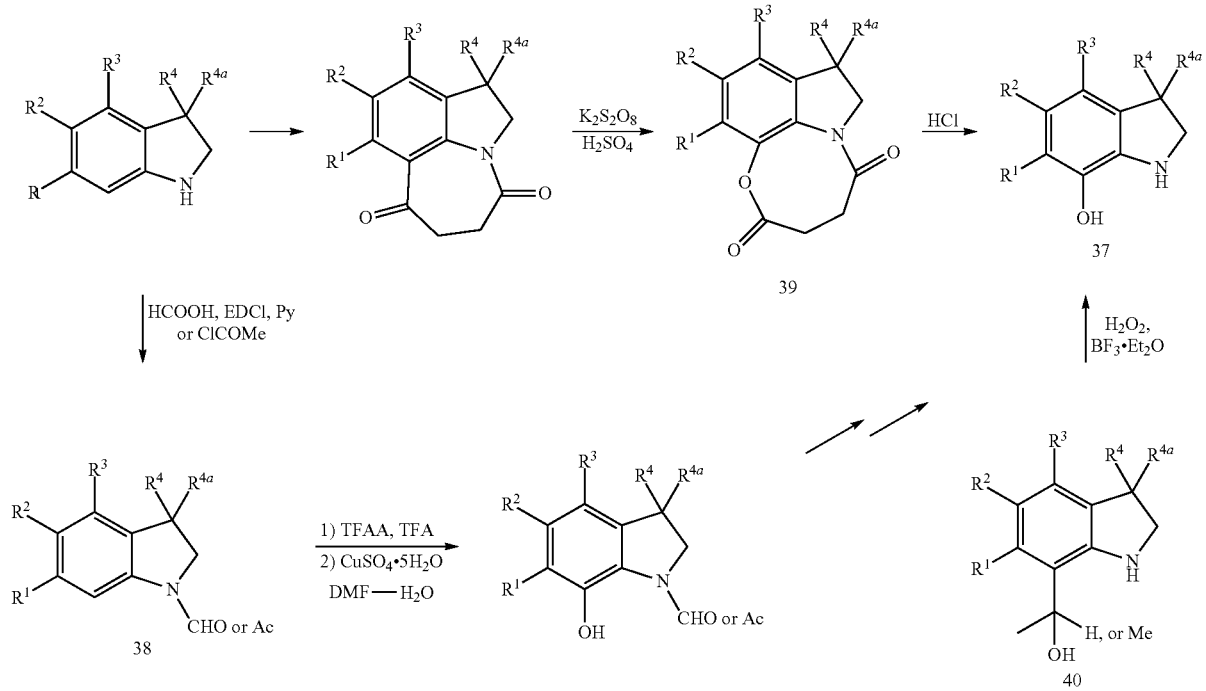

Scheme 13

Scheme 14 illustrates the synthesis of compounds in the present invention wherein, $R^3$ is a trifluoromethyl group. Protection of phenol 41 with either a benzyl or a methyl group followed by reduction of the nitro group afforded the aniline 42. Diazotization of 42 followed by reduction formed the hydrazine 43. Hydrazone formation of 43 with the aldehyde 44 followed by cyclic imine formation under Fischer indole condition and subsequently reducing the imine afforded indoline intermediate 45. Pd-catalyzed cross-shown in Schemes 1-4 afforded compound 52 of the present of the invention. Alternatively, reduction of the nitro intermediate 48 led to aniline 53, which was then reacted with chloroformate followed by displacement of the resulting carbonate with aniline 54 gave the urea intermediate 55. Demethylation of 55 with $BCl_3$/TBAI or debenzylation of 55 under hydrogenation condition yielded the desired compound 52 of the present of the invention.

Scheme 14

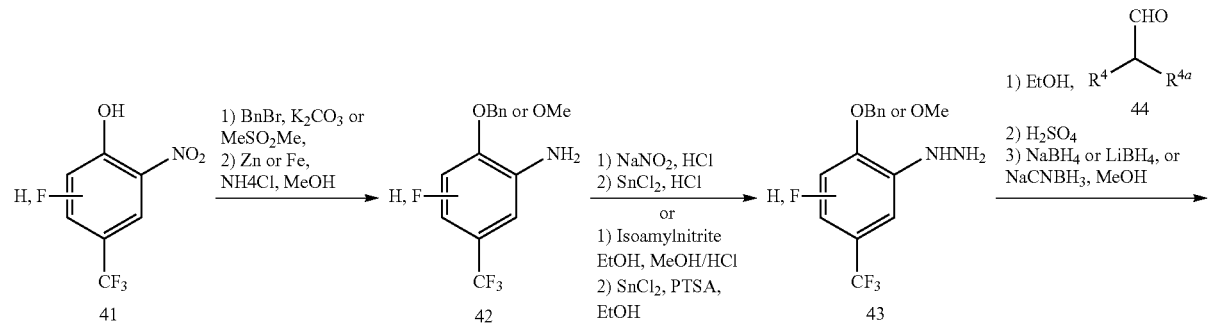

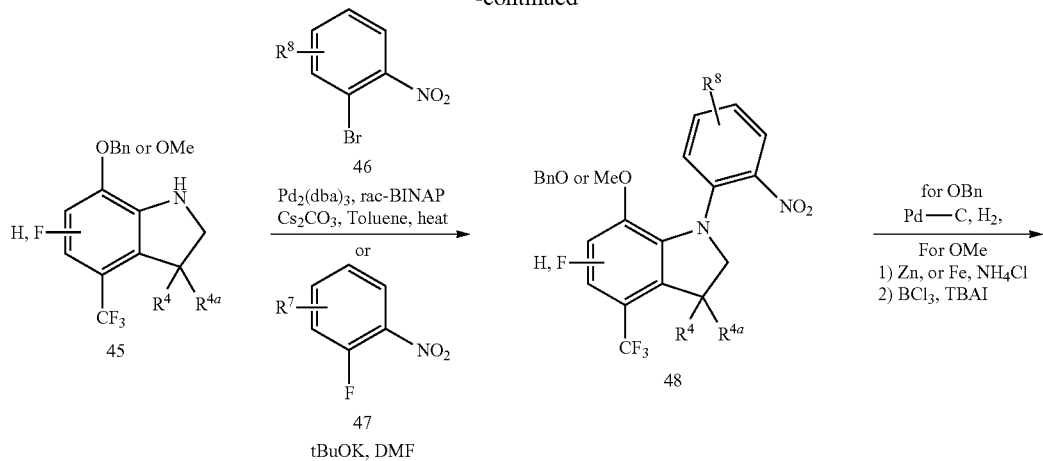

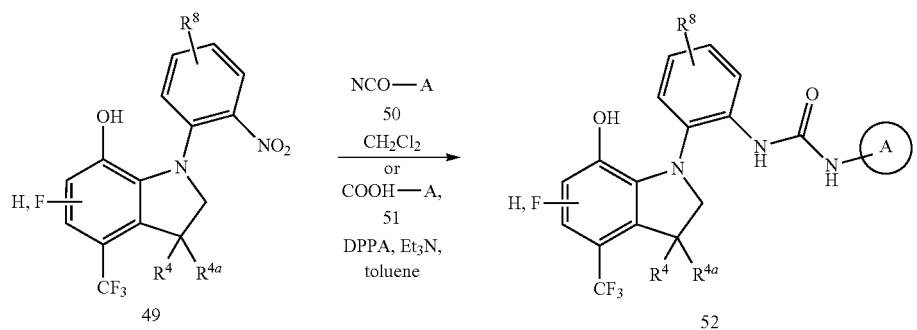

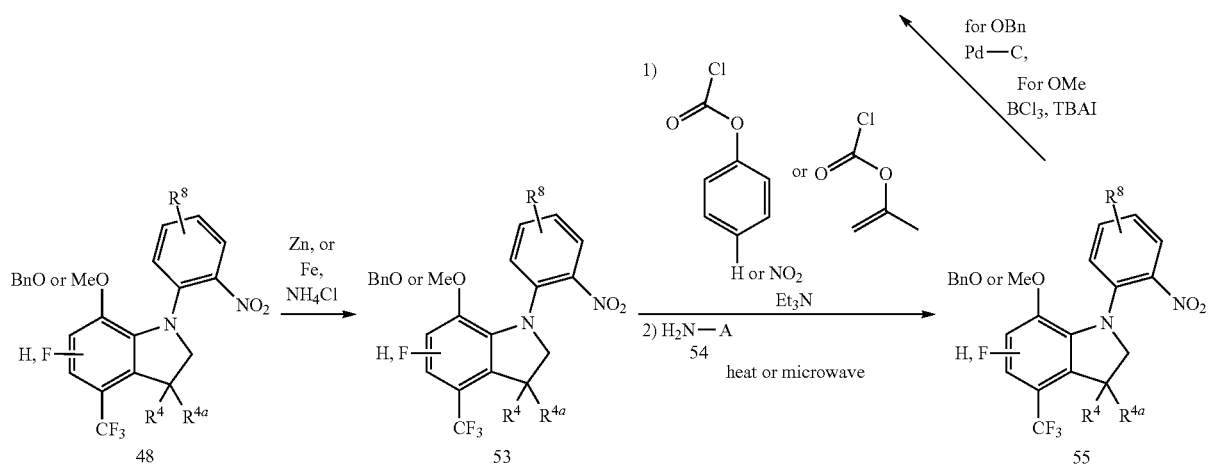

Subsequently, the trifluoromethyl group in 52 can be hydrolyzed in aqueous NaOH in the presence of variety of nucleophiles such as NH—R, SH—R, OH—R, to form amides (56), carboxylic acid or esters (57), nitriles (58), monocyclic or bicyclic heterocycles (59 or 60), such as oxazolidines, benzoxazoles, benzimidazoles, benzithiazoles (Scheme 15). The partially saturated heterocycles such as oxazolidines can be aromatized to form 61 using methods known to the skill of art of organic synthesis.

Scheme 15

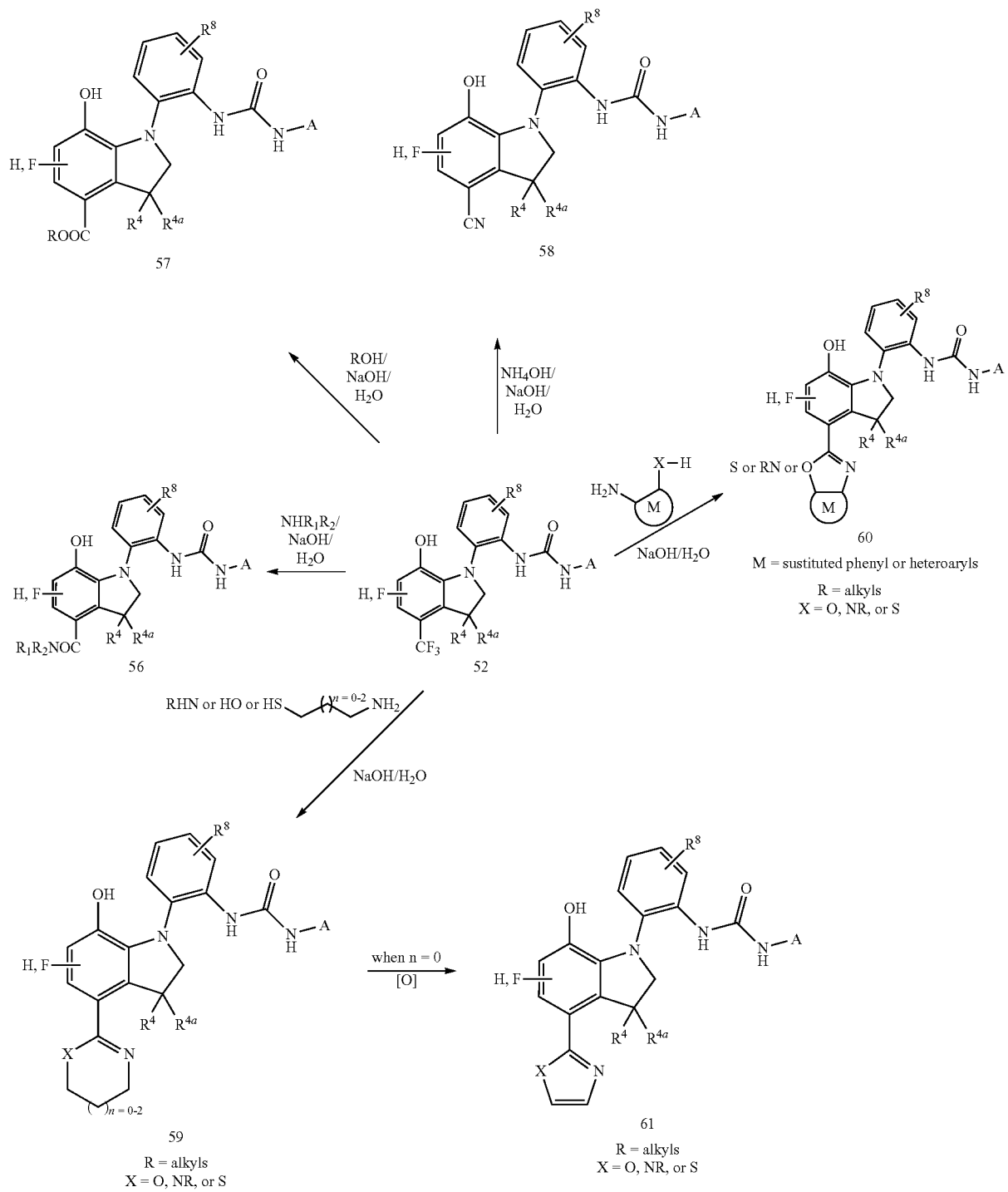

The synthesis of compounds 62 in the present invention wherein, $R^3$ is a bromo group is essentially similar to those procedures illustrated in Scheme 14. Scheme 16 illustrates compounds of the present invention (66) with a variety heteroaryl or aryl or alkyl type of $R^3$ substituents can be obtained from the bromo derivative 62 by using methods known to one skilled in the art of organic synthesis. For instance, the bromo group can be transferred to other groups such as aryl, heteroaryl, alkyl groups via palladium chemistry such as Suzuki coupling (Suzuki, *Pure Appl. Chem.,* 63:419-422 (1991). Miyaura et al., *Chemistry Reviews,* 95:2457-2483 (1995)), Heck reaction (Semmelhack, M. F., *Comprehensive Organic Synthesis,* Vol. 4, Pergamon Press, Oxford (1991)), Hiyama cross-coupling reaction (Hiyama, *Metal Catalyzed Cross-coupling Reactions, Chapter* 10, p. 421, Wiley-VCH, Weinhein (1998)), and Negishi cross-coupling reaction (Negishi, *Acc. Chem. Res.*, 15:340 (1982)), or via organocopper chemistry such as Ullman coupling (Hassan et al., *Chemical Reviews*, 102:1359-1469 (2002)).
Alternatively, compounds of the present invention wherein $R^3$ is a heteroaryl, such as pyrazole, oxazole, oxadiazole, can be obtained as shown in Scheme 17 by using methods known to one skilled in the art of organic synthesis.
Scheme 16
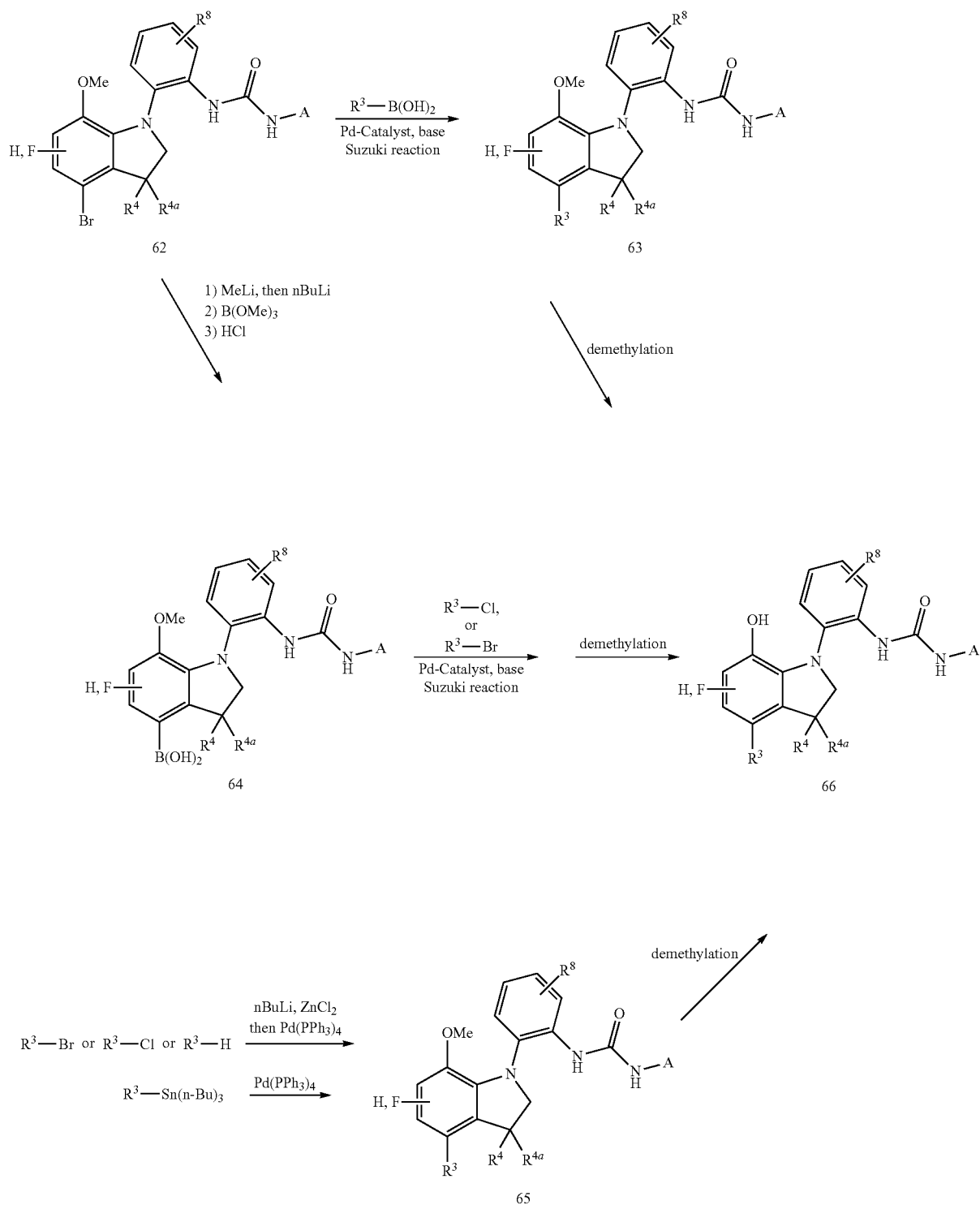

Scheme 17

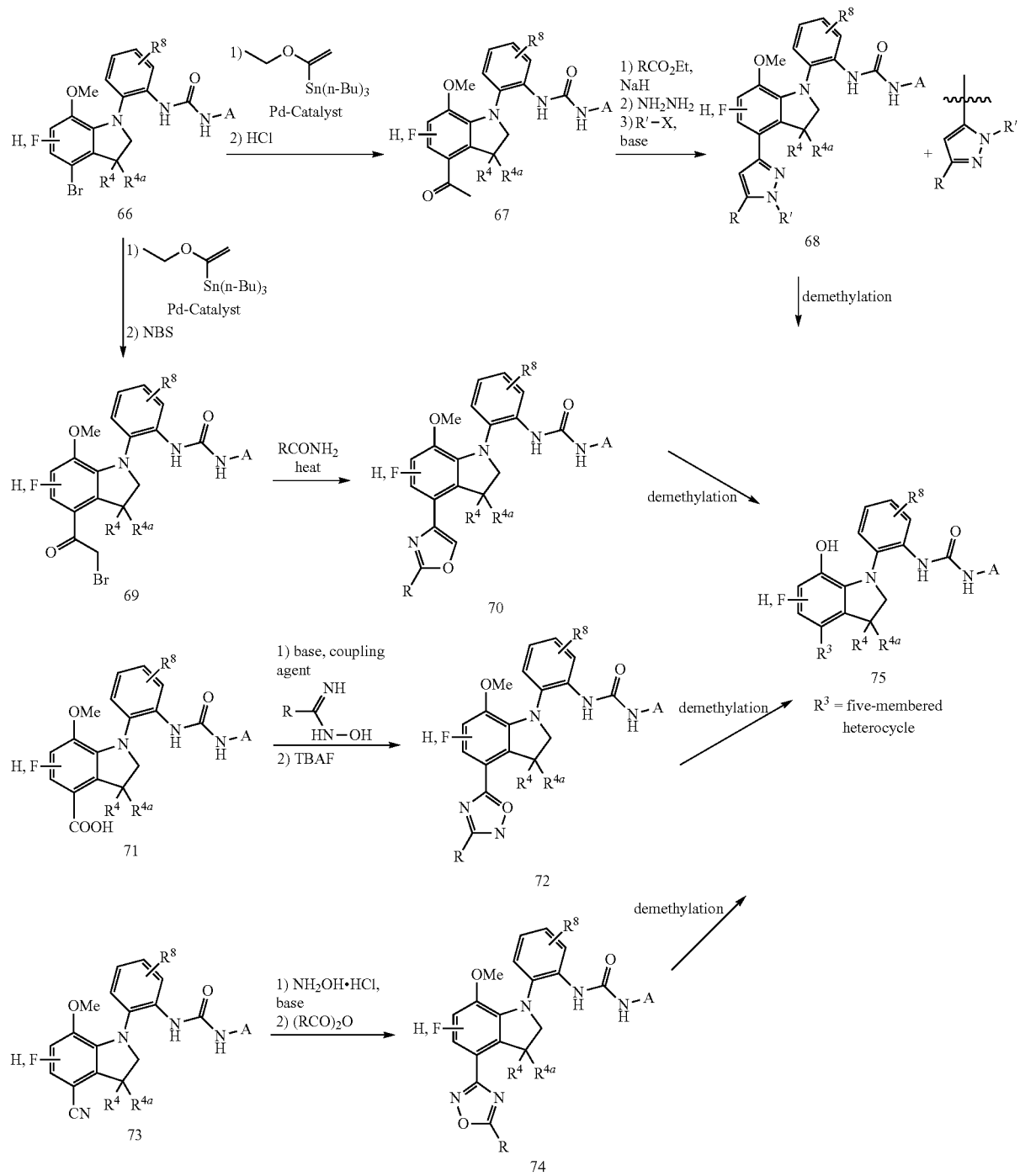

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% H$_3$PO$_4$; B: 10% water, 89.9% methanol, 0.1% H$_3$PO$_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% NH$_4$OAc; B: 10% water, 89.9% methanol, 0.1% NH$_4$OAc, UV 220 nm). Purification of intermediates and final products was carried out via either normal or reverse phase chromatography. Normal phase chromatography was carried out using prepacked SiO$_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a VARIAN® ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running Discovery VP software, coupled with a Waters ZQ mass spectrometer running MassLynx version 3.5 software using:

Method A: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: Luna C-18 5μ (4.5×30 mm) Flow rate was 4 ml/min. and UV detection was set to 220 nm. The LC column was maintained at room temperature.

Method B: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: L XTERRA® C-8 (4.5×30 mm) Flow rate was 4 ml/min. and UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×50 mm) Flow rate was 4 ml/min. and UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5u C18 (4.5×30 mm) Flow rate was 4 ml/min. and UV detection was set to 220 nm. The LC column was maintained at room temperature.

Method E: A linear gradient using solvent A (10% acetonitrile, 90% water, 10 mM NH$_4$OAc) and solvent B (90% acetonitrile, 10% water, 10 mM NH$_4$OAc); 0-100% of solvent B over 4 min and then 100% of solvent B over 1 min. Column: PHENOMENEX® Luna 5u C18 (4.5×50 mm) Flow rate was 4 ml/min. and UV detection was set to 220 nm. The LC column was maintained at room temperature.

Method F: A linear gradient using solvent A (10% acetonitrile, 90% water, 0.1% TFA) and solvent B (90% acetonitrile, 10% water, 0.1% TFA); 0-100% of solvent B over 2 min and then 100% of solvent B over 1 min. Column: PHENOMENEX® Luna 5u C18 (4.6×30 mm) Flow rate was 5 ml/min. and UV detection was set to 220 nm. The LC column was maintained at room temperature.

Method G: A linear gradient using solvent A (10% acetonitrile, 90% water, 0.05% of NH$_4$OAc) and solvent B (90% acetonitrile, 10% water, 0.05% of NH$_4$OAc); 0-100% of solvent B over 2 min and then 100% of solvent B over 1 min. Column: Luna C-18 (50 (4.6×30 mm) Flow rate was 4 ml/min. and UV detection was set to 220 nm. The LC column was maintained at room temperature.

Method H: A linear gradient using solvent A (10% acetonitrile, 90% water, 0.05% of NH$_4$OAc) and solvent B (90% acetonitrile, 10% water, 0.05% of NH$_4$OAc); 0-100% of solvent B over 2 min and then 100% of solvent B over 1 min. Column: XTERRA® C-8 (4.6×30 mm) Flow rate was 4 ml/min. and UV detection was set to 220 nm. The LC column was maintained at room temperature.

Method I: A linear gradient using solvent A (10% acetonitrile, 90% water, 0.05% of TFA) and solvent B (90% acetonitrile, 10% water, 0.05% of TFA); 0-100% of solvent B over 8 min and then 100% of solvent B over 3 min. Column: ZORBAX® SB C18 (4.6×75 mm) Flow rate was 2.5 ml/min. and UV detection was set to 220 nm. The LC column was maintained at room temperature.

Method J: A linear gradient using solvent A (10% MeOH, 90% water, 0.1% of TFA) and solvent B (90% MeOH, 10% water, 0.1% of TFA); 0-100% of solvent B over 2 min and then 100% of solvent B over 1 min. Column: PHENOMENEX® C18 10 micron (3×50 mm) Flow rate was 5 ml/min. and UV detection was set to 220 nm. The LC column was maintained at room temperature.

Method K: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5u C18 (4.5×30 mm) Flow rate was 5 ml/min. and UV detection was set to 220 nm. The LC column was maintained at room temperature.

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 μm (4.6×150 mm) Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 μm (4.6×150 mm) Flow rate was 2 ml/min. and UV detection was set to 220 nm. The LC column was maintained at room temperature.

Method C: A linear gradient using solvent A (0.1% DEA in H$_2$O, pH adjusted to 8.5 with dil. OPA) and solvent B (acetonitrile); 10-100% of solvent B over 12 min and then 100% of solvent B over 6 min. Column: Sunfire C18 3.5 µm (4.6×150 mm) Flow rate was 1 ml/min. and UV detection was set to 220 nm. The LC column was maintained at room temperature.

Method D: A linear gradient using solvent A (0.1% DEA in $H_2O$, pH adjusted to 8.5 with dil. OPA) and solvent B (acetonitrile); 10-100% of solvent B over 12 min and then 100% of solvent B over 6 min. Column: Xbridge Phenyl 3.5 µm (4.6×150 mm) Flow rate was 1 ml/min. and UV detection was set to 220 nm. The LC column was maintained at room temperature.

IV. Biology

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for $P2Y_1$ antagonists have been recently reviewed (Burnstock, G. et al., *J. Pharm. Exp. Ther.*, 295:862-869 (2000)) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

It is also desirable and preferable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-platelet agent, e.g., a P2Y1 antagonist. Exemplary subjects include human beings of any age with risk factors for platelet associated disorders. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

P2Y$_1$ Assays

Binding Assay A

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al., *Current Protocols in Molecular Biology*, John Wiley and Sons, NY, NY (1995)). The essential coding sequences were subcloned into pCDNA 3.1 (Invitrogen) to produce a P2Y$_1$ expression construct. This construct was then transfected into the human embryonic kidney cell line HEK-293 and stable transfectants selected in GENETICIN® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FLASHPLATE®s (PerkinElmer Life Sciences, Cat # SMP105A) in a volume of 200 μL containing ~45 fmol of P2Y$_1$ receptor (5 μg of total protein), 0.5 nM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 14 nM.

Binding Assay B—Scintillation Proximity Assay (SPA) for P2Y$_1$ Binding

A SPA membrane binding assay was used to identify inhibitors of [$^{33}$P] 2MeS-ADP binding to cloned human P2Y$_1$ receptors (The P2Y$_1$ receptor membranes were provided by Biology and the cloning of the receptor and P2Y$_1$ receptor membrane preparation is same as described by Biology). Binding reactions were performed in 384-well OptiPlates (PerkinElmer Life Sciences, Cat #6007299) in a volume of 50 μL containing ~15 fmol of P2Y$_1$ receptor (1.7 μg of total protein), 0.3 nM [$^{33}$P] 2MeS-ADP (PerkinElmer; 2,000 Ci/mmol), various concentrations of the test compound (usually between 10 μM and 160 pM) in Buffer B containing 1% DMSO in assay buffer (15 mM, HEPES, 145 mM potassium chloride, 5 mM sodium chloride, 5 mM EDTA, 0.1 mM MgCl$_2$, pH 7.4) and 100 μg of SPA bead (WGA polystyrene Image beads, #RPNQ 0260V, Amersham). Reactions were allowed to proceed to completion at room temperature for 1 hour followed by centrifugation of the plate for 5 min. About 40 μL of the aqueous solution was aspirated. Plates were sealed and the [$^{33}$P] 2MeS-ADP bound to the P2Y$_1$ receptor membranes that were bound to the SPA bead were determined in a Gen 4 LEADSEEKER© (Amersham) Image Reader. Dose-response curves (IC$_{50}$) were fit by non-linear regression (Toolset an in house data processing program) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

ADP Induced Platelet Aggregation Assay

The ability of P2Y$_1$ antagonists covered in the present invention to inhibit platelet aggregation induced by 10 μM ADP was tested using human platelet rich plasma (PRP) as described in *Platelet Protocols: Research and Clinical Laboratory Procedures* (White, M. M. et al., Academic Press (1999)). Human blood was collected in 30 μM (final concentration in blood) argatroban (GSK) as the anticoagulant at a ratio of 1 mL per 9 mL of blood. The PRP was isolated by centrifugation at 170 g for 12 minutes. The platelet poor plasma (PPP) was used as the blank for optical aggregometry. Compounds of the present invention in DMSO solution was preincubated with 250 μL PRP at 37° C. for 1 minute with stirring speed of 1000 rpm. Aggregation was initiated by addition of 2.5 μL of 1 mM ADP (Chronolog, Havertown, Pa.) for a final ADP concentration of 10 μM. Platelet aggregation was monitored using Optical Aggregometer (Chrono-log, Havertown, Pa.) and the area under the curve (AUC) at 5 minute was measured. IC$_{50}$ was calculated using vehicle control as 0% inhibition.

The effectiveness of compounds of the present invention as antithrombotic agents and can be determined using relevant in vivo thrombosis models, including in vivo rat FeCl$_2$-induced carotid artery thrombosis, in vivo rabbit electrically-induced carotid artery thrombosis, and in vivo rabbit arterio-venous shunt thrombosis models. The potential of compounds of the present invention to have an undesirable bleeding liability can be determined using relevant in vivo rat models of cuticle and mesenteric bleeding time or in vivo rabbit cuticle bleeding model. An ideal compound from the present invention will demonstrate strong antithrombotic activity at doses that minimize the bleeding liability.

In Vivo FeCl$_2$-Induced Carotid Artery Thrombosis (FeAT) Model

The FeAT model described by Schumacher et al. (*J. Pharmacol. Exp. Ther.*, 322:369-377 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP and measuring drug concentration. The right carotid artery is exposed and fitted with transit time doppler probe attached to a T206 flowmeter (Transonic Systems Inc., Ithaca, N.Y.). A piece of parafilm "M" (American National Can, Greenwich, Conn.) is inserted under the vessel and, following baseline flow measurements, a 2 mm by 5 mm strip of filter paper saturated with a 50% solution of FeCl$_2$ is placed on top of the artery for 10 min. The carotid artery is dissected free 60 min after filter paper application and opened lengthwise to expose the thrombus, which is removed, blotted dry and weighed on an AE50 balance (Mettler, Toledo, Ind.). Carotid blood flow is monitored continuously on a TA4000 physiologic recorder (Gould, Cleveland, Ohio). Integrated blood flow is determined as an area under the curve and normalized as percent of baseline (0 min) flow over 60 min to provide a measure of average blood flow over the duration of thrombus formation.

In Vivo Rabbit Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid E equation (DeltaGraph; SPSS Inc., Chicago, Ill.).

In Vivo Rabbit Arterio-Venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid E equation (DeltaGraph; SPSS Inc., Chicago, Ill.).

In Vivo Rat Cuticle Bleeding Time (CBT) and Mesenteric Bleeding Time (MBT) Model The CBT and MBT models described by Schumacher et al. (*J. Pharmacol. Exp. Ther.*, 322:1-9 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP.

For the MBT the abdomen is opened via a midline incision and the small intestine is exteriorized. The jejunum is exposed, held in place with clamps and superfused with Ringer's solution maintained at 37° C. Small arteries that branch perpendicular to the mesenteric artery and course over the surface of the jejunum are observed through an SZH10 stereomicroscope (Olympus Corp., Lake Success, N.Y.). These vessels are punctured with a 30-gauge hypodermic needle, and the time in sec from puncturing until bleeding stopped and remained stopped for 30 sec is recorded. The maximum bleeding time recorded is 10 min and 3 to 5 replicate bleed times are determined For the CBT toenails are cut with a single edged razor blade at the location where the quick meets the nail. The cuticle is immediately superfused with Ringer's solution maintained at 37° C., and the time until bleeding stopped and remained stopped for 30 sec is recorded. The maximum bleeding time recorded is 15 min. Three replicate bleeding times are determined on the hind paw.

In Vivo Rabbit Cuticle Bleeding Time Model

The rabbit cuticle bleeding time model, described by Wong et al. (Wong, P. C. et al., *J. Pharmacol. Exp. Ther.*, 303:993-1000 (2002)), can be used in this study. Male rabbits were anesthetized with ketamine (50 mg/kg+50 mg/kg/h IM) and xylazine (10 mg/kg+10 mg/kg/h IM). These anesthetics are supplemented as needed, and their hind paws were shaved. A standard cut was made at the apex of the cuticle with a razor blade. Blood was allowed to flow freely by keeping the bleeding site in contact with 37° C. warm Lactated Ringer's solution. Bleeding time was defined as the time after transection when bleeding was ceased. It was measured by averaging the bleeding time of three nail cuticles in the control period and at 60 min of the treatment period. Compound or vehicle was infused i. v. 1 h before the cuticle bleeding and continuously during the bleeding time measurement period.

Comparator Compounds

The following comparator compounds and their preparations are disclosed in U.S. Patent Publication No. 2005/0261244 A1:

| Comparator No. (Example No. in US 2005/0261244 A1) | Structure |
|---|---|
| Comparator 1 (Example 36 in US 2005/0261244 A1) | 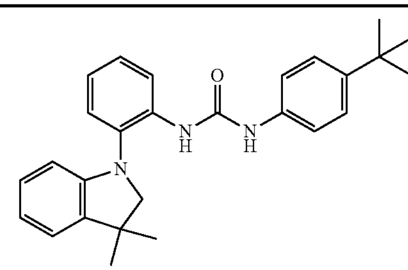 |

| Comparator No. (Example No. in US 2005/ 0261244 A1) | Structure |
|---|---|
| Comparator 2 (Example 37 in US 2005/ 0261244 A1) | 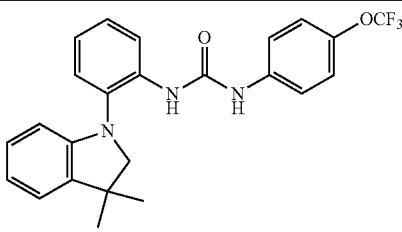 |
| Comparator 3 (Example 82 in US 2005/ 0261244 A1) | 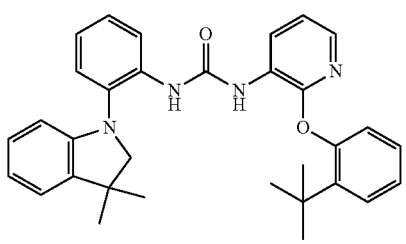 [SMILES: CC(C)(C)c1ccccc1Oc1ncccc1NC(=O)Nc1ccccc1N1CC(C)(C)c2ccccc21] |
The following representative in vitro biological data was measured in a binding assay for the Comparator Compound and the exemplified examples herein:
TABLE 1
| Example No. | P2Y$_1$ K$_i$ (nM) using binding assay B | PA IC$_{50}$ (μM) @ 10 μM ADP |
|---|---|---|
| Comparator 1 | 12.9 | >20 |
| Comparator 2 | 8.7 | >20 |
| Comparator 3 | 759.2 | >>20 |
| 1 | 10.8 | 0.47 |
| 2 | 3.4 | 0.13 |
| 3 | 4.9 | 3.10 |
| 4 | 5.6 | 0.36 |
| 5 | 16.0 | 1.05 |
| 6 | 24.4 | 0.31 |
| 7 | 8.6 | 0.55 |
| 8 | 18.6 | 0.31 |
| 9 | 14.2 | 0.39 |
| 10 | 7.6 | 0.54 |
| 11 | 36.8 | 1.08 |
| 12 | 5.0 | 0.20 |
| 13 | 8.2 | 0.13 |
| 14 | 5.2 | 0.48 |
| 15 | 7.3 | 0.95 |
| 16 | 6.2 | 0.12 |
| 17 | 16.4 | 0.27 |
| 18 | 12.4 | 0.17 |
| 19 | 23.6 | 0.12 |
| 20 | 18.6 | 0.95 |
| 21 | 7.9 | 0.07 |
| 22 | 8.0 | 0.21 |
| 23 | 10.4 | 1.01 |
| 24 | 7.6 | 0.22 |
| 25 | 6.3 | 0.26 |
| 26 | 5.1 | 0.98 |
| 27 | 3.1 | 1.02 |
| 28 | 8.1 | 0.54 |
| 29 | 3.6 | 0.30 |
| 30 | 5.1 | 0.28 |
| 31 | 3.3 | 0.53 |
| 32 | NT | 0.37 |
| 33 | 7.6 | 0.55 |
| 34 | 9.8 | 1.07 |
| 35 | 13.8 | 0.38 |
| 36 | 5.7* | 0.21 |
| 37 | 8.7 | 0.89 |
| 38 | 14.8 | 0.43 |
| 39 | 18.8 | 0.51 |
| 40 | 13.8 | 0.53 |
| 41 | 10.6 | 0.47 |
| 42 | 27.7 | 0.45 |
| 43 | 7.8 | 0.47 |
| 44 | 6.9 | 0.45 |
| 45 | 6.7 | 0.39 |
| 46 | 9.5 | 1.00 |
| 47 | 18.6 | 3.35 |
| 48 | 7.0* | 0.48 |
| 49 | 6.6* | 0.18 |
| 50 | 6.6 | 0.86 |
| 51 | 14.1 | 0.41 |
| 52 | 12.6 | 0.28 |
| 53 | 5.0 | 0.28 |
| 54 | 13.3 | 0.15 |
| 55 | 16.2 | 0.63 |
| 56 | 8.7 | 0.87 |
| 57 | 8.3 | 0.90 |
| 58 | 4.1 | 0.32 |
| 59 | 5.7 | 0.24 |
| 60 | 10.6 | 0.62 |
| 61 | 5.2 | 0.54 |
| 62 | 14.6 | 0.75 |
| 63 | 20.8 | 0.18 |
| 64 | 13.0 | 0.21 |
| 65 | 14.1 | 0.83 |
| 66 | 21.3 | 0.75 |
| 67 | 13.8 | 0.77 |
| 68 | 7.5 | 0.60 |
| 69 | 18.1 | 0.83 |
| 70 | 31.3 | 0.78 |
| 71 | 6.8 | 0.50 |
| 72 | 32.2 | 1.05 |
| 73 | 4.5 | 0.90 |
| 74 | 19.8 | 3.11 |
| 75 | 7.1 | 0.56 |
| 76 | 11.5 | 0.40 |
| 77 | 12.9 | 0.61 |
| 78 | 7.7 | 2.92 |
| 79 | 9.7 | 0.83 |
| 80 | 9.0 | 0.84 |
| 81 | 8.6 | 0.91 |
| 82 | 15.8 | 0.99 |
| 83 | 14.7 | 0.86 |
| 84 | 16.7 | 0.58 |
| 85 | 23.5 | 0.38 |
| 86 | 22.2 | 5.00 |
| 87 | 42.9 | 0.27 |
| 88 | 39.7 | 4.15 |
| 89 | 12.3 | 0.99 |
| 90 | 56.7 | 0.43 |
| 91 | 65.1 | 0.33 |
| 92 | 36.6 | 0.20 |
| 93 | 52.0 | 0.80 |
| 94 | 39.5 | 0.48 |
| 95 | 33.3 | 0.46 |
| 96 | 22.2 | 2.99 |
| 97 | 20.7 | 1.52 |
| 98 | 26.7 | 0.79 |
| 99 | 28.1 | 0.89 |
| 100 | 38.4 | 0.27 |
| 101 | 31.9 | 0.67 |
| 102 | 11.2 | 0.97 |
| 103 | 11.1 | 1.03 |
| 104 | 9.1 | 0.46 |
| 105 | 8.8 | 1.57 |
| 106 | 363.9 | 3.28 |
| 107 | 24.0 | 3.85 |
| 108 | 9.7 | 0.19 |
| 109 | 22.0 | 0.13 |
| 110 | 15.4 | 0.31 |
| 111 | 7.5 | 0.14 |
| 112 | 9.0 | 0.43 |
| 113 | 5.9 | 0.35 |

TABLE 1-continued

| Example No. | P2Y$_1$ K$_i$ (nM) using binding assay B | PA IC$_{50}$ (μM) @ 10 μM ADP |
|---|---|---|
| 114 | 26.5 | 0.53 |
| 115 | 13.2 | 0.31 |
| 116 | 22.4 | 0.50 |
| 117 | 36.0 | 0.51 |
| 118 | 9.9 | 0.60 |
| 119 | 3.3 | 0.47 |
| 120 | 7.9 | 0.14 |
| 121 | 113.1 | 0.20 |
| 122 | NT | 0.51 |
| 123 | 4.5* | 0.43 |
| 124 | 3.4* | 0.82 |
| 125 | 4.8* | 0.15 |
| 126 | 4.1* | 0.3 |
| 127 | 4.7* | 0.28 |
| 128 | 107.6 | 0.24 |
| 129 | 15.3 | 0.71 |
| 130 | 93.5 | 1.80 |
| 131 | 9.1 | 0.42 |
| 132 | 18.8 | 1.29 |
| 133 | 10.2 | 0.69 |
| 134 | 73.8 | 0.19 |
| 135 | 8.7 | 0.15 |
| 136 | 12.9 | 0.50 |
| 137 | 77.6 | 1.06 |
| 138 | 47.5 | 0.47 |
| 139 | 89.6 | 0.57 |
| 140 | NT | 0.17 |
| 141 | 38.7 | 0.55 |
| 142 | 9.5 | 0.13 |
| 143 | 15.6 | 0.33 |
| 144 | 10.0 | 0.50 |
| 145 | 8.2 | 0.13 |
| 146 | 47.2 | 0.30 |
| 147 | 70.8 | 0.77 |
| 148 | 83.0 | 0.68 |
| 149 | 13.0 | 0.11 |
| 150 | 32.7 | 0.41 |
| 151 | 24.1 | 0.48 |
| 152 | 25.4 | 0.30 |
| 153 | 15.4 | 0.23 |
| 154 | 22.5 | 0.35 |
| 155 | 38.0 | 0.60 |
| 156 | 97.8 | 0.97 |
| 157 | 18.7 | 0.28 |
| 158 | 5.7 | 0.20 |
| 159 | 7.4 | 0.30 |
| 160 | 13.1 | 0.09 |
| 161 | 6.6 | 0.16 |
| 162 | 6.4 | 0.25 |
| 163 | 43.1 | 0.26 |
| 164 | 10.8 | 0.95 |
| 165 | 26.8 | 0.21 |
| 166 | NT | 1.25 |
| 167 | 13.4 | 0.47 |
| 168 | 29.4 | 0.45 |
| 169 | NT | 0.10 |
| 170 | 14.1 | 0.25 |
| 171 | 8.7* | 0.36 |
| 172 | 16.7* | 0.26 |
| 173 | 20.7* | 0.50 |
| 174 | 6.3* | 0.32 |
| 175 | 17.6* | 0.35 |
| 176 | 13.0* | 0.35 |
| 177 | 51.8 | 2.30 |
| 178 | 17.9 | 0.74 |
| 179 | 22.6 | 0.49 |
| 180 | 28.4 | 0.56 |
| 181 | 9.7 | 0.49 |
| 182 | 15.7 | 0.51 |
| 183 | 11.3 | 0.21 |
| 184 | 10.7 | 0.26 |
| 185 | 13.3 | 0.16 |
| 186 | 17.6 | 0.67 |
| 187 | 19.2 | 1.07 |
| 188 | 4.7 | 0.38 |
| 189 | 7.2 | 0.25 |
| 190 | 10.6 | 0.48 |
| 191 | 12.3 | 0.19 |
| 192 | 8.8 | 0.26 |
| 193 | 6.9 | 0.12 |
| 194 | 6.7 | 0.26 |
| 195 | 9.0 | 0.18 |
| 196 | 8.0 | 0.23 |
| 197 | 5.1 | 0.18 |
| 198 | 4.9 | 0.09 |
| 199 | 10.1 | 0.18 |
| 200 | 4.6 | 0.05 |
| 201 | 5.8 | 0.43 |
| 202 | 5.7 | 0.09 |
| 203 | 8.0 | 0.16 |
| 204 | 7.7 | 0.40 |
| 205 | 6.7 | 0.14 |
| 206 | 8.5 | 0.24 |
| 207 | 8.7 | 0.08 |
| 208 | 11.4 | 0.25 |
| 209 | 13.0 | 0.23 |
| 210 | 12.4 | 0.08 |
| 211 | 27.1 | 0.46 |
| 212 | 4.9 | 0.16 |
| 213 | 25.4 | 0.38 |
| 214 | 13.7 | 0.21 |
| 215 | 15.0 | 0.14 |
| 216 | 54.7 | 0.14 |
| 217 | 8.0* | 0.16 |
| 218 | 9.3* | 0.37 |
| 219 | 25.4 | 0.36 |
| 220 | 13.7 | 0.24 |
| 221 | 15.0 | 0.13 |
| 222 | 35.0 | 0.14 |
| 223 | 34.4 | 0.37 |
| 224 | 26.1 | 0.34 |
| 225 | 34.7 | 0.36 |
| 226 | 26.6 | 0.46 |
| 227 | 21.6 | 0.56 |
| 228 | 13.6 | 0.30 |
| 229 | 15.3 | 0.22 |
| 230 | 16.3 | 0.30 |
| 231 | 15.2 | 0.30 |
| 232 | 14.7 | 0.39 |
| 233 | 9.4 | 0.31 |
| 234 | 40.8 | 0.29 |
| 235 | 19.5 | 0.23 |
| 236 | 17.0 | 0.23 |
| 237 | 21.5 | 0.48 |
| 238 | 16.3 | 0.40 |
| 239 | 11.3 | 0.05 |
| 240 | 13.7 | 0.31 |
| 241 | 33.3 | 0.15 |
| 242 | 12.6 | 0.06 |
| 243 | 20.3 | 0.10 |
| 244 | NT | 0.30 |
| 245 | 11.4 | 0.19 |
| 246 | 14.2 | 0.25 |
| 247 | 10.0 | 0.87 |
| 248 | 7.4 | 0.43 |
| 249 | 12.2 | 0.70 |
| 250 | 29.5 | 0.22 |
| 251 | 16.9 | 0.93 |
| 252 | 18.3 | 0.42 |
| 253 | 33.4 | 0.12 |
| 254 | 13.7 | 0.87 |
| 255 | 16.8 | 2.7 |
| 256 | 6.6 | 0.76 |
| 257 | 86.2 | 0.29 |
| 258 | 7.5 | 0.52 |
| 259 | 46.3 | 0.58 |
| 260 | 18.8 | 0.40 |
| 261 | 5.5 | 1.99 |
| 262 | 12.9 | 0.92 |
| 263 | 20.5 | 0.84 |
| 264 | 18.2 | 0.62 |
| 265 | 49.9 | 0.40 |
| 266 | 41.1 | 0.13 |
| 267 | 16.4 | 0.51 |

TABLE 1-continued

| Example No. | P2Y$_1$ K$_f$ (nM) using binding assay B | PA IC$_{50}$ (µM) @ 10 µM ADP |
|---|---|---|
| 268 | 18.1 | 0.45 |
| 269 | 1.2 | 0.39 |
| 270 | 17.3 | 0.43 |
| 271 | 12.4 | 0.07 |
| 272 | 16.7 | 0.18 |
| 273 | 9.4 | 0.05 |
| 274 | 7.4 | 3.39 |
| 275 | NT | 5.69 |
| 276 | 48.7 | 0.64 |
| 277 | 54.9 | 0.26 |
| 278 | 8.1 | 0.21 |

*Using binding assay A.
NT: Not tested.

The platelet aggregation assay measures the in vitro antiplatelet activity of a compound in platelet rich plasma. The assay is sensitive to plasma protein binding, and is believed to be a better predictor of actual in vivo activity. Surprisingly, it was discovered that the compounds of the present invention are unexpectedly significantly more active in the platelet aggregation assay than those exemplified in U.S. Patent Publication No. US 2005/0261244 A1.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., other anti-platelet agents or other pharmaceutically active material. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving $P2Y_1$ or anti-platelet activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

Other features of the invention should become apparent in the course of the above descriptions of exemplary embodiments that are given for illustration of the invention and are not intended to be limiting thereof

EXAMPLES

The following Examples have been prepared, isolated and characterized using the methods disclosed herein. The following Examples demonstrate a partial scope of the invention and are not meant to be limiting of the scope of the invention.

Intermediate 1

2-(3,3-Diethyl-7-methoxyindolin-1-yl)aniline

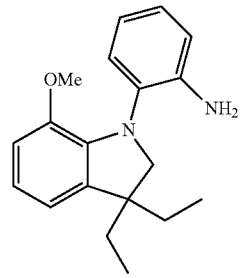 [SMILES: CCC1(CC)CN(c2ccccc2N)c2c(OC)cccc21]

Intermediate 1A.

3,3-Diethyl-7-methoxyindoline

To 2-ethyl butyraldehyde (7.6 mL, 57 mmol) in ethanol (150 mL) was added the (2-methoxyphenyl)hydrazine hydrochloride (10 g, 57 mmol) and the mixture was stirred at 0° C. for 30 min. Sulfuric acid (3.2 mL, 57 mmol) was added slowly and the mixture was stirred at 0° C. for 1 h and at 20° C. for 2 h. After cooled to 0° C., $NaBH_4$ (2.2 g, 57 mmol) was added carefully. After pouring into water and 1 M NaOH, the aqueous layer was extracted with ethyl acetate (2×). The combined organics were dried over $MgSO_4$, filtered and concentrated in vacuo. The crude material was purified by flash chromatography (5-10% ethyl acetate/95-90% hexanes) to give Intermediate 1A (980 mg, 12.0%). LCMS (ESI) m/z 206 (M+H)$^+$, RT=0.9 min (Method A).

Intermediate 1B.

3,3-Diethyl-7-methoxy-1-(2-nitrophenyl)indoline

To a sealable flask containing Intermediate 1A (700 mg, 3.40 mmol), 1-bromo-2-nitrobenzene (688 mg, 3.40 mmol), Pd$_2$(dba)$_3$ (156 mg, 0.170 mmol), rac-BINAP (318 mg, 0.510 mmol) and cesium carbonate (1.55 g, 4.76 mmol) was added toluene (20 mL) and sparged with argon for 30 min. The reaction was sealed and heated to 100° C. for 18 h. The reaction was cooled, filtered through CELITE®, and concentrated in vacuo. The crude material was purified by flash chromatography (10-25% ethyl acetate/90-75% hexanes) to give Intermediate 1B (0.66 g, 59%). LCMS (ESI) m/z 327 (M+H)$^+$, RT=2.08 min (Method A).

Intermediate 1

To Intermediate 1B (0.66 g, 2.0 mmol) in ethyl acetate (10 mL) was added the 10% Pd/C (60 mg). Air was removed and the reaction was stirred under hydrogen atmosphere (balloon) at 60° C. The solution was filtered through CELITE®, rinsed with ethyl acetate (50 mL), and concentrated to give Intermediate 1 (0.54 g, 92%). LCMS (ESI) m/z 297 (M+H)$^+$, RT=1.54 min (Method A).

Intermediate 2

1-(2-Aminophenyl)-3,3-dimethyl-4-(trifluoromethyl)indolin-7-ol

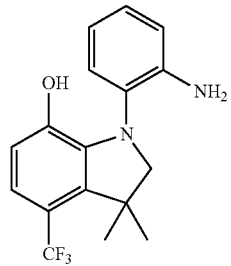 [SMILES: CC1(C)CN(c2ccccc2N)c2c(O)ccc(C(F)(F)F)c21]

Intermediate 2A.

2-(Benzyloxy)-5-(trifluoromethyl)aniline

Benzyl bromide (6.3 mL, 53 mmol) was added to a solution of potassium carbonate (6.67 g, 48.3 mmol) and 4-trifluoromethyl-2-nitrophenol (10 g, 48 mmol) in DMF (50 mL) and stirred at room temperature for 3 h. The reaction was diluted with water and EtOAc/hexanes (1:2). The organics were washed with saturated NaHCO$_3$ solution, brine, dried over MgSO$_4$, filtered, and evaporated to give crude product. The crude was taken up in ethanol (500 mL) and zinc (31.6 g, 483 mmol) and ammonium chloride (25.8 g, 483 mmol) were added. The reaction mixture was stirred at room temperature for 16 h. The reaction was diluted with EtOAc, filtered through CELITE®, and concentrated to give Intermediate 2A which was taken on to the next step without further purification. LCMS (ESI) m/z 268 (M+H)$^+$, RT=1.97 min (Method A). $^1$H NMR (400 MHz, CDCl$_3$) δ ppm 3.93 (br s, 2H), 5.13 (s, 2H), 6.89 (d, J=8.3 Hz, 1H), 6.96-7.00 (m, 2H), 7.35-7.47 (m, 5H).

Intermediate 2B.

(2-(Benzyloxy)-5-(trifluoromethyl)phenyl)hydrazine

A suspension of Intermediate 2A (12.5 g, 47.0 mmol) in 6 M HCl (25 mL) was cooled to −10° C. with mechanical stirring and a solution of sodium nitrite (3.8 g, 56 mmol) in water (10 mL) was added slowly to keep the temperature below 0° C. After the addition, the reaction was stirred for additional 20 min at −10 to 0° C. A solution of tin (II) chloride (26.6 g, 140 mmol) in conc. HCl (50 mL) was added slowly, resulting in precipitation. After 20 min, water (100 mL) was added and the reaction was stirred for another 1 h. Ether was added and the aqueous layer was extracted with ether. The combined organics were dried over MgSO$_4$, filtered, and evaporated. The crude product was purified by flash chromatography using EtOAc/hexanes/Et$_3$N (10:89:1 to 60:39:1) to give the oil which was taken up in EtOAc. TFA (20 mL) was added. The solution was concentrated and triturated with EtOAc/hexanes (1:9) to give the TFA salt of Intermediate 2B (4.1 g, 22%) as a light tan solid. LCMS (ESI) m/z 266 (M-NH$_3$+H)$^+$, RT=1.40 min (Method A).

Intermediate 2C.

7-(Benzyloxy)-3,3-dimethyl-4-(trifluoromethyl)indoline

Sulfuric acid (1.42 mL, 25.2 mmol) was added to a solution of 2-ethyl butyraldehyde (1.0 mL, 10 mmol) and the TFA salt of Intermediate 2B (4.0 g, 10 mmol) in ethanol (50 mL) at 0° C. The reaction was stirred at room temperature for 24 h. The reaction was diluted with EtOAc (200 mL) and washed with saturated NaHCO$_3$ solution and brine. The organics were dried over MgSO$_4$, filtered, and concentrated to give crude imine. The crude was taken up in MeOH (50 mL) and cooled to 0° C. Sodium borohydride (0.38 g, 10 mmol) was added. After 30 min, the reaction was quenched with water and extracted with EtOAc. The organics were dried over MgSO$_4$, filtered, and concentrated to give crude indoline. The crude was purified by flash chromatography (5-20% EtOAc/hexanes) to give Intermediate 2C (2.2 g, 68%) as a yellow oil. LCMS (ESI) m/z 322 (M+H)$^+$, RT=2.07 min (Method A). $^1$H NMR (400 MHz, CDCl$_3$) δ ppm 1.40 (s, 6H), 3.32 (s, 2H), 4.00 (br s, 1H), 5.09 (s, 2H), 6.74 (d, J=8.3 Hz, 1H), 6.98 (d, J=8.6 Hz, 1H), 7.30-7.45 (m, 5H).

Intermediate 2D.

7-(Benzyloxy)-3,3-dimethyl-1-(2-nitrophenyl)-4-(trifluoromethyl)indoline

A solution of Intermediate 2C (2.2 g, 6.85 mmol) in toluene (50 mL) was sparged with argon for 30 min and added to a sealable flask containing 2-bromo-1-nitrobenzene (1.66 g, 8.22 mmol), Pd$_2$(dba)$_3$ (380 mg, 0.410 mmol), rac-BINAP (770 mg, 1.23 mmol), and Cs$_2$CO$_3$ (2.68 g, 8.22 mmol). The vessel was sealed and heated to 120° C. for 2 days. The reaction was cooled, filtered through CELITE®, washed with EtOAc, and concentrated. The residue was purified by flash chromatography (5-30% EtOAc/hexanes) to give Intermediate 2D (2.3 g, 76%) as a red solid. LCMS (ESI) m/z 433 (M+H)$^+$, RT=2.56 min (Method A).

Intermediate 2

Palladium on carbon (0.55 g, 10% w/w, 0.52 mmol) was added to a solution of Intermediate 2D (2.3 g, 5.2 mmol) in ethanol (50 mL) and EtOAc (10 mL). The reaction was stirred under hydrogen atmosphere for 5 days. The reaction was filtered through CELITE® and concentrated. The residue was purified by flash chromatography (10-50% EtOAc/ hexanes) to give Intermediate 2 (0.71 g, 42%) as a yellow solid. LCMS (ESI) m/z 323 (M+H)$^+$, RT=1.62 min (Method A).

Intermediate 3

2-(7-Methoxy-3,3-dimethyl-4-(trifluoromethyl)indolin-1-yl)aniline

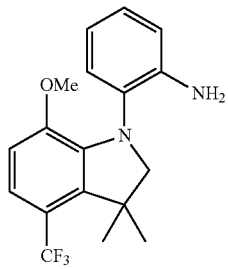

Intermediate 3 was prepared according to the procedures described in Intermediate 2 using 2-methoxy-5-(trifluoromethyl)aniline and isobutyraldehyde as the starting material. MS (ESI) m/z 337.0 (M+H)$^+$.

Intermediate 4

2-(3,3-Diethyl-7-methoxy-4-(trifluoromethyl)indolin-1-yl)aniline

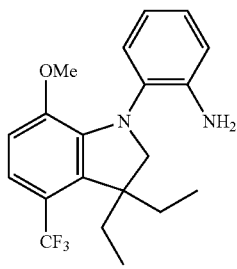 [SMILES: CCC1(CC)CN(c2ccccc2N)c2c(OC)ccc(C(F)(F)F)c21]

Intermediate 4 was prepared according to the procedures described in Intermediate 2 using 2-methoxy-5-(trifluoromethyl)aniline as the starting material. LCMS (ESI) m/z 365.1 (M+H)$^+$, RT=2.12 min (Method A).

Intermediate 5

1-(2-Aminophenyl)-3,3-diethyl-4-fluoroindolin-7-ol

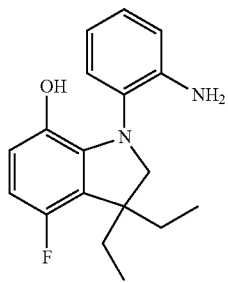 [SMILES: CCC1(CC)CN(c2ccccc2N)c2c(O)ccc(F)c21]

Intermediate 5A.

2-(Benzyloxy)-5-fluoroaniline

Benzyl bromide (8.3 mL, 70 mmol) was added to a solution of potassium carbonate (8.8 g, 64 mmol) and 4-fluoro-2-nitrophenol (10 g, 64 mmol) in DMF (100 mL) and stirred at room temperature for 3 days. The reaction was diluted with water and EtOAc. The aqueous layer was extracted with EtOAc and then the combined organics were washed with saturated NaHCO$_3$ solution, brine, dried over MgSO$_4$, filtered and evaporated to give the crude. The crude was taken up in ethanol (500 mL). Zinc (41.6 g, 636 mmol) and ammonium chloride (34.1 g, 636 mmol) were added and stirred at room temperature for 5 h. The reaction was diluted with EtOAc, filtered through CELITE®, and concentrated to give Intermediate 5A (12.15 g, 88%). LCMS (ESI) m/z 218 (M+H)$^+$, RT=1.74 min (Method A). $^1$H NMR (400 MHz, CDCl$_3$) δ ppm 3.87 (m, 2H), 5.03 (s, 2H), 6.36 (t, J=8.6 Hz, 1H), 6.45 (d, J=9.9 Hz, 1H), 6.75 (dd, J=5.0, 8.5 Hz, 1H), 7.35-7.45 (m, 5H).

Intermediate 5B.

(2-(Benzyloxy)-5-fluorophenyl)hydrazine

A suspension of Intermediate 5A (12.2 g, 55.9 mmol) in 6 M HCl (35 mL) was cooled to −10° C. with mechanical stirring and a solution of sodium nitrite (4.0 g, 59 mmol) in water (10 mL) was added slowly to keep the temperature below 0° C. After the addition, the reaction was stirred for an additional 20 min at −10 to 0° C. A solution of tin (II) chloride (31.8 g, 168 mmol) in conc. HCl (50 mL) was added slowly, resulting in precipitation. After 20 min, a gum was resulted and the solution was decanted off. The gum was suspended in 10% NaOH solution, and extracted with ether (2×). The combined organics were dried over MgSO$_4$, filtered, and evaporated to give Intermediate 5B, which was used directly in the next step. LCMS (ESI) m/z 216.1 (M-NH$_3$+H)$^+$, RT=1.30 min (Method A).

Intermediate 5C.

7-(Benzyloxy)-3,3-diethyl-4-fluoroindoline

Sulfuric acid (2.9 mL, 51.7 mmol) was added to a solution of 2-ethyl butyraldehyde (6.9 mL, 52 mmol) and Intermediate 5B (12 g, 52 mmol) in ethanol (100 mL) at 0° C. The reaction was stirred at room temperature for 2 days. After the reaction was cooled to −10° C., sodium borohydride (2.0 g, 52 mmol) was added portionwise. The reaction mixture was stirred for 15 min and then warmed to room temperature for 30 min. The reaction was carefully quenched with water (50 mL) and partially concentrated to remove EtOH. The residue was taken up in EtOAc and water. The aqueous layer was basified with NaOH solution and then extracted with EtOAc. The combined organics were dried over MgSO$_4$, filtered, and concentrated. The crude was purified by flash chromatography (5-10% EtOAc/hexanes) to give Intermediate 5C (2.0 g, 13%) as yellow oil. LCMS (ESI) m/z 300 (M+H)$^+$, RT=1.90 min (Method A).

Intermediate 5D.

2-(7-(Benzyloxy)-3,3-diethyl-4-fluoroindolin-1-yl)aniline

A solution of Intermediate 5C (2.0 g, 6.7 mmol) in toluene (75 mL) was sparged with argon for 30 min and added to a sealable tube containing 2-bromo-1-nitrobenzene (2.02 g, 10.0 mmol), Pd$_2$(dba)$_3$ (0.24 g, 0.27 mmol), rac-BINAP (0.50 g, 0.80 mmol), and potassium phosphate (2.13 g, 10.0 mmol). The vessel was sealed and heated to 120° C. for 66 h. The reaction was cooled, filtered through CELITE®, and concentrated. The residue was taken up in EtOH (100 ml). Zinc (4.37 g, 66.8 mmol) and ammonium chloride (3.57 g, 66.8 mmol) were added and allowed to stir at room temperature for 3 h. The reaction was diluted with EtOAc, filtered through CELITE®, and concentrated to give crude product. The crude was purified by flash chromatography (5-10% EtOAc/hexanes) to give Intermediate 5D (1.5 g, 56%). LCMS (ESI) m/z 391 (M+H)$^+$, RT=2.26 min (Method A).

Intermediate 5

Palladium on carbon (0.40 g, 10% w/w, 0.37 mmol) was added to a solution of Intermediate 5D (1.5 g, 3.7 mmol) in ethanol (40 mL). The reaction mixture was stirred under hydrogen atmosphere (balloon) for 16 h. The reaction was filtered through CELITE® and concentrated. The residue was purified by flash chromatography on BIOTAGE® (10-20% EtOAc/hexanes) to give Intermediate 5 (0.53 g, 48%) as a white solid. LCMS (ESI) m/z 301 (M+H)$^+$, RT=1.63 min (Method A). $^1$H NMR (400 MHz, DMSO-$d_6$) δ ppm 0.73 (t, J=7.5 Hz, 3H), 0.82 (t, J=7.5 Hz, 3H), 1.55 (m, 1H), 1.65-1.80 (m, 3H), 2.91 (d, J=10.4 Hz, 1H), 3.90 (d, J=10.3 Hz, 1H), 4.72 (s, 2H), 6.34-6.45 (m, 2H), 6.49 (m, 1H), 6.52 (m, 2H), 6.79 (t, J=7.2 Hz, 1H), 8.63 (s, 1H).

Intermediate 6

2-(7-(Benzyloxy)-4-fluoro-3,3-dimethylindolin-1-yl) aniline

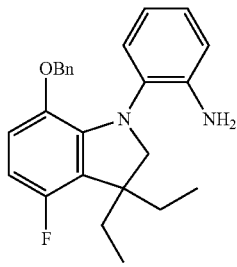 [SMILES: CCC1(CC)CN(c2ccccc2N)c2c(OCc3ccccc3)ccc(F)c21]

Intermediate 6 was prepared according to the procedures described in Intermediate 2 using 4-fluoro-2-nitrophenol and isobutyraldehyde as the starting material. LCMS (ESI) m/z 363.1 (M+H)$^+$, RT=2.04 min (Method A).

Intermediate 7

1-(2-Aminophenyl)-6-fluoro-3,3-dimethylindolin-7-ol

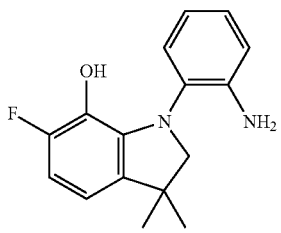 [SMILES: CC1(C)CN(c2ccccc2N)c2c1ccc(F)c2O]

Intermediate 7A.

6-Fluoro-7-methoxy-3,3-dimethyl-1-(2-nitrophenyl) indoline 7A was prepared according to the procedures described in Intermediates 2A-2C using 3-fluoro-2-methoxyaniline and isobutyraldehyde as the starting material. LCMS (ESI) m/z 317.1 (M+H)$^+$, RT=2.23 min (Method B).

Intermediate 7

A mixture of 7A (0.12 g, 0.38 mmol) and palladium on carbon (10% w/w) in EtOAc (5 mL) was stirred under hydrogen atmosphere for 2 h at 50° C. and 8 h at room temperature. The reaction was filtered through CELITE® and concentrated. The crude was taken up in DCM (5 mL) and BBr$_3$ (1.52 mL, 1.52 mmol, 1.0 M in DCM) was added. The mixture was stirred at room temperature for 8 h. The reaction was quenched with NH$_4$OH, extracted with DCM (2×), dried over MgSO$_4$ and concentrated. The residue was purified by Prep HPLC to give Intermediate 7 (52 mg, 50%). LCMS (ESI) m/z 273 (M+H)$^+$, RT=1.35 min (Method B).

Intermediate 8

2-(5-Bromo-3,3-diethyl-7-methoxyindolin-1-yl)aniline

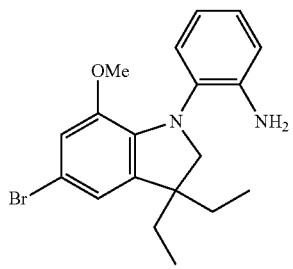 [SMILES: CCC1(CC)CN(c2ccccc2N)c2c(OC)cc(Br)cc21]

Intermediate 8A.

tert-Butyl 3,3-diethyl-7-methoxyindoline-1-carboxylate

To 2-ethyl butyraldehyde (7.7 mL, 63 mmol) in ethanol (60 mL) was added the (2-methoxyphenyl)hydrazine hydrochloride (10 g, 57 mmol) and the mixture was stirred at room temperature. Sulfuric acid (0.30 mL, 5.7 mmol) was added slowly and the mixture was stirred at room temperature for 3 h. More sulfuric acid (1.5 mL, 29 mmol) was added. After 1 h, NaBH$_4$ (2.2 g, 58 mmol) was added carefully. After poured into water and 1 M NaOH, the aqueous layer was extracted with ethyl acetate (2×). Organic layers were combined, dried over MgSO$_4$, filtered and concentrated in vacuo. Crude material was purified by flash chromatography to give a red oil. To this crude in dioxane (50 mL), 1 M Na$_2$CO$_3$ solution (100 mL) was added followed by Boc$_2$O (12.5 g, 57.3 mmol). The reaction was stirred at room temperature for 16 h. The reaction was concentrated and then partitioned between EtOAc and water. The aqueous layer was extracted with EtOAc. The combined organics were dried over MgSO$_4$, filtered, and evaporated. The crude product was purified by flash chromatography (5-10%

EtOAc/hexanes) to give Intermediate 8A (2.2 g, 13%) as a yellow solid. LCMS (ESI) m/z 206 (M-Boc+H)⁺, RT=1.09 min (Method A).

Intermediate 8B.

5-Bromo-3,3-diethyl-7-methoxyindoline

N-bromosuccinimide (1.10 g, 6.22 mmol) was added to a solution of Intermediate 8A (1.90 g, 6.22 mmol) in acetone (12 mL) and stirred at room temperature for 1 h. Hexane was added to the reaction to precipitate the succinimide. The mixture was filtered and concentrated. The crude was dissolved in dichloromethane (20 mL) and TFA (20 mL). The reaction was stirred at room temperature for 30 min. The reaction was concentrated and purified by flash chromatography (20-50% EtOAc/hexanes) to give Intermediate 8B (1.7 g, 96%) as a dark foam. LCMS (ESI) m/z 284, 286 (M+H)⁺, RT=1.43 min (Method A).

Intermediate 8

A solution of Intermediate 8B (1.7 g, 6.0 mmol) in toluene (70 mL) was sparged with argon for 30 min and added to a sealable tube containing 2-bromo-1-nitrobenzene (1.45 g, 7.18 mmol), Pd₂(dba)₃ (0.11 g, 0.12 mmol), rac-BINAP (0.22 g, 0.36 mmol), and Cs₂CO₃ (2.34 g, 7.18 mmol). The vessel was sealed and heated to 110° C. for 16 h. The reaction was cooled, filtered through CELITE®, and concentrated. The residue was taken up in EtOH (70 mL) and zinc (3.91 g, 59.8 mmol) and ammonium chloride (3.20 g, 59.8 mmol) were added. The reaction was stirred at room temperature for 2 h. The reaction was diluted with EtOAc, filtered through CELITE®, and concentrated to give crude product. The crude was purified by flash chromatography (10-20% EtOAc/hexanes) to give Intermediate 8 (1.4 g, 62%). LCMS (ESI) m/z 375, 377 (M+H, M+2+H)⁺, RT=2.05 min (Method A).

Intermediate 9

2-(6-Bromo-3,3-diethyl-7-methoxyindolin-1-yl)aniline

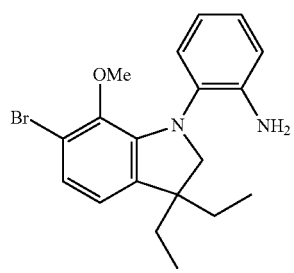 [SMILES: CCC1(CC)CN(c2ccccc2N)c2c1ccc(Br)c2OC]

Intermediate 9A.

3-Bromo-2-methoxyaniline

Potassium carbonate (6.47 g, 46.8 mmol) and methyl iodide (2.86 mL, 46.8 mmol) were added to a solution of 2-bromo-6-nitrophenol (5.10 g, 23.4 mmol) in DMF (100 mL) at room temperature and the resulting reaction mixture was stirred for 16 h. The reaction was quenched with water (100 mL) and diluted with EtOAc (500 mL). The aqueous layer was extracted with EtOAc. The combined organics were washed with saturated NaHCO₃ solution and brine, dried over MgSO₄, filtered, and evaporated. The crude was dissolved in EtOH (100 mL) and zinc (15.30 g, 233.9 mmol) and ammonium chloride (12.52 g, 233.9 mmol) were added. The reaction mixture was stirred at room temperature for 6 h. The reaction was diluted with EtOAc, filtered through CELITE®, and evaporated. The crude was purified by flash chromatography (10-20% EtOAc/hexanes) to give Intermediate 9A (4.6 g, 97%) as a yellow oil. LCMS (ESI) m/z 202, 204 (M+H, M+2+H)⁺, RT=1.38 min (Method A).

Intermediate 9B.

(3-Bromo-2-methoxyphenyl)hydrazine

A suspension of Intermediate 9A (4.0 g, 20 mmol) in 6 M HCl was cooled to −10° C. and a solution of sodium nitrite (1.41 g, 20.8 mmol) in water (5 mL) was added slowly to keep the temperature below 0° C. After the addition, the reaction was stirred for additional 20 min at −10° C. A solution of tin (II) chloride (11.26 g, 59.39 mmol) in conc. HCl (20 mL) was added slowly, resulting in precipitation. After 30 min, the precipitate was filtered, washed with conc. HCl and then water, suspended in 10% NaOH solution, and extracted with EtOAc. The combined organics were dried over MgSO₄, filtered, and evaporated to give Intermediate 9B (1.8 g, 42%), which was used directly in the next step. LCMS (ESI) m/z 200, 202 (M-NH₃+H, M-NH₃+2+H)⁺, RT=1.09 min (Method A).

Intermediate 9C.

6-Bromo-3,3-diethyl-7-methoxyindoline

Sulfuric acid (0.50 mL, 8.3 mmol) was added to a solution of 2-ethyl butyraldehyde (1.1 mL, 8.3 mmol) and Intermediate 9B (1.8 g, 8.3 mmol) in ethanol (20 mL) at 0° C. The reaction was stirred at 0° C. for 10 min and then at room temperature for 16 h. The reaction was cooled to −10° C. and sodium borohydride (0.30 g, 8.3 mmol) was added portionwise. The reaction was stirred for 10 min and then warmed to room temperature for 30 min. The reaction was quenched with water (20 mL) and partially concentrated to remove EtOH. The residue was taken up in EtOAc and water. The aqueous layer was basified with NaOH solution and extracted with EtOAc. The combined organics were extracted with 1 M HCl solution (3×), dried over MgSO₄, filtered, and evaporated. The residue was purified by flash chromatography (1-10% EtOAc/hexanes) to give Intermediate 9C (0.90 g, 36%) as a light yellow oil. LCMS (ESI) m/z 284, 286 (M+H, M+2+H)⁺, RT=1.90 min (Method A).

Intermediate 9

A solution of Intermediate 9C (0.70 g, 2.5 mmol) in toluene (25 mL) was sparged with argon for 30 min and added to a sealable tube containing 2-bromo-1-nitrobenzene (0.75 g, 3.7 mmol), Pd₂(dba)₃ (0.05 g, 0.05 mmol), rac-BINAP (0.09 g, 0.15 mmol), and Cs₂CO₃ (1.20 g, 3.69 mmol). The vessel was sealed and heated to 120° C. for 16 h. The reaction was cooled, filtered through CELITE®, and concentrated. The residue was taken up in EtOH (50 mL) and zinc (1.61 g, 24.6 mmol) and ammonium chloride (1.32 g, 24.6 mmol) were added and stirred at room temperature for 4 h. The reaction was diluted with EtOAc, filtered through CELITE®, and concentrated. The crude was purified by flash chromatography (10-20% EtOAc/hexanes) to give Intermediate 9 (0.57 g, 62%). LCMS (ESI) m/z 375, 377 (M+H, M+2+H)$^+$, RT=2.19 min (Method A).

Intermediate 10

2-(4-Bromo-3,3-diethyl-7-methoxyindolin-1-yl)aniline

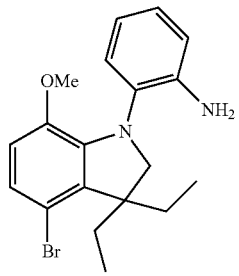 [SMILES: CCC1(CC)CN(c2ccccc2N)c2c(OC)ccc(Br)c21]

Intermediate 10A.

(5-Bromo-2-methoxyphenyl)hydrazine

A suspension of 5-bromo-2-methoxyaniline (5.0 g, 25 mmol) in 6 M HCl (13 mL) was cooled to −10° C. and a solution of sodium nitrite (1.77 g, 26.0 mmol) in water (5 mL) was added slowly to keep the temperature below 0° C. After the addition, the reaction was stirred for an additional 20 min at −10 to 0° C. A solution of tin (II) chloride (14.1 g, 74.2 mmol) in conc. HCl (25 mL) was added slowly, resulting in precipitation. The precipitate was filtered, suspended in 10% NaOH solution, and extracted with ether (3×). The combined organics were dried over MgSO$_4$, filtered and evaporated to give Intermediate 10A (4.1 g, 76%) which was used directly in the next step. LCMS (ESI) m/z 200, 202 (M-NH$_3$+H, M-NH$_3$+2+H)$^+$, RT=1.01 min (Method A).

Intermediate 10B.

4-Bromo-3,3-diethyl-7-methoxyindoline

Sulfuric acid (1.0 mL, 18 mmol) was added to a solution of 2-ethyl butyraldehyde (2.5 mL, 18 mmol) and Intermediate 10A (4.0 g, 18 mmol) in ethanol (50 mL) at 0° C. The reaction was stirred at room temperature for 2 days. The reaction was cooled to −10° C. and sodium borohydride (0.70 g, 18 mmol) was added portionwise. The reaction was stirred for 15 min, and then warmed to room temperature for 30 min. The reaction was quenched with water (50 mL) and partially concentrated to remove EtOH. The residue was taken up in EtOAc and water. The aqueous layer was basified with NaOH solution, extracted with EtOAc. The combined organics were dried over MgSO$_4$, filtered, and concentrated. The crude was purified by flash chromatography (1-10% EtOAc/hexanes) to give Intermediate 10B (1.9 g, 35%) as a yellow oil. LCMS (ESI) m/z 284, 286 (M+H, M+2+H)$^+$, RT=1.60 min (Method A). $^1$H NMR (400 MHz, CDCl$_3$) δ ppm 0.79 (t, J=7.4 Hz, 6H), 1.55 (m, 2H), 2.06 (m, 2H), 3.42 (s, 2H), 3.07 (br s, 1H), 3.78 (s, 3H), 6.49 (d, J=8.5 Hz, 1H), 6.74 (d, J=8.3 Hz, 1H).

Intermediate 10

A solution of Intermediate 10B (1.7 g, 6.0 mmol) in toluene (60 mL, sparged with argon for 30 min) was added to a sealable tube containing 2-bromo-1-nitrobenzene (1.81 g, 9.00 mmol), Pd$_2$(dba)$_3$ (110 mg, 0.120 mmol), rac-BINAP (220 mg, 0.360 mmol), and Cs$_2$CO$_3$ (2.92 g, 9.00 mmol). The vessel was sealed and heated to 120° C. for 24 h. The reaction was cooled, filtered through CELITE®, and concentrated. The residue was taken up in EtOH (100 ml), and zinc (3.91 g, 59.8 mmol) and ammonium chloride (3.20 g, 59.8 mmol) were added. The reaction was stirred at room temperature for 4 h, diluted with EtOAc, filtered through CELITE®, and concentrated. The crude was purified by flash chromatography (10-20% EtOAc/hexanes) to give Intermediate 10 (0.77 g, 34%). LCMS (ESI) m/z 375, 377 (M+H, M+2+H)$^+$, RT=1.99 min (Method A).

Intermediate 11

2-(4-Bromo-7-methoxy-3,3-dimethylindolin-1-yl)aniline

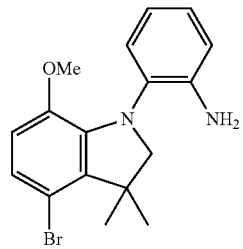 [SMILES: COc1ccc(Br)c2c1N(c1ccccc1N)CC2(C)C]

Intermediate 11A.

4-Bromo-1-methoxy-2-nitrobenzene

The mixture of 4-bromo-1-methoxy-2-nitrobenzene (2.00 g, 8.62 mmol), zinc (5.64 g, 86.0 mmol), and ammonium chloride (4.61 g, 86.0 mmol) in ethanol (65 mL) was stirred together at room temperature for 2 h. The reaction was then diluted with EtOAc, filtered through CELITE®, and evaporated to give Intermediate 11A (1.74 g, 100%) as a grayish-white solid. LCMS (ESI) m/z 202, 204 (M+H, M+2+H)$^+$, RT=0.70 min (Method J).

Intermediate 11B.

(5-Bromo-2-methoxyphenyl)hydrazine

A suspension of Intermediate 11A (1.74 g, 8.62 mmol) in 6 M HCl (30 mL) was cooled to −10° C. and a solution of sodium nitrite (0.714 g, 10.4 mmol) in water (3 mL) was added dropwise. After the addition, the reaction was stirred for an additional 30 min at −10° C. A solution of tin (II) chloride (4.90 g, 25.9 mmol) in conc. HCl (10 mL) was added slowly, resulting in precipitation. After 30 min, the precipitate was filtered, washed with 1 M HCl, suspended in 10% NaOH solution, and extracted with ether (3×). The combined organics were dried over MgSO$_4$ and evaporated to give Intermediate 11B, which was used directly in the next step without further purification. LCMS (ESI) m/z 200, 202 (M-NH$_3$+H, M-NH$_3$+2+H)$^+$, RT=0.70 min (Method J).

Intermediate 11C.

4-Bromo-7-methoxy-3,3-dimethylindoline

A solution of Intermediate 11B (1.60 g, 7.37 mmol) and isobutyraldehyde (0.673 mL, 7.37 mmol) in ethanol (30 mL) was stirred at room temperature. Sulfuric acid (1.97 mL, 36.9 mmol) was added to the reaction mixture at 0° C. for 0.5 h. The reaction was stirred at room temperature for 2 h, and then diluted with EtOAc, and washed with saturated NaHCO$_3$. The combined organics were dried over MgSO$_4$, filtered, and evaporated. The crude was dissolved in MeOH and cooled to 0° C. Sodium borohydride (0.558 g, 14.7 mmol) was added portionwise and stirred for 15 min and then warmed to room temperature for 30 min. The reaction was quenched with water and separated with EtOAc. The combined organics were dried over MgSO$_4$ and evaporated to give the crude product. The crude was purified by flash chromatography, eluting with EtOAc/hexanes to give Intermediate 11C (0.45 g, 24%). LCMS (ESI) m/z 256, 258 (M+H, M+2+H)$^+$, RT=1.11 min (Method J). $^1$H NMR (300 MHz, CDCl$_3$) δ ppm 1.46 (s, 6H), 3.36 (s, 2H), 3.83 (s, 3H), 6.52 (d, J=8.78 Hz, 1H), 6.74-6.89 (m, 1H).

Intermediate 11

A solution of Intermediate 11C (1.13 g, 4.41 mmol) in toluene (40 mL) was sparged with nitrogen for 30 min and added to a sealable flask containing 1-bromo-2-nitrobenzene (0.980 g, 4.85 mmol), Pd$_2$(dba)$_3$ (0.242 g, 0.265 mmol), rac-BINAP (0.494 g, 0.794 mmol), and Cs$_2$CO$_3$ (1.73 g, 5.29 mmol). The reaction was sealed and heated to 110° C. for 18 h. The reaction was cooled, filtered through CELITE®, and concentrated. The crude material was taken up in ethanol (40 mL). Zinc (2.95 g, 45.1 mmol) and ammonium chloride (2.41 g, 45.1 mmol) were added and stirred at room temperature. The reaction was filtered through CELITE® and concentrated. The crude was purified by flash chromatography, eluting with EtOAc/hexanes to give Intermediate 11 (1.195 g, 76%). LCMS (ESI) m/z 347, 349 (M+H, M+2+H)+, RT=1.57 min (Method J). $^1$H NMR (300 MHz, CDCl$_3$) δ ppm 1.50 (d, J=11.71 Hz, 6H), 3.24 (d, J=9.88 Hz, 1H), 3.48 (s, 3H), 3.70 (d, 1H), 6.58 (d, J=8.78 Hz, 1H), 6.68 (dt, 1H), 6.77 (dd, 1H), 6.88 (dd, J=7.68, 1.46 Hz, 1H), 6.94 (d, J=8.78 Hz, 1H), 6.99 (td, 1H).

Intermediate 12

1-(2-Aminophenyl)-4-cyano-3,3-diethyl-7-hydroxyindoline

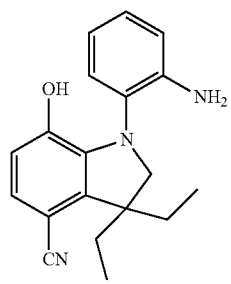 [SMILES: CCC1(CC)CN(c2ccccc2N)c2c(O)ccc(C#N)c21]

Intermediate 12A.

3-Amino-4-(benzyloxy)benzonitrile

Benzyl bromide (3.23 mL, 26.8 mmol) was added to a solution of potassium carbonate (3.40 g, 24.5 mmol) and 4-hydroxy-3-nitrobenzonitrile (4.00 g, 24.4 mmol) in DMF (50 mL) and stirred at room temperature for 16 h. The reaction was diluted with water and EtOAc. The aqueous layer was extracted with EtOAc. The combined organics were washed with saturated NaHCO$_3$ solution and brine, dried over MgSO$_4$, filtered, and concentrated. The crude was taken up in ethanol (200 mL) and zinc (15.9 g, 243 mmol) and ammonium chloride (13.0 g, 243 mmol) were added. The reaction was stirred at room temperature for 24 h. The reaction was diluted in EtOAc, filtered through CELITE®, and concentrated to give Intermediate 12A (5.4 g, 100%), which was taken directly on to the next step. LCMS (ESI) m/z 225 (M+H)$^+$, RT=1.77 min (Method A).

Intermediate 12B.

4-(Benzyloxy)-3-hydrazinylbenzonitrile

A suspension of Intermediate 12A (5.4 g, 24 mmol) in 6 M HCl (15 mL) was cooled to −10° C. with mechanical stirring and a solution of sodium nitrite (1.7 g, 25 mmol) in water (10 mL) was added slowly to keep the temperature below 0° C. After the addition, the reaction was stirred for additional 20 min at −10 to 0° C. A solution of tin (II) chloride (13.9 g, 73.0 mmol) in conc. HCl (25 mL) was added slowly, resulting in precipitation. The precipitate was filtered, suspended in 10% NaOH solution, and extracted with ether (2×). The combined organics were dried over MgSO$_4$, filtered, and evaporated to give Intermediate 12B (4.9 g, 84%). LCMS (ESI) m/z 223 (M-NH$_3$+H)$^+$, RT=1.23 min (Method A).

Intermediate 12C.

7-(Benzyloxy)-4-cyano-3,3-diethylindoline

Sulfuric acid (1.0 mL, 18 mmol) was added to a solution of 2-ethyl butyraldehyde (2.5 mL, 18 mmol) and Intermediate 12B (4.4 g, 18 mmol) in ethanol (50 mL) at 0° C. The reaction was stirred at room temperature for 3 days. The reaction was cooled to −10° C. and sodium borohydride (0.70 g, 18 mmol) was added portionwise. The reaction was stirred for 15 min and then warmed to room temperature for 30 min. The reaction was quenched with water (50 mL) and partially concentrated to remove EtOH. The residue was taken up in EtOAc and water. The aqueous layer was basified with NaOH solution and extracted with EtOAc. The combined organics were dried over MgSO$_4$, filtered, and concentrated to give crude product. The crude was purified by flash chromatography (5-10% EtOAc/hexanes) to give Intermediate 12C (3.1 g, 54%) as yellow oil. LCMS (ESI) m/z 307 (M+H)$^+$, RT=2.08 min (Method A).

Intermediate 12D.

1-(2-Aminophenyl)-7-(benzyloxy)-3,3-diethylindoline-4-carbonitrile

A solution of Intermediate 12C (3.0 g, 9.8 mmol) in toluene (100 mL) was sparged with argon for 30 min and added to a sealable tube containing 2-bromo-1-nitrobenzene (2.97 g, 14.7 mmol), Pd$_2$(dba)$_3$ (0.18 g, 0.20 mmol), rac-BINAP (0.37 g, 0.60 mmol), and Cs$_2$CO$_3$ (4.79 g, 14.7 mmol). The vessel was sealed and heated to 120° C. for 66 h. The reaction was cooled, filtered through CELITE®, and concentrated. The residue was taken up in EtOH (100 ml) and zinc (6.4 g, 98 mmol) and ammonium chloride (5.2 g, 98 mmol) were added. The reaction mixture was stirred at room temperature for 2 h. The reaction was diluted with EtOAc, filtered through CELITE®, and concentrated to give crude product. The crude was purified by flash chromatography (5-10% EtOAc/hexanes) to give Intermediate 12D (0.88 g, 23%). LCMS (ESI) m/z 398 (M+H)$^+$, RT=1.85 min (Method A).

Intermediate 12

Palladium on carbon (0.24 g, 10% w/w, 0.22 mmol) was added to a solution of Intermediate 12D (0.88 g, 2.2 mmol) in ethanol (20 mL). The reaction mixture was stirred under hydrogen atmosphere (balloon) for 4 h. The reaction was filtered through CELITE® and concentrated. The residue was purified by Prep HPLC (TFA) to give Intermediate 12 as a white solid (TFA salt). LCMS (ESI) m/z 308 (M+H)$^+$, RT=1.55 min (Method A). $^1$H NMR (400 MHz, CDCl$_3$) δ ppm 0.85 (t, J=7.6 Hz, 3H), 0.90 (t, J=7.4 Hz, 3H), 1.80 (m, 2H), 2.00 (m, 1H), 2.15 (m, 1H), 3.41 (d, J=10.1 Hz, 1H), 3.82 (d, J=10.1 Hz, 1H), 4.06 (br s, 1H), 6.70 (d, J=8.1 Hz, 1H), 6.95 (m, 2H), 7.08 (m, 2H), 7.15 (m, 1H).

Intermediate 13

1-(2-Aminophenyl)-7-methoxy-3,3-dimethylindoline-4-carbonitrile

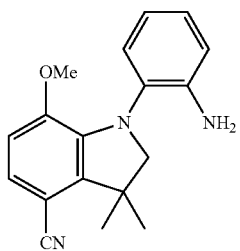 [SMILES: COc1ccc(C#N)c2c1N(c1ccccc1N)CC2(C)C]

Intermediate 13 was prepared according to the procedures described in Intermediate 9 using 4-hydroxy-3-nitrobenzonitrile and isobutyraldehyde as the starting material. LCMS (ESI) m/z 294.2 (M+H)$^+$, RT=1.41 min (Method D).

Intermediate 14

2-(4-Chloro-3,3-diethyl-7-methoxyindolin-1-yl)aniline

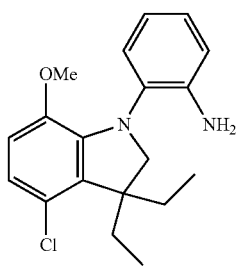 [SMILES: CCC1(CC)CN(c2ccccc2N)c2c(OC)ccc(Cl)c21]

Intermediate 14 was prepared according to the procedures described in Intermediate 9 using 5-chloro-2-methoxyaniline as the starting material. LCMS (ESI) m/z 331, 333 (M+H, M+2+H)$^+$, RT=1.86 min (Method D).

Intermediate 15

2-(4-Chloro-7-methoxy-3,3-dimethylindolin-1-yl)aniline

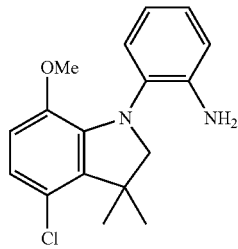 [SMILES: COc1ccc(Cl)c2c1N(c1ccccc1N)CC2(C)C]

Intermediate 15 was prepared according to the procedures described in Intermediate 9 using 5-chloro-2-methoxyaniline and isobutyraldehyde as the starting material. LCMS (ESI) m/z 303 (M+H)$^+$, RT=3.06 min (Method A).

Intermediate 16

Ethyl 1-(2-aminophenyl)-4-chloro-7-methoxy-3-methylindoline-3-carboxylate

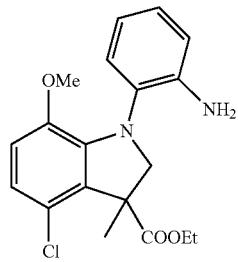 [SMILES: CCOC(=O)C1(C)CN(c2ccccc2N)c2c(OC)ccc(Cl)c21]

Intermediate 16A.

Ethyl 4-chloro-7-methoxy-3-methylindoline-3-carboxylate

A solution of (5-chloro-2-methoxyphenyl)hydrazine hydrochloride (1.29 g, 6.17 mmol) and ethyl 2-methyl-3-oxopropanoate hydrochloride (800 mg, 6.15 mmol) in 10 mL of dichloromethane was stirred at room temperature for 16 h before 6 mL of HCl (4 M in dioxane) was added. After 2 h, the reaction mixture was concentrated and EtOH (10 mL) was added. At 0° C., NaBH$_4$ (930 mg, 24.6 mmol) was added portionwise. After 10 min, the reaction mixture was quenched with water, adjusted pH with 1 M HCl to pH ~7, concentrated, extracted with EtOAc (2×), dried over MgSO$_4$, concentrated, and purified by flash chromatography, eluting with EtOAc/hexanes to give Intermediate 16A (292 mg, 18% yield). LCMS (ESI) m/z 270.1 (M+H)$^+$, RT=2.50 min (Method C).

Intermediate 16B.

Ethyl 4-chloro-7-methoxy-3-methyl-1-(2-nitrophenyl)indoline-3-carboxylate

A mixture of Intermediate 16A (292 mg, 1.08 mmol), 1-bromo-2-nitrobenzene (262 mg, 1.30 mmol), rac-BINAP (47 mg, 0.076 mmol), $Pd_2(dba)_3$ (30 mg, 0.032 mmol), $Cs_2CO_3$ (847 mg, 2.60 mmol) in 10 mL of toluene was sparged with argon for three times, sealed and heated at 85° C. for 8 h. Another 1-bromo-2-nitrobenzene (260 mg, 1.30 mmol), rac-BINAP (47 mg, 0.076 mmol), and $Pd_2(dba)_3$ (30 mg, 0.032 mmol) were added to the reaction mixture, sparged with argon for three times, sealed and heated at 110° C. for 16 h. After cooled to room temperature, the reaction mixture was filtered, concentrated and purified by flash chromatography, eluting with EtOAc/hexanes to give Intermediate 16B (0.28 g, 65% yield) as an orange solid. LCMS (ESI) m/z 391.2 $(M+H)^+$, RT=2.85 min (Method C).

Intermediate 16

To Intermediate 16B (275 mg, 0.704 mmol) in MeOH (5 mL) and EtOAc (5 mL) was added zinc (920 mg, 14.1 mmol) and $NH_4Cl$ (753 mg, 14.1 mmol). The reaction mixture was stirred at room temperature. After 1 h, the reaction mixture was filtered, concentrated, dissolved in dichloromethane, and filtered. The filtrate was concentrated and purified by flash chromatography, eluting with EtOAc/hexanes to give Intermediate 16 (210 mg, 83% yield) as an off-white solid. LCMS (ESI) m/z 361.1 $(M+H)^+$, RT=2.86 min (Method C).

Intermediate 17

2-(7-(Benzyloxy)-4,5-difluoro-3,3-dimethylindolin-1-yl)aniline

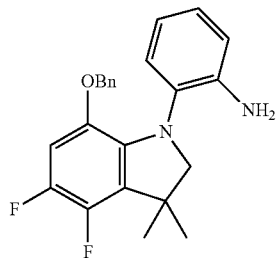 [SMILES: CC1(C)CN(c2ccccc2N)c2c(OCc3ccccc3)cc(F)c(F)c21]

Intermediate 17A.

4,5-Difluoro-2-nitrophenol

Ferric nitrate (31 g, 77 mmol) was added to a solution of 3,4-difluorophenol (10 g, 77 mmol) in ethanol (80 mL) and heated to reflux for 16 h. The reaction was cooled and 50 mL of 1 M HCl was added. This was extracted with EtOAc (2×) and the combined organics were dried over $MgSO_4$, filtered and evaporated to give Intermediate 17A (10 g, 74%) which was used directly in the next step.

Intermediate 17B.

2-(Benzyloxy)-4,5-difluoroaniline

Benzyl bromide (6.8 mL, 57.1 mmol) was added to a solution of potassium carbonate (7.89 g, 57.1 mmol) and Intermediate 17A (10.0 g, 57.1 mmol) in DMF (60 mL) and stirred at room temperature for 16 h. The reaction was diluted with water and EtOAc. The aqueous layer was extracted with EtOAc and then the combined organics were washed with saturated $NaHCO_3$ solution, brine, and then dried over $MgSO_4$, filtered and evaporated to give crude ether product. This was taken up in ethanol (500 mL) and zinc (37.35 g, 571.1 mmol) and ammonium chloride (30.56 g, 571.1 mmol) were added and stirred at room temperature for 4 h. The reaction was diluted in EtOAc, filtered through CELITE®, concentrated, and purified by flash chromatography on BIOTAGE® (5-20% EtOAc/hexanes) to give Intermediate 17B (7.0 g, 52%) as a light brown solid. LCMS (ESI) m/z 236.2 $(M+H)^+$, RT=2.35 min (Method C).

Intermediate 17C.

(2-(Benzyloxy)-4,5-difluorophenyl)hydrazine

A mixture of Intermediate 17B (2.30 g, 9.78 mmol) in 6 M HCl (10 mL) was stirred at 0° C. A solution of sodium nitrite (0.89 g, 13 mmol) in water (1.1 mL) was added dropwise. The mixture was stirred at 0° C. for 2 h. To this stirred mixture was added a cold solution of tin (II) chloride dihydrate (6.62 g, 29.3 mmol) in hydrochloric acid, 37% (10 mL). The resulting suspension was stirred for 30 min, and water (40 mL) was added. The resulting mixture was stirred for another 30 min. DCM was added, followed by the addition of 3 M NaOH (150 mL). The organic layer was washed with water, brine, dried over $MgSO_4$, filtered, and concentrated to give Intermediate 17C as light yellow solids (1.6 g, 64% yield). LCMS (ESI) m/z 234.2 $(M+H)^+$, RT=2.43 min (Method C).

Intermediate 17D.

7-(Benzyloxy)-4,5-difluoro-3,3-dimethylindoline

To Intermediate 17C (250 mg, 0.999 mmol) in ethanol (2 mL) at room temperature under argon, isobutyraldehyde (72.0 mg, 0.999 mmol) was added and the reaction mixture was stirred for 2 h. LC-MS showed the hydrazone formation. At 0° C., $H_2SO_4$ (0.160 mL, 3.00 mmol) was added to the above stirred mixture dropwise. The resulting mixture was stirred at room temperature under argon for 16 h. MeOH (2 mL) was added, followed by addition of $NaBH_4$ (37.8 mg, 0.999 mmol) portionwise. The mixture was stirred at −10° C. till LC-MS showed the completion of the reduction. Water was added carefully to quench the reaction, followed by the addition of DCM. The organic layer was washed with water, dried over $MgSO_4$, filtered and concentrated. The residue was purified by flash chromatography, eluting with EtOAc/hexanes to give Intermediate 17D (0.10 g, 35% yield). LCMS (ESI) m/z 290.3 $(M+H)^+$, RT=1.60 min (Method D).

Intermediate 17E.

7-(Benzyloxy)-4,5-difluoro-3,3-dimethyl-1-(2-nitrophenyl)indoline

A mixture of Intermediate 17D (100 mg, 0.346 mmol), 1-bromo-2-nitrobenzene (91 mg, 0.45 mmol), $Pd_2(dba)_3$ (21 mg, 0.023 mmol), rac-BINAP (43 mg, 0.069 mmol), and Cs$_2$CO$_3$ (146 mg, 0.449 mmol) in toluene (1 mL) was degassed twice and was stirred for 16 h at 120° C. under argon for 6 h. After cooling, EtOAc and water were added. The organic layer was separated. The aqueous phase was extracted one more time with EtOAc. The combined organics were washed with water, then brine, dried over MgSO$_4$, filtered, and concentrated. The crude was purified by flash chromatography, eluting with EtOAc/hexanes to give Intermediate 17E (0.12 g, 85% yield). LCMS (ESI) m/z 411.4 (M+H)$^+$, RT=3.83 min (Method C).

Intermediate 17

To a solution of Intermediate 17E (100 mg, 0.244 mmol) in MeOH (10 mL) was added ammonium chloride (91 mg, 1.7 mmol), followed by zinc (112 mg, 1.71 mmol). The reaction mixture was stirred at room temperature for 30 min. The reaction was filtered and the solvents were evaporated. The residue was washed with EtOAc to give Intermediate 17 (80 mg, 87% yield) in oil form. LCMS (ESI) m/z 381.4 (M+H)$^+$, RT=3.39 min (Method C).

Intermediate 18

2-(4,6-Difluoro-7-methoxy-3,3-dimethylindolin-1-yl)aniline

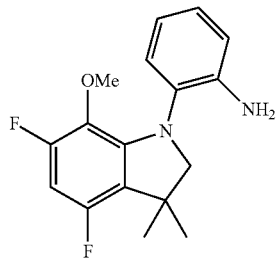 [SMILES: COc1c(F)cc(F)c2c1N(c1ccccc1N)CC2(C)C]

Intermediate 18A.

1-(3,5-Difluoro-2-methoxyphenyl)-2-(diphenylmethylene)hydrazine

To a mixture of palladium (II) acetate (0.040 g, 0.18 mmol) and xantphos (0.104 g, 0.179 mmol) in toluene (1 mL), 1-bromo-3,5-difluoro-2-methoxybenzene (4.0 g, 18 mmol), (diphenylmethylene)hydrazine (3.52 g, 17.9 mmol) and sodium tert-butoxide (2.41 g, 25.1 mmol) were added followed by the addition of toluene (4 mL). The mixture was degassed twice and stirred for 6 h at 100° C. under argon. After cooling to room temperature, EtOAc and water were added. The organic layer was separated. The aqueous layer was extracted one more time with EtOAc. The combined organics were washed with water and brine, dried over MgSO$_4$, filtered, and concentrated. The crude was purified by flash chromatography, eluting with EtOAc/hexanes to give Intermediate 18A (6.0 g, 84% yield). LCMS (ESI) m/z 339.4 (M+H)$^+$, RT=2.33 min (Method D). $^1$H NMR (400 MHz, CDCl$_3$) δ ppm 3.63 (br. s, 3 H), 6.14-6.38 (m, 1 H), 7.08-7.20 (m, 5 H), 7.45-7.68 (m, 5 H), 7.97 (s, 1 H). $^{19}$F NMR (376.5 MHz, acetone-d$_6$) δ ppm −115.46, −129.88.

Intermediate 18B.

(3,5-Difluoro-2-methoxyphenyl)hydrazine hydrochloride

A solution of Intermediate 18A (4.7 g, 14 mmol) in ethanol (50 mL) and hydrochloric acid, 37% (50 mL) was heated at 100° C. for 2 h. After cooled to room temperature, the solvents were evaporated, extracted with Et$_2$O (3×) and concentrated. The residue was azeotroped with toluene (3×) and Et$_2$O was added. The residue was filtered to give Intermediate 18B (2.0 g, 68% yield) as an off white solid. LCMS (ESI) m/z 158.1 (M+H)$^+$, RT=0.85 min (Method D).

Intermediate 18C.

4,6-Difluoro-7-methoxy-3,3-dimethylindoline

To Intermediate 18B (220 mg, 1.05 mmol) in ethanol (2 mL) at room temperature under argon, isobutyraldehyde (75 mg, 1.0 mmol) was added and the reaction mixture was stirred for 2 h. H$_2$SO$_4$ (0.167 mL, 3.13 mmol) was added to the above stirred mixture dropwise. The resulting mixture was stirred at room temperature under argon for 16 h. MeOH (2 mL) was added, followed by addition of NaBH$_4$ (39.5 mg, 1.05 mmol) portionwise. The mixture was stirred at −10° C. till LC-MS showed the completion of the reduction. Water was added carefully to quench the reaction, followed by the addition of DCM. The organic layer was washed with water, dried over MgSO$_4$, filtered and concentrated. The residue was purified by flash chromatography, eluting with EtOAc/hexanes to give Intermediate 18C (80 mg, 36% yield). LCMS (ESI) m/z 214.3 (M+H)$^+$, RT=1.65 min (Method D). $^1$H NMR (400 MHz, CDCl$_3$) δ ppm 1.42 (s, 6 H), 3.38 (s, 2 H), 3.86 (s, 3 H), 6.14 (dd, J=11.9, 9.3 Hz, 1 H). $^{19}$F NMR (376.5 MHz, acetone-d$_6$) δ ppm −127.11, −132.18.

Intermediate 18D.

4,6-Difluoro-7-methoxy-3,3-dimethyl-1-(2-nitrophenyl)indoline

A mixture of Intermediate 18C (80 mg, 0.38 mmol), 1-bromo-2-nitrobenzene (99 mg, 0.49 mmol), Pd$_2$(dba)$_3$ (23 mg, 0.025 mmol), rac-BINAP (47 mg, 0.075 mmol), and Cs$_2$CO$_3$ (159 mg, 0.488 mmol) in toluene (5 mL) was degassed twice and was stirred for 16 h at 120° C. under argon. After cooling, EtOAc and water were added. The organic layer was separated. The aqueous phase was extracted one more time with EtOAc. The combined organics were washed with water, then brine, dried over MgSO$_4$, filtered, and concentrated. The crude was purified by flash chromatography, eluting with EtOAc/hexanes to give Intermediate 18D (90 mg, 72% yield). LCMS (ESI) m/z 335.5 (M+H)$^+$, RT=2.08 min (Method D). $^1$H NMR (400 MHz, CDCl$_3$) δ ppm 1.32 (s, 3 H), 1.39 (s, 3 H), 3.28 (s, 3 H), 3.40 (d, J=9.3 Hz, 1 H), 3.81 (d, J=9.9 Hz, 1 H), 6.24 (dd, J=11.1, 9.4 Hz, 1H), 7.12 (t, J=7.1 Hz, 1 H), 7.19 (d, J=8.2 Hz, 1 H), 7.29-7.50 (m, 1 H), 7.91 (d, J=8.2 Hz, 1 H). $^{19}$F NMR (376.5 MHz, acetone-d$_6$) δ ppm −125.40, −130.15.

Intermediate 18

A mixture of Intermediate 18D (90 mg, 0.27 mmol), ammonium chloride (144 mg, 2.69 mmol), and zinc (160 mg, 2.45 mmol) was stirred in methanol (15 mL) at room temperature for 30 min. It was filtered through CELITE® and rinsed with DCM. The organic layer was concentrated to give crude product. The crude was purified by flash chromatography, eluting with EtOAc/hexanes to give Intermediate 18 (50 mg, 61% yield). LCMS (ESI) m/z 305.4 (M+H)$^+$, RT=1.74 min (Method D). $^1$H NMR (400 MHz, CDCl$_3$) δ ppm 1.46 (s, 3 H), 1.53 (s, 3 H), 3.30 (s, 3 H), 3.41 (d, J=9.6 Hz, 1 H), 3.71 (d, J=9.6 Hz, 1 H), 3.97 (br. s., 2 H), 6.26 (dd, J=11.4, 9.3 Hz, 1 H), 6.61-6.92 (m, 2 H), 6.94-7.17 (m, 2 H). $^{19}$F NMR (376.5 MHz, acetone-d$_6$) δ ppm −126.65, −130.69.

Intermediate 19

2-(4-Chloro-6-fluoro-7-methoxy-3,3-dimethylindolin-1-yl)aniline

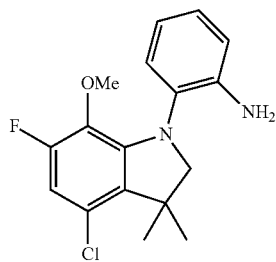 [SMILES: COc1c(F)cc(Cl)c2c1N(c1ccccc1N)CC2(C)C]

Intermediate 19A.

1-(5-Chloro-3-fluoro-2-methoxyphenyl)-2-(diphenylmethylene)-hydrazine

To palladium (II) acetate (0.038 g, 0.17 mmol) and xantphos (0.097 g, 0.17 mmol) in toluene (1 mL) at room temperature, 1-bromo-5-chloro-3-fluoro-2-methoxybenzene (4.0 g, 17 mmol), (diphenylmethylene)hydrazine (3.28 g, 16.7 mmol) and sodium tert-butoxide (2.25 g, 23.4 mmol) were added followed by the addition of toluene (4 mL). The mixture was degassed twice and was stirred for 6 h at 100° C. under argon. After cooling, EtOAc and water were added. The mixture was filtered through CELITE®. The organic layer was separated. The aqueous phase was extracted one more time with EtOAc. The combined organics were washed with water, then brine, dried over MgSO$_4$, filtered, and concentrated to give Intermediate 19A (5.9 g, 90% yield) as a light tan solid, which was used directly in the next reaction without purification. LCMS (ESI) m/z 355.3 (M+H)$^+$, RT=2.45 min (Method D).

Intermediate 19B.

(5-Chloro-3-fluoro-2-methoxyphenyl)hydrazine hydrochloride

Intermediate 19A (5.8 g, 16 mmol) was heated at 100° C. in ethanol (450 mL) and hydrochloric acid, 37% (150 mL) for 3 h. After cooling, the solvents were removed and aqueous layer was extracted with Et$_2$O (3×). The organic layer was removed. The aqueous layer was azeotroped with toluene (3×), and Et$_2$O was added. The resulting mixture was filtered and rinsed with ether to give Intermediate 19B (3.4 g, 92% yield) as slightly tan solids. LCMS (ESI) m/z 174.1 (M-NH$_3$+H)$^+$, RT=1.75 min (Method C).

Intermediate 19C.

4-Chloro-6-fluoro-7-methoxy-3,3-dimethylindoline

To Intermediate 19B (300 mg, 1.32 mmol) in ethanol (3 mL) at room temperature under argon, isobutyraldehyde (95 mg, 1.3 mmol) was added and the reaction mixture was stirred for 3 h. H$_2$SO$_4$ (0.211 mL, 3.96 mmol) was added to the above stirred mixture dropwise. The resulting mixture was stirred at room temperature under argon for 16 h. MeOH (3 mL) was added, followed by addition of NaBH$_4$ (75.0 mg, 1.98 mmol) portionwise. The mixture was stirred at −10° C. for 1 min. Water was added carefully to quench the reaction, followed by the addition of DCM. The organic layer was washed with water, dried over MgSO$_4$, filtered and concentrated. The residue was purified by flash chromatography, eluting with EtOAc/hexanes in to give Intermediate 19C (120 mg, 39.5% yield). LCMS (ESI) m/z 230.3 (M+H)$^+$, RT=3.36 min (Method C).

Intermediate 19D.

4-Chloro-6-fluoro-7-methoxy-3,3-dimethyl-1-(2-nitrophenyl)indoline

A mixture of 19C (115 mg, 0.501 mmol), 1-bromo-2-nitrobenzene (131 mg, 0.651 mmol), Pd$_2$(dba)$_3$ (31 mg, 0.034 mmol), rac-BINAP (62.4 mg, 0.100 mmol), and Cs$_2$CO$_3$ (212 mg, 0.651 mmol) in toluene (2 mL) was degassed twice and stirred for 16 h at 110° C. under argon. After cooling, EtOAc and water were added. The organic layer was separated. The aqueous phase was extracted one more time with EtOAc. The combined organics were washed with water, then brine, dried over MgSO$_4$, filtered, and concentrated. The crude was purified by flash chromatography, eluting with EtOAc/hexanes to give Intermediate 19D (100 mg, 56.9% yield). LCMS (ESI) m/z 351.3 (M+H)$^+$, RT=2.16 min (Method D).

Intermediate 19

Intermediate 19D (0.10 g, 0.29 mmol), ammonium chloride (0.152 g, 2.85 mmol), and zinc (0.093 g, 1.4 mmol) were stirred in methanol (10 mL) at room temperature for 30 min. It was filtered through CELITE® and rinsed with DCM. The organic layer was concentrated to give crude amine. The crude was purified by flash chromatography, eluting with EtOAc/hexanes to give Intermediate 19 (65 mg, 71.1% yield) as light tan solids. LCMS (ESI) m/z 321.4 (M+H)$^+$, RT=3.38 min (Method C).

Intermediate 20

4-Bromo-5-fluoro-7-methoxy-3,3-dimethyl-1-(2-nitrophenyl)indoline

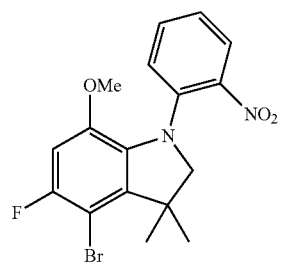 [SMILES: COc1cc(F)c(Br)c2c1N(c1ccccc1[N+](=O)[O-])CC2(C)C]

Intermediate 20A.

5-Bromo-4-fluoro-2-methoxyaniline

To a solution of 1-bromo-2-fluoro-4-methoxy-5-nitrobenzene (24.5 g, 98.0 mmol) in ethanol (100 mL) was added zinc (8.97 mL, 980 mmol) and ammonium chloride (34.5 mL, 980 mmol) in a portion and the resulting solution was stirred for 1 h at 25° C. The reaction mixture was filtered and organic solution was concentrated in vacuo, yielding a dark oily residue. It was partitioned in EtOAc (50 mL) and brine (20 mL). Organic solution was dried over $Na_2SO_4$ and concentrated in vacuo to provide Intermediate 20A as a dark brown oil, which was subjected to the following reaction without further purification. LCMS (ESI) m/z 220, 222 (M+H, M+2+H)$^+$, RT=1.12 min (Method D).

Intermediate 20B.

(5-Bromo-4-fluoro-2-methoxyphenyl)hydrazine

To a solution of Intermediate 20A (6.50 g, 29.5 mmol) in 4 mL of 3 M HCl was added sodium nitrite (2.24 g, 32.5 mmol) portionwise and the resulting solution was stirred for 1 h at 0° C. To the solution was added tin (II) chloride dihydrate (6.15 mL, 73.9 mmol) in conc. HCl) 2 mL) dropwise. After this addition, the mixture was stirred for an additional 1 h at 0° C. The mixture was poured into ice and basified by adding aqueous NaOH. The basic solution was extracted with $Et_2O$ (2×). Organic solution was dried over $Na_2SO_4$ and concentrated in vacuo to provide Intermediate 20B, which was subjected to the following reaction without further purification. LCMS (ESI) m/z 218, 220 (M-$NH_3$+H, M-$NH_3$+2+H)$^+$, RT=0.52 min (Method D).

Intermediate 20C.

4-Bromo-5-fluoro-7-methoxy-3,3-dimethylindoline

To a solution of Intermediate 20B (4.35 g, 16.0 mmol) suspended in DCM (50 mL) and MeOH (16.7 mL) was added isobutyraldehyde (1.46 mL, 16.0 mmol). The reaction mixture was stirred at room temperature for 3 h. The reaction mixture was cooled to 0° C. and added aqueous HCl (16.02 mL, 64.1 mmol). The reaction mixture was stirred at 0° C. for 4 h and at room temperature for 16 h. An aliquot of this material was heated at 50° C. for 2 h. The reaction mixture was then heated at 50° C. for 16 h. After cooling to room temperature, the layers were separated and the aqueous layer was washed with DCM. The combined organics were dried over $Na_2SO_4$ and concentrated. The residue was dissolved in MeOH (40 mL), cooled to 0° C. and $NaBH_4$ (1.52 g, 40.1 mmol) was added portionwise. The reaction mixture was stirred at 0° C. until the reduction was complete. The reaction was quenched with $H_2O$ and extracted with DCM. The solvent was evaporated and the crude product was purified by flash chromatography, eluting with EtOAc/hexanes to give Intermediate 20C (3.8 g, 86% yield). LCMS (ESI) m/z 274 (M+H)$^+$, RT=1.26 min (Method D).

Intermediate 20

To a solution of 1-bromo-2-nitrobenzene (5.54 g, 27.4 mmol) in toluene (100 mL) was added Intermediate 20C (3.76 g, 13.7 mmol), rac-BINAP (1.03 g, 1.65 mmol), $Pd_2(dba)_3$ (0.628 g, 0.686 mmol). The reaction mixture was stirred at room temperature under argon for 20 min and added $Cs_2CO_3$ (10.7 g, 32.9 mmol). The reaction mixture was reflux for 16 h. The reaction mixture was filtered and purified by flash chromatography using a 30 minutes gradient from 0-100% EtOAc in hexanes to give Intermediate 20 (4.4 g, 81% yield) as red oil. LCMS (ESI) m/z 395, 397 (M+H, M+2+H)$^+$, RT=1.82 min (Method D).

Intermediate 21

4-Bromo-6-fluoro-7-methoxy-3,3-dimethyl-1-(2-nitrophenyl)indoline

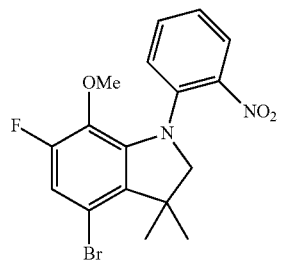 [SMILES: COc1c(F)cc(Br)c2c1N(c1ccccc1[N+](=O)[O-])CC2(C)C]

Intermediate 21 was prepared according to the procedures described in Intermediate 20 using 4-bromo-2-fluoro-6-nitroanisole as the starting material.

Example 1

1-(2-(4-Bromo-7-hydroxy-3,3-dimethylindolin-1-yl)phenyl)-3-(6-fluorobenzo[d]thiazol-2-yl)urea

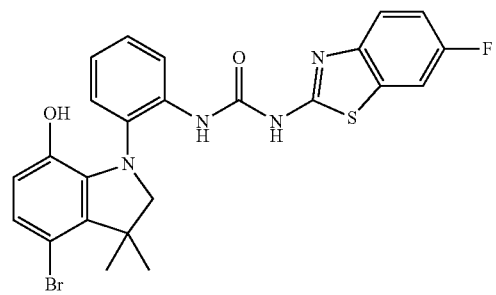 [SMILES: CC1(C)CN(c2ccccc2NC(=O)Nc2nc3ccc(F)cc3s2)c2c(O)ccc(Br)c21]

Example 1A

4-Nitrophenyl 2-(4-bromo-7-methoxy-3,3-dimethylindolin-1-yl)phenylcarbamate A mixture of Intermediate 11 (100 mg, 0.288 mmol), 4-nitrophenyl chloroformate (58.0 mg, 0.288 mmol), and potassium carbonate (43.8 mg, 0.317 mmol) in DCM (3.5 mL) was stirred at room temperature for 1 h. The crude material Example 1A was taken directly onto the next step. LCMS (ESI) m/z 512, 514 (M+H, M+2+H)$^+$, RT=1.54 min (Method J).

Example 1B

1-(2-(4-Bromo-7-methoxy-3,3-dimethylindolin-1-yl)phenyl)-3-(6-fluorobenzo[d]thiazol-2-yl)urea To a suspension of Example 1A (148 mg, 0.289 mmol) in DCM (4.5 mL), 6-fluorobenzo[d]thiazol-2-amine (58.3 mg, 0.347 mmol) and DMAP (7.1 mg, 0.058 mmol) were added and the reaction was heated at 80° C. in the microwave for 30 min. The reaction was diluted with DCM. The organic layer was washed with brine, dried over MgSO$_4$, and evaporated. The crude was purified by Prep HPLC (TFA) to give Example 1B (54 mg, 35% yield). LCMS (ESI) m/z 543, 545 (M+H, M+2+H)$^+$, RT=2.27 min (Method J).

Example 1

To a solution of Example 1B (54.1 mg, 0.100 mmol) in DCM (1.5 mL) was added tetrabutylammonium iodide (258 mg, 0.699 mmol), degassed, refilled with nitrogen, and cooled down to −78° C. Boron trichloride (0.699 mL, 0.699 mmol, 1.0 M solution in DCM) was added over 2 min. After 1 h, the cold bath was removed and the reaction was gradually warmed up to room temperature. Conc. NH$_4$OH (2 mL) was added and then water and DCM. The aqueous layer was extracted with DCM. Combined organics were washed with water, dried over MgSO$_4$, filtered and concentrated. The crude was purified by Prep HPLC (TFA) to give Example 1 (9.1 mg, 17%). LCMS (ESI) m/z 527, 529 (M+H, M+2+H)$^+$, RT=2.25 min (Method J). $^1$H NMR (300 MHz, DMSO-d$_6$) δ ppm 1.36 (s, 3H), 1.48 (s, 3H), 3.09 (d, J=9.88 Hz, 1H), 3.86 (d, J=10.25 Hz, 1H), 6.55 (d, J=8.78 Hz, 1H), 6.80-7.03 (m, 3H), 7.06-7.30 (m, 2H), 7.59 (dd, J=8.78, 4.76 Hz, 1H), 7.84 (dd, J=8.78, 2.56 Hz, 1H), 8.07 (d, J=6.95 Hz, 1H), 8.97 (br. s, 1H), 9.25 (br. s, 1H), 11.39 (br. s, 1H).

Example 2

1-(2-(7-Hydroxy-3,3-dimethyl-4-(trifluoromethyl)indolin-1-yl)phenyl)-3-(4-(1-neopentylpiperidin-4-yl)phenyl)urea

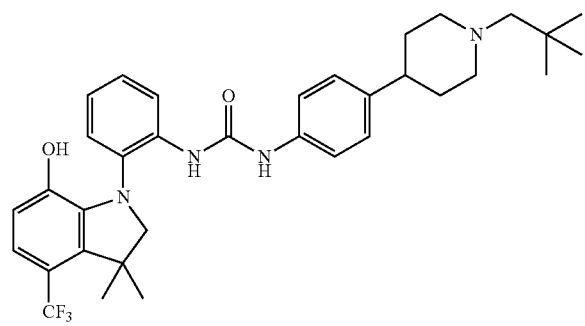 [SMILES: CC(C)(C)CN1CCC(c2ccc(NC(=O)Nc3ccccc3N3CC(C)(C)c4c(C(F)(F)F)ccc(O)c43)cc2)CC1]

Example 2A 4-(4-Nitrophenyl)piperidine

To 4-phenylpiperidine (8.7 g, 50 mmol) in conc. H$_2$SO$_4$ (50 mL) at 0° C., a mixture of fuming HNO$_3$ (2.1 mL, 50 mL) was slowly added, keeping temperature below 15° C. The mixture was slowly warmed up to 25° C. for 3 h. The mixture was poured over crushed ice and slowly basified using NaOH pellets (~85 g). The mixture was extracted with DCM (3×). The combined organics were dried over MgSO$_4$, concentrated, and purified by flash chromatography to give Example 2A (2.8 g, 25%). LCMS (ESI) m/z 207.1 (M+H)$^+$, RT=0.15 min (Method A).

Example 2B

1-Neopentyl-4-(4-nitrophenyl)piperidine

A mixture of Example 2A (1.4 g, 6.8 mmol), pivalaldehyde (2.24 mL, 20.4 mmol), and PS—BH$_3$CN (2.65 g, 10.9 mmol) in DCM (50 mL) and acetic acid (5 mL) was stirred for 18 h. The mixture was filtered and concentrated. The crude was dissolved in EtOAc, washed with saturated NaHCO$_3$. The organic phase was dried over MgSO$_4$, concentrated and purified by flash chromatography to give 2B (1.4 g, 72%). LCMS (ESI) m/z 277.2 (M+H)$^+$, RT=1.29 min (Method A).

Example 2C 4-(1-Neopentylpiperidin-4-yl)aniline

To Example 2B (1.4 g, 4.9 mmol) in EtOAc (25 mL) was added palladium on carbon (10% w/w, 130 mg). The mixture was stirred under hydrogen atmosphere (balloon) at 50° C. for 2 h and 20° C. for 18 h. The mixture was filtered and concentrated to give Example 2C (980 mg, 81%). LCMS (ESI) m/z 247.2 (M+H)$^+$, RT=1.07 min (Method A).

Example 2D 4-nitrophenyl 4-(1-neopentylpiperidin-4-yl)phenylcarbamate

To Example 2C (202.5 mg, 0.822 mmol) in chloroform (4 mL) was added 4-nitrophenylchloroformate (169.0 mg, 0.838 mmol). The reaction was stirred for 3 h at 23° C. The reaction was diluted with hexanes (10 mL), filtered, and concentrated to give Example 2D (370 mg, 100%). LCMS (ESI) m/z 412 (M+H)$^+$, RT=1.48 min (Method A).

Example 2

DMF (2 mL) was added to a flask containing Intermediate 2 (45 mg, 0.14 mmol) and Example 2D (57 mg, 0.13 mmol). Triethylamine (0.053 mL, 0.38 mmol) was added and stirred at room temperature for 24 h. The reaction was purified by Prep HPLC (TFA) to give the TFA salt of Example 2 (25 mg, 28%) as a yellow solid. LCMS (ESI) m/z 595 (M+H)$^+$, RT=1.81 min (Method A). $^1$H NMR (400 MHz, DMSO-d$_6$) δ ppm 1.07 (s, 9H), 1.29 (s, 3H), 1.40 (s, 3H), 1.90 (m, 2H), 2.03 (m, 2H), 3.00-3.30 (m, 7H), 3.56 (m, 1H), 3.82 (d, J=10.1 Hz, 1H), 6.75 (d, J=8.4 Hz, 1H), 6.85 (m, 2H), 7.04-7.24 (m, 4H), 7.42 (d, J=8.3 Hz, 2H), 8.05 (m, 1H), 8.24 (br s, 1H), 9.31 (s, 1H), 9.92 (s, 1H).

Example 3

1-(2-(7-Hydroxy-3,3-dimethyl-4-(trifluoromethyl)indolin-1-yl)phenyl)-3-(1-(2,2,2-trifluoroethyl)piperidin-4-yl)urea

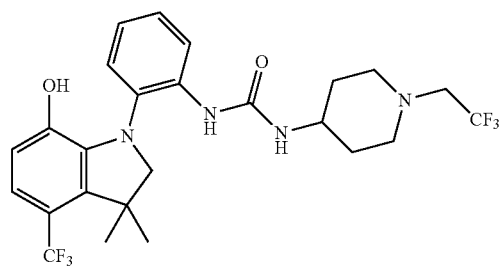 [SMILES: CC1(C)CN(c2ccccc2NC(=O)NC2CCN(CC(F)(F)F)CC2)c2c(O)ccc(C(F)(F)F)c21]

Example 3A 1-(2-(7-Hydroxy-3,3-dimethyl-4-(trifluoromethyl) indolin-1-yl)phenyl)-3-isopropylurea To a solution of Intermediate 2 (500 mg, 1.55 mmol) in DCM (6 mL) was added isopropyl isocyanate (0.152 mL, 1.55 mmol) dropwise. The reaction mixture was stirred at room temperature for 1 h. The reaction mixture was stirred at room temperature for 16 h. Another portion of isocyanate (0.060 mL, 0.62 mmol) was added to the reaction mixture and stirred at room temperature for 2 h. The reaction mixture was diluted with DCM and washed with H$_2$O. The organic layer was dried over Na$_2$SO$_4$ and the solvent was evaporated to give Example 3A (520 mg, 82.0% yield). LCMS (ESI) m/z 408.1 (M+H)$^+$, RT=3.69 min (Method C).

Example 3B. 1-(1-Benzylpiperidin-4-yl)-3-(2-(7-hydroxy-3,3-dimethyl-4-(trifluoromethyl)indolin-1-yl)phenyl) urea: To a solution of Example 3A (300 mg, 0.736 mmol) in THF (2 mL) and DMSO (0.5 mL) was added 4-amino-1-benzylpiperidine (0.452 mL, 2.21 mmol). The reaction mixture was stirred at 150° C. under microwave for 20 min. The crude product was purified by flash chromatography, eluting with EtOAc/hexanes to give Example 3B (0.33 g, 83% yield). LCMS (ESI) m/z 539.2 (M+H)$^+$, RT=3.26 min (Method C). $^1$H NMR (400 MHz, MeOD) δ ppm 1.33 (s, 3H), 1.41 (s, 3H), 1.48 (m, 1H), 1.81-1.92 (m, 2H), 2.15 (m, 2H), 2.65 (m, 1H), 2.82 (m, 2H), 3.14 (d, J=9.89 Hz, 1H), 3.51 (s, 2H), 3.58 (m, 1H), 3.73 (d, J=9.89 Hz, 1H), 6.67 (d, J=8.79 Hz, 1H), 6.85-6.88 (m, 1H), 6.90-6.95 (m, 1H), 7.04 (d, J=8.25 Hz, 1H), 7.07 (d, J=8.24 Hz, 1H), 7.24-7.27 (m, 1H), 7.29-7.32 (m, 5H), 7.71 (d, J=8.25 Hz, 1H).

Example 3C. 1-(2-(7-Hydroxy-3,3-dimethyl-4-(trifluoromethyl)indolin-1-yl)phenyl)-3-(piperidin-4-yl)urea: To a solution of Example 3B (250 mg, 0.464 mmol) in MeOH (5 mL) was added palladium on carbon (4.9 mg, 0.046 mmol). The reaction mixture was stirred under hydrogen atmosphere for 2 h. There was no desired product formed. Ammonium formate (5.9 mg, 0.093 mmol) was added and the reaction mixture was stirred at room temperature under hydrogen atmosphere for 16 h. Then the catalyst was removed and the reaction was run using Pearlman's catalyst with a small amount of 1 M HCl under a hydrogen atmosphere for 16 h. The catalyst was removed and the solvent was evaporated to give Example 3C (0.15 g, 73% yield). LCMS (ESI) m/z 449.2 (M+H)$^+$, RT=3.10 min (Method C). $^1$H NMR (400 MHz, MeOD) δ ppm 1.33 (s, 3H), 1.42 (s, 3H), 1.63-1.78 (m, 2H), 2.07-2.16 (m, 2H), 3.04-3.12 (m, 2H), 3.15 (d, J=9.89 Hz, 1H), 3.34-3.43 (m, 2H), 3.76 (d, J=9.89 Hz, 1H), 3.80-3.89 (m, 1H), 6.70 (d, J=8.24 Hz, 1H), 6.86-6.90 (m, 1H), 6.95 (t, J=7.42 Hz, 1H), 7.07 (t, J=9.07 Hz, 2H), 7.69-7.74 (m, 1H), 8.49 (s, 2H).

Example 3: To a solution of Example 3C (22 mg, 0.049 mmol) in THF (1 mL) was added sodium bicarbonate (4.1 mg, 0.049 mmol), followed by 2,2,2-trifluoroethyl trifluoromethanesulfonate (11 mg, 0.049 mmol) at 40° C. The reaction mixture was stirred at room temperature for 16 h and then at 40° C. for additional 8 h. The crude was purified by Prep HPLC to give Example 3 (8.3 mg, 24%). LCMS (ESI) m/z 531.2 (M+H)$^+$, RT=3.43 min (Method C). $^1$H NMR (400 MHz, MeOD) δ ppm 1.35 (s, 3H), 1.43 (s, 3H), 1.53-1.69 (m, 2H), 1.95-2.05 (m, 2H), 2.75-2.84 (m, 2H), 3.15 (m, 2H), 3.16 (d, J=9.89 Hz, 1H), 3.44-3.51 (m, 2H), 3.68 (m, 1H), 3.74 (d, J=9.89 Hz, 1H), 6.68 (d, J=8.24 Hz, 1H), 6.87-6.90 (m, 1H), 6.92-6.97 (m, 1H), 7.04-7.11 (m, 2H), 7.73 (d, J=6.60 Hz, 1H).

Example 4

1-(2-(3,3-Diethyl-4-fluoro-7-hydroxyindolin-1-yl) phenyl)-3-(4-(1-neopentylpiperidin-4-yl)phenyl)urea

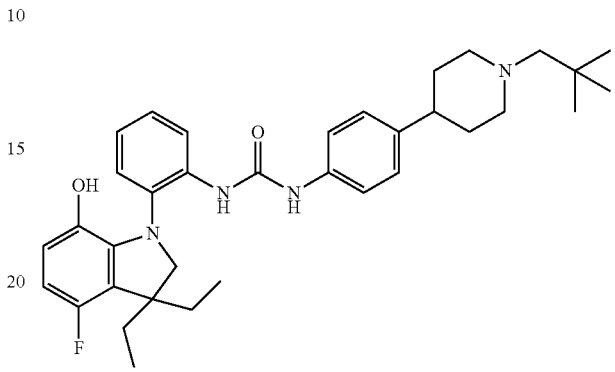

Example 4A.

1-(2-(3,3-Diethyl-4-fluoro-7-hydroxyindolin-1-yl) phenyl)-3-(4-(piperidin-4-yl)phenyl)urea A solution of tert-butyl 4-(4-aminophenyl)piperidine-1-carboxylate (121 mg, 0.440 mmol) in dichloromethane (3 mL) was added dropwise to a solution of triphosgene (142 mg, 0.480 mmol) and triethylamine (0.11 mL, 0.80 mmol) in dichloromethane (7 mL) at 0° C. and stirred for 30 min. The reaction was quenched with cold water and then diluted with dichloromethane. The organics were washed with saturated NaHCO$_3$ solution, dried over MgSO$_4$, filtered and evaporated to give crude isocyanate. A solution of Intermediate 5 (0.12 g, 0.40 mmol) in THF (5 mL) was added to the isocyanate at room temperature and this was stirred for 3 h. The reaction was concentrated and taken up in dichloromethane (5 mL). TFA (5 mL) was added and the reaction was stirred for 30 min. The reaction was concentrated and purified by Prep HPLC (TFA) to give the TFA salt of Example 4A (0.20 g, 81%). LCMS (ESI) m/z 503.2 (M+H)$^+$, RT=1.72 min (Method A).

Example 4

Resin bounded cyanoborohydride (50 mg) was added to a solution of Example 4A TFA salt (35 mg, 0.060 mmol) and trimethylacetaldehyde (0.019 mL, 0.17 mmol) in dichloromethane(1 mL) and acetic acid (0.1 mL) in a vial. This was placed on a shaker at room temperature for 16 h. The reaction was filtered, concentrated, and purified by Prep HPLC (TFA) to give the TFA salt of the Example 4 (13 mg, 33%) as white solid. LCMS (ESI) m/z 573 (M+H)$^+$, RT=2.10 min (Method H). $^1$H NMR (400 MHz, CDCl$_3$) δ ppm 0.70 (t, J=7.1 Hz, 3H), 0.80 (t, J=7.4 Hz, 3H), 1.07 (s, 9H), 1.50-1.85 (m, 6H), 2.10 (m, 2H), 2.40-2.75 (m, 5H), 3.09 (d, J=9.8 Hz, 1H), 3.54 (m, 2H), 3.82 (d, J=10.4 Hz, 1H), 6.40 (t, J=8.9 Hz, 1H), 6.60 (dd, J=4.3, 8.6 Hz, 1H), 6.79 (m, 2H), 7.04 (m, 5H), 7.67 (m, 1H), 7.82 (s, 1H), 8.05 (s, 1H), 10.10 (br s, 1H).

Example 5

1-(2-(3,3-Diethyl-5-fluoro-7-hydroxyindolin-1-yl)phenyl)-3-(4-(trifluoromethoxy)phenyl)urea

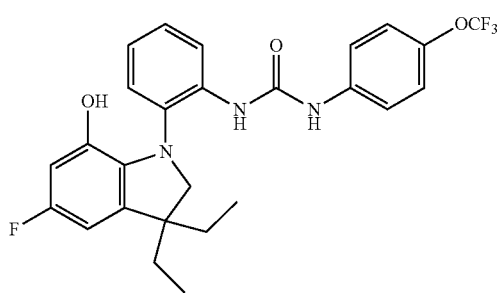 [SMILES: CCC1(CC)CN(c2ccccc2NC(=O)Nc2ccc(OC(F)(F)F)cc2)c2c(O)cc(F)cc21]

Example 5A.

1-(2-(3,3-Diethyl-5-bromo-7-methoxyindolin-1-yl)phenyl)-3-(4-(trifluoromethoxy)-phenyl)urea Example 5A (0.74 g, 38% yield) was prepared as a white solid following a similar procedure as described in Example 1. LCMS (ESI) m/z 578.2, 580.2 (M+H, M+2+H)$^+$, RT=2.80 min (Method H).

Example 5: To Example 5A (50 mg, 0.090 mmol) in THF (2 mL) at −78° C. was added MeLi (0.11 mL, 0.17 mmol, 1.6 M in ether). After 5 min, BuLi (0.11 mL, 0.17 mmol, 1.6 M in hexanes) was added and stirred for 15 min at −78° C. A solution of N-fluorobenzenesulfonimide (55 mg, 0.17 mmol) in THF (0.5 mL) was added and the reaction was stirred at −78° C. for 15 min and then warmed to room temperature slowly. The reaction was quenched with water and extracted with EtOAc. The combined organics were dried over MgSO$_4$, filtered and concentrated. The crude was purified by Prep HPLC to give the fluorobenzene product. The product was dissolved in DCM (1 mL) and BBr$_3$ solution (0.43 mL, 0.43 mmol, 1.0 M in DCM) was added at −78° C. The mixture was stirred at −78° C. for 5 min, then allowed to reach room temperature and stirred for 15 min. Conc. NH$_4$OH (2 mL) was added and then water and EtOAc. The layers were separated and the aqueous layer was extracted with EtOAc. Combined organics were washed with water, dried over MgSO$_4$, filtered and concentrated. The crude was purified by Prep HPLC to give Example 5 (3 mg, 6%) as a white solid. LCMS (ESI) m/z 504.1 (M+H)$^+$, RT=2.19 min (Method H). HRMS Calcd for (C$_{26}$H$_{26}$N$_3$O$_3$F$_4$) [M+H]+504.1910. found 504.1895.

Example 6

1-(2-(4-Bromo-7-hydroxy-3,3-dimethylindolin-1-yl)phenyl)-3-(2-chlorothiazol-4-yl)urea

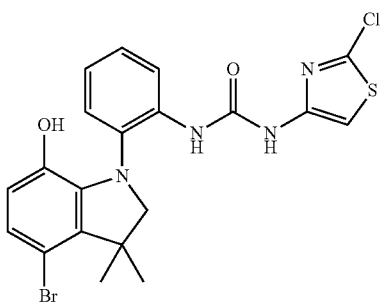 [SMILES: CC1(C)CN(c2ccccc2NC(=O)Nc2csc(Cl)n2)c2c(O)ccc(Br)c21]

Example 6A.

1-(2-Aminophenyl)-4-bromo-3,3-dimethylindolin-7-ol

To a solution of Intermediate 11 (0.25 g, 0.72 mmol) in DCM (6 mL) was added tetrabutylammonium iodide (1.86 g, 5.04 mmol) and sealed under nitrogen. The reaction was then cooled to −78° C., degassed and then kept under constant nitrogen flow. Boron trichloride (5.04 mL, 5.04 mmol, 1.0 M solution in DCM) was added slowly and allowed to stir at −78° C. for 1 h before warming up to room temperature. The reaction was then quenched with water and separated with DCM, washed with saturated NaHCO$_3$, saturated NH$_4$Cl, water, and then brine. The organic layer was collected, dried over MgSO$_4$, filtered and evaporated. The crude product was purified by flash chromatography, eluting with EtOAc/hexanes to give Example 6A (126 mg, 53% yield) as a greenish brown oil. LCMS (ESI) m/z 333, 335 (M+H, M+2+H)$^+$, RT=1.49 min (Method J).

Example 6

A solution of 2-chlorothiazole-4-carboxylic acid (148 mg, 0.906 mmol), diphenyl phosphorazidate (0.20 mL, 1.0 mmol) in toluene (3 mL) was stirred at room temperature for 5 min before slowly warming up to 100° C. When the reaction reached 40° C., Example 6A (23.7 mg) in toluene (3 mL) was added. The reaction mixture was heated at 100° C. for 90 min before gradually cooling down to room temperature. The reaction was then concentrated and purified by Prep HPLC (TFA) to give Example 6 (48 mg, 22% yield) as a brown solid. LCMS (ESI) m/z 493, 495 (M+H, M+2+H)$^+$, RT=2.05 min (Method J). $^1$H NMR (300 MHz, DMSO-d$_6$) δ ppm 1.38 (s, 3H), 1.48 (s, 3H), 3.03 (d, J=10.25 Hz, 1H), 3.85 (d, J=9.88 Hz, 1H), 6.54 (d, J=8.42 Hz, 1H), 6.79-6.96 (m, 3H), 7.00-7.17 (m, 1H), 7.28 (s, 1H), 8.06 (d, J=7.68 Hz, 1H), 8.52 (s, 1H), 9.18 (s, 1H), 10.20 (s, 1H).

Examples 7 to 47 were prepared similarly according the procedures described in Examples 1 to 6 by using the appropriate Intermediate amines and the appropriate isocyanates.

| Example No. | Compound Name | Compound Structure | LC-MS (ESI) m/z |
|---|---|---|---|
| 7 | 1-(2-(3,3-Diethyl-7-hydroxyindolin-1-yl)phenyl)-3-(4-(1-neopentylpyrrolidin-2-yl)phenyl)urea | 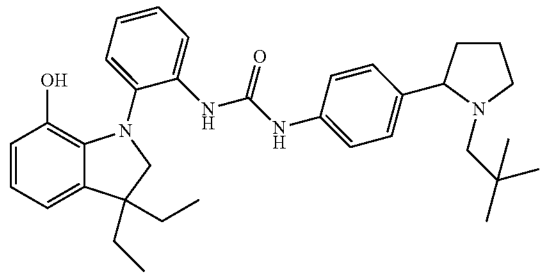 [SMILES: CCC1(CC)CN(c2ccccc2NC(=O)Nc2ccc(C3CCCN3CC(C)(C)C)cc2)c2c(O)cccc21] | m/z 541.0 (M + H)+, RT = 1.75 min (Method A) |
| 8 | 1-(2-(3,3-Diethylindolin-1-yl)phenyl)-3-(4-(1-isobutylpyrrolidin-2-yl)phenyl)urea | 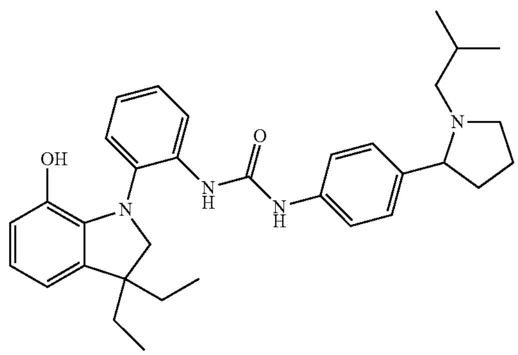 [SMILES: CCC1(CC)CN(c2ccccc2NC(=O)Nc2ccc(C3CCCN3CC(C)C)cc2)c2c(O)cccc21] | m/z 527.0 (M + H)+, RT = 2.07 min (Method H) |
| 9 | 1-(6-Chlorobenzo[d]thiazol-2-yl)-3-(2-(3,3-diethyl-7-hydroxyindolin-1-yl)phenyl)urea | 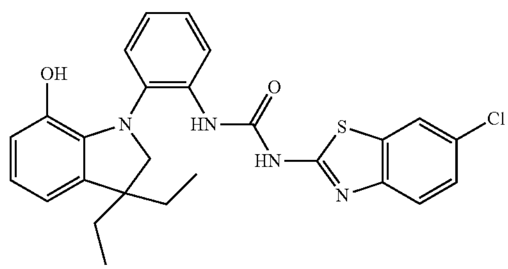 [SMILES: CCC1(CC)CN(c2ccccc2NC(=O)Nc2nc3ccc(Cl)cc3s2)c2c(O)cccc21] | m/z 493.0 (M + H)+, RT = 2.37 min (Method D) |
| 10 | 1-(2-(3,3-Diethyl-7-hydroxyindolin-1-yl)phenyl)-3-(6-methylbenzo[d]thiazol-2-yl)urea | 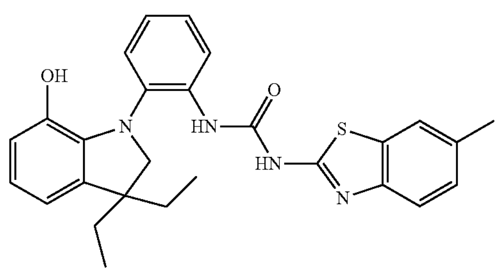 [SMILES: CCC1(CC)CN(c2ccccc2NC(=O)Nc2nc3ccc(C)cc3s2)c2c(O)cccc21] | m/z 473.1 (M + H)+, RT = 2.27 min (Method D) |
| 11 | 1-(2-(7-Hydroxy-3,3-dimethylindolin-1-yl)phenyl)-3-(4-(1-isobutylpyrrolidin-2-yl)phenyl)urea | 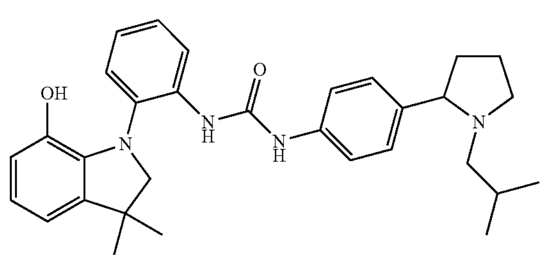 [SMILES: CC(C)CN1CCCC1c1ccc(NC(=O)Nc2ccccc2N2CC(C)(C)c3cccc(O)c32)cc1] | m/z 499.0 (M + H)+, RT = 5.18 min (Method I) |

-continued

| Example No. | Compound Name | Compound Structure | LC-MS (ESI) m/z |
|---|---|---|---|
| 12 | 1-(2-(7-Hydroxy-3,3-dimethyl-4-(trifluoromethyl)indolin-1-yl)phenyl)-3-(4-(trifluoromethoxy)phenyl)urea | 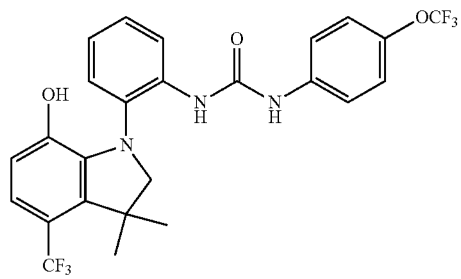 [SMILES: CC1(C)CN(c2ccccc2NC(=O)Nc2ccc(OC(F)(F)F)cc2)c2c(O)ccc(C(F)(F)F)c21] | m/z 526 (M + H)+, RT = 2.41 min (Method A) |
| 13 | 1-(4-tert-Butylphenyl)-3-(2-(7-hydroxy-3,3-dimethyl-4-(trifluoromethyl)indolin-1-yl)phenyl)urea | 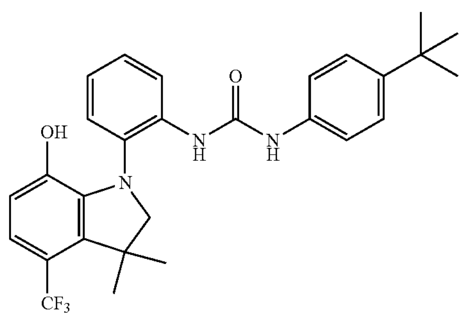 [SMILES: CC(C)(C)c1ccc(NC(=O)Nc2ccccc2N2CC(C)(C)c3c(C(F)(F)F)ccc(O)c32)cc1] | m/z 498 (M + H)+, RT = 2.49 min (Method A) |
| 14 | 1-(2,4-Difluorophenyl)-3-(2-(7-hydroxy-3,3-dimethyl-4-(trifluoromethyl)indolin-1-yl)phenyl)urea | 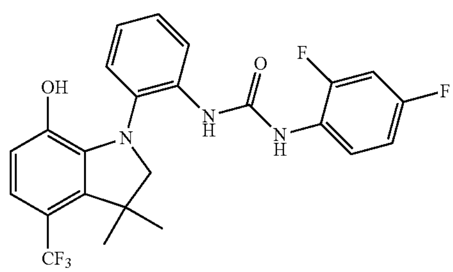 [SMILES: CC1(C)CN(c2ccccc2NC(=O)Nc2ccc(F)cc2F)c2c(O)ccc(C(F)(F)F)c21] | m/z 478.4 (M + H)+, RT = 2.14 min (Method D) |
| 15 | 1-(2-(7-Hydroxy-3,3-dimethyl-4-(trifluoromethyl)indolin-1-yl)phenyl)-3-(2-methylthiazol-4-yl)urea | 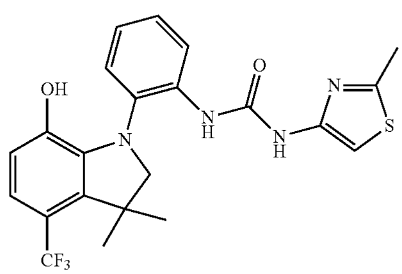 [SMILES: Cc1nc(NC(=O)Nc2ccccc2N2CC(C)(C)c3c(C(F)(F)F)ccc(O)c32)cs1] | m/z 463.4 (M + H)+, RT = 2.03 min (Method D) |
| 16 | 1-(2-Chlorothiazol-4-yl)-3-(2-(7-hydroxy-3,3-dimethyl-4-(trifluoromethyl)indolin-1-yl)phenyl)urea | 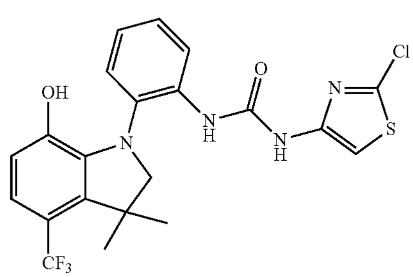 [SMILES: CC1(C)CN(c2ccccc2NC(=O)Nc2csc(Cl)n2)c2c(O)ccc(C(F)(F)F)c21] | m/z 483.4 (M + H)+, RT = 2.14 min (Method D) |

| Example No. | Compound Name | Compound Structure | LC-MS (ESI) m/z |
|---|---|---|---|
| 17 | 1-(2-(7-Hydroxy-3,3-dimethyl-4-(trifluoromethyl)indolin-1-yl)phenyl)-3-(4-(trifluoromethyl)phenyl)urea | 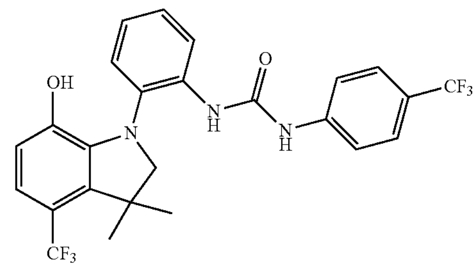 [SMILES: CC1(C)CN(c2ccccc2NC(=O)Nc2ccc(C(F)(F)F)cc2)c2c(O)ccc(C(F)(F)F)c21] | m/z 510.3 (M + H)+, RT = 3.71 min (Method E) |
| 18 | 1-(6-Fluorobenzo[d]thiazol-2-yl)-3-(2-(7-hydroxy-3,3-dimethyl-4-(trifluoromethyl)indolin-1-yl)phenyl)urea | 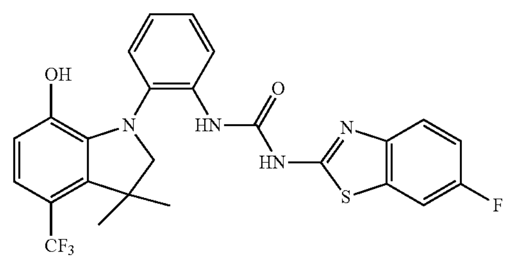 [SMILES: CC1(C)CN(c2ccccc2NC(=O)Nc2nc3ccc(F)cc3s2)c2c(O)ccc(C(F)(F)F)c21] | m/z 517.4 (M + H)+, RT = 4.22 min (Method C) |
| 19 | 1-(6-Chlorobenzo[d]thiazol-2-yl)-3-(2-(7-hydroxy-3,3-dimethyl-4-(trifluoromethyl)indolin-1-yl)phenyl)urea | 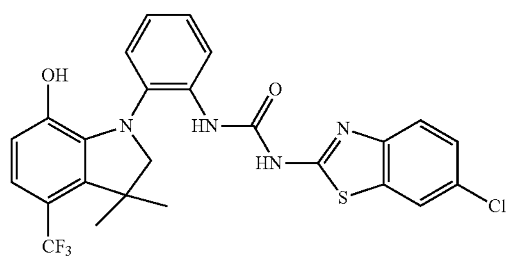 [SMILES: CC1(C)CN(c2ccccc2NC(=O)Nc2nc3ccc(Cl)cc3s2)c2c(O)ccc(C(F)(F)F)c21] | m/z 533.4 (M + H)+, RT = 2.32 min (Method D) |
| 20 | 1-(5-Ethyl-4,5,6,7-tetrahydrothiazolo[5,4-c]pyridin-2-yl)-3-(2-(7-hydroxy-3,3-dimethyl-4-(trifluoromethyl)indolin-1-yl)phenyl)urea | 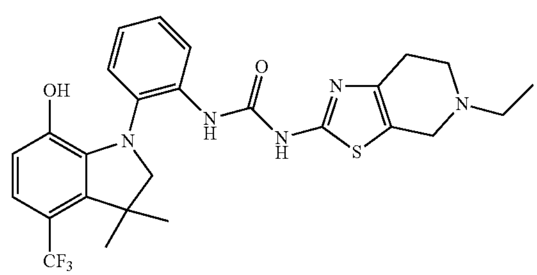 [SMILES: CCN1CCc2nc(NC(=O)Nc3ccccc3N3CC(C)(C)c4c(C(F)(F)F)ccc(O)c43)sc2C1] | m/z 532.6 (M + H)+, RT = 3.24 min (Method C) |
| 21 | 1-(2-(7-Hydroxy-3,3-dimethyl-4-(trifluoromethyl)indolin-1-yl)phenyl)-3-(5-isobutyl-4,5,6,7-tetrahydrothiazolo[5,4-c]pyridin-2-yl)urea | 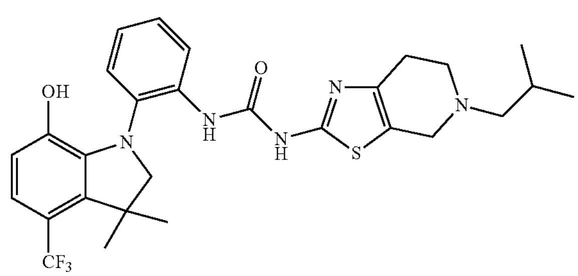 [SMILES: CC(C)CN1CCc2nc(NC(=O)Nc3ccccc3N3CC(C)(C)c4c(C(F)(F)F)ccc(O)c43)sc2C1] | m/z 560.6 (M + H)+, RT = 3.26 min (Method C) |

-continued

| Example No. | Compound Name | Compound Structure | LC-MS (ESI) m/z |
|---|---|---|---|
| 22 | 1-(2-(7-Hydroxy-3,3-dimethyl-4-(trifluoromethyl)indolin-1-yl)phenyl)-3-(5-neopentyl-4,5,6,7-tetrahydrothiazolo[5,4-c]pyridin-2-yl)urea | 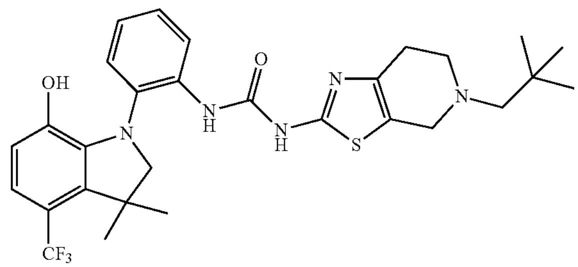 [SMILES: CC(C)(C)CN1CCc2nc(NC(=O)Nc3ccccc3N3CC(C)(C)c4c(C(F)(F)F)ccc(O)c43)sc2C1] | m/z 574.6 (M + H)+, RT = 3.50 min (Method C) |
| 23 | 1-(5-(Cyclopropylmethyl)-4,5,6,7-tetrahydrothiazolo[5,4-c]pyridin-2-yl)-3-(2-(7-hydroxy-3,3-dimethyl-4-(trifluoromethyl)indolin-1-yl)phenyl)urea | 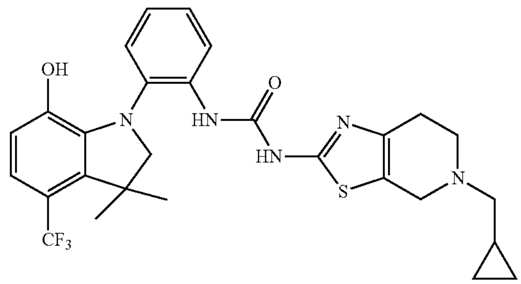 [SMILES: CC1(C)CN(c2ccccc2NC(=O)Nc2nc3c(s2)CN(CC2CC2)CC3)c2c(O)ccc(C(F)(F)F)c21] | m/z 558.5 (M + H)+, RT = 1.81 min (Method D) |
| 24 | 1-(2-(3,3-Diethyl-7-hydroxy-4-(trifluoromethyl)indolin-1-yl)phenyl)-3-(4-(trifluoromethoxy)phenyl)urea | 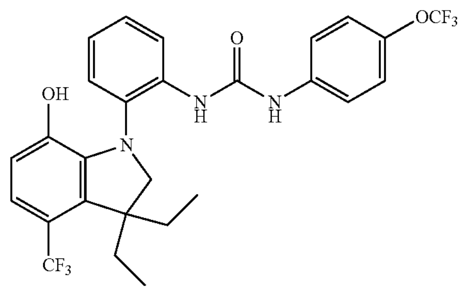 [SMILES: CCC1(CC)CN(c2ccccc2NC(=O)Nc2ccc(OC(F)(F)F)cc2)c2c(O)ccc(C(F)(F)F)c21] | m/z 554 (M + H)+, RT = 2.24 min (Method H) |
| 25 | 1-(2-(3,3-Diethyl-7-hydroxy-4-(trifluoromethyl)indolin-1-yl)phenyl)-3-(4-(1-neopentylpiperidin-4-yl)phenyl)urea | 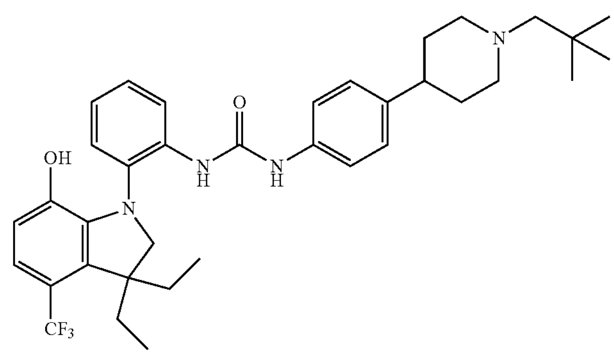 [SMILES: CCC1(CC)CN(c2ccccc2NC(=O)Nc2ccc(C3CCN(CC(C)(C)C)CC3)cc2)c2c(O)ccc(C(F)(F)F)c21] | m/z 623 (M + H)+, RT = 2.22 min (Method H) |
| 26 | 1-(4-tert-Butylphenyl)-3-(2-(3,3-diethyl-4-fluoro-7-hydroxyindolin-1-yl)phenyl)urea | 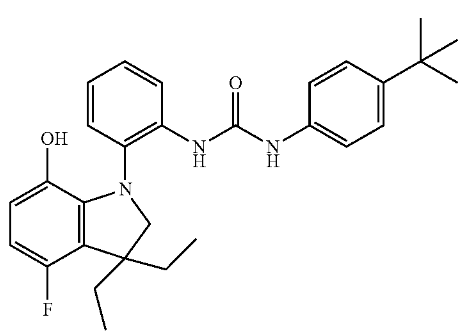 [SMILES: CCC1(CC)CN(c2ccccc2NC(=O)Nc2ccc(C(C)(C)C)cc2)c2c(O)ccc(F)c21] | m/z 476 (M + H)+, RT = 2.21 min (Method H) |

| Example No. | Compound Name | Compound Structure | LC-MS (ESI) m/z |
|---|---|---|---|
| 27 | 1-(2-(3,3-Diethyl-4-fluoro-7-hydroxyindolin-1-yl)phenyl)-3-(4-ethylphenyl)urea | 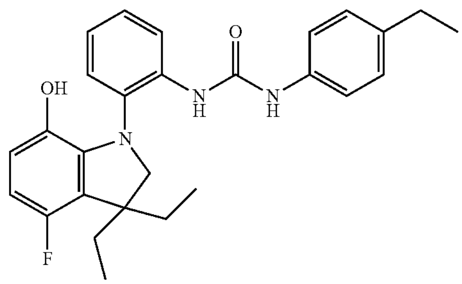 [SMILES: CCc1ccc(NC(=O)Nc2ccccc2N2CC(CC)(CC)c3c(F)ccc(O)c32)cc1] | m/z 448 (M + H)+, RT = 2.14 min (Method H) |
| 28 | 1-(2-(3,3-Diethyl-4-fluoro-7-hydroxyindolin-1-yl)phenyl)-3-(4-(1-isobutylpiperidin-4-yl)phenyl)urea | 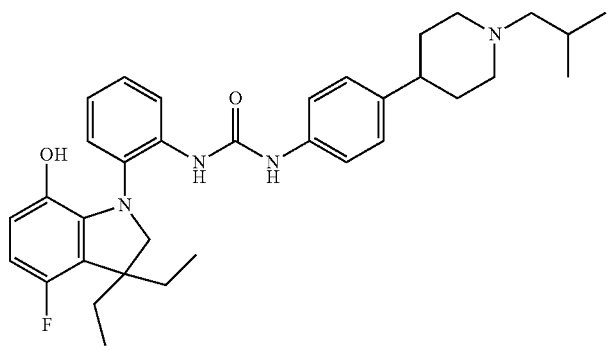 [SMILES: CCC1(CC)CN(c2ccccc2NC(=O)Nc2ccc(C3CCN(CC(C)C)CC3)cc2)c2c(O)ccc(F)c21] | m/z 559 (M + H)+, RT = 1.92 min (Method H) |
| 29 | 1-(2-(3,3-Diethyl-4-fluoro-7-hydroxyindolin-1-yl)phenyl)-3-(4-(1-neopentylpyrrolidin-2-yl)phenyl)urea | 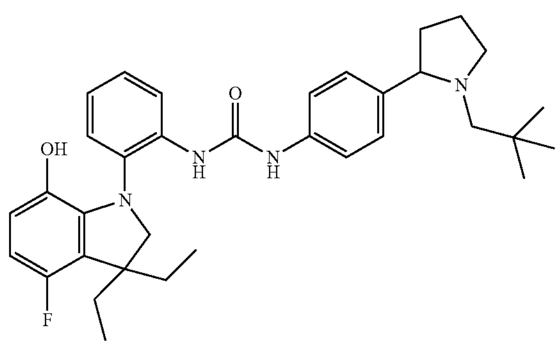 [SMILES: CCC1(CC)CN(c2ccccc2NC(=O)Nc2ccc(C3CCCN3CC(C)(C)C)cc2)c2c(O)ccc(F)c21] | m/z 559 (M + H)+, RT = 2.12 min (Method H) |
| 30 | 1-(2-(3,3-Diethyl-4-fluoro-7-hydroxyindolin-1-yl)phenyl)-3-(4-(1-isobutylpyrrolidin-2-yl)phenyl)urea | 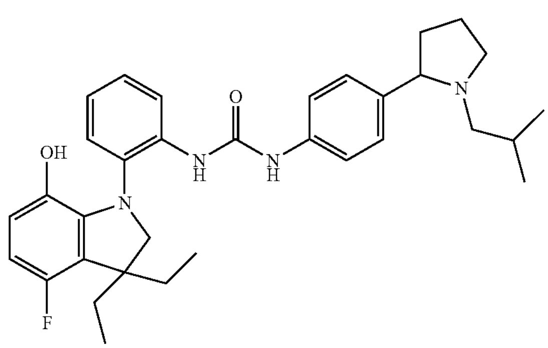 [SMILES: CCC1(CC)CN(c2ccccc2NC(=O)Nc2ccc(C3CCCN3CC(C)C)cc2)c2c(O)ccc(F)c21] | m/z 545 (M + H)+, RT = 2.02 min (Method H) |

| Example No. | Compound Name | Compound Structure | LC-MS (ESI) m/z |
|---|---|---|---|
| 31 | 1-(2-Chlorothiazol-4-yl)-3-(2-(3,3-diethyl-4-fluoro-7-hydroxyindolin-1-yl)phenyl)urea | 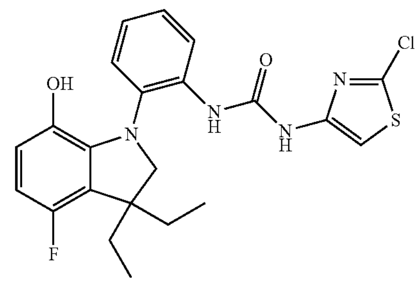 [SMILES: CCC1(CC)CN(c2ccccc2NC(=O)Nc2csc(Cl)n2)c2c(O)ccc(F)c21] | m/z 461.4 (M + H)+, RT = 2.17 min (Method D) |
| 32 | 1-(2-(3,3-Diethyl-4-fluoro-7-hydroxyindolin-1-yl)phenyl)-3-(6-fluorobenzo[d]thiazol-2-yl)urea | 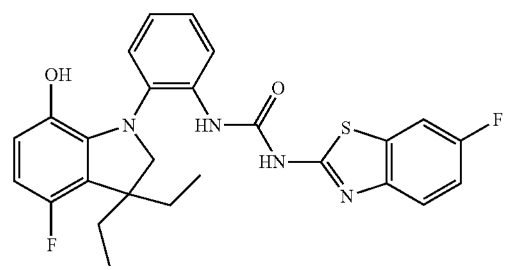 [SMILES: CCC1(CC)CN(c2ccccc2NC(=O)Nc2nc3ccc(F)cc3s2)c2c(O)ccc(F)c21] | m/z 495.0 (M + H)+, RT = 2.29 min (Method D) |
| 33 | 1-(2-(3,3-Diethyl-4-fluoro-7-hydroxyindolin-1-yl)phenyl)-3-(3-(ethylthio)-1,2,4-thiadiazol-5-yl)urea | 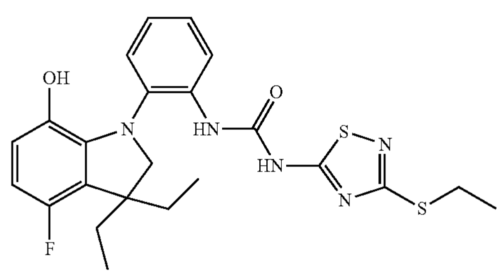 [SMILES: CCSc1nsc(NC(=O)Nc2ccccc2N2CC(CC)(CC)c3c(F)ccc(O)c32)n1] | m/z 488.0 (M + H)+, RT = 2.30 min (Method D) |
| 34 | 1-(2-(4-Fluoro-7-hydroxy-3,3-dimethylindolin-1-yl)phenyl)-3-(4-(1-isobutylpyrrolidin-2-yl)phenyl)urea | 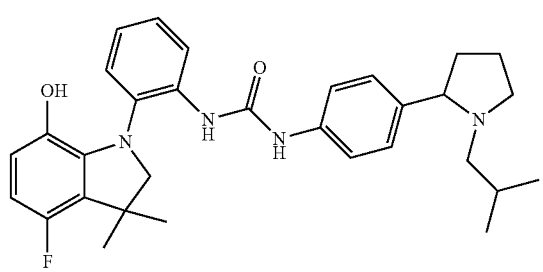 [SMILES: CC(C)CN1CCCC1c1ccc(NC(=O)Nc2ccccc2N2CC(C)(C)c3c(F)ccc(O)c32)cc1] | m/z 517.2 (M + H)+ |
| 35 | 1-(2-(3,3-Diethyl-6-fluoro-7-hydroxyindolin-1-yl)phenyl)-3-(4-(trifluoromethoxy)phenyl)urea | 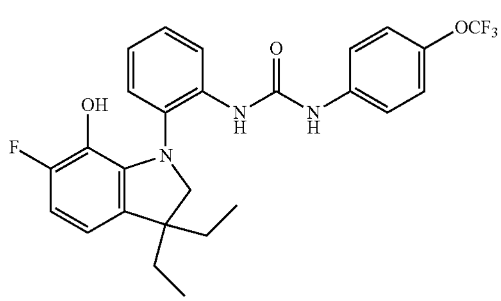 [SMILES: CCC1(CC)CN(c2ccccc2NC(=O)Nc2ccc(OC(F)(F)F)cc2)c2c1ccc(F)c2O] | m/z 504 (M + H)+, RT = 2.17 min (Method H) |

| Example No. | Compound Name | Compound Structure | LC-MS (ESI) m/z |
|---|---|---|---|
| 36 | 1-(2-(3,3-Diethyl-6-fluoro-7-hydroxyindolin-1-yl)phenyl)-3-(4-(1-isobutylpyrrolidin-2-yl)phenyl)urea | 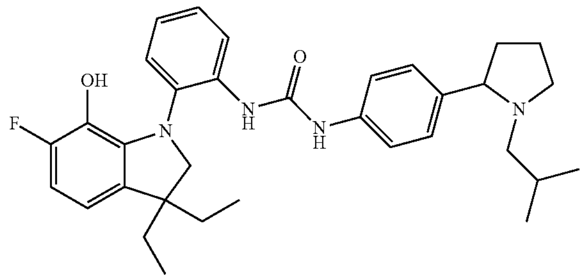 [SMILES: CCC1(CC)CN(c2ccccc2NC(=O)Nc2ccc(C3CCCN3CC(C)C)cc2)c2c1ccc(F)c2O] | m/z 545.0 (M + H)+, RT = 1.76 min (Method B) |
| 37 | 1-(2-(3,3-Diethyl-6-fluoro-7-hydroxyindolin-1-yl)phenyl)-3-(4-(1-neopentylpiperidin-4-yl)phenyl)urea | 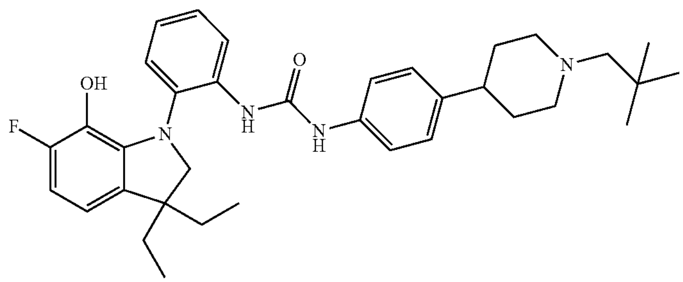 [SMILES: CCC1(CC)CN(c2ccccc2NC(=O)Nc2ccc(C3CCN(CC(C)(C)C)CC3)cc2)c2c1ccc(F)c2O] | m/z 573.0 (M + H)+, RT = 1.76 min (Method B) |
| 38 | 1-(4-tert-Butylphenyl)-3-(2-(3,3-diethyl-6-fluoro-7-hydroxyindolin-1-yl)phenyl)urea | 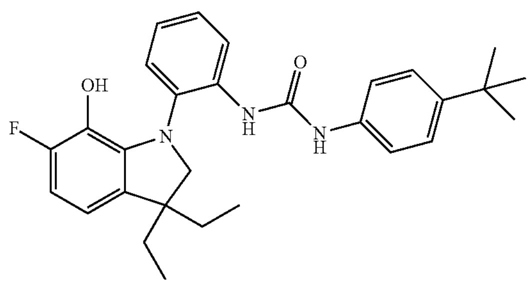 [SMILES: CCC1(CC)CN(c2ccccc2NC(=O)Nc2ccc(C(C)(C)C)cc2)c2c1ccc(F)c2O] | m/z 476.4 (M + H)+, RT = 4.33 min (Method C) |
| 39 | 1-(2-(3,3-Diethyl-4-bromo-7-hydroxyindolin-1-yl)phenyl)-3-(4-(trifluoromethoxy)phenyl)urea | 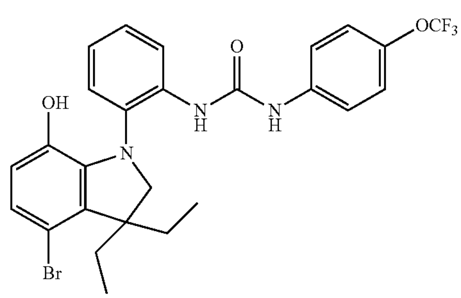 [SMILES: CCC1(CC)CN(c2ccccc2NC(=O)Nc2ccc(OC(F)(F)F)cc2)c2c(O)ccc(Br)c21] | m/z 564, 566 (M + H, M + 2 + H)+, RT = 2.26 min (Method H) |
| 40 | 1-(2-(4-Bromo-7-hydroxy-3,3-dimethylindolin-1-yl)phenyl)-3-(4-(trifluoromethoxy)phenyl)urea | 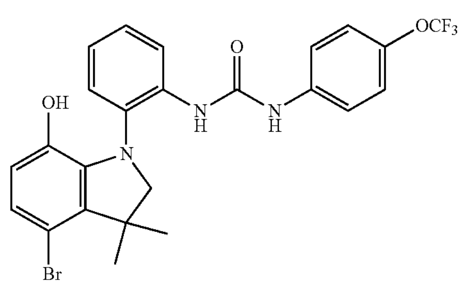 | m/z 536, 538 (M + H, M + 2 + H)+, RT = 2.12 min (Method A) |

-continued

| Example No. | Compound Name | Compound Structure | LC-MS (ESI) m/z |
|---|---|---|---|
| 41 | 1-(2-(4-Bromo-7-hydroxy-3,3-dimethylindolin-1-yl)phenyl)-3-(6-chlorobenzo[d]thiazol-2-yl)urea | 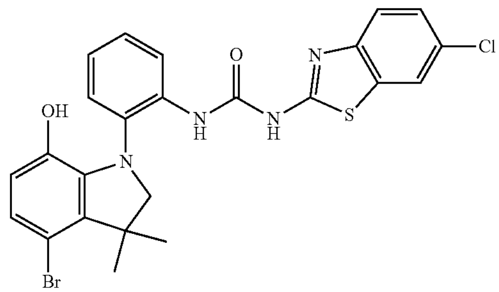 [SMILES: CC1(C)CN(c2ccccc2NC(=O)Nc2nc3ccc(Cl)cc3s2)c2c(O)ccc(Br)c21] | m/z 543, 545 (M + H, M + 2 + H)+, RT = 2.24 min (Method J) |
| 42 | 1-(2-(4-Bromo-7-hydroxy-3,3-dimethylindolin-1-yl)phenyl)-3-(6-bromobenzo[d]thiazol-2-yl)urea | 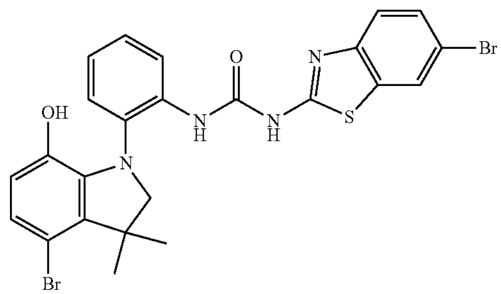 [SMILES: CC1(C)CN(c2ccccc2NC(=O)Nc2nc3ccc(Br)cc3s2)c2c(O)ccc(Br)c21] | m/z 589 (M + H)+, RT = 2.26 min (Method J) |
| 43 | 1-(2-(3,3-Diethyl-4-cyano-7-hydroxyindolin-1-yl)phenyl)-3-(4-(trifluoromethoxy)phenyl)urea | 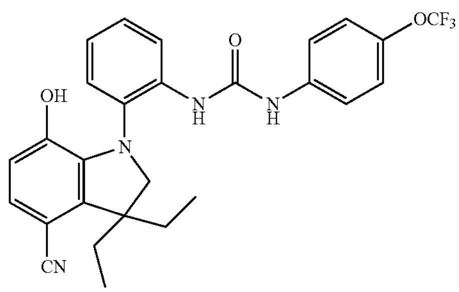 [SMILES: CCC1(CC)CN(c2ccccc2NC(=O)Nc2ccc(OC(F)(F)F)cc2)c2c(O)ccc(C#N)c21] | m/z 511 (M + H)+, RT = 2.10 min (Method H) |
| 44 | 1-(4-tert-Butylphenyl)-3-(2-(4-cyano-3,3-diethyl-7-hydroxyindolin-1-yl)phenyl)urea | 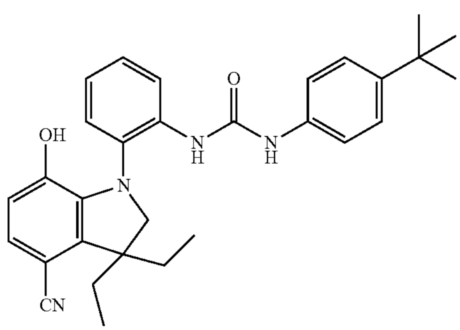 [SMILES: CCC1(CC)CN(c2ccccc2NC(=O)Nc2ccc(C(C)(C)C)cc2)c2c(O)ccc(C#N)c21] | m/z 483 (M + H)+, RT = 2.12 min (Method H) |
| 45 | 1-(2-(4-Cyano-3,3-diethyl-7-hydroxyindolin-1-yl)phenyl)-3-(4-(1-neopentylpiperidin-4-yl)phenyl)urea | 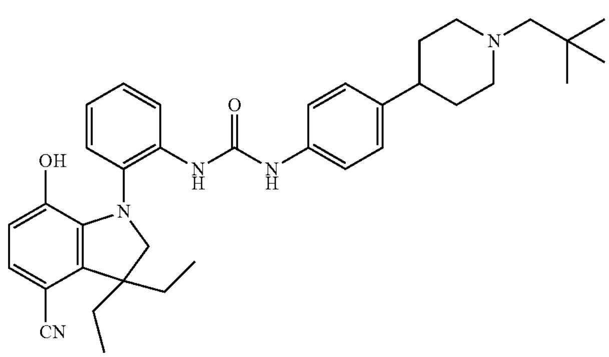 [SMILES: CCC1(CC)CN(c2ccccc2NC(=O)Nc2ccc(C3CCN(CC(C)(C)C)CC3)cc2)c2c(O)ccc(C#N)c21] | m/z 580 (M + H)+, RT = 1.77 min (Method H) |

-continued

| Example No. | Compound Name | Compound Structure | LC-MS (ESI) m/z |
|---|---|---|---|
| 46 | 1-(2-(4-Cyano-3,3-diethyl-7-hydroxyindolin-1-yl)phenyl)-3-(4-(1-isobutylpiperidin-4-yl)phenyl)urea | 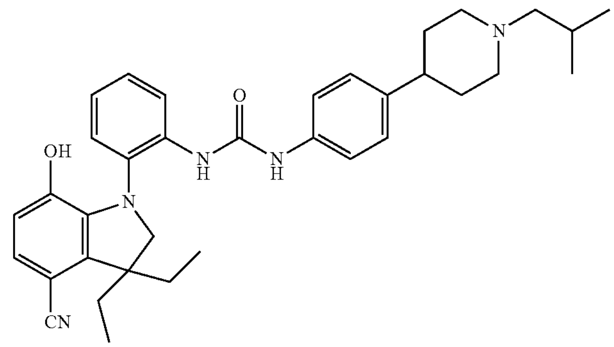 [SMILES: CCC1(CC)CN(c2ccccc2NC(=O)Nc2ccc(C3CCN(CC(C)C)CC3)cc2)c2c(O)ccc(C#N)c21] | m/z 566 (M + H)+, RT = 1.85 min (Method H) |
| 47 | 1-(2-(4-Cyano-7-hydroxy-3,3-dimethylindolin-1-yl)phenyl)-3-(4-(trifluoromethoxy)phenyl)urea | 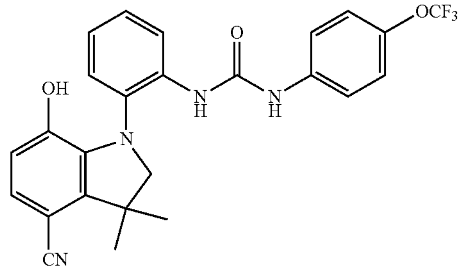 [SMILES: CC1(C)CN(c2ccccc2NC(=O)Nc2ccc(OC(F)(F)F)cc2)c2c(O)ccc(C#N)c21] | m/z 483 (M + H)+, RT = 1.94 min (Method J) |

Examples 48 to 70 were prepared according the procedures described in Examples 1 to 6 by using the appropriate Intermediate amines and reacting with the appropriate isocyanate.

| Example No. | Compound Name | Compound Structure | LC-MS (ESI) m/z |
|---|---|---|---|
| 48 | 1-(2-(4-Chloro-3,3-diethyl-7-hydroxyindolin-1-yl)phenyl)-3-(3-isopropyl-1,2,4-thiadiazol-5-yl)urea | 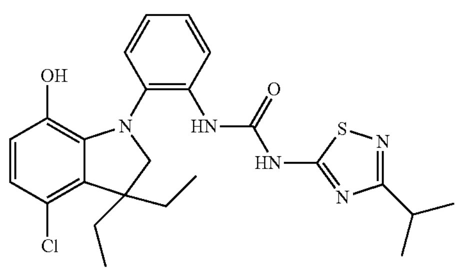 [SMILES: CCC1(CC)CN(c2ccccc2NC(=O)Nc2nc(C(C)C)ns2)c2c(O)ccc(Cl)c21] | m/z 485.9 (M + H)+, RT = 2.33 min (Method D) |
| 49 | 1-(2-(4-Chloro-3,3-diethyl-7-hydroxyindolin-1-yl)phenyl)-3-(6-fluorobenzo[d]thiazol-2-yl)urea | 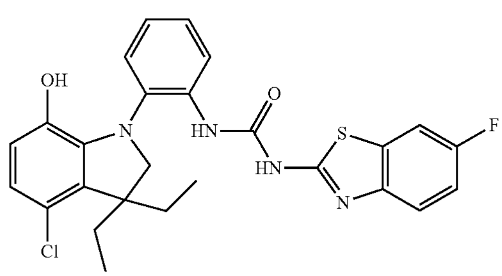 [SMILES: CCC1(CC)CN(c2ccccc2NC(=O)Nc2nc3ccc(F)cc3s2)c2c(O)ccc(Cl)c21] | m/z 510.9 (M + H)+, RT = 2.38 min (Method D) |

| Example No. | Compound Name | Compound Structure | LC-MS (ESI) m/z |
|---|---|---|---|
| 50 | 1-(2-(4-Chloro-3,3-diethyl-7-hydroxyindolin-1-yl)phenyl)-3-(4-(1-isobutylpiperidin-4-yl)phenyl)urea | 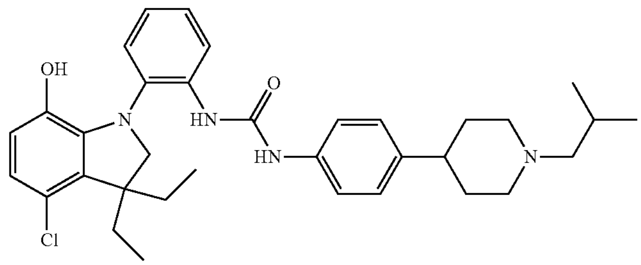 [SMILES: CCC1(CC)CN(c2ccccc2NC(=O)Nc2ccc(C3CCN(CC(C)C)CC3)cc2)c2c(O)ccc(Cl)c21] | m/z 575.4 (M + H)+, RT = 1.76 min (Method D) |
| 51 | 1-(2-(4-Chloro-3,3-diethyl-7-hydroxyindolin-1-yl)phenyl)-3-(4-(trifluoromethoxy)phenyl)urea | 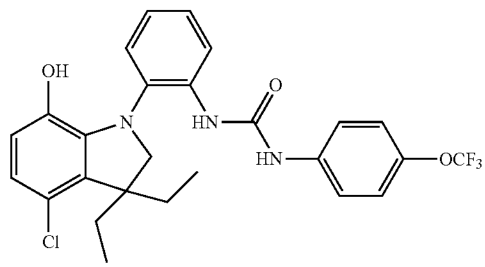 [SMILES: CCC1(CC)CN(c2ccccc2NC(=O)Nc2ccc(OC(F)(F)F)cc2)c2c(O)ccc(Cl)c21] | m/z 520.4 (M + H)+, RT = 4.37 min (Method C) |
| 52 | 1-(2-(4-Chloro-3,3-diethyl-7-hydroxyindolin-1-yl)phenyl)-3-(4-(trifluoromethyl)phenyl)urea | 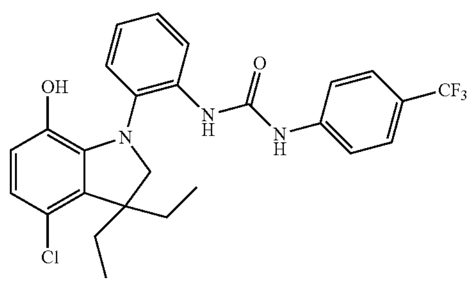 [SMILES: CCC1(CC)CN(c2ccccc2NC(=O)Nc2ccc(C(F)(F)F)cc2)c2c(O)ccc(Cl)c21] | m/z 504.5 (M + H)+, RT = 4.32 min (Method C) |
| 53 | 1-(2-(4-Chloro-3,3-diethyl-7-hydroxyindolin-1-yl)phenyl)-3-(2-chlorothiazol-4-yl)urea | 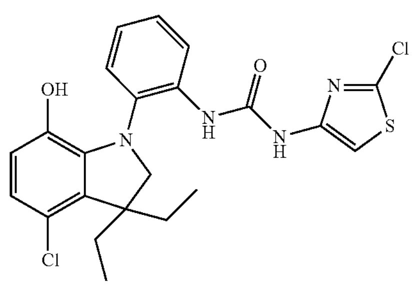 [SMILES: CCC1(CC)CN(c2ccccc2NC(=O)Nc2csc(Cl)n2)c2c(O)ccc(Cl)c21] | m/z 477.3 (M + H)+, RT = 4.27 min (Method C) |
| 54 | 1-(2-(4-Chloro-3,3-diethyl-7-hydroxyindolin-1-yl)phenyl)-3-(5-isobutyl-4,5,6,7-tetrahydrothiazolo[5,4-c]pyridin-2-yl)urea | 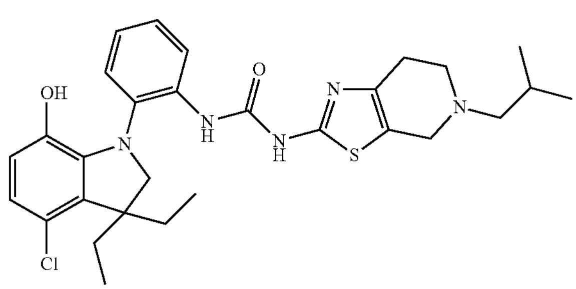 [SMILES: CCC1(CC)CN(c2ccccc2NC(=O)Nc2nc3c(s2)CN(CC(C)C)CC3)c2c(O)ccc(Cl)c21] | m/z 554.5 (M + H)+, RT = 3.83 min (Method E) |

-continued

| Example No. | Compound Name | Compound Structure | LC-MS (ESI) m/z |
|---|---|---|---|
| 55 | 1-(2-(4-Chloro-3,3-diethyl-7-hydroxyindolin-1-yl)phenyl)-3-(5-(2,2,2-trifluoroethyl)-4,5,6,7-tetrahydrothiazolo[5,4-c]pyridin-2-yl)urea | 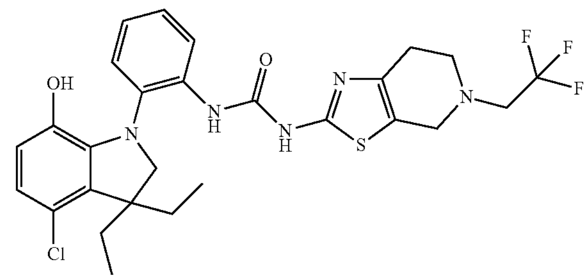 [SMILES: CCC1(CC)CN(c2ccccc2NC(=O)Nc2nc3c(s2)CN(CC(F)(F)F)CC3)c2c(O)ccc(Cl)c21] | m/z 580.5 (M + H)$^+$, RT = 3.50 min (Method E) |
| 56 | 1-(2-(4-Chloro-7-hydroxy-3,3-dimethylindolin-1-yl)phenyl)-3-(4-(trifluoromethoxy)phenyl)urea | 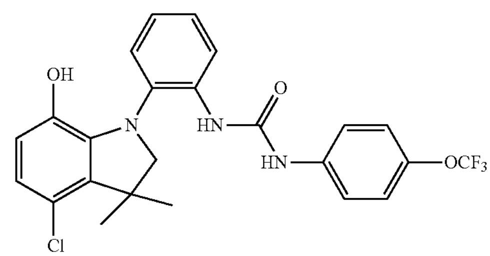 [SMILES: CC1(C)CN(c2ccccc2NC(=O)Nc2ccc(OC(F)(F)F)cc2)c2c(O)ccc(Cl)c21] | m/z 492.4 (M + H)$^+$, RT = 4.17 min (Method C) |
| 57 | 1-(2-(4-Chloro-7-hydroxy-3,3-dimethylindolin-1-yl)phenyl)-3-(4-(trifluoromethyl)phenyl)urea | 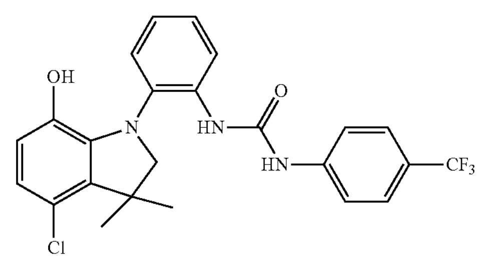 [SMILES: CC1(C)CN(c2ccccc2NC(=O)Nc2ccc(C(F)(F)F)cc2)c2c(O)ccc(Cl)c21] | m/z 476.4 (M + H)$^+$, RT = 4.16 min (Method C) |
| 58 | 1-(2-(4-Chloro-7-hydroxy-3,3-dimethylindolin-1-yl)phenyl)-3-(2-chlorothiazol-4-yl)urea | 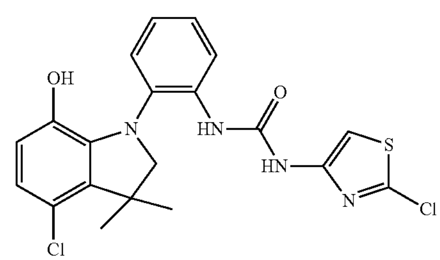 [SMILES: CC1(C)CN(c2ccccc2NC(=O)Nc2csc(Cl)n2)c2c(O)ccc(Cl)c21] | m/z 449.3 (M + H)$^+$, RT = 4.03 min (Method C) |
| 59 | 1-(2,4-Difluorophenyl)-3-(4-fluoro-2-(7-hydroxy-3,3-dimethyl-4-(trifluoromethyl)indolin-1-yl)phenyl)urea | 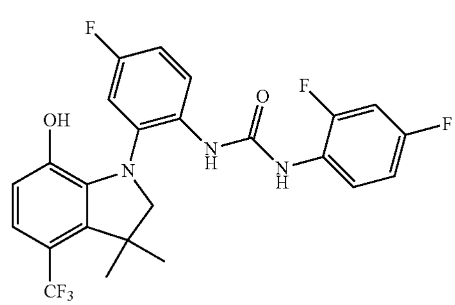 [SMILES: CC1(C)CN(c2cc(F)ccc2NC(=O)Nc2ccc(F)cc2F)c2c(O)ccc(C(F)(F)F)c21] | m/z 496.4 (M + H)$^+$, RT = 4.03 min (Method C) |

-continued

| Example No. | Compound Name | Compound Structure | LC-MS (ESI) m/z |
|---|---|---|---|
| 60 | 1-(2,4-Difluorophenyl)-3-(5-fluoro-2-(7-hydroxy-3,3-dimethyl-4-(trifluoromethyl)indolin-1-yl)phenyl)urea | 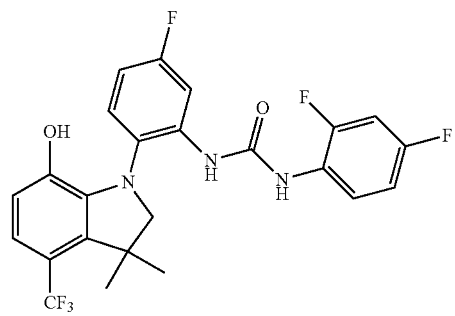 [SMILES: CC1(C)CN(c2ccc(F)cc2NC(=O)Nc2ccc(F)cc2F)c2c(O)ccc(C(F)(F)F)c21] | m/z 496.4 (M + H)+, RT = 4.08 min (Method C) |
| 61 | 1-(2,4-Difluorophenyl)-3-(2-fluoro-6-(7-hydroxy-3,3-dimethyl-4-(trifluoromethyl)indolin-1-yl)phenyl)urea | 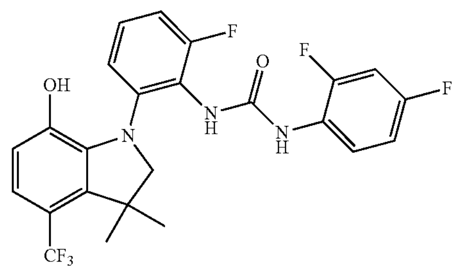 [SMILES: CC1(C)CN(c2cccc(F)c2NC(=O)Nc2ccc(F)cc2F)c2c(O)ccc(C(F)(F)F)c21] | m/z 496.4 (M + H)+, RT = 3.83 min (Method C) |
| 62 | 1-(2,4-Difluorophenyl)-3-(3-fluoro-2-(7-hydroxy-3,3-dimethyl-4-(trifluoromethyl)indolin-1-yl)phenyl)urea | 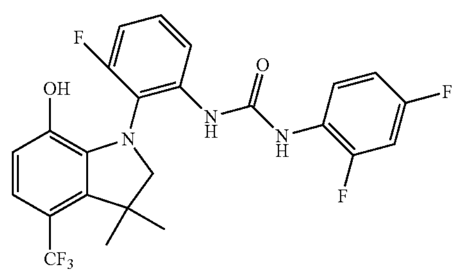 [SMILES: CC1(C)CN(c2c(F)cccc2NC(=O)Nc2ccc(F)cc2F)c2c(O)ccc(C(F)(F)F)c21] | m/z 496.6 (M + H)+, RT = 3.96 min (Method C) |
| 63 | 1-(5-Fluoro-2-(7-hydroxy-3,3-dimethyl-4-(trifluoromethyl)indolin-1-yl)phenyl)-3-(6-fluorobenzo[d]thiazol-2-yl)urea | 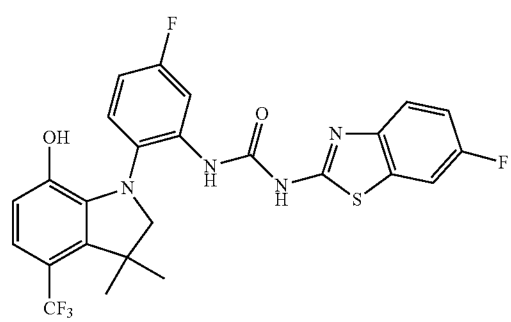 [SMILES: CC1(C)CN(c2ccc(F)cc2NC(=O)Nc2nc3ccc(F)cc3s2)c2c(O)ccc(C(F)(F)F)c21] | m/z 535.4 (M + H)+, RT = 2.15 min (Method D) |
| 64 | 1-(4-Fluoro-2-(7-hydroxy-3,3-dimethyl-4-(trifluoromethyl)indolin-1-yl)phenyl)-3-(6-fluorobenzo[d]thiazol-2-yl)urea | 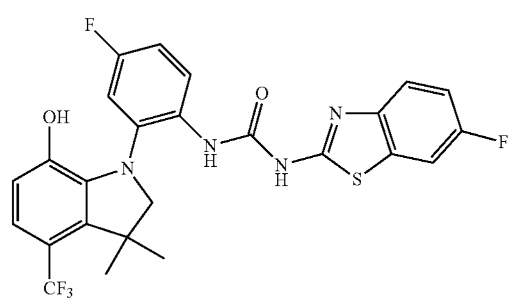 [SMILES: CC1(C)CN(c2cc(F)ccc2NC(=O)Nc2nc3ccc(F)cc3s2)c2c(O)ccc(C(F)(F)F)c21] | m/z 535.4 (M + H)+, RT = 4.29 min (Method C) |

| Example No. | Compound Name | Compound Structure | LC-MS (ESI) m/z |
|---|---|---|---|
| 65 | 1-(2-(4-Chloro-6-fluoro-7-hydroxy-3,3-dimethylindolin-1-yl)phenyl)-3-(4-(trifluoromethoxy)phenyl)urea | 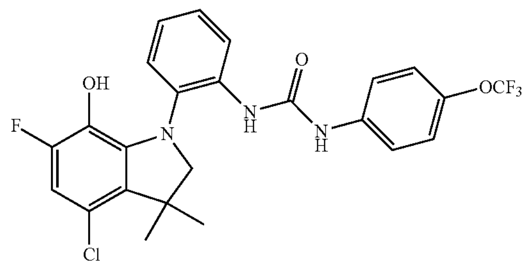 [SMILES: CC1(C)CN(c2ccccc2NC(=O)Nc2ccc(OC(F)(F)F)cc2)c2c(O)c(F)cc(Cl)c21] | m/z 510.4 (M + H)+, RT = 2.21 min (Method D) |
| 66 | 1-(2-(4-Bromo-6-fluoro-7-hydroxy-3,3-dimethylindolin-1-yl)phenyl)-3-(6-chlorobenzo[d]thiazol-2-yl)urea | 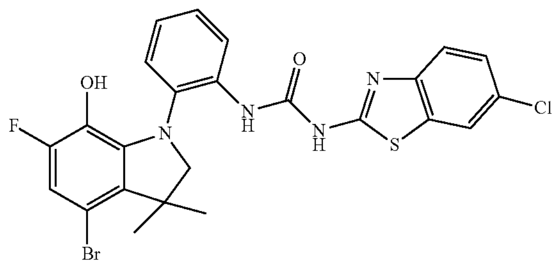 [SMILES: CC1(C)CN(c2ccccc2NC(=O)Nc2nc3ccc(Cl)cc3s2)c2c(O)c(F)cc(Br)c21] | m/z 561.0 (M + H)+, RT = 2.35 min (Method K) |
| 67 | 1-(2-(4-Bromo-5-fluoro-7-hydroxy-3,3-dimethylindolin-1-yl)phenyl)-3-(6-fluorobenzo[d]thiazol-2-yl)urea | 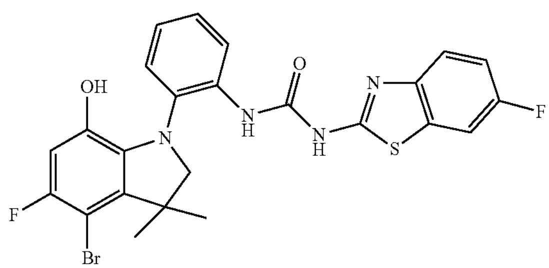 [SMILES: CC1(C)CN(c2ccccc2NC(=O)Nc2nc3ccc(F)cc3s2)c2c(O)cc(F)c(Br)c21] | m/z 545.0 (M + H)+, RT = 2.28 min (Method K) |
| 68 | 1-(2-(4-Bromo-5-fluoro-7-hydroxy-3,3-dimethylindolin-1-yl)phenyl)-3-(2-chlorothiazol-4-yl)urea | 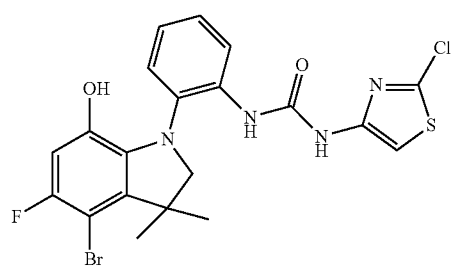 [SMILES: CC1(C)CN(c2ccccc2NC(=O)Nc2csc(Cl)n2)c2c(O)cc(F)c(Br)c21] | m/z 511.0 (M + H)+, RT = 2.22 min (Method K) |
| 69 | 1-(2-(4-Bromo-6-fluoro-7-hydroxy-3,3-dimethylindolin-1-yl)phenyl)-3-(4-(trifluoromethoxy)phenyl)urea | 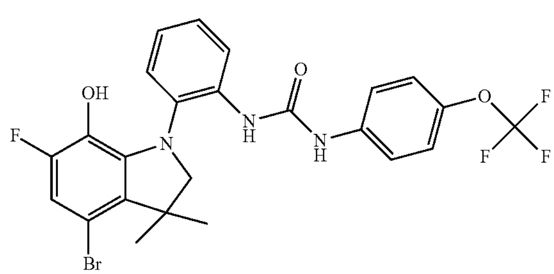 [SMILES: CC1(C)CN(c2ccccc2NC(=O)Nc2ccc(OC(F)(F)F)cc2)c2c(O)c(F)cc(Br)c21] | m/z 551.9 (M − H)+, RT = 2.42 min (Method K) |

| Example No. | Compound Name | Compound Structure | LC-MS (ESI) m/z |
|---|---|---|---|
| 70 | 1-(2-(4-Bromo-5-fluoro-7-hydroxy-3,3-dimethylindolin-1-yl)phenyl)-3-(6-chlorobenzo[d]thiazol-2-yl)urea | 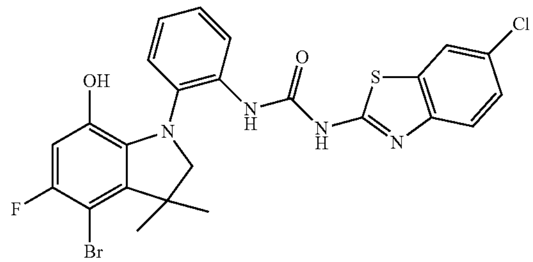 [SMILES: CC1(C)CN(c2ccccc2NC(=O)Nc2nc3ccc(Cl)cc3s2)c2c(O)cc(F)c(Br)c21] | m/z 561.0 (M + H)+, RT = 2.39 min (Method D) |

Example 71

1-(2-(3,3-Diethyl-7-hydroxy-4-methylindolin-1-yl)phenyl)-3-(4-(trifluoromethoxy)phenyl)urea

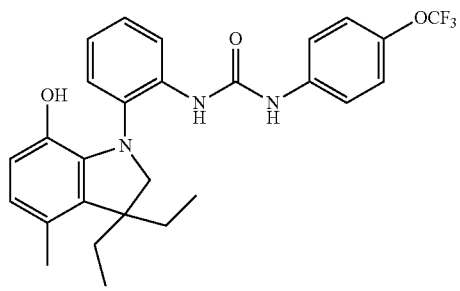 [SMILES: CCC1(CC)CN(c2ccccc2NC(=O)Nc2ccc(OC(F)(F)F)cc2)c2c(O)ccc(C)c21]

Palladium tetrakis(triphenylphosphine) (16 mg, 0.010 mmol) was added to Example 39 (50 mg, 0.090 mmol) and trimethylboroxine (89 mg, 0.71 mmol) in DME (2.7 mL) and 2 M $Na_2CO_3$ solution (0.3 mL) in a sealable vessel. This was sealed and heated to 100° C. in an oil bath for 5 h. The reaction was cooled and filtered through a nylon frit and purified by Prep HPLC (TFA) to give Example 71 as a white solid. LCMS (ESI) m/z 500 (M+H)+, RT=2.19 min (Method H). $^1$H NMR (400 MHz, DMSO-$d_6$) δ ppm 0.62 (t, J=7.2 Hz, 3H), 0.81 (t, J=7.4 Hz, 3H), 1.42-1.88 (m, 4H), 2.18 (s, 3H), 2.85 (d, J=10.6 Hz, 1H), 3.98 (d, J=10.6 Hz, 1H), 6.49 (m, 2H), 6.71 (d, J=7.9, 1H), 6.83 (t, J=7.6, 1H), 6.98 (t, J=7.69, 1H), 7.28 (d, J=8.8, 2H), 7.55 (d, J=8.8, 2H), 7.94 (d, J=8.1, 1H), 8.19 (s, 1H), 8.75 (s, 1H), 9.58 (s, 1H).

Example 72

1-(2-(4-(tert-Butylthio)-7-hydroxy-3,3-dimethylindolin-1-yl)phenyl)-3-(4-(trifluoromethoxy)phenyl)urea

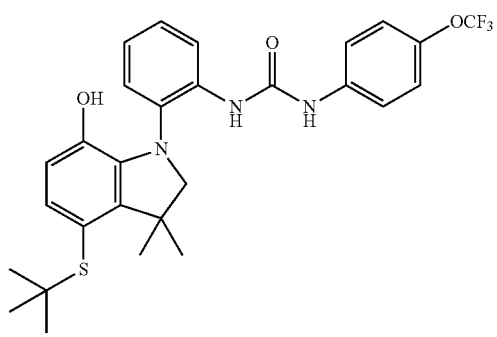 [SMILES: CC(C)(C)Sc1ccc(O)c2c1C(C)(C)CN2c1ccccc1NC(=O)Nc1ccc(OC(F)(F)F)cc1]

Example 72A.

1-(2-(4-(tert-Butylthio)-7-methoxy-3,3-dimethylindolin-1-yl)phenyl)-3-(4-(trifluoromethoxy)phenyl)urea To 1-(2-(4-bromo-7-methoxy-3,3-dimethylindolin-1-yl)phenyl)-3-(4-(trifluoromethoxy)phenyl)urea (Example 40A, 100 mg, 0.182 mmol), palladium (II) acetate (8.2 mg, 0.036 mmol), 1,1'-bis(diisopropylphosphino)ferrocene (19 mg, 0.044 mmol), and sodium tert-butoxide (21 mg, 0.22 mmol) in dioxane (2 mL) was sparged with nitrogen for 30 min, and stirred at room temperature for 1 h. Then 2-methyl-2-propanethiol (0.025 mL, 0.22 mmol) was added and stirred at 100° C. for 16 h. The reaction was diluted with EtOAc and filtered through CELITE®. The organic layer was dried with $MgSO_4$ and evaporated. The product was purified by flash chromatography, eluting with EtOAc/hexanes to give 72A (53 mg, 52% yield). LCMS (ESI) m/z 560 (M+H)+, RT=2.30 min (Method J).

Example 72

To a solution of Example 72A (0.053 g, 0.095 mmol) in DCM (2 mL) was added tetrabutylammonium iodide (0.245 g, 0.663 mmol), degassed, refilled with nitrogen, and cooled down to −78° C. Boron trichloride (0.663 mL, 0.663 mmol, 1.0 M solution in DCM) was added. After 1 h, the cold bath was removed and the reaction was gradually warmed up to room temperature. Conc. $NH_4OH$ (2 mL) was added and then water and DCM. The layers were separated and the aqueous layer was extracted with DCM. Combined organics were washed with water, dried over $MgSO_4$, filtered and concentrated. The crude was purified by Prep HPLC to give Example 72 (3 mg, 6% yield). LCMS (ESI) m/z 546 (M+H)+, RT=2.21 min (Method J). $^1$H NMR (300 MHz, DMSO-$d_6$) δ ppm 1.33 (s, 9H), 1.37 (s, 3H), 1.54 (s, 3H), 2.95 (d, J=10.25 Hz, 1H), 3.86 (d, J=10.25 Hz, 1H), 6.64 (d, J=8.42 Hz, 1H), 6.76-6.94 (m, 3H), 6.97-7.11 (m, 1H), 7.28 (m, J=8.78 Hz, 2H), 7.56 (m, J=8.78 Hz, 2H), 8.05 (d, J=6.95 Hz, 1H), 8.32 (s, 1H), 9.22 (br. s, 1H), 9.56 (s, 1H).

Example 73

1-(2-(3,3-Diethyl-4-formyl-7-hydroxyindolin-1-yl)phenyl)-3-(4-(trifluoromethoxy)phenyl)urea

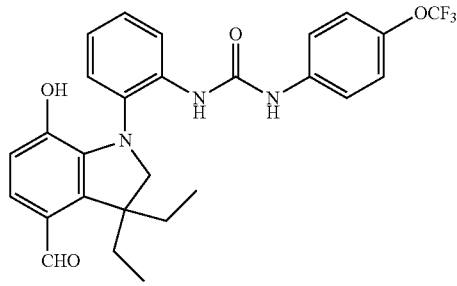 [SMILES: CCC1(CC)CN(c2ccccc2NC(=O)Nc2ccc(OC(F)(F)F)cc2)c2c(O)ccc(C=O)c21]

DIBAL-H (1.9 mL, 3.0 mmol) was added to a solution of Example 43 (150 mg, 0.290 mmol) in toluene (2 mL) at −78° C. and then warmed to 0° C. for 30 min. The reaction was quenched with 1.0 M HCl and diluted with EtOAc and stirred for 1 h. The aqueous layer was extracted with EtOAc and the combined organics were dried over MgSO$_4$, filtered and evaporated to give crude product. The crude was purified by Prep HPLC to give Example 73 (130 mg, 86.0%) as a yellow solid. LCMS (ESI) m/z 514 (M+H)$^+$, RT=2.04 min (Method H). $^1$H NMR (400 MHz, DMSO-d$_6$) δ ppm 0.64 (t, J=7.3 Hz, 3H), 0.80 (t, J=7.3 Hz, 3H), 1.56 (m, 1H), 1.69 (m, 1H), 1.96 (m, 1H), 2.07 (m, 1H), 2.98 (d, J=10.6 Hz, 1H), 4.05 (d, J=10.6 Hz, 1H), 6.73 (dd, J=1.5, 8.0 Hz, 1H), 6.80 (d, J=8.3 Hz, 1H), 6.87 (td, J=1.3, 7.7 Hz, 1H), 7.05 (m, 1H), 7.28 (d, J=8.4 Hz, 2H), 7.41 (d, J=8.3 Hz, 1H), 7.56 (d, J=9.1 Hz, 2H), 7.99 (dd, J=1.5, 8.1 Hz, 1H), 8.23 (s, 1H), 9.56 (s, 1H), 10.00 (s, 1H), 10.26 (s, 1H).

Example 74

Ethyl 4-chloro-7-hydroxy-3-methyl-1-(2-(3-(4-(trifluoromethoxy)phenyl)ureido)phenyl)indoline-3-carboxylate

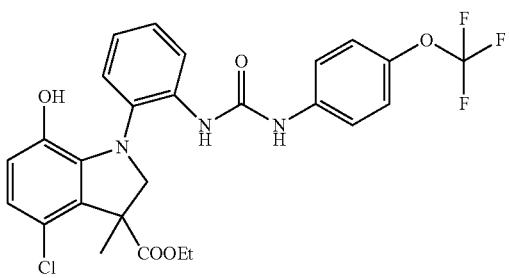 [SMILES: CCOC(=O)C1(C)CN(c2ccccc2NC(=O)Nc2ccc(OC(F)(F)F)cc2)c2c(O)ccc(Cl)c21]

Example 74A.

Ethyl 4-chloro-7-methoxy-3-methyl-1-(2-(3-(4-(trifluoromethoxy)phenyl)ureido)phenyl)indoline-3-carboxylate A solution of Intermediate 16 (52 mg, 0.14 mmol) and 1-isocyanato-4-(trifluoromethoxy)benzene (35 mg, 0.17 mmol) in dichloromethane (2 mL) was stirred at room temperature for 16 h. The reaction mixture was concentrated and purified by flash chromatography, eluting with EtOAc/hexanes to give Example 74A (78 mg, 96% yield) as pale yellow solid. LCMS (ESI) m/z 564.1 (M+H)$^+$, RT=4.03 min (Method C).

Example 74

To Example 74A (78 mg, 0.14 mmol) in DCM (3 mL) was added tetrabutylammonium iodide (257 mg, 0.696 mmol) at −78° C. under argon, BCl$_3$ (1 M solution in DCM, 0.7 mL, 0.7 mmol) was added dropwise. The reaction mixture was gradually warmed up to room temperature and stirred for 16 h. The reaction mixture was concentrated and purified by flash chromatography, eluting with EtOAc/hexanes to give Example 72 as a white solid (37 mg, 49% yield). LCMS (ESI) m/z 550.2 (M+H)$^+$, RT=3.41 min (Method C).

Example 75

Ethyl 4-chloro-1-(2-(3-(2-chlorothiazol-4-yl)ureido)phenyl)-7-hydroxy-3-methylindoline-3-carboxylate

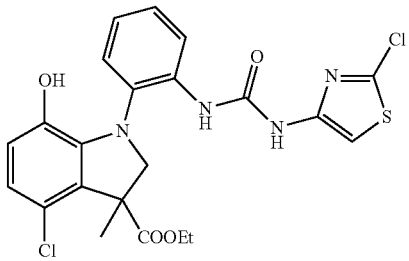 [SMILES: CCOC(=O)C1(C)CN(c2ccccc2NC(=O)Nc2csc(Cl)n2)c2c(O)ccc(Cl)c21]

Example 75 was prepared as a white solid according the procedures described in Example 74. LCMS (ESI) m/z 507.1 (M+H)$^+$, RT=3.13 min (Method E).

Example 76

Ethyl 4-chloro-1-(2-(3-(6-fluorobenzo[d]thiazol-2-yl)ureido)phenyl)-7-hydroxy-3-methylindoline-3-carboxylate

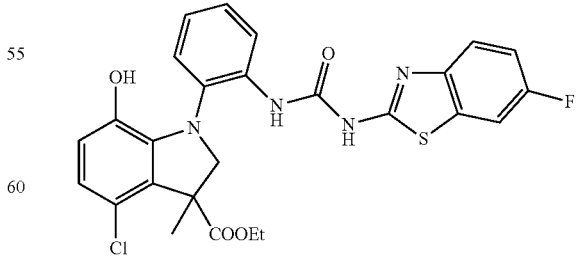

Example 76 was prepared as a white solid according the procedures described in Example 74. LCMS (ESI) m/z 541.1 (M+H)$^+$, RT=3.98 min (Method C).

Example 77

Ethyl 4-chloro-1-(2-(3-(5-chlorothiazolo[5,4-b]pyridin-2-yl)ureido)phenyl)-7-hydroxy-3-methylindoline-3-carboxylate

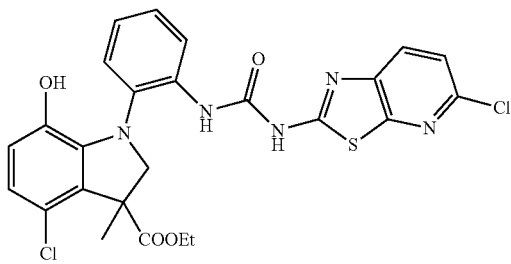 [SMILES: CCOC(=O)C1(C)CN(c2ccccc2NC(=O)Nc2nc3ccc(Cl)nc3s2)c2c(O)ccc(Cl)c21]

Example 77 was prepared as a white solid according to the procedures described in Example 74. LCMS (ESI) m/z 557.9 (M+H)$^+$, RT=3.96 min (Method C).

Example 78

1-(2-(4-Chloro-7-hydroxy-3-methyl-3-(2,2,2-trifluoroethyl)indolin-1-yl)phenyl)-3-(4-(trifluoromethoxy)phenyl)urea

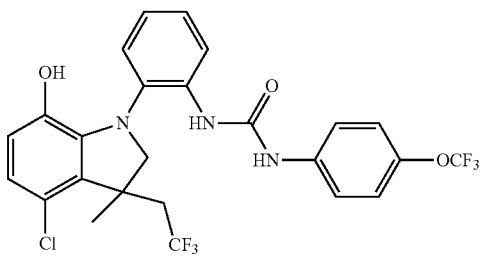 [SMILES: CC1(CC(F)(F)F)CN(c2ccccc2NC(=O)Nc2ccc(OC(F)(F)F)cc2)c2c(O)ccc(Cl)c21]

Example 78A.

4,4,4-Trifluoro-2-methylbutanal

To a suspension of pyridinium chlorochromate (2.28 g, 10.6 mmol) in DCM (14 mL) was added 4,4,4-trifluoro-2-methylbutan-1-ol (1.0 g, 7.0 mmol) in DCM (1.5 mL). The reaction was stirred at room temperature for 3 h. Ether (15 mL) was added, filtered through a short silica gel plug, and concentrated to give Example 78A (520 mg, 53.0%) as a light brownish oil.

Example 78B.

2-(4-Chloro-7-methoxy-3-methyl-3-(2,2,2-trifluoroethyl)indolin-1-yl)aniline

Example 78B was prepared according to the procedures described in Intermediate 16 using 4,4,4-trifluoro-2-methylbutanal as the starting material. LCMS (ESI) m/z 371.2 (M+H)$^+$, RT=1.69 min (Method D).

Example 78

Example 78 was prepared as a white solid according the procedures described in Example 74 by replacing Intermediate 16 with Example 78B. LCMS (ESI) m/z 560.2 (M+H)$^+$, RT=2.15 min (Method D).

Example 79

1-(2-(6-Fluoro-7-hydroxy-3,3-dimethyl-4-(2,2,2-trifluoroethyl)indolin-1-yl)phenyl)-3-(4-(trifluoromethoxy)phenyl)urea

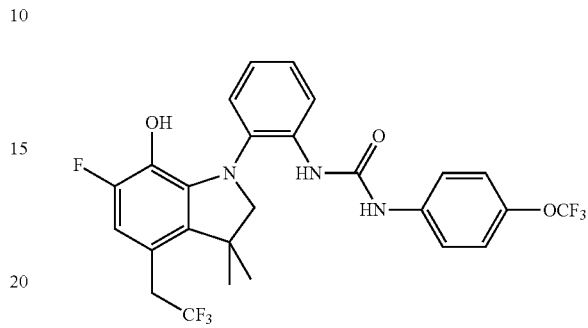

Example 79A.

2,2,2-Trifluoro-1-(3-fluoro-4-methoxyphenyl)ethanone

At −5° C., (3-fluoro-4-methoxyphenyl)magnesium bromide (0.5 M in THF, 50 mL, 25 mmol) was added dropwise over 1 h to trifluoroacetic anhydride (6.95 mL, 50.0 mmol). After the addition, the reaction was stirred at room temperature for 16 h. The reaction was heated to reflux for 2 h and then the reaction was concentrated and partitioned between ether and saturated NH$_4$Cl solution. The organic layer was washed with 1 M HCl, 1 M NaOH, water, brine and then dried over MgSO$_4$, filtered and evaporated to give Example 79A (4.5 g, 81%).

Example 79B.

2,2,2-Trifluoro-1-(3-fluoro-4-methoxyphenyl)ethanol

Sodium borohydride (0.77 g, 20 mmol) was added to a solution of Example 79A (4.5 g, 20 mmol) in methanol (100 mL) at 0° C. and stirred for 3 h and then allowed to warm to room temperature for 1 h. The reaction was quenched with water and extracted with EtOAc. The organics were washed with brine, dried over MgSO$_4$, filtered and evaporated. The crude was purified by flash chromatography, eluting with EtOAc/hexanes to give Example 79B (2.32 g, 51.0%) as a colorless oil. $^1$H NMR (300 MHz, CDCl$_3$) δ ppm 2.85 (d, J=4.76 Hz, 1H), 3.88 (s, 3H), 4.83-5.04 (m, 1H), 6.96 (t, J=8.42 Hz, 1H), 7.11-7.28 (m, 2H).

Example 79C.

2-Fluoro-1-methoxy-4-(2,2,2-trifluoroethyl)benzene

A solution of 1,1'-thiocarbonyldiimidazole (2.77 g, 15.5 mmol) and Example 79B (2.32 g, 10.4 mmol) in tetrahydrofuran (50 mL) was heated to reflux for 2 h. The reaction was diluted with EtOAc and washed with brine, dried over MgSO$_4$, filtered and evaporated. This was taken up in toluene (100 mL) and tri-n-butyltin hydride (4.1 mL, 15 mmol) and AIBN (0.33 g, 2.03 mmol) were added. This was heated to 85° C. for 3 h under nitrogen. The reaction was cooled to room temperature, concentrated and purified by flash chromatography, eluting with EtOAc/hexanes to give Example 79C (1.05 g, 50%) as a light brown oil. $^1$H NMR (300 MHz, CDCl$_3$) δ ppm 3.28 (q, J=10.61 Hz, 2H), 3.88 (s, 3H), 6.91-7.10 (m, 3H).

Example 79D.

1-Fluoro-2-methoxy-3-nitro-5-(2,2,2-trifluoroethyl)benzene

Nitronium tetrafluoroborate (0.638 g, 4.80 mmol) was added portionwise to a solution of Example 79C (1.0 g, 4.8 mmol) in acetonitrile (5 mL) at 0° C. After the addition, the reaction was allowed to warm to room temperature for 16 h. The reaction was diluted with Et$_2$O and water, and then the organics were washed with brine, dried over MgSO$_4$, filtered and evaporated to give Example 79D (1.20 g, 100%). $^1$H NMR (300 MHz, CDCl$_3$) δ ppm 3.37 (q, J=10.25 Hz, 2H), 4.07 (d, J=1.83 Hz, 3H), 7.29 (dd, J=10.98, 1.83 Hz, 1H), 7.52 (s, 1H).

Example 79E.

3-Fluoro-2-methoxy-5-(2,2,2-trifluoroethyl)aniline

Zinc (3.10 g, 47.4 mmol) and ammonium chloride (2.54 g, 47.4 mmol) were added to a solution of Example 79D (1.20 g, 4.74 mmol) in ethanol (50 mL) and stirred at room temperature for 16 h. The reaction was diluted with EtOAc and filtered through CELITE® and concentrated to give Example 79E (1.1 g, 104%). LCMS (ESI) m/z 224 (M+H)$^+$, RT=1.15 min (Method J).

Example 79

Example 79 was prepared as a tan solid according the procedures described in Example 1 by replacing Intermediate 1 with Example 79E. LCMS (ESI) m/z 558 (M+H)$^+$, RT=2.02 min (Method J). $^1$H NMR (300 MHz, DMSO-d$_6$) δ ppm 1.32 (s, 3H), 1.42 (s, 3H), 3.05 (d, J=9.88 Hz, 1H), 3.52-3.69 (m, 2H), 3.84 (d, J=10.61 Hz, 1H), 6.63 (d, J=12.08 Hz, 1H), 6.84-6.96 (m, 2H), 7.08 (d, J=8.05 Hz, 1H), 7.28 (d, J=8.78 Hz, 2H), 7.56 (d, J=7.32 Hz, 2H), 8.07 (d, J=8.05 Hz, 1H), 8.31 (s, 1H), 9.14 (br. s, 1H), 9.55 (s, 1H).

Example 80

Methyl 7-hydroxy-3,3-dimethyl-1-(2-(3-(4-(trifluoromethoxy)phenyl)ureido)phenyl)indoline-4-carboxylate

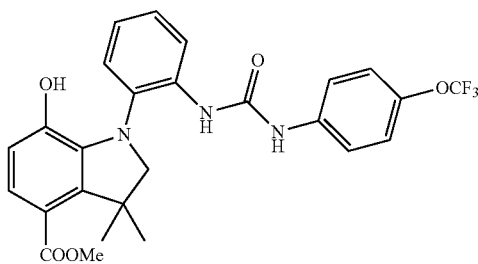 [SMILES: COC(=O)c1ccc(O)c2c1C(C)(C)CN2c1ccccc1NC(=O)Nc1ccc(OC(F)(F)F)cc1]

Example 12 (22 mg, 0.042 mmol) was added to 1 N NaOH (2 mL, 2 mmol) at room temperature. MeOH (0.3 mL, 7 mmol) was added to the suspension, and the reaction mixture became clear. The mixture was stirred at 40° C. in a capped vial for 1 h. After cooling, 1 M HCl was added to neutralize the reaction. It was extracted with CH$_2$Cl$_2$ (2×), washed with H$_2$O, brine, dried over MgSO$_4$, filtered and concentrated. The residue was purified by flash chromatography, eluting with EtOAc/hexanes to give Example 80 (18 mg, 83% yield). LCMS (ESI) m/z 516.2 (M+H)$^+$, RT=3.88 min (Method C). $^1$H NMR (400 MHz, CDCl$_3$) δ ppm 1.33 (s, 3H), 1.41 (s, 3H), 3.18 (d, J=9.9 Hz, 1H), 3.64 (d, J=9.6 Hz, 1H), 3.87 (s, 3H), 6.62 (s, 1H), 6.95-7.07 (m, 4H), 7.13 (s, 1H), 7.19-7.31 (m, 1H), 7.32-7.39 (m, 2H), 7.45 (s, 1H), 7.75 (d, J=7.8 Hz, 1H). $^{19}$F NMR (376.5 MHz, acetone-d$_6$) δ ppm −58.63.

Example 81

Ethyl 7-hydroxy-3,3-dimethyl-1-(2-(3-(4-(trifluoromethoxy)-phenyl)-ureido)phenyl)indoline-4-carboxylate

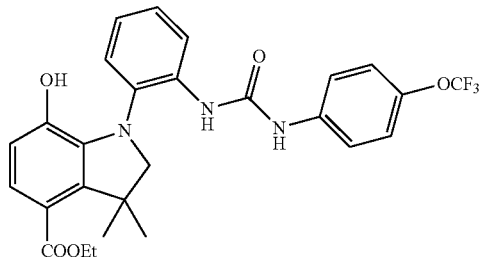 [SMILES: CCOC(=O)c1ccc(O)c2c1C(C)(C)CN2c1ccccc1NC(=O)Nc1ccc(OC(F)(F)F)cc1]

Example 12 (22 mg, 0.042 mmol) was added to 1 N NaOH (3 mL, 3 mmol) at room temperature. EtOH (1.0 mL, 17 mmol) was added to the suspension, and the reaction mixture became clear. The mixture was stirred at 40° C. in a capped vial for 3 h. The mixture was evaporated. After cooling, 1 M HCl was added to neutralize the reaction. CH$_3$CN was added. The clear solution purified by Prep HPLC (CH$_3$CN/H$_2$O with no TFA) to give Example 81 (12 mg, 54% yield). LCMS (ESI) m/z 530.5 (M+H)$^+$, RT=4.03 min (Method C). $^1$H NMR (400 MHz, acetone-d$_6$) δ ppm 1.27 (t, J=7.2 Hz, 3H), 1.38 (br. s, 3H), 1.40 (br. s, 3H), 3.09 (d, J=10.4 Hz, 1H), 3.73 (d, J=9.9 Hz, 1H), 4.15-4.30 (m, 2H), 6.63 (d, J=8.3 Hz, 1H), 6.79-6.90 (m, 2H), 6.94-7.07 (m, 1H), 7.10-7.19 (m, 2H), 7.29 (d, J=8.3 Hz, 1H), 7.56 (d, 2H), 7.99 (s, 1H), 8.05 (s, 1H), 8.36 (br. s, H), 8.83 (s, 1H). $^{19}$F NMR (376.5 MHz, acetone-d$_6$) δ ppm 118.12.

Example 82

1-(2-(4-(Benzo[d]oxazol-2-yl)-7-hydroxy-3,3-dimethylindolin-1-yl)phenyl)-3-(4-(trifluoromethoxy)phenyl)urea

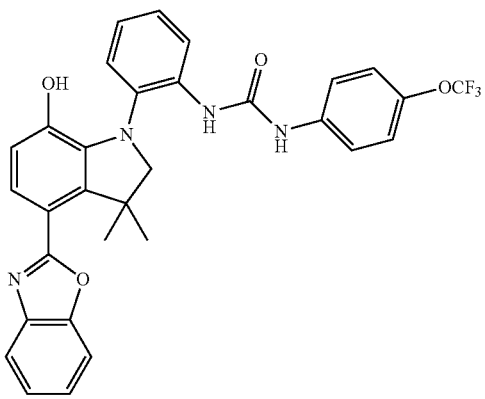 [SMILES: CC1(C)CN(c2ccccc2NC(=O)Nc2ccc(OC(F)(F)F)cc2)c2c(O)ccc(-c3nc4ccccc4s3)c21]

To Example 12 (20 mg, 0.038 mmol) and 2-aminophenol (90 mg, 0.83 mmol) were added 1 N NaOH (4 mL). The reaction was stirred for 16 h. While cooling in a dry ice bath, conc. HCl was added to neutralize the reaction. It was extracted with $CH_2Cl_2$ (2×), washed with $H_2O$, and concentrated. The residue was dissolved in MeOH and was purified with RP HPLC (30-90% $CH_3CN/H_2O$ with 0.1% TFA 12 min then 90% $CH_3CN/H_2O$ for additional 5 min to give Example 82 (16 mg, 0.028 mmol, 73% yield). $^1$H NMR (400 MHz, acetone-$d_6$) δ ppm 1.60 (s, 3 H), 1.61 (s, 3 H), 3.28 (d, J=9.9 Hz, 1 H), 3.91 (d, J=10.1 Hz, 1 H), 6.89 (d, J=8.3 Hz, 1 H), 6.99 (m, 1 H), 7.06 (m, 1 H), 7.15 (m, 1 H), 7.26 (d, J=8.6 Hz, 2 H), 7.35-7.48 (m, 2 H), 7.59 (d, J=8.3 Hz, 1 H), 7.65-7.75 (m, 2 H), 7.75-7.85 (m, 3 H), 8.15 (s, 1 H), 8.19 (dd, J=8.2, 1.4 Hz, 1 H), 8.97 (s, 1 H). $^{19}$F NMR (376.5 MHz, acetone-$d_6$) δ ppm −60.66. LCMS (ESI) m/z 575.5 (M+H)$^+$, RT=4.18 min (Method C).

Example 83

(1-(2-(4-(Benzo[d]thiazol-2-yl)-7-hydroxy-3,3-dimethylindolin-1-yl)phenyl)-3-(4-(trifluoromethoxy)phenyl)urea

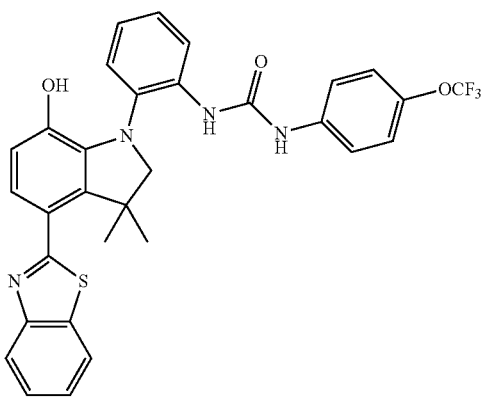

To Example 12 (20 mg, 0.038 mmol) and 2-aminobenzenethiol (70 mg, 0.56 mmol) were added to 1 N NaOH (3 mL, 3 mmol) at rt. The mixture was stirred at 40° C. in a capped vial for 16 h. After cooling, conc. HCl was added to neutralize the reaction. It was extracted with $CH_2Cl_2$ (2×), and concentrated. The residue was purified by RP HPLC ($CH_3CN/H_2O$/TFA) to give Example 83 (17 mg, 0.029 mmol, 76% yield). $^1$H NMR (400 MHz, acetone-$d_6$) δ ppm 1.48 (s, 3 H), 1.51 (s, 3 H), 6.84 (d, J=8.3 Hz, 1 H), 7.00 (dd, J=7.3, 1.5 Hz, 1 H), 7.09 (dd, J=7.8, 1.5 Hz, 1 H), 7.16 (s, 2 H), 7.26 (d, J=8.3 Hz, 2 H), 7.45-7.52 (m, 1 H), 7.56 (dd, J=8.1, 1.3 Hz, 1 H), 7.69 (s, 2 H), 8.09 (t, J=9.1 Hz, 2 H), 8.15 (s, 1 H), 8.19 (dd, 1 H), 8.97 (s, 1 H). $^{19}$F NMR (376.5 MHz, acetone-$d_6$) δ ppm −60.61. LCMS (ESI) m/z 591.5 (M+H)$^+$, RT=4.25 min (Method C).

Example 84

1-(2-(4-(5-Chlorobenzo[d]oxazol-2-yl)-7-hydroxy-3,3-dimethylindolin-1-yl)phenyl)-3-(4-(trifluoromethoxy)phenyl)urea

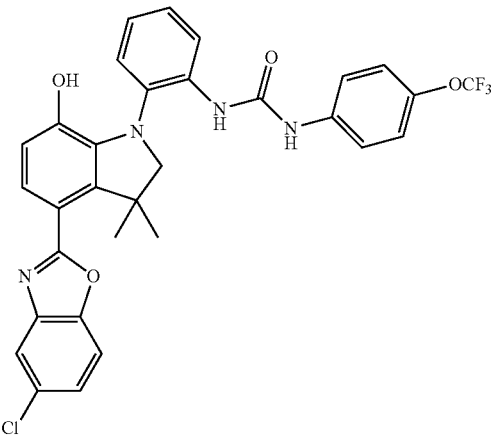 [SMILES: CC1(C)CN(c2ccccc2NC(=O)Nc2ccc(OC(F)(F)F)cc2)c2c(O)ccc(-c3nc4cc(Cl)ccc4s3)c21]

Example 84 (14 mg, 0.023 mmol, 45% yield) was prepared following the same procedure as described in Example 82 from Example 12 (27 mg, 0.051 mmol), 1 N NaOH (3 mL, 3 mmol) and 2-amino-4-chlorophenol (37 mg, 0.26 mmol) was added to the suspension. $^1$H NMR (400 MHz, acetone-$d_6$) δ ppm 1.59 (s, 3 H), 1.61 (s, 3 H), 3.28 (d, J=9.9 Hz, 1 H), 3.91 (d, J=10.1 Hz, 1 H), 6.89 (d, J=8.3 Hz, 1 H), 6.99 (dd, J=7.3, 1.5 Hz, 1 H), 7.01-7.09 (m, 1 H), 7.09-7.20 (m, 1 H), 7.26 (d, J=8.1 Hz, 2 H), 7.45 (dd, J=8.6, 2.0 Hz, 1 H), 7.60 (d, J=8.3 Hz, 1 H), 7.68 (m, 2 H), 7.75 (d, J=8.6 Hz, 1 H), 7.82 (d, J=1.8 Hz, 1 H), 8.09-8.28 (m, 2 H), 8.97 (s, 1 H). LCMS (ESI) m/z 607.6 (M−H)$^+$, 609.5 (M+H)$^+$, RT=2.94 min (Method E).

Example 85

1-(2-(4-(5-Chlorobenzo[d]thiazol-2-yl)-7-hydroxy-3,3-dimethylindolin-1-yl)phenyl)-3-(4-(trifluoromethoxy)phenyl)urea

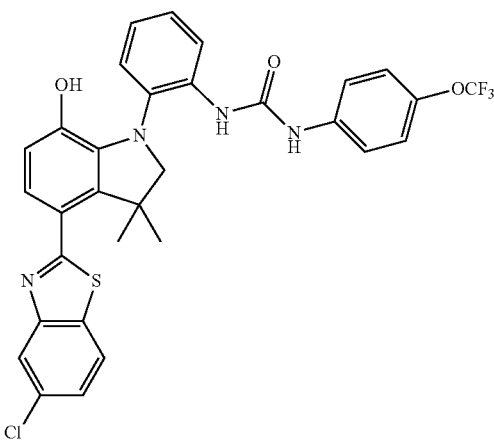

Example 85 (16 mg, 0.026 mmol, 64% yield) was obtained following the same procedure as described in Example 83 from Example 12 (21 mg, 0.040 mmol), 1 N NaOH (2 mL, 2 mmol) and 2-amino-4-chlorobenzenethiol (50 mg, 0.31 mmol). $^1$H NMR (400 MHz, acetone-$d_6$) δ ppm 1.48 (s, 3 H), 1.51 (s, 3 H), 3.24 (d, J=9.9 Hz, 1 H), 3.84 (d, J=9.9 Hz, 1 H), 6.84 (d, J=8.3 Hz, 1 H), 7.00 (s, 1 H), 7.09 (s, 1 H), 7.12-7.20 (m, 2 H), 7.26 (d, J=8.3 Hz, 2 H), 7.50 (dd, J=8.5, 2.1 Hz, 1 H), 7.68 (s, 2 H), 7.88-8.32 (m, 4 H), 8.96 (s, 1 H). $^{19}$F NMR (376.5 MHz, acetone-$d_6$) δ ppm −60.72. LCMS (ESI) m/z 623.5 (M−H)$^+$, 625.5 (M+H)$^+$, RT=3.30 min (Method E).

Example 86

1-(2-(7-Hydroxy-3,3-dimethyl-4-(5-methyl-1,3,4-oxadiazol-2-yl)indolin-1-yl)phenyl)-3-(4-(trifluoromethoxy)phenyl)urea

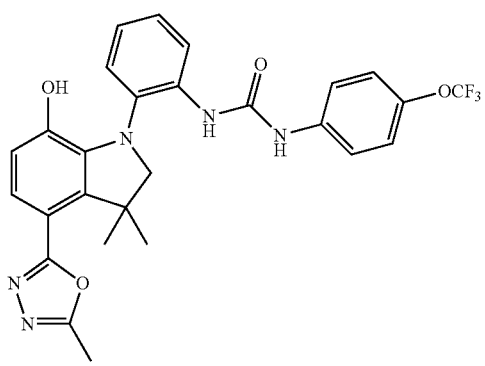

Example 12 (21 mg, 0.040 mmol) was added to 1 N NaOH (0.2 mL, 0.200 mmol) at rt. Acetohydrazide was added to the suspension. The mixture was stirred at 40° C. in a capped vial for 1 week. After cooling, saturated NH$_4$Cl was added to neutralize the reaction. It was extracted with CH$_2$Cl$_2$ (2×), washed with H$_2$O, brine, dried over MgSO$_4$, filtered and concentrated. The residue was added to a silica gel column (12 g) and was eluted with hexanes/EtOAc to give pure 1-(2-(4-cyano-7-hydroxy-3,3-dimethylindolin-1-yl)phenyl)-3-(4-(trifluoromethoxy)phenyl)urea (10.6 mg, 0.022 mmol, 55% yield) and the title compound 86 (3.0 mg, 5.56 µmol, 14% yield). $^1$H NMR (400 MHz, acetone-$d_6$) δ ppm 1.45 (s, 3 H), 1.48 (s, 3 H), 2.58 (s, 3 H), 3.21 (d, J=9.9 Hz, 1H), 3.85 (d, J=9.9 Hz, 1 H), 6.81 (d, J=8.2 Hz, 1 H), 6.94 (s, 1 H), 7.00 (s, 1 H), 7.12 (t, J=7.7 Hz, 1 H), 7.24 (s, 3 H), 7.65 (s, 2 H), 8.10 (s, 1 H), 8.16 (d, J=6.6 Hz, 1H), 8.48 (br. s., 1H), 8.92 (s, 1H). $^{19}$F NMR (376.5 MHz, acetone-$d_6$) δ ppm −58.82. LCMS (ESI) m/z 538.6 (M−H)$^+$, 540.5 (M+H)$^+$, RT=3.00 min (Method E).

Example 87

1-(2-(7-Hydroxy-3,3-dimethyl-4-(5-(trifluoromethyl)benzo[d]thiazol-2-yl)indolin-1-yl)phenyl)-3-(4-trifluoromethoxyl)phenyl)urea

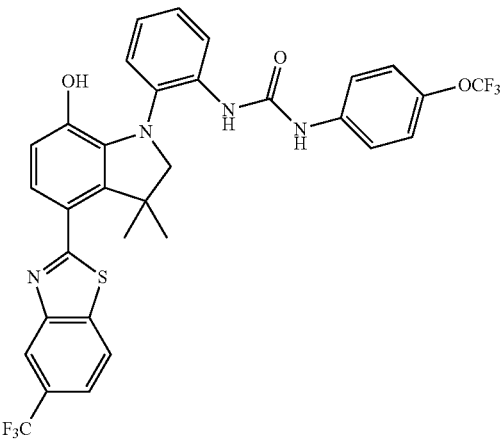 [SMILES: CC1(C)CN(c2ccccc2NC(=O)Nc2ccc(OC(F)(F)F)cc2)c2c(O)ccc(-c3nc4cc(C(F)(F)F)ccc4s3)c21]

Example 87 (16 mg, 0.024 mmol, 61% yield) was obtained following the same procedure as described in Example 83 from Example 12 (21 mg, 0.040 mmol), 1 N NaOH (6 mL, 6 mmol) and 2-amino-4-(trifluoromethyl)benzenethiol (180 mg, 0.932 mmol). $^1$H NMR (400 MHz, acetone-$d_6$) δ ppm 1.47 (s, 3 H), 1.51 (s, 3 H), 3.23 (d, J=9.9 Hz, 1 H), 3.83 (d, J=9.3 Hz, 1 H), 6.84 (d, J=8.2 Hz, 1 H), 6.92-7.00 (m, 1 H), 7.07 (s, 1 H), 7.13 (m, 1 H), 7.19 (d, J=8.2 Hz, 1 H), 7.24 (d, J=8.2 Hz, 2 H), 7.66 (d, J=8.8 Hz, 2 H), 7.77 (d, J=7.1 Hz, 1 H), 8.15 (s, 2 H), 8.34 (s, 1 H), 8.36 (d, J=3.3 Hz, 1 H), 8.95 (s, 1 H). $^{19}$F NMR (376.5 MHz, acetone-$d_6$) δ ppm −58.82, −62.05. LCMS (ESI) m/z 659.5 (M+H)$^+$, RT=2.34 min (Method D).

Example 88

1-(2-(7-Hydroxy-3,3-dimethyl-4-(1-methyl-1H-benzo[d]imidazol-2-yl)indolin-1-yl)phenyl)-3-(4-(trifluoromethoxy)phenyl)urea

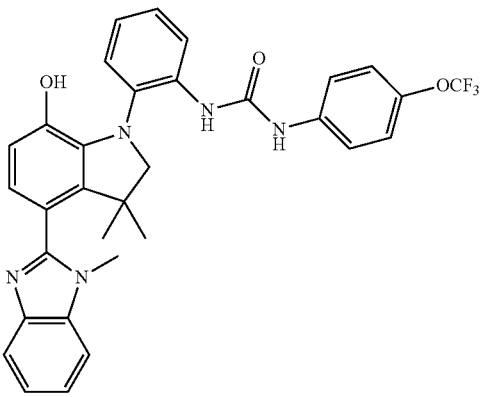 [SMILES: Cn1c(-c2ccc(O)c3c2C(C)(C)CN3c2ccccc2NC(=O)Nc2ccc(OC(F)(F)F)cc2)nc2ccccc21]

Example 12 (20 mg, 0.038 mmol) was added to 1 N NaOH (3 mL, 3 mmol) at rt. $N^1$-methylbenzene-1,2-diamine (90 mg, 0.74 mmol) was added to the suspension. The mixture was stirred at 40° C. in a capped vial for 2 days. After cooling, the mixture was neutralized with conc. HCl, and CH₃CN was added. It was filtered and purified via HPLC (CH₃CN/H₂O/TFA) to give Example 88 (3.0 mg, 5.11 μmol, 13% yield). ¹H NMR (400 MHz, acetone-d₆) δ ppm 1.14 (s, 3 H), 1.23 (s, 3 H), 3.25 (d, J=9.9 Hz, 1 H), 3.86 (d, J=9.9 Hz, 1 H), 3.97 (s, 3 H), 6.94 (d, J=8.2 Hz, 1 H), 6.96-7.05 (m, 1 H), 7.08 (d, J=8.2 Hz, 1 H), 7.11-7.22 (m, 2 H), 7.27 (d, J=8.8 Hz, 2 H), 7.51-7.67 (m, 2H), 7.67-7.80 (m, 2 H), 7.84-7.96 (m, 1 H), 8.03-8.21 (m, 2 H), 8.36 (s, 1 H), 9.25 (s, 1 H). ¹⁹F NMR (376.5 MHz, acetone-d₆) δ ppm −58.82, −76.15 (TFA). LCMS (ESI) m/z 588.5 (M+H)⁺, RT=1.70 min (Method D).

Example 89

1-(2-(7-Hydroxy-3,3-dimethyl-4-(oxazolo[5,4-b]pyridin-2-yl)indolin-1-yl)phenyl)-3-(4-(trifluoromethoxy)phenyl)urea

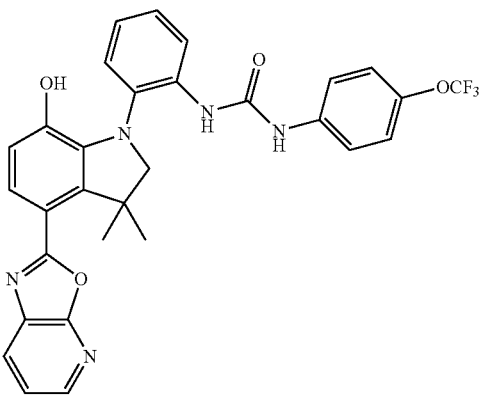 [SMILES: CC1(C)CN(c2ccccc2NC(=O)Nc2ccc(OC(F)(F)F)cc2)c2c(O)ccc(-c3nc4cccnc4o3)c21]

Example 12 (27 mg, 0.051 mmol) was added to 1 N NaOH (3 mL, 3 mmol) at rt. 3-Aminopyridin-2-ol (37 mg, 0.34 mmol) was added to the suspension. The mixture was stirred at 40° C. in a capped vial for 16 h. After cooling, 1 N HCl was added to neutralize the reaction. It was extracted with CH₂Cl₂ (2×), washed with H₂O, brine, dried over MgSO₄, filtered and concentrated. The residue was added to a silica gel column (12 g) and was eluted with Hexanes/EtOAc to give Example 89 (14 mg, 0.024 mmol, 47% yield). ¹H NMR (400 MHz, acetone-d₆) δ ppm 1.60 (s, 3 H), 1.61 (s, 3 H), 3.26 (d, J=9.9 Hz, 1 H), 3.89 (d, J=9.9 Hz, 1 H), 6.89 (d, J=8.2 Hz, 1 H), 6.95 (t, J=8.2 Hz, 1 H), 7.04 (d, J=6.6 Hz, 1 H), 7.13 (s, 1 H), 7.24 (d, J=8.8 Hz, 2 H), 7.47 (dd, J=8.2, 4.9 Hz, 1 H), 7.64 (m, 3 H), 8.16 (m, 3 H), 8.35 (d, J=4.9 Hz, 1 H), 8.94 (s, 1H). ¹⁹F NMR (376.5 MHz, acetone-d₆) δ ppm −58.82. LCMS (ESI) m/z 576.4 (M+H)⁺, RT=2.09 min (Method D).

Example 90

1-(2-(7-Hydroxy-3,3-dimethyl-4-(4-methylbenzo[d]oxazol-2-yl)indolin-1-yl)phenyl)-3-(4-(trifluoromethoxy)phenyl)urea

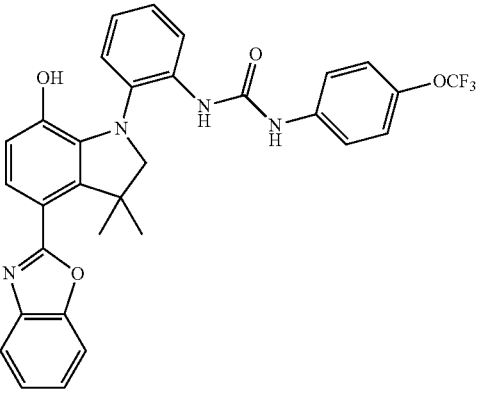

Example 90 (14 mg, 0.024 mmol, 63% yield) was obtained following the same procedure as described in Example 82 from Example 12 (20 mg, 0.038 mmol), 1 N NaOH (3 mL, 3 mmol) and 2-amino-3-methylphenol (80 mg, 0.65 mmol). ¹H NMR (400 MHz, acetone-d₆) δ ppm 1.632 (s, 3 H), 1.635 (s, 3 H), 2.64 (s, 3 H), 3.28 (d, J=10.1 Hz, 1 H), 3.92 (d, J=10.1 Hz, 1 H), 6.88 (d, J=8.3 Hz, 1 H), 6.92-7.02 (m, 1 H), 7.01-7.08 (m, 1 H), 7.09-7.19 (m, 1 H), 7.19-7.36 (m, 4 H), 7.51 (d, J=8.1 Hz, 1 H), 7.60 (d, J=8.6 Hz, 1 H), 7.64-7.72 (m, 2 H), 8.15 (s, 1 H), 8.19 (dd, J=8.1, 1.3 Hz, 1 H), 8.97 (s, 1 H). ¹⁹F NMR (376.5 MHz, acetone-d₆) δ ppm −60.68. LCMS (ESI) m/z 589.4 (M+H)⁺, RT=2.28 min (Method D).

Example 91

1-(2-(4-(6-Chlorobenzo[d]oxazol-2-yl)-7-hydroxy-3,3-dimethylindolin-1-yl)phenyl)-3-(4-(trifluoromethoxy)phenyl)urea

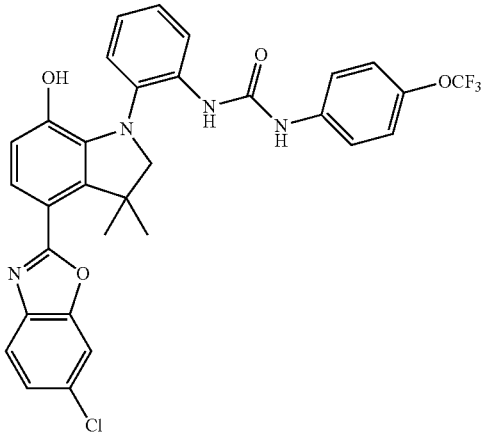 [SMILES: CC1(C)CN(c2ccccc2NC(=O)Nc2ccc(OC(F)(F)F)cc2)c2c(O)ccc(-c3nc4ccc(Cl)cc4o3)c21]

Example 91 (16 mg, 0.026 mmol, 69% yield) was obtained following the same procedure as described in example 82 from Example 12 (20 mg, 0.038 mmol), 1 N NaOH (3 mL, 3 mmol), and 2-amino-5-chlorophenol (80 mg, 0.56 mmol). $^1$H NMR (400 MHz, acetone-$d_6$) δ ppm 1.59 (s, 3 H), 1.61 (s, 3 H), 3.28 (d, J=9.9 Hz, 1 H), 3.91 (d, J=9.9 Hz, 1 H), 6.89 (d, J=8.3 Hz, 1 H), 6.93-7.02 (m, 1 H), 7.02-7.08 (m, 1 H), 7.11-7.20 (m, 1 H), 7.26 (d, J=8.3 Hz, 2 H), 7.45 (dd, J=8.5, 1.9 Hz, 1 H), 7.59 (d, J=8.3 Hz, 1 H), 7.68 (m, 2 H), 7.79 (d, J=8.3 Hz, 1 H), 7.83 (d, J=2.0 Hz, 1 H), 8.07-8.35 (m, 2 H), 8.97 (s, 1 H). $^{19}$F NMR (376.5 MHz, acetone-$d_6$) δ ppm −60.70. LCMS (ESI) m/z 609.3 (M+H)$^+$, RT=2.32 min (Method D).

Example 92

1-(2-(4-(6-Fluorobenzo[d]oxazol-2-yl)-7-hydroxy-3,3-dimethylindolin-1-yl)phenyl)-3-(4-(trifluoromethoxy)phenyl)urea

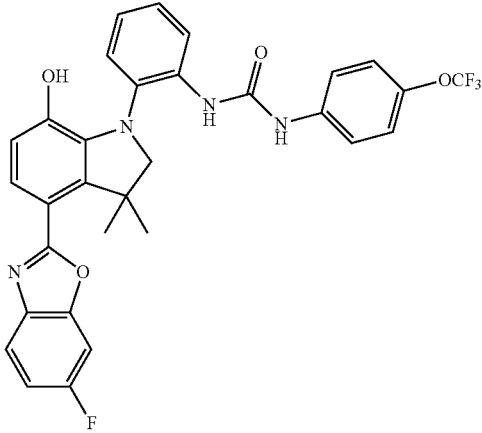 [SMILES: CC1(C)CN(c2ccccc2NC(=O)Nc2ccc(OC(F)(F)F)cc2)c2c(O)ccc(-c3nc4ccc(F)cc4o3)c21]

Example 92 (11 mg, 0.019 mmol, 49% yield) was obtained following the same procedure as described in Example 82 from Example 12 (20 mg, 0.038 mmol), 1 N NaOH (3 mL, 3 mmol) and 2-amino-5-fluorophenol (70 mg, 0.55 mmol). $^1$H NMR (400 MHz, acetone-$d_6$) δ ppm 1.59 (s, 3 H), 1.60 (s, 3 H), 3.27 (d, J=9.9 Hz, 1 H), 3.91 (d, J=9.9 Hz, 1 H), 6.89 (d, J=8.3 Hz, 1 H), 6.92-7.01 (m, 1 H), 7.05 (dd, J=8.1, 1.7 Hz, 1 H), 7.11-7.19 (m, 1 H), 7.19-7.30 (m, 3 H), 7.43-7.63 (m, 2 H), 7.69 (m, 2 H), 7.79 (dd, J=8.8, 4.8 Hz, 1 H), 8.08-8.27 (m, 2 H), 8.97 (s, 1 H). $^{19}$F NMR (376.5 MHz, acetone-$d_6$) δ ppm −60.84, −119.26. LCMS (ESI) m/z 593.4 (M+H)$^+$, RT=2.25 min (Method D).

Example 93

1-(2-(7-Hydroxy-3,3-dimethyl-4-(7-methylbenzo[d]oxazol-2-yl)indolin-1-yl)phenyl)-3-(4-(trifluoromethoxy)phenyl)urea

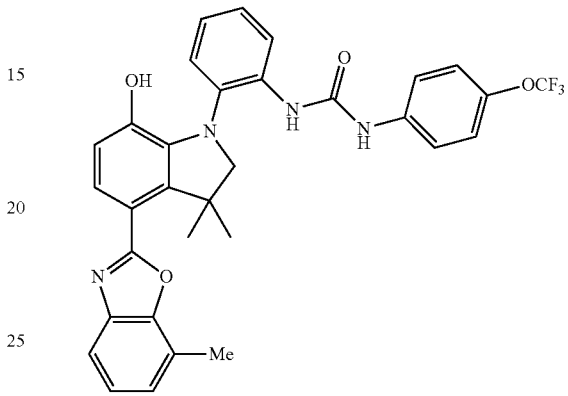

Example 93 (6.0 mg, 10 μmol, 27% yield) was obtained following the same procedure as described in Example 82 from Example 12 (20 mg, 0.038 mmol), 1 N NaOH (3 mL, 3 mmol) and 2-amino-6-methylphenol (75 mg, 0.61 mmol). $^1$H NMR (400 MHz, acetone-$d_6$) δ ppm 1.607 (s, 3 H), 1.614 (s, 3 H), 2.60 (s, 3 H), 3.28 (d, J=9.9 Hz, 1 H), 3.91 (d, J=9.9 Hz, 1 H), 6.89 (d, J=8.3 Hz, 1 H), 6.93-7.01 (m, 1 H), 7.01-7.10 (m, 1 H), 7.06 (dd, J=8.0, 1.6 Hz, 1 H), 7.11-7.20 (m, 1 H), 7.20-7.35 (m, 4 H), 7.61 (m, 2 H), 7.65-7.78 (m, 2 H), 8.19 (m, 2 H), 8.98 (s, 1 H). $^{19}$F NMR (376.5 MHz, acetone-$d_6$) δ ppm −60.74. LCMS (ESI) m/z 589.5 (M+H)$^+$, RT=2.29 min (Method D).

Example 94

1-(2-(7-Hydroxy-4-(6-methoxybenzo[d]oxazol-2-yl)-3,3-dimethylindolin-1-yl)phenyl)-3-(4-(trifluoromethoxy)phenyl)urea

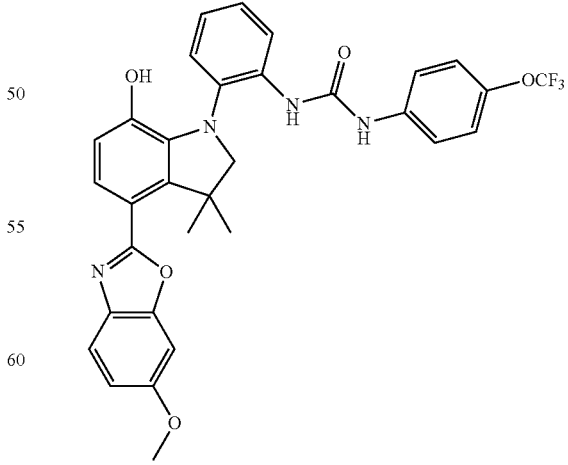

Example 94 (9.0 mg, 0.015 mmol, 44% yield) was obtained following the same procedure as described in Example 82 from Example 12 (18 mg, 0.034 mmol), 1 N NaOH (3 mL, 3 mmol) and 2-amino-5-methoxyphenol (70 mg, 0.50 mmol). $^1$H NMR (400 MHz, acetone-$d_6$) δ ppm 1.59 (s, 3 H), 1.60 (s, 3 H), 1.60 (s, 3 H), 3.26 (d, J=9.9 Hz, 1 H), 3.89 (d, J=9.9 Hz, 1 H), 3.92 (s, 3 H), 6.87 (d, J=8.6 Hz, 1 H), 6.91-7.10 (m, 3 H), 7.14 (m, 1 H), 7.26 (d, J=8.8 Hz, 2 H), 7.32 (d, J=2.5 Hz, 1 H), 7.53 (d, J=8.3 Hz, 1 H), 7.60-7.77 (m, 3 H), 7.92-8.35 (dd, J=8.3, 1.4 Hz, 1 H), 8.97 (s, 1 H). $^{19}$F NMR (376.5 MHz, acetone-$d_6$) δ ppm −60.70. LCMS (ESI) m/z 605.4. (M+H)$^+$, RT=2.20 min (Method D).

Example 95

1-(2-(7-Hydroxy-3,3-dimethyl-4-(6-methylbenzo[d]oxazol-2-yl)indolin-1-yl)phenyl)-3-(4-(trifluoromethoxy)phenyl)-urea

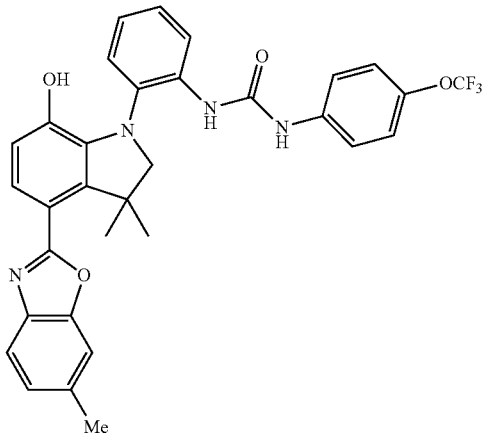 [SMILES: Cc1ccc2nc(-c3ccc(O)c4c3C(C)(C)CN4c3ccccc3NC(=O)Nc3ccc(OC(F)(F)F)cc3)oc2c1]

Example 95 (9.0 mg, 0.015 mmol, 47% yield) was obtained following the same procedure as described in Example 83 from Example 12 (17 mg, 0.032 mmol), 1 N NaOH (3 mL, 3 mmol) and 2-amino-5-methylphenol (60 mg, 0.49 mmol). $^1$H NMR (400 MHz, acetone-$d_6$) δ ppm 1.59 (s, 3 H), 1.60 (s, 3 H), 1.60 (s, 3 H), 3.27 (d, J=10.1 Hz, 1H), 3.90 (d, J=10.1 Hz, 1 H), 6.87 (d, J=8.3 Hz, 3 H), 6.87 (d, 1 H), 6.92-7.02 (m, 1H), 6.93-7.01 (m, 1 H), 7.05 (d, J=7.9, 1.5 Hz, 1 H), 7.08-7.19 (m, 1 H), 7.25 (m, 3H), 7.54 (m, 2 H), 7.65 (d, J=8.1 Hz, 1 H), 7.66-7.75 (m, 2 H), 7.80-8.31 (m, 2 H), 8.97 (s, 1 H). $^{19}$F NMR (376.5 MHz, acetone-$d_6$) δ ppm −60.68. LCMS (ESI) m/z 589.4. (M+H)$^+$, RT=2.26 min (Method D).

Example 96

1-(2-(7-Hydroxy-3,3-dimethyl-4-(oxazolo[4,5-c]pyridin-2-yl)indolin-1-yl)phenyl)-3-(4-(trifluoromethoxy)phenyl)urea

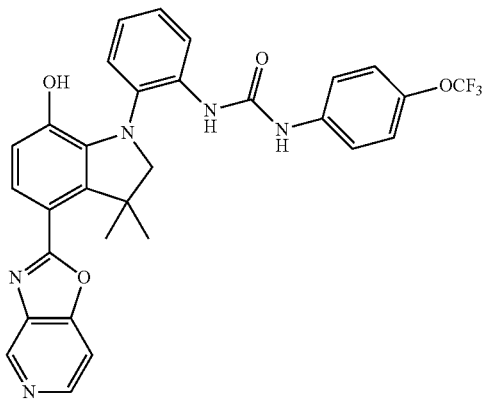 [SMILES: CC1(C)CN(c2ccccc2NC(=O)Nc2ccc(OC(F)(F)F)cc2)c2c(O)ccc(-c3nc4cnccc4o3)c21]

Example 96 (9 mg, 0.016 mmol, 41% yield) was obtained following the same procedure as described in Example 82 from Example 12 (20 mg, 0.038 mmol), 1 N NaOH (2 mL, 2 mmol) and 3-aminopyridin-4-ol (60 mg, 0.55 mmol). $^1$H NMR (400 MHz, acetone-$d_6$) δ ppm 1.60 (s, 3 H), 1.62 (s, 3 H), 3.27 (d, J=10.4 Hz, 1 H), 3.91 (d, J=9.9 Hz, 1 H), 6.91 (d, J=8.7 Hz, 1 H), 6.96-7.07 (m, 2 H), 7.14 (td, J=7.8, 1.7 Hz, 1H), 7.24 (d, J=8.2 Hz, 2 H), 7.67 (m, 3 H), 8.05 (d, J=6.0 Hz, 1 H), 8.14 (d, J=8.2 Hz, 1 H), 8.21 (s, 1 H), 8.77 (d, J=6.0 Hz, 1 H), 9.00 (s, 1 H), 9.26 (s, 1 H). LCMS (ESI) m/z 576.1. (M+H)$^+$, RT=3.26 min (Method C).

Example 97

1-(2-(7-Hydroxy-3,3-dimethyl-4-(3-methyl-1,2,4-oxadiazol-5-yl)indolin-1-yl)phenyl)-3-(4-(trifluoromethoxy)phenyl)urea

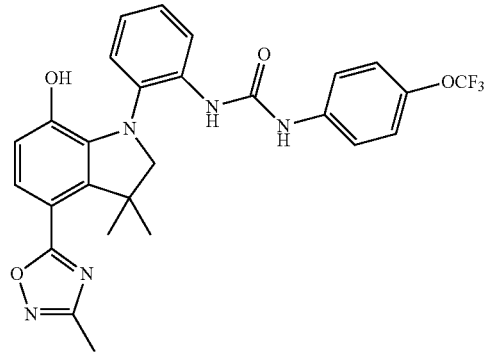 [SMILES: Cc1noc(-c2ccc(O)c3c2C(C)(C)CN3c2ccccc2NC(=O)Nc2ccc(OC(F)(F)F)cc2)n1]

Example 12 (24 mg, 0.046 mmol) was added to 1 N NaOH (1 mL, 1 mmol) at rt. (E)-N'-hydroxyacetimidamide (100 mg, 1.35 mmol) was added to the suspension. The mixture was stirred at 40° C. in a capped vial for 3 weeks. After cooling, saturated NH$_4$Cl was added. The reaction was extracted with CH$_2$Cl$_2$ and concentrated to dryness. The residue was purified by flash column chromatography (hexanes/EtOAc) to give (E)-7-hydroxy-N-(1-(hydroxyimino)ethyl)-3,3-dimethyl-1-(2-(3-(4-(trifluoromethoxy)-phenyl)ureido)phenyl)indoline-4-carboxamide (5 mg, 8.97 μmol, 19.63% yield) and Example 97 (2.0 mg, 3.71 μmol, 8.1% yield). $^1$H NMR (400 MHz, acetone-$d_6$) δ ppm 1.47 (br. s., 3 H), 1.49 (s, 3 H), 2.41 (s, 3 H), 3.23 (d, J=9.9 Hz, 1 H), 3.86 (d, J=9.9 Hz, 1 H), 6.83 (d, J=8.2 Hz, 1 H), 6.91-6.97 (m, 1 H), 6.97-7.05 (m, 1 H), 7.13 (t, J=7.7 Hz, 1 H), 7.24 (d, J=8.2 Hz, 2 H), 7.40 (d, J=8.2 Hz, 1 H), 7.61-7.74 (m, 2 H), 8.11 (s, 1 H), 8.16 (d, J=8.2 Hz, 1 H), 8.91 (s, 1H). $^{19}$F NMR (376.5 MHz, acetone-$d_6$) δ ppm −58.82. LCMS (ESI) m/z 540.4. (M+H)$^+$, RT=2.11 min (Method D).

Example 98

1-(2-(4-(5-Fluorobenzo[d]oxazol-2-yl)-7-hydroxy-3,3-dimethylindolin-1-yl)phenyl)-3-(4-(trifluoromethoxy)phenyl)urea

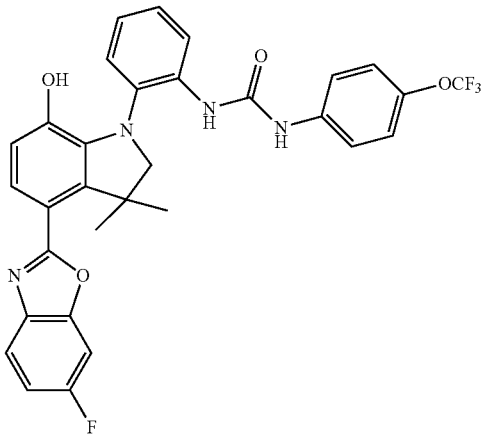 [SMILES: CC1(C)CN(c2ccccc2NC(=O)Nc2ccc(OC(F)(F)F)cc2)c2c(O)ccc(-c3nc4ccc(F)cc4o3)c21]

Example 98 (27 mg, 0.046 mmol, 80% yield) was obtained following the same procedure as described in Example 82 from Example 12 (30 mg, 0.057 mmol), 1 N NaOH (4 mL, 4 mmol) and 2-amino-4-fluorophenol (70 mg, 0.55 mmol). $^1$H NMR (400 MHz, acetone-$d_6$) δ ppm 1.57 (s, 3 H), 1.58 (s, 3 H), 3.25 (d, J=9.9 Hz, 1 H), 3.88 (d, J=9.9 Hz, 1 H), 6.86 (d, J=8.8 Hz, 1 H), 6.95 (s, 1 H), 7.03 (s, 1 H), 7.13 (t, J=7.7 Hz, 1 H), 7.16-7.31 (m, 3 H), 7.45-7.60 (m, 2 H), 7.66 (d, J=8.8 Hz, 2 H), 7.72 (dd, J=8.8, 4.4 Hz, 1 H), 8.12 (s, 1 H), 8.17 (d, J=8.2 Hz, 1 H), 8.59 (br. s., 1 H), 8.94 (s, 1 H). LCMS (ESI) m/z 593.4. (M+H)$^+$, RT=2.26 min (Method D).

Example 99

1-(2-(4-(5,6-Difluorobenzo[d]oxazol-2-yl)-7-hydroxy-3,3-dimethylindolin-1-yl)phenyl)-3-(4-(trifluoromethoxy)phenyl)urea

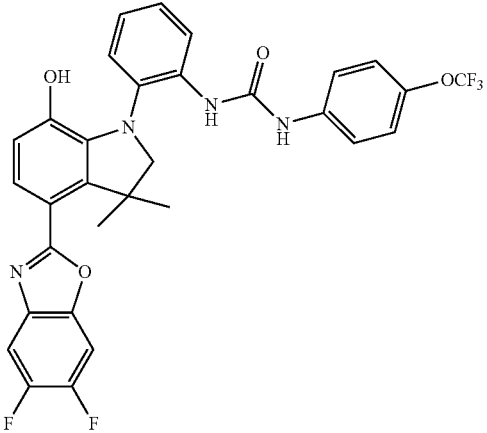 [SMILES: CC1(C)CN(c2ccccc2NC(=O)Nc2ccc(OC(F)(F)F)cc2)c2c(O)ccc(-c3nc4cc(F)c(F)cc4o3)c21]

Example 99 (16 mg, 0.026 mmol, 57% yield) was obtained following the same procedure as described in Example 82 from Example 12 (24 mg, 0.046 mmol), 1 N NaOH (4 mL, 4 mmol) and 2-amino-4,5-difluorophenol (70 mg, 0.48 mmol). $^1$H NMR (400 MHz, acetone-$d_6$) δ ppm 1.55 (s, 3 H), 1.58 (s, 3 H), 3.24 (d, J=9.9 Hz, 1 H), 3.88 (d, J=9.9 Hz, 1 H), 6.86 (d, J=8.2 Hz, 1 H), 6.95 (s, 1 H), 6.99-7.05 (m, 1 H), 7.13 (t, J=7.7 Hz, 1 H), 7.24 (d, J=8.2 Hz, 2 H), 7.54 (d, J=8.8 Hz, 1 H), 7.66 (m, 2 H), 7.70-7.86 (m, 2 H), 8.11 (s, 1 H), 8.17 (d, J=8.2 Hz, 1 H), 8.59 (br. s., 1 H), 8.92 (s, 1 H). LCMS (ESI) m/z 611.4. (M+H)$^+$, RT=2.29 min (Method D).

Example 100

1-(2-(4-(5-Chlorobenzo[d]thiazol-2-yl)-7-hydroxy-3,3-dimethylindolin-1-yl)phenyl)-3-(6-fluorobenzo[d]thiazol-2-yl)urea

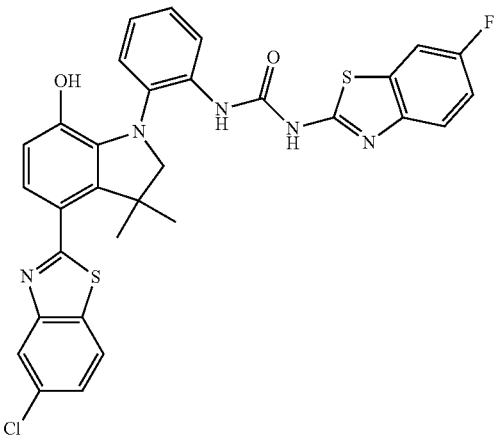 [SMILES: CC1(C)CN(c2ccccc2NC(=O)Nc2nc3ccc(F)cc3s2)c2c(O)ccc(-c3nc4cc(Cl)ccc4s3)c21]

Example 100 was obtained (16 mg, 0.026 mmol, 67% yield) as off-white solids following the same procedure as described in Example 83 from 1-(6-fluorobenzo[d]thiazol-2-yl)-3-(2-(7-hydroxy-3,3-dimethyl-4-(trifluoromethyl)indolin-1-yl)phenyl)urea (20 mg, 0.039 mmol). $^1$H NMR (400 MHz, MeOD) δ ppm 1.41 (br, s, 6H), 3.23 (d, J=9.85 Hz, 1 H), 3.82 (d, J=9.85 Hz, 1 H), 6.73 (d, J=8.08 Hz, 1 H), 7.00-7.12 (m, 4 H), 7.13-7.20 (m, 1 H), 7.35-7.41 (m, 1 H), 7.44 (dd, J=8.34, 2.02 Hz, 1 H), 7.57 (dd, J=8.34, 2.53 Hz, 1 H), 7.96-8.02 (m, 2 H), 8.06 (d, J=7.83 Hz, 1H). LCMS (ESI) m/z 616.4 (M+H)$^+$, RT=4.50 min (Method C).

Example 101

1-(2-(4-(6-Fluorobenzo[d]oxazol-2-yl)-7-hydroxy-3,3-dimethylindolin-1-yl)phenyl)-3-(6-fluorobenzo[d]thiazol-2-yl)urea

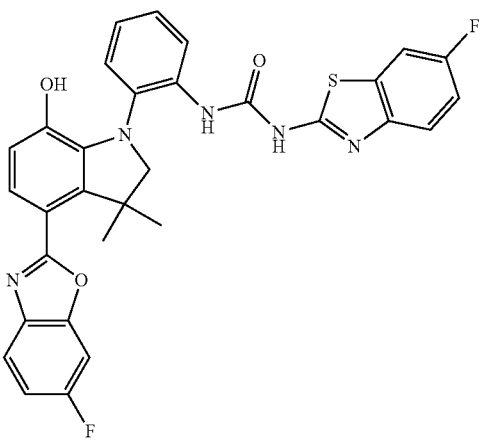 [SMILES: CC1(C)CN(c2ccccc2NC(=O)Nc2nc3ccc(F)cc3s2)c2c(O)ccc(-c3nc4ccc(F)cc4o3)c21]

Example 101 was obtained (5.7 mg, 9.77 μmol, 25% yield) as off-white solids following the same procedure as described in Example 82 from 1-(6-fluorobenzo[d]thiazol-2-yl)-3-(2-(7-hydroxy-3,3-dimethyl-4-(trifluoromethyl)indolin-1-yl)phenyl)urea (20 mg, 0.039 mmol). $^1$H NMR (400 MHz, MeOD) δ ppm 1.51 (s, 6 H), 3.23 (d, J=9.85 Hz, 1 H), 3.87 (d, J=9.85 Hz, 1 H), 6.76 (d, J=8.34 Hz, 1 H), 7.00-7.10 (m, 3 H), 7.13-7.21 (m, 3 H), 7.44 (d, J=8.59 Hz, 1 H), 7.48 (dd, J=8.21, 2.40 Hz, 1 H), 7.57 (dd, J=8.34, 2.78 Hz, 1 H), 7.71 (dd, J=8.72, 4.93 Hz, 1 H), 8.06 (dd, J=8.21, 1.14 Hz, 1 H). LCMS (ESI) m/z 584.4 (M+H)$^+$, RT=4.26 min (Method C).

Example 102

1-(2-(7-Hydroxy-3,3-dimethyl-4-(6-methyloxazolo[5,4-b]pyridin-2-yl)indolin-1-yl)phenyl)-3-(4-(trifluoromethoxy)phenyl)urea

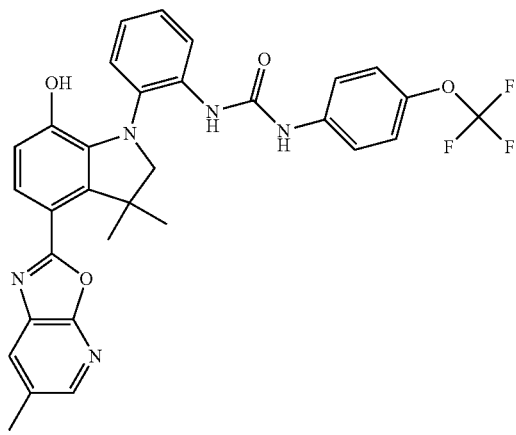 [SMILES: Cc1cnc2oc(-c3ccc(O)c4c3C(C)(C)CN4c3ccccc3NC(=O)Nc3ccc(OC(F)(F)F)cc3)nc2c1]

Example 102A.

3-Amino-5-methylpyridin-2-ol

To a solution of 5-methyl-3-nitropyridin-2-ol (50 mg, 0.32 mmol) in MeOH (5 mL) was added ammonium chloride (174 mg, 3.24 mmol) and zinc (106 mg, 1.62 mmol). The reaction mixture was colored and stirred at rt for 1 h. The suspension was removed by a filter and washed the filter with MeOH. The solvent was evaporated under reduced pressure. The crude product was triturated with a mixed solvent of MeOH and EtOAc (1:1). The suspension was filtered and the solvent was removed under reduced pressure to Example 1013A (16 mg, 0.13 mmol, 40% yield). $^1$H NMR (400 MHz, MeOD) δ ppm 2.03 (s, 3 H), 6.56 (s, 1 H), 6.63 (s, 1 H).

Example 102

To a suspension of Example 12 (42 mg, 0.081 mmol) in sodium hydroxide (806 μL, 0.806 mmol) was added Example 102A (10 mg, 0.081 mmol). The reaction mixture was stirred at 40° C. for over the weekend. The reaction was quenched with 1 N HCl and MeOH. The organic layer was reduced in vacuo, and was purified using a 10 minutes gradient from 0 to 100% B (Column: PHENOMENEX® Axia Luna 100×20 mm 5u (10 min gradient). Solvent A: 10% ACN-90% H$_2$O-0.1% TFA, Solvent B: 90% ACN-10% H$_2$O-0.1% TFA) to give Example 102 (19 mg, 32% yield). $^1$H NMR (400 MHz, MeOD) δ ppm 1.55 (s, 3H), 1.56 (s, 3H), 2.50 (s, 3 H), 3.25-3.27 (m, 1 H), 3.88 (d, J=9.85 Hz, 1 H), 6.78 (d, J=8.34 Hz, 1 H), 6.96-6.99 (m, 2H), 7.09-7.13 (m, 1 H), 7.17 (d, J=9.09 Hz, 2 H), 7.50-7.55 (m, 3 H), 7.93 (d, J=8.08 Hz, 1 H), 7.98 (m, 1 H), 8.16 (m, 1 H). LCMS (ESI) m/z 590.0 (M+H)$^+$, RT=4.26 min (Method C).

Example 103

1-(2-(7-Hydroxy-3,3-dimethyl-4-(7-methyloxazolo[5,4-b]pyridin-2-yl)indolin-1-yl)phenyl)-3-(4-(trifluoromethoxy)phenyl)urea

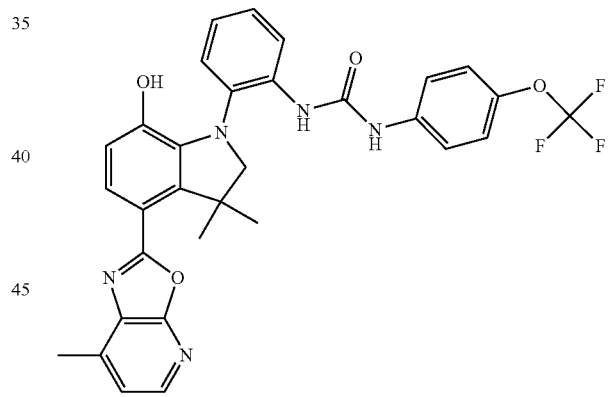

Following the same procedure as that for Example 102, Example 103 was obtained (10 mg, 0.014 mmol, 32% yield) as off-white solids from Example 12 (25 mg, 0.044 mmol). $^1$H NMR (400 MHz, MeOD) δ ppm 1.27 (s, 3 H), 1.41 (s, 3 H), 3.21 (d, J=9.89 Hz, 1 H), 3.81 (d, J=9.89 Hz, 1 H), 6.76 (d, J=8.24 Hz, 1 H), 7.01-7.05 (m, 1 H), 7.05-7.14 (m, 4 H), 7.37 (d, J=8.25 Hz, 2 H), 7.42 (dd, J=8.79, 2.20 Hz, 1 H), 7.77 (d, J=6.60 Hz, 1 H), 7.89 (d, J=8.79 Hz, 2 H), 7.96 (m, 1 H). LCMS (ESI) m/z 590.0 (M+H)$^+$, RT=4.08 min (Method C).

Examples 104 to 110 were prepared following similar procedures as described in Examples 83 to 104.

| Example No. | Compound Name | Compound Structure | LC-MS |
|---|---|---|---|
| 104 | 1-(2-(4-(4-tert-Butyl-4,5-dihydrooxazol-2-yl)-7-hydroxy-3,3-dimethylindolin-1-yl)phenyl)-3-(4-(trifluoromethoxy)phenyl)urea | 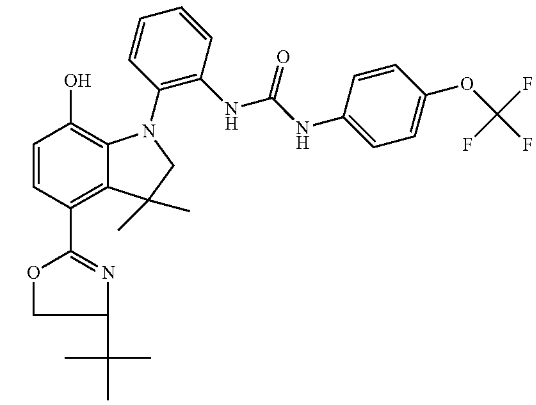 [SMILES: CC1(C)CN(c2ccccc2NC(=O)Nc2ccc(OC(F)(F)F)cc2)c2c(O)ccc(C3=NC(C(C)(C)C)CO3)c21] | MS (ESI) m/z 583.23 (M + H)$^+$ |
| 105 | 1-(2-(7-Hydroxy-3,3-dimethyl-4-(5-(trifluoromethyl)-4,5-dihydrooxazol-2-yl)indolin-1-yl)phenyl)-3-(4-(trifluoromethoxy)phenyl)urea | 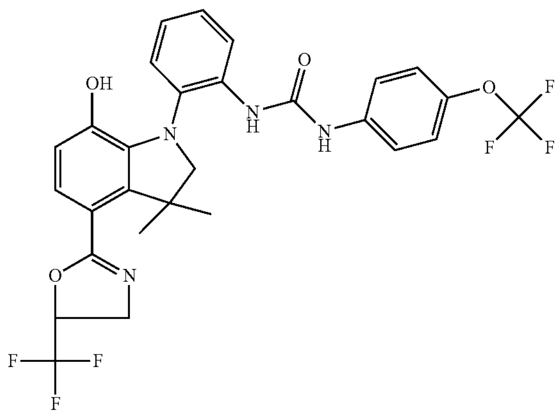 [SMILES: CC1(C)CN(c2ccccc2NC(=O)Nc2ccc(OC(F)(F)F)cc2)c2c(O)ccc(C3=NCC(C(F)(F)F)O3)c21] | MS (ESI) m/z 595.15 (M + H)$^+$ |
| 106 | 1-(2-(7-Hydroxy-4-(4-(hydroxymethyl)benzo[d]oxazol-2-yl)-3,3-dimethylindolin-1-yl)phenyl)-3-(4-(trifluoromethoxy)phenyl)urea | 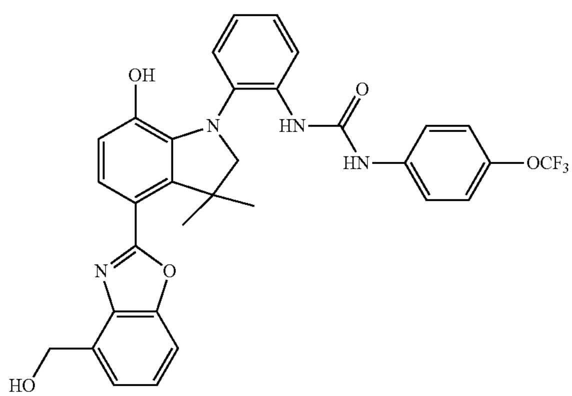 [SMILES: CC1(C)CN(c2ccccc2NC(=O)Nc2ccc(OC(F)(F)F)cc2)c2c(O)ccc(-c3nc4c(CO)cccc4o3)c21] | m/z 605.0 (M + H)$^+$, RT = 3.85 min (Method C) |
| 107 | 1-(2-(7-Hydroxy-3,3-dimethyl-4-(7-(methylamino)oxazolo[5,4-d]pyrimidin-2-yl)indolin-1-yl)phenyl)-3-(4-(trifluoromethoxy)phenyl)urea | 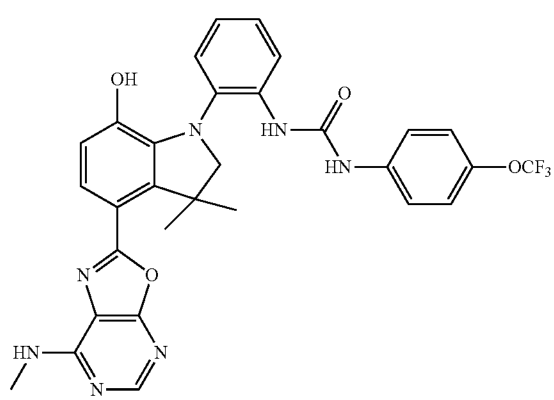 [SMILES: CNc1ncnc2oc(-c3ccc(O)c4c3C(C)(C)CN4c3ccccc3NC(=O)Nc3ccc(OC(F)(F)F)cc3)nc12] | m/z 606.0 (M + H)$^+$, RT = 3.10 min (Method C) |

-continued

| Example No. | Compound Name | Compound Structure | LC-MS |
|---|---|---|---|
| 108 | 1-(2-(4-(6-Chlorobenzo[d]oxazol-2-yl)-7-hydroxy-3,3-dimethylindolin-1-yl)phenyl)-3-(5-fluorothiazolo[5,4-b]pyridin-2-yl)urea | 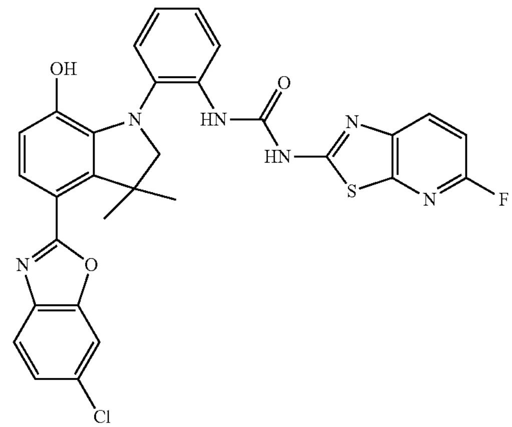 [SMILES: CC1(C)CN(c2ccccc2NC(=O)Nc2nc3ccc(F)nc3s2)c2c(O)ccc(-c3nc4ccc(Cl)cc4o3)c21] | m/z 600.9 (M + H)+, RT = 4.33 min (Method C) |
| 109 | 1-(2-(4-(6-Chlorobenzo[d]oxazol-2-yl)-7-hydroxy-3,3-dimethylindolin-1-yl)phenyl)-3-(4-(1-neopentylpyrrolidin-2-yl)phenyl)urea | 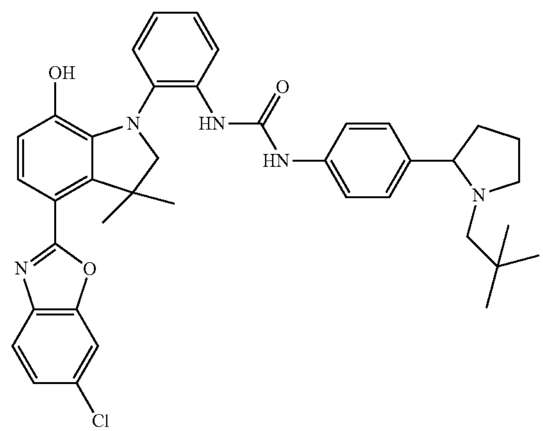 [SMILES: CC(C)(C)CN1CCCC1c1ccc(NC(=O)Nc2ccccc2N2CC(C)(C)c3c(-c4nc5ccc(Cl)cc5o4)ccc(O)c32)cc1] | m/z 664.1 (M + H)+, RT = 3.68 min (Method C) |
| 110 | 1-(2-(4-(6-Chlorobenzo[d]oxazol-2-yl)-7-hydroxy-3,3-dimethylindolin-1-yl)phenyl)-3-(5-methoxythiazolo[5,4-b]pyridin-2-yl)urea | 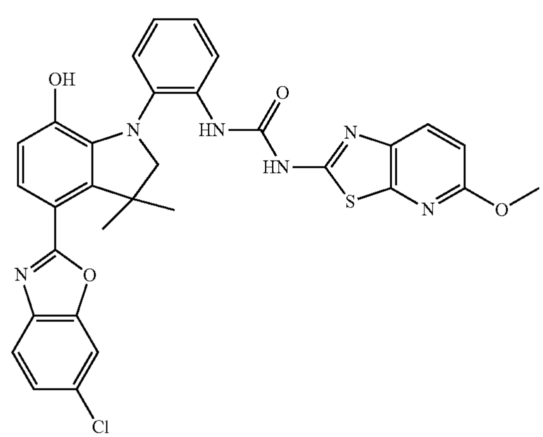 [SMILES: COc1ccc2nc(NC(=O)Nc3ccccc3N3CC(C)(C)c4c(-c5nc6ccc(Cl)cc6o5)ccc(O)c43)sc2n1] | m/z 613.0 (M + H)+, RT = 4.41 min (Method C) |

Example 111

1-(2-(4-(2,6-Difluoropyridin-4-yl)-7-hydroxy-3,3-dimethylindolin-1-yl)phenyl)-3-(4-(trifluoromethoxy)phenyl)urea, TFA

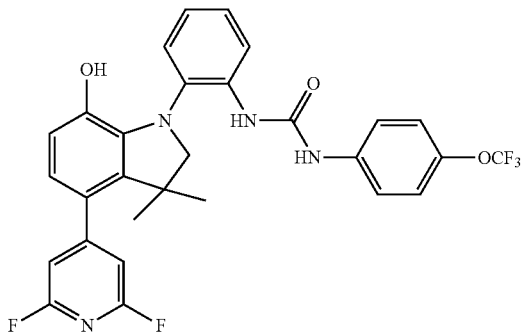 [SMILES: CC1(C)CN(c2ccccc2NC(=O)Nc2ccc(OC(F)(F)F)cc2)c2c(O)ccc(-c3cc(F)nc(F)c3)c21]

Example 111A.

4-(2,6-Difluoropyridin-4-yl)-7-methoxy-3,3-dimethyl-1-(2-nitrophenyl)indoline

To a solution of 4-bromo-7-methoxy-3,3-dimethyl-1-(2-nitrophenyl)indoline (60 mg, 0.16 mmol) and 2,6-difluoropyridin-4-ylboronic acid (30.3 mg, 0.191 mmol) in THF (2.5 mL) was added $Cs_2CO_3$ (62.2 mg, 0.191 mmol) and $Pd(PPh_3)_4$ (37 mg, 0.032 mmol). The reaction was stirred at 110° C. under argon for 5 h. The desired product was purified by flash chromatography to Example 111A (60 mg, 0.15 mmol, 92% yield). LCMS (ESI) m/z 412.0 (M+H)$^+$, RT=3.73 min (Method C).

Example 111B.

2-(4-(2,6-Difluoropyridin-4-yl)-7-methoxy-3,3-dimethylindolin-1-yl)aniline

To a solution of Example 111A (65 mg, 0.16 mmol) in DCM (1 mL) and MeOH (5 mL) was added ammonium chloride (50.7 mg, 0.948 mmol) and zinc (51.7 mg, 0.790 mmol). The reaction mixture was stirred at rt for 20 minutes. It was filtered and the solvent was evaporated via reduced pressure. The crude product was triturated with EtOAc and concentrated in vacuo to give Example 111B (58 mg, 0.152 mmol, 96% yield). LCMS (ESI) m/z 382.1 (M+H)$^+$, RT=3.09 min (Method C).

Example 111C.

1-(2-(4-(2,6-Difluoropyridin-4-yl)-7-methoxy-3,3-dimethylindolin-1-yl)phenyl)-3-(4-(trifluoromethoxy)phenyl)urea To a solution of Example 111B (59 mg, 0.16 mmol) in DCM (1 mL) was added DMAP (18.9 mg, 0.155 mmol) and 1-isocyanato-4-(trifluoromethoxy)benzene (0.028 mL, 0.19 mmol). The reaction mixture was stirred at room temperature for 1 h and was partitioned between DCM and $H_2O$. The layer was separated and dried over $Na_2SO_4$. The solvent was evaporated under reduced pressure. The crude was purified by flash chromatography to give Example 111C (29 mg, 0.050 mmol, 32% yield). LCMS (ESI) m/z 585.4 (M+H)$^+$, RT=2.17 min (Method D).

Example 111

To a solution of Example 111C (32 mg, 0.055 mmol) in DCM (1 mL) was added TBAI (142 mg, 0.383 mmol) and boron trichloride (0.438 mL, 0.438 mmol) at −20° C. The reaction mixture was stirred at rt for 2 h. The reaction mixture was quenched with ice and MeOH. The solvent was evaporated under reduced pressure. The crude product was purified by flash chromatography and preparative HPLC using a 10 minutes gradient from 0 to 100% B to afford Example 111 (31 mg, 0.045 mmol, 83% yield). $^1$H NMR (400 MHz, MeOD) δ ppm 1.06 (s, 3 H), 1.08 (s, 3 H), 3.07 (d, J=9.9 Hz, 1 H), 3.66 (d, J=9.9 Hz, 1 H), 6.46 (d, J=8.3 Hz, 1 H), 6.55-6.64 (m, 1 H), 6.86 (s, 2 H), 6.88-6.93 (m, 2 H), 6.97-7.05 (m, 1 H), 7.08 (d, J=8.3 Hz, 2 H), 7.34-7.48 (m, 2 H), 7.79 (d, J=7.6 Hz, 1 H). LCMS (ESI) m/z 571.3 (M+H)$^+$, RT=2.13 min (Method D).

Examples 112 to 119 were prepared following similar procedures as described in Example 111.

| Example No. | Compound Name | Compound Structure | LC-MS |
|---|---|---|---|
| 112 | 1-(2-(4-(2-Fluoropyridin-4-yl)-7-hydroxy-3,3-dimethylindolin-1-yl)phenyl)-3-(4-(trifluoromethoxy)phenyl)urea | 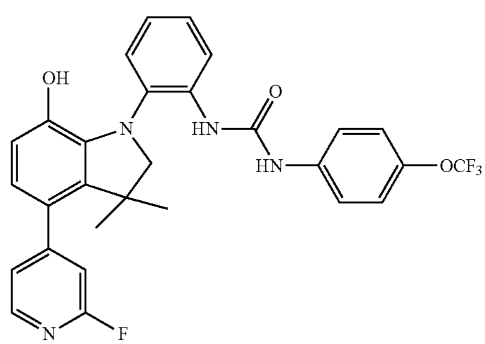 [SMILES: CC1(C)CN(c2ccccc2NC(=O)Nc2ccc(OC(F)(F)F)cc2)c2c(O)ccc(-c3ccnc(F)c3)c21] | m/z 553.0 (M + H)$^+$, RT = 3.86 min (Method C) |

-continued

| Example No. | Compound Name | Compound Structure | LC-MS |
|---|---|---|---|
| 113 | 1-(2-(7-Hydroxy-3,3-dimethyl-4-(pyridin-4-yl)indolin-1-yl)phenyl)-3-(4-(trifluoromethoxy)phenyl)urea | 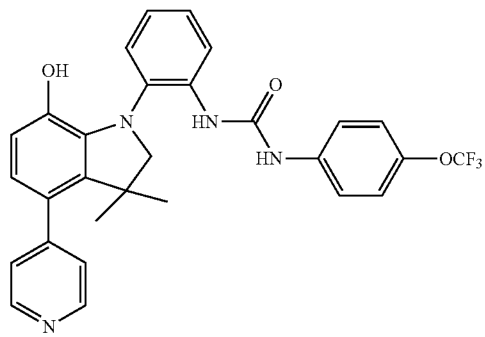 [SMILES: CC1(C)CN(c2ccccc2NC(=O)Nc2ccc(OC(F)(F)F)cc2)c2c(O)ccc(-c3ccncc3)c21] | m/z 535.1 (M + H)+, RT = 3.06 min (Method C) |
| 114 | 1-(2-(4-(3-Chloropyridin-4-yl)-7-hydroxy-3,3-dimethylindolin-1-yl)phenyl)-3-(4-(trifluoromethoxy)phenyl)urea | 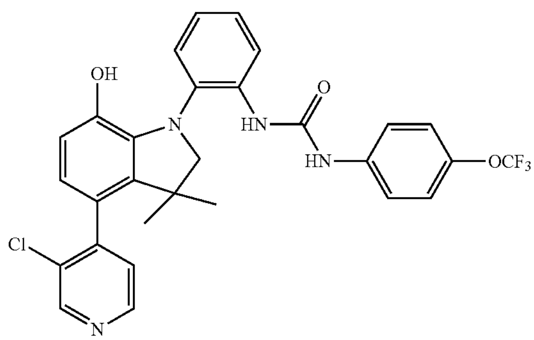 [SMILES: CC1(C)CN(c2ccccc2NC(=O)Nc2ccc(OC(F)(F)F)cc2)c2c(O)ccc(-c3ccncc3Cl)c21] | m/z 569.0 (M + H)+, RT = 4.04 min (Method C) |
| 115 | 1-(2-(4-(6-Fluoropyridin-3-yl)-7-hydroxy-3,3-dimethylindolin-1-yl)phenyl)-3-(4-(trifluoromethoxy)phenyl)urea | 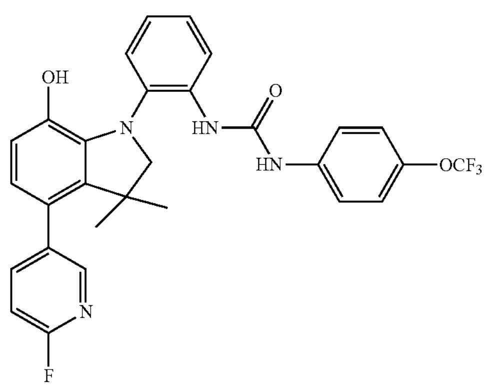 [SMILES: CC1(C)CN(c2ccccc2NC(=O)Nc2ccc(OC(F)(F)F)cc2)c2c(O)ccc(-c3ccc(F)nc3)c21] | m/z 554.0 (M + H)+, RT = 3.85 min (Method C) |
| 116 | 1-(2-(4-(5-Chloropyridin-3-yl)-7-hydroxy-3,3-dimethylindolin-1-yl)phenyl)-3-(4-(trifluoromethoxy)phenyl)urea | 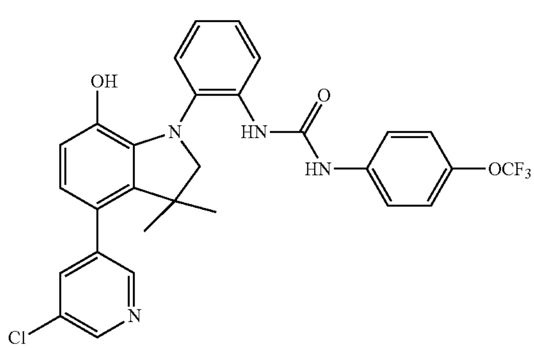 [SMILES: CC1(C)CN(c2ccccc2NC(=O)Nc2ccc(OC(F)(F)F)cc2)c2c(O)ccc(-c3cncc(Cl)c3)c21] | m/z 569.0 (M + H)+, RT = 4.11 min (Method C) |

-continued

| Example No. | Compound Name | Compound Structure | LC-MS |
|---|---|---|---|
| 117 | 1-(2-(4-(5-Fluoropyridin-3-yl)-7-hydroxy-3,3-dimethylindolin-1-yl)phenyl)-3-(4-(trifluoromethoxy)phenyl)urea | 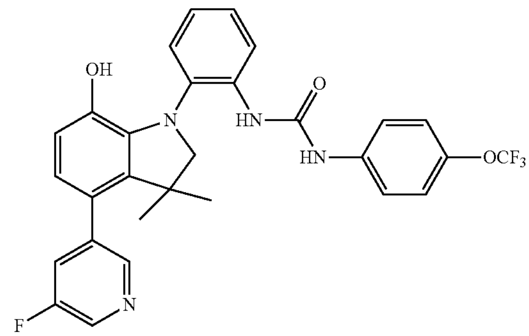 [SMILES: CC1(C)CN(c2ccccc2NC(=O)Nc2ccc(OC(F)(F)F)cc2)c2c(O)ccc(-c3cncc(F)c3)c21] | m/z 553.1 (M + H)$^+$, RT = 3.84 min (Method C) |
| 118 | 1-(2-(7-Hydroxy-4-(5-methoxypyridin-3-yl)-3,3-dimethylindolin-1-yl)phenyl)-3-(4-(trifluoromethoxy)phenyl)urea | 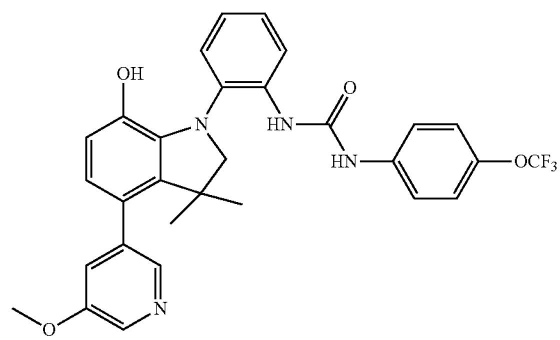 [SMILES: COc1cncc(-c2ccc(O)c3c2C(C)(C)CN3c2ccccc2NC(=O)Nc2ccc(OC(F)(F)F)cc2)c1] | m/z 566.1 (M + H)$^+$, RT = 3.10 min (Method C) |
| 119 | 1-(2-(4-(6-Fluoro-5-methylpyridin-3-yl)-7-hydroxy-3,3-dimethylindolin-1-yl)phenyl)-3-(4-(trifluoromethoxy)phenyl)urea | 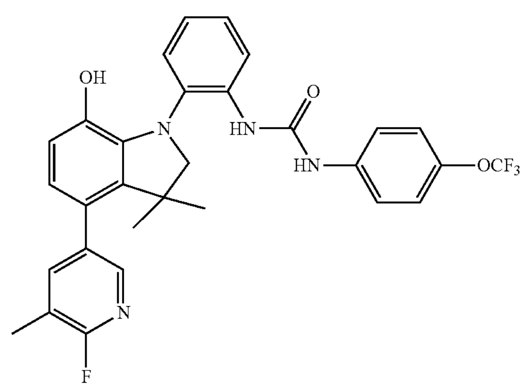 [SMILES: Cc1cc(-c2ccc(O)c3c2C(C)(C)CN3c2ccccc2NC(=O)Nc2ccc(OC(F)(F)F)cc2)cnc1F] | m/z 567.4 (M + H)$^+$, RT = 2.09 min (Method D) |

Example 120

1-(2-(7-Hydroxy-3,3-dimethyl-4-(6-(trifluoromethyl)pyridin-3-yl)indolin-1-yl)phenyl)-3-(4-(trifluoromethoxy)phenyl)urea,TFA

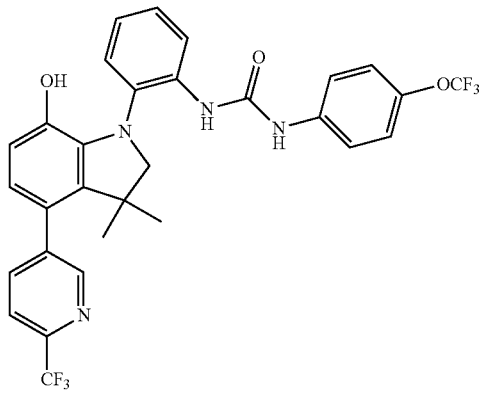 [SMILES: CC1(C)CN(c2ccccc2NC(=O)Nc2ccc(OC(F)(F)F)cc2)c2c(O)ccc(-c3ccc(C(F)(F)F)nc3)c21]

Example 120A.

4-(5,5-Dimethyl-1,3,2-dioxaborinan-2-yl)-7-methoxy-3,3-dimethyl-1-(2-nitrophenyl)indoline To a solution of 4-bromo-7-methoxy-3,3-dimethyl-1-(2-nitrophenyl)indoline (900 mg, 2.39 mmol), 5,5,5',5'-tetramethyl-2,2'-bi(1,3,2-dioxaborinane) (808 mg, 3.58 mmol) and potassium acetate (1171 mg, 11.93 mmol) in DMSO (18 mL) under argon was added (1,1'-bis(diphenylphosphino)-ferrocene)-dichloropalladium(II) (196 mg, 0.239 mmol). The reaction mixture was stirred at 80° C. for 16 h. It was partition between H₂O and EtOAc. The organic layer was dried over Na₂SO₄. The crude product was isolated via column chromatography using a 15 minutes gradient from 0 to 100% EtOAc in hexane on a 12 g cartridge to give Example 120A (660 mg, 1.61 mmol, 67.4% yield).

Example 120B.

7-Methoxy-3,3-dimethyl-1-(2-nitrophenyl)-4-(6-(trifluoromethyl)pyridin-3-yl)indoline To a solution of Example 120A (40 mg, 0.098 mmol), 5-bromo-2-(trifluoromethyl)pyridine (25.4 mg, 0.112 mmol) and cesium carbonate (54.9 mg, 0.168 mmol) in THF (1 mL) was added tetrakis(triphenylphosphine)-palladium(O) (13 mg, 0.011 mmol). The reaction mixture was reflux for 3 h and then 16 h. The desired product was isolated via silica gel column chromatography to give Example 120B (50 mg, quant.). LCMS (ESI) m/z 444.2 (M+H)⁺, RT=3.73 min (Method C).

Example 120C.

2-(7-Methoxy-3,3-dimethyl-4-(6-(trifluoromethyl)pyridin-3-yl)indolin-1-yl)aniline Example 120C was prepared (42 mg, 0.10 mmol, 90% yield) following the same procedure as described in Example 111B by replacing Example 111A with Example 120B (50 mg, 0.11 mmol). LCMS (ESI) m/z 414.3 (M+H)⁺, RT=3.12 min (Method C).

Example 120D.

1-(2-(7-Methoxy-3,3-dimethyl-4-(6-(trifluoromethyl)pyridin-3-yl)indolin-1-yl)phenyl)-3-(4-(trifluoromethoxy)phenyl)urea Crude Example 120D was prepared following the same procedure as described in Example 111C by replacing Example 111B with Example 120C (50 mg, 0.12 mmol). LCMS (ESI) m/z 617.3 (M+H)⁺, RT=4.17 min (Method C).

Example 120

TFA salt of Example 120 (28 mg, 0.038 mmol, 59% yield) was prepared following the same procedure as described in Example 111 by replacing Example 111C with Example 120D (40 mg, 0.065 mmol). ¹H NMR (400 MHz, MeOD) δ ppm 0.99 (s, 3 H), 1.01 (s, 3 H), 3.06 (d, J=9.9 Hz, 1 H), 3.67 (d, J=9.9 Hz, 1 H), 6.48 (d, J=8.1 Hz, 1 H), 6.60 (d, J=8.1 Hz, 1 H), 6.77-6.97 (m, 2 H), 6.96-7.04 (m, 1H), 7.08 (d, J=8.3 Hz, 2 H), 7.28-7.55 (m, 2 H), 7.66-7.84 (m, 2 H), 7.90 (dd, J=8.0, 1.6 Hz, 1 H), 8.57 (d, J=1.5 Hz, 1 H). LCMS (ESI) m/z 603.4 (M+H)⁺, RT=2.08 min (Method D).

Examples 121 to 192 were prepared following similar procedures as described in Example 111 and Example 120.

| Example No. | Compound Name | Compound Structure | LC-MS |
|---|---|---|---|
| 121 | 1-(2-(4-(5-Chlorothiophen-2-yl)-7-hydroxy-3,3-dimethylindolin-1-yl)phenyl)-3-(4-(trifluoromethoxy)phenyl)urea | 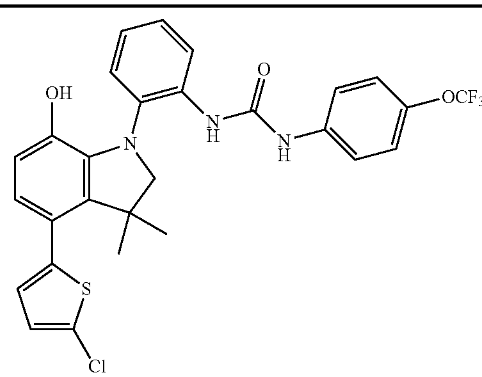 | m/z 574.3 (M + H)⁺, RT = 2.26 min (Method D) |

-continued

| Example No. | Compound Name | Compound Structure | LC-MS |
|---|---|---|---|
| 122 | 1-(2-(4-(5-Chloropyridin-2-yl)-7-hydroxy-3,3-dimethylindolin-1-yl)phenyl)-3-(4-(trifluoromethoxy)phenyl)urea | 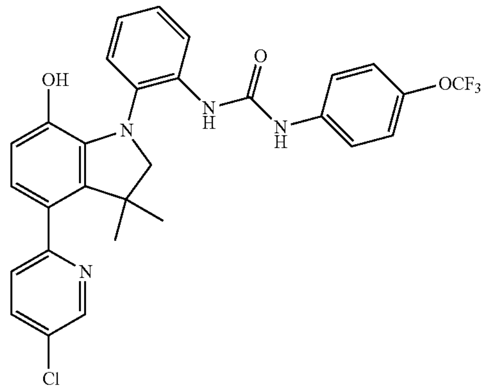 [SMILES: CC1(C)CN(c2ccccc2NC(=O)Nc2ccc(OC(F)(F)F)cc2)c2c(O)ccc(-c3ccc(Cl)cn3)c21] | m/z 569.3 (M + H)+, RT = 2.12 min (Method D) |
| 123 | 1-(2-(4-(5-Fluoropyridin-2-yl)-7-hydroxy-3,3-dimethylindolin-1-yl)phenyl)-3-(4-(trifluoromethoxy)phenyl)urea | 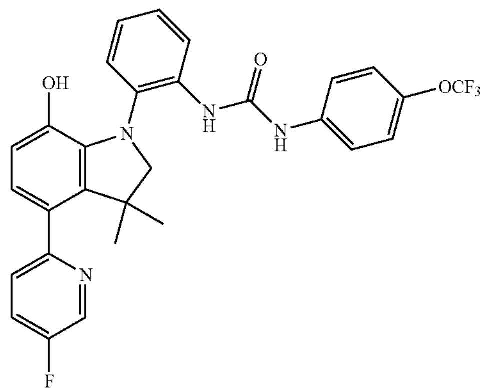 [SMILES: CC1(C)CN(c2ccccc2NC(=O)Nc2ccc(OC(F)(F)F)cc2)c2c(O)ccc(-c3ccc(F)cn3)c21] | m/z 553.5 (M + H)+, RT = 2.04 min (Method D) |
| 124 | 1-(2-(7-Hydroxy-3,3-dimethyl-4-(thiazol-2-yl)indolin-1-yl)phenyl)-3-(4-(trifluoromethoxy)phenyl)urea | 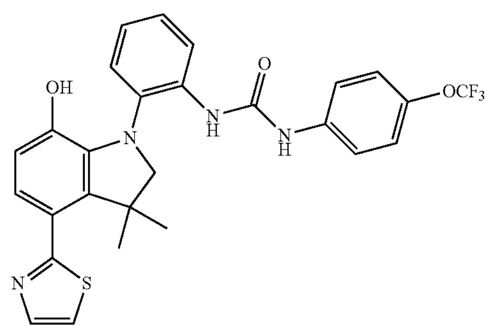 [SMILES: CC1(C)CN(c2ccccc2NC(=O)Nc2ccc(OC(F)(F)F)cc2)c2c(O)ccc(-c3nccs3)c21] | m/z 541.3 (M + H)+, RT = 3.89 min (Method C) |
| 125 | 1-(2-(7-Hydroxy-3,3-dimethyl-4-(5-(trifluoromethyl)pyridin-2-yl)indolin-1-yl)phenyl)-3-(4-(trifluoromethoxy)phenyl)urea | 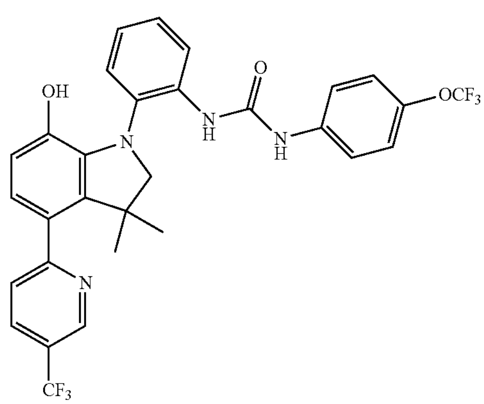 [SMILES: CC1(C)CN(c2ccccc2NC(=O)Nc2ccc(OC(F)(F)F)cc2)c2c(O)ccc(-c3ccc(C(F)(F)F)cn3)c21] | m/z 603.3 (M + H)+, RT = 4.11 min (Method C) |

-continued

| Example No. | Compound Name | Compound Structure | LC-MS |
|---|---|---|---|
| 126 | 1-(2-(7-Hydroxy-4-(5-isopropylpyrimidin-2-yl)-3,3-dimethylindolin-1-yl)phenyl)-3-(4-(trifluoromethoxy)phenyl)urea | 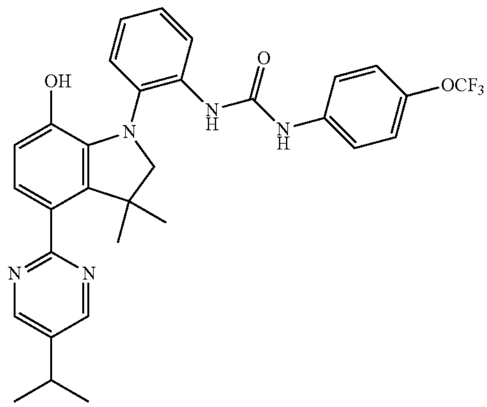 [SMILES: CC(C)c1cnc(-c2ccc(O)c3c2C(C)(C)CN3c2ccccc2NC(=O)Nc2ccc(OC(F)(F)F)cc2)nc1] | m/z 578.5 (M + H)+, RT = 2.09 min (Method D) |
| 127 | 1-(2-(7-Hydroxy-4-(2-isopropylthiazol-4-yl)-3,3-dimethylindolin-1-yl)phenyl)-3-(4-(trifluoromethoxy)phenyl)urea | 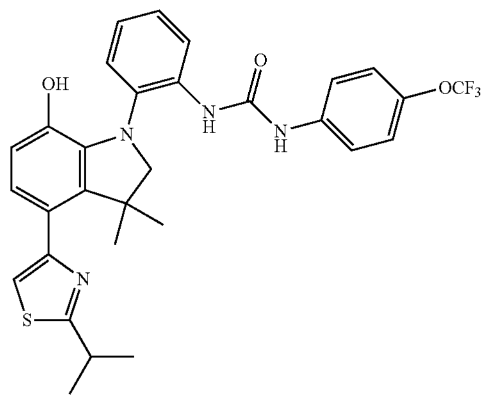 [SMILES: CC(C)c1nc(-c2ccc(O)c3c2C(C)(C)CN3c2ccccc2NC(=O)Nc2ccc(OC(F)(F)F)cc2)cs1] | m/z 583.5 (M + H)+, RT = 2.15 min (Method D) |
| 128 | 1-(6-Chlorobenzo[d]thiazol-2-yl)-3-(2-(4-(6-fluorobenzo[d]thiazol-2-yl)-7-hydroxy-3,3-dimethylindolin-1-yl)phenyl)urea | 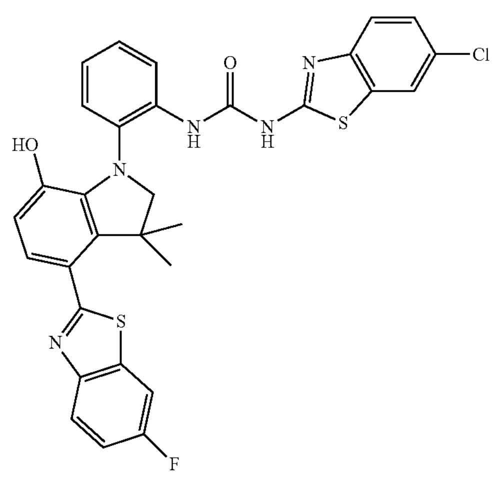 [SMILES: CC1(C)CN(c2ccccc2NC(=O)Nc2nc3ccc(Cl)cc3s2)c2c(O)ccc(-c3nc4ccc(F)cc4s3)c21] | m/z 616.4 (M + H)+, RT = 2.13 min (Method D) |

-continued

| Example No. | Compound Name | Compound Structure | LC-MS |
|---|---|---|---|
| 129 | 1-(2-(6-Fluoro-7-hydroxy-3,3-dimethyl-4-(5-(trifluoromethyl)pyridin-2-yl)indolin-1-yl)phenyl)-3-(4-(trifluoromethoxy)phenyl)urea | 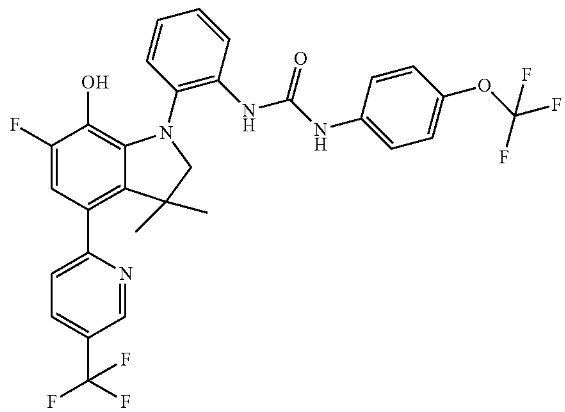 [SMILES: CC1(C)CN(c2ccccc2NC(=O)Nc2ccc(OC(F)(F)F)cc2)c2c(O)c(F)cc(-c3ccc(C(F)(F)F)cn3)c21] | m/z 621.0 (M + H)+, RT = 2.13 min (Method D) |
| 130 | 1-(2-(4-(6-Chlorobenzo[d]thiazol-2-yl)-6-fluoro-7-hydroxy-3,3-dimethylindolin-1-yl)phenyl)-3-(4-(trifluoromethoxy)phenyl)urea | 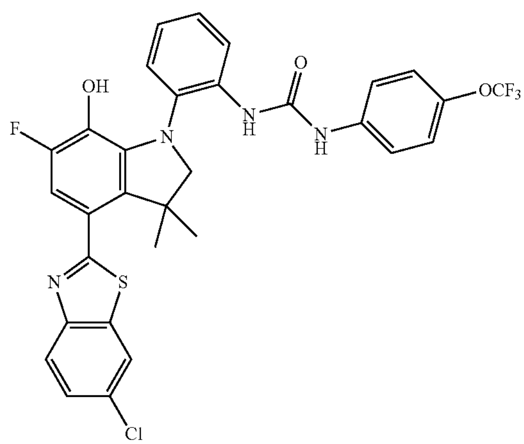 [SMILES: CC1(C)CN(c2ccccc2NC(=O)Nc2ccc(OC(F)(F)F)cc2)c2c(O)c(F)cc(-c3nc4ccc(Cl)cc4s3)c21] | m/z 643.0 (M + H)+, RT = 2.29 min (Method D) |
| 131 | 1-(2-(4-(5-Chloropyrazin-2-yl)-7-hydroxy-3,3-dimethylindolin-1-yl)phenyl)-3-(4-(trifluoromethoxy)phenyl)urea | 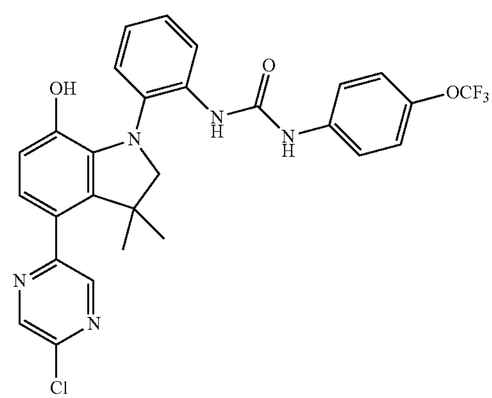 [SMILES: CC1(C)CN(c2ccccc2NC(=O)Nc2ccc(OC(F)(F)F)cc2)c2c(O)ccc(-c3cnc(Cl)cn3)c21] | m/z 570.0 (M + H)+, RT = 2.14 min (Method D) |
| 132 | 1-(2-(7-Hydroxy-3,3-dimethyl-4-(pyrazin-2-yl)indolin-1-yl)phenyl)-3-(4-(trifluoromethoxy)phenyl)urea | 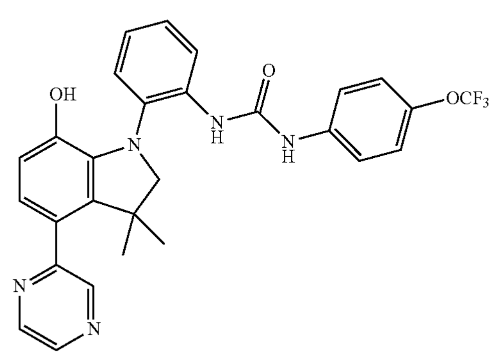 [SMILES: CC1(C)CN(c2ccccc2NC(=O)Nc2ccc(OC(F)(F)F)cc2)c2c(O)ccc(-c3cnccn3)c21] | m/z 536.0 (M + H)+, RT = 1.95 min (Method D) |

-continued

| Example No. | Compound Name | Compound Structure | LC-MS |
|---|---|---|---|
| 133 | 1-(2-(4-(5-Fluoropyrimidin-2-yl)-7-hydroxy-3,3-dimethylindolin-1-yl)phenyl)-3-(4-(trifluoromethoxy)phenyl)urea | 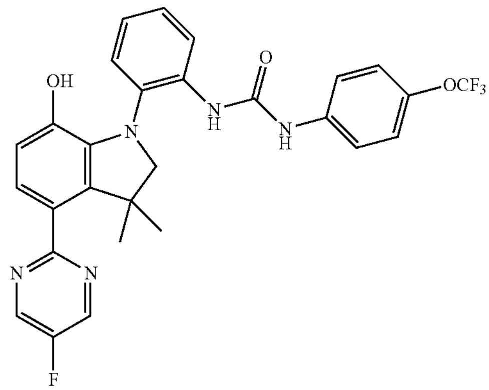 [SMILES: CC1(C)CN(c2ccccc2NC(=O)Nc2ccc(OC(F)(F)F)cc2)c2c(O)ccc(-c3ncc(F)cn3)c21] | m/z 554.0 (M + H)+, RT = 3.84 min (Method C) |
| 134 | 1-(2-(4-(6-Chlorobenzo[d]oxazol-2-yl)-7-hydroxy-3,3-dimethylindolin-1-yl)phenyl)-3-(6-fluorobenzo[d]thiazol-2-yl)urea | 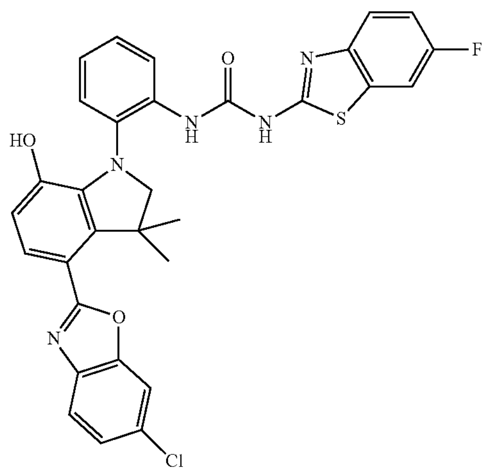 [SMILES: CC1(C)CN(c2ccccc2NC(=O)Nc2nc3ccc(F)cc3s2)c2c(O)ccc(-c3nc4ccc(Cl)cc4o3)c21] | m/z 600.0 (M + H)+, RT = 2.30 min (Method D) |
| 135 | 1-(2-(5-Fluoro-7-hydroxy-3,3-dimethyl-4-(6-(trifluoromethyl)pyridin-3-yl)indolin-1-yl)phenyl)-3-(4-(trifluoromethoxy)phenyl)urea | 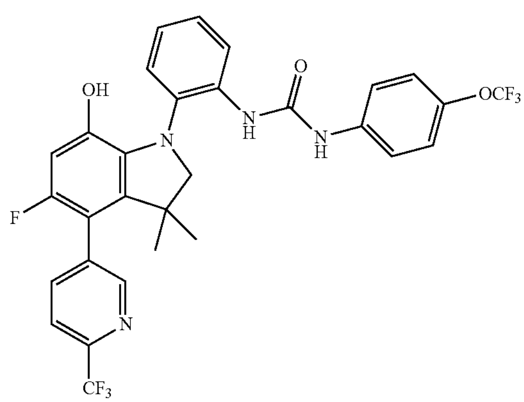 [SMILES: CC1(C)CN(c2ccccc2NC(=O)Nc2ccc(OC(F)(F)F)cc2)c2c(O)cc(F)c(-c3ccc(C(F)(F)F)nc3)c21] | m/z 621.0 (M + H)+, RT = 4.00 min (Method C) |

-continued

| Example No. | Compound Name | Compound Structure | LC-MS |
|---|---|---|---|
| 136 | 1-(2-(4-(6-Chlorobenzo[d]thiazol-2-yl)-7-hydroxy-3,3-dimethylindolin-1-yl)phenyl)-3-(4-(trifluoromethoxy)phenyl)urea | 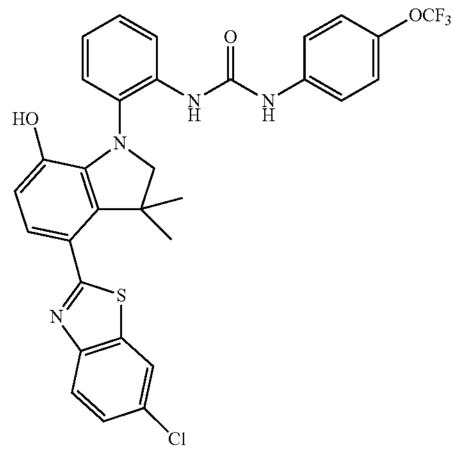 [SMILES: CC1(C)CN(c2ccccc2NC(=O)Nc2ccc(OC(F)(F)F)cc2)c2c(O)ccc(-c3nc4ccc(Cl)cc4s3)c21] | m/z 626.0 (M + H)+, RT = 2.30 min (Method D) |
| 137 | 1-(2-(4-(6-Chlorobenzo[d]thiazol-2-yl)-7-hydroxy-3,3-dimethylindolin-1-yl)phenyl)-3-(6-fluorobenzo[d]thiazol-2-yl)urea | 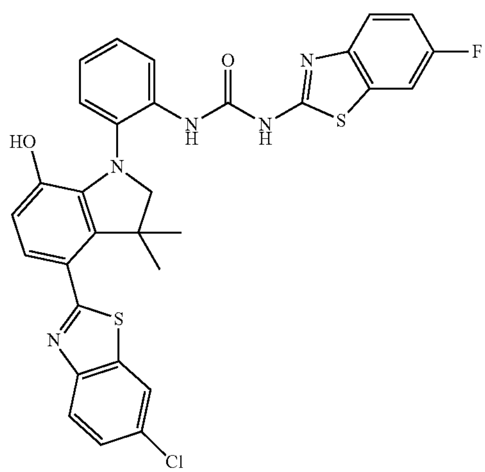 [SMILES: CC1(C)CN(c2ccccc2NC(=O)Nc2nc3ccc(F)cc3s2)c2c(O)ccc(-c3nc4ccc(Cl)cc4s3)c21] | m/z 617.0 (M + H)+, RT = 4.39 min (Method C) |
| 138 | 1-(2-(4-(5-Chlorobenzo[d]thiazol-2-yl)-5-fluoro-7-hydroxy-3,3-dimethylindolin-1-yl)phenyl)-3-(6-fluorobenzo[d]thiazol-2-yl)urea | 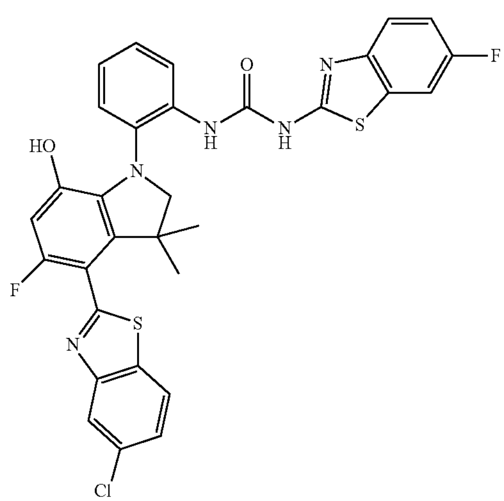 [SMILES: CC1(C)CN(c2ccccc2NC(=O)Nc2nc3ccc(F)cc3s2)c2c(O)cc(F)c(-c3nc4cc(Cl)ccc4s3)c21] | m/z 635.0 (M + H)+, RT = 4.38 min (Method C) |

-continued

| Example No. | Compound Name | Compound Structure | LC-MS |
|---|---|---|---|
| 139 | 1-(6-Chlorobenzo[d]thiazol-2-yl)-3-(2-(5-fluoro-4-(6-fluorobenzo[d]thiazol-2-yl)-7-hydroxy-3,3-dimethylindolin-1-yl)phenyl)urea | 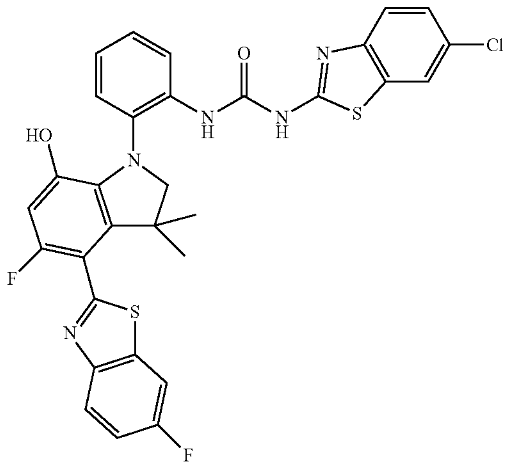 [SMILES: CC1(C)CN(c2ccccc2NC(=O)Nc2nc3ccc(Cl)cc3s2)c2c(O)cc(F)c(-c3nc4ccc(F)cc4s3)c21] | m/z 635.0 (M + H)+, RT = 4.38 min (Method C) |
| 140 | 1-(2-(4-(5-Chlorothiophen-2-yl)-5-fluoro-7-hydroxy-3,3-dimethylindolin-1-yl)phenyl)-3-(6-fluorobenzo[d]thiazol-2-yl)urea | 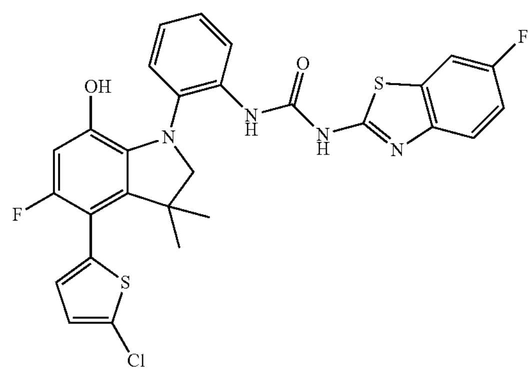 [SMILES: CC1(C)CN(c2ccccc2NC(=O)Nc2nc3ccc(F)cc3s2)c2c(O)cc(F)c(-c3ccc(Cl)s3)c21] | m/z 583.0 (M + H)+, RT = 2.27 min (Method D) |
| 141 | 1-(2-(4-(5-Chlorobenzo[d]thiazol-2-yl)-5-fluoro-7-hydroxy-3,3-dimethylindolin-1-yl)phenyl)-3-(5-chlorothiazolo[5,4-b]pyridin-2-yl)urea | 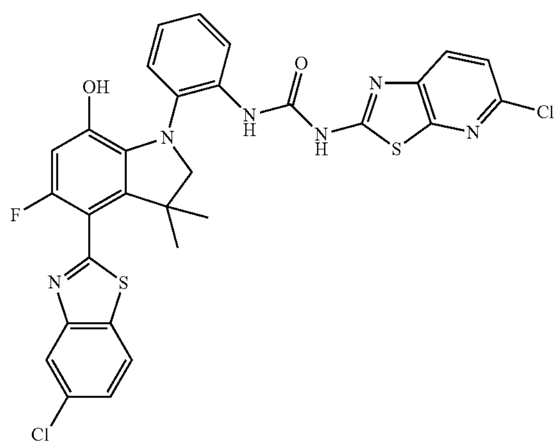 [SMILES: CC1(C)CN(c2ccccc2NC(=O)Nc2nc3ccc(Cl)nc3s2)c2c(O)cc(F)c(-c3nc4cc(Cl)ccc4s3)c21] | m/z 652.0 (M + H)+, RT = 3.97 min (Method C) |

| Example No. | Compound Name | Compound Structure | LC-MS |
|---|---|---|---|
| 142 | 1-(2-(4-(5-Chlorothiophen-2-yl)-5-fluoro-7-hydroxy-3,3-dimethylindolin-1-yl)phenyl)-3-(4-(trifluoromethoxy)phenyl)urea | 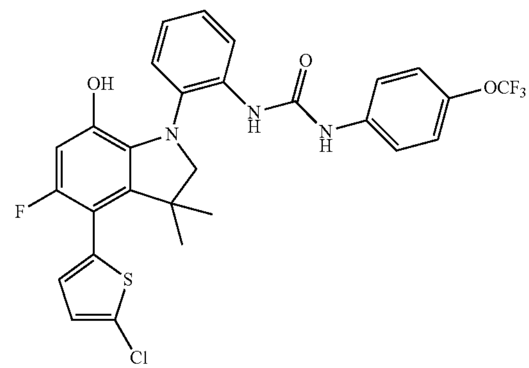 [SMILES: CC1(C)CN(c2ccccc2NC(=O)Nc2ccc(OC(F)(F)F)cc2)c2c(O)cc(F)c(-c3ccc(Cl)s3)c21] | m/z 593.0 (M + H)$^+$, RT = 2.20 min (Method D) |
| 143 | 1-(5-Chlorothiazolo[5,4-b]pyridin-2-yl)-3-(2-(5-fluoro-4-(6-fluorobenzo[d]thiazol-2-yl)-7-hydroxy-3,3-dimethylindolin-1-yl)phenyl)urea | 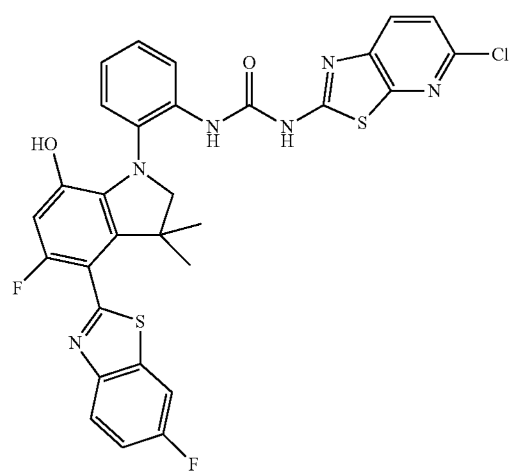 [SMILES: CC1(C)CN(c2ccccc2NC(=O)Nc2nc3ccc(Cl)nc3s2)c2c(O)cc(F)c(-c3nc4ccc(F)cc4s3)c21] | m/z 636.0 (M + H)$^+$, RT = 2.20 min (Method D) |
| 144 | 1-(2-(5-Fluoro-4-(6-fluorobenzo[d]thiazol-2-yl)-7-hydroxy-3,3-dimethylindolin-1-yl)phenyl)-3-(4-(trifluoromethoxy)phenyl)urea | 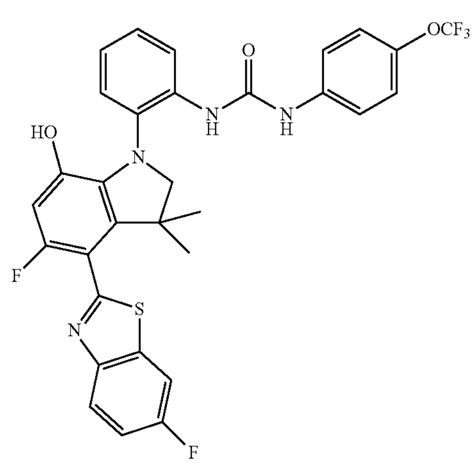 [SMILES: CC1(C)CN(c2ccccc2NC(=O)Nc2ccc(OC(F)(F)F)cc2)c2c(O)cc(F)c(-c3nc4ccc(F)cc4s3)c21] | m/z 627.0 (M + H)$^+$, RT = 2.17 min (Method D) |

-continued

| Example No. | Compound Name | Compound Structure | LC-MS |
|---|---|---|---|
| 145 | 1-(5-Chlorothiazolo[5,4-b]pyridin-2-yl)-3-(2-(4-(5-chlorothiophen-2-yl)-5-fluoro-7-hydroxy-3,3-dimethylindolin-1-yl)phenyl)urea | 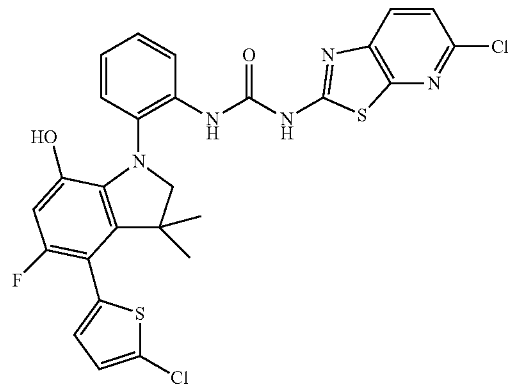 [SMILES: CC1(C)CN(c2ccccc2NC(=O)Nc2nc3ccc(Cl)nc3s2)c2c(O)cc(F)c(-c3ccc(Cl)s3)c21] | m/z 601.0 (M + H)+, RT = 2.24 min (Method D) |
| 146 | 1-(2-(5-Fluoro-4-(6-fluorobenzo[d]thiazol-2-yl)-7-hydroxy-3,3-dimethylindolin-1-yl)phenyl)-3-(6-fluorobenzo[d]thiazol-2-yl)urea | 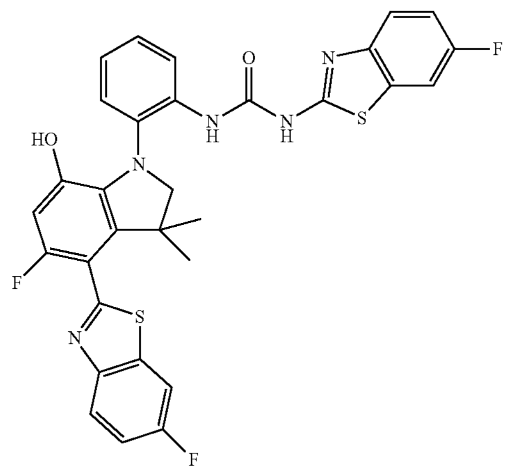 [SMILES: CC1(C)CN(c2ccccc2NC(=O)Nc2nc3ccc(F)cc3s2)c2c(O)cc(F)c(-c3nc4ccc(F)cc4s3)c21] | m/z 618.0 (M + H)+, RT = 2.19 min (Method D) |
| 147 | 1-(2-(4-(5-Chlorobenzo[d]thiazol-2-yl)-7-hydroxy-3,3-dimethylindolin-1-yl)phenyl)-3-(2-chlorothiazol-4-yl)urea | 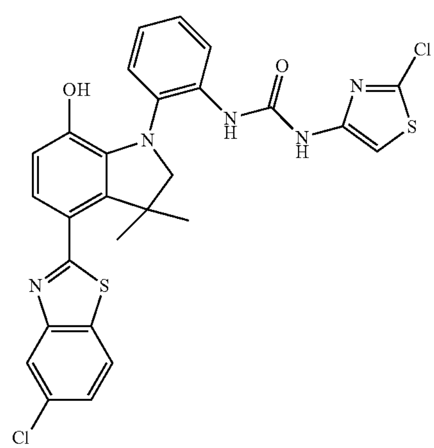 [SMILES: CC1(C)CN(c2ccccc2NC(=O)Nc2csc(Cl)n2)c2c(O)ccc(-c3nc4cc(Cl)ccc4s3)c21] | m/z 582.0 (M + H)+, RT = 2.27 min (Method D) |

-continued

| Example No. | Compound Name | Compound Structure | LC-MS |
|---|---|---|---|
| 148 | 1-(2-(4-(6-Chlorobenzo[d]thiazol-2-yl)-5-fluoro-7-hydroxy-3,3-dimethylindolin-1-yl)phenyl)-3-(4-(trifluoromethoxy)phenyl)urea | 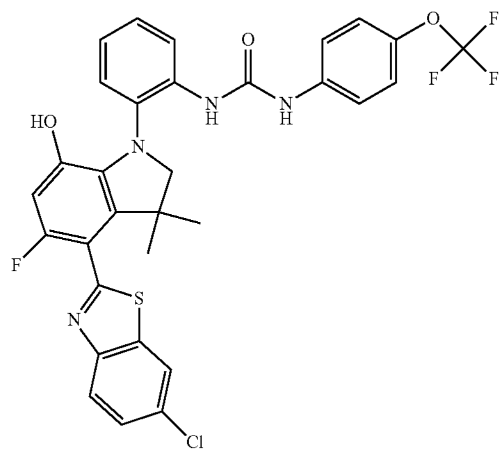 [SMILES: CC1(C)CN(c2ccccc2NC(=O)Nc2ccc(OC(F)(F)F)cc2)c2c(O)cc(F)c(-c3nc4ccc(Cl)cc4s3)c21] | m/z 643.1 (M + H)+, RT = 4.42 min (Method C) |
| 149 | 1-(2-(5-Fluoro-7-hydroxy-3,3-dimethyl-4-(5-(trifluoromethyl)pyridin-2-yl)indolin-1-yl)phenyl)-3-(4-(trifluoromethoxy)phenyl)urea | 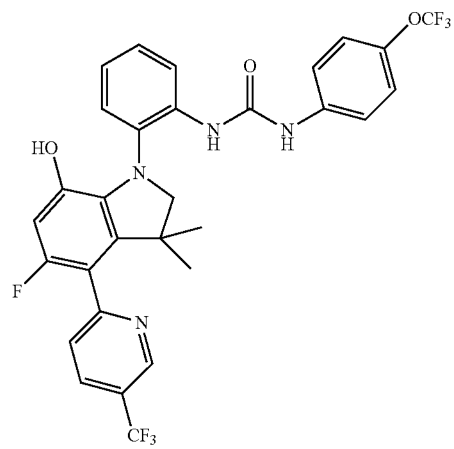 [SMILES: CC1(C)CN(c2ccccc2NC(=O)Nc2ccc(OC(F)(F)F)cc2)c2c(O)cc(F)c(-c3ccc(C(F)(F)F)cn3)c21] | m/z 621.0 (M + H)+, RT = 2.07 min (Method D) |
| 150 | 1-(2-Chlorothiazol-4-yl)-3-(2-(5-fluoro-4-(6-fluorobenzo[d]thiazol-2-yl)-7-hydroxy-3,3-dimethylindolin-1-yl)phenyl)urea | 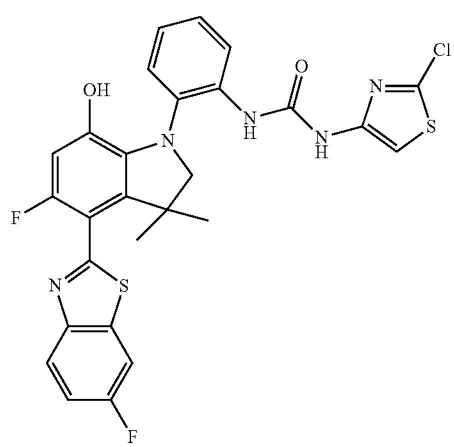 [SMILES: CC1(C)CN(c2ccccc2NC(=O)Nc2csc(Cl)n2)c2c(O)cc(F)c(-c3nc4ccc(F)cc4s3)c21] | m/z 584.0 (M + H)+, RT = 3.66 min (Method C) |

-continued

| Example No. | Compound Name | Compound Structure | LC-MS |
|---|---|---|---|
| 151 | 1-(2-(5-Fluoro-4-(5-fluorobenzo[d]thiazol-2-yl)-7-hydroxy-3,3-dimethylindolin-1-yl)phenyl)-3-(4-(trifluoromethoxy)phenyl)urea | 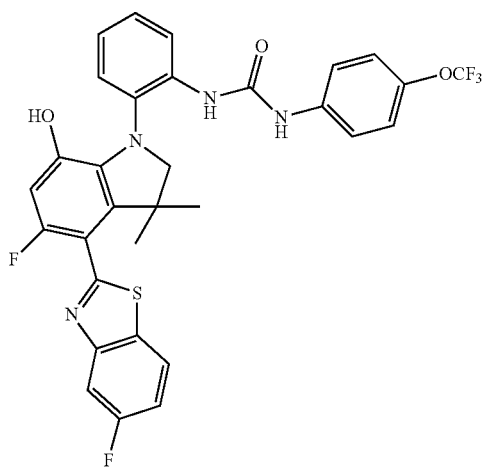 [SMILES: CC1(C)CN(c2ccccc2NC(=O)Nc2ccc(OC(F)(F)F)cc2)c2c(O)cc(F)c(-c3nc4cc(F)ccc4s3)c21] | m/z 626.9 (M + H)+, RT = 2.19 min (Method D) |
| 152 | 1-(2-(5-Fluoro-4-(5-fluorobenzo[d]thiazol-2-yl)-7-hydroxy-3,3-dimethylindolin-1-yl)phenyl)-3-(6-fluorobenzo[d]thiazol-2-yl)urea | 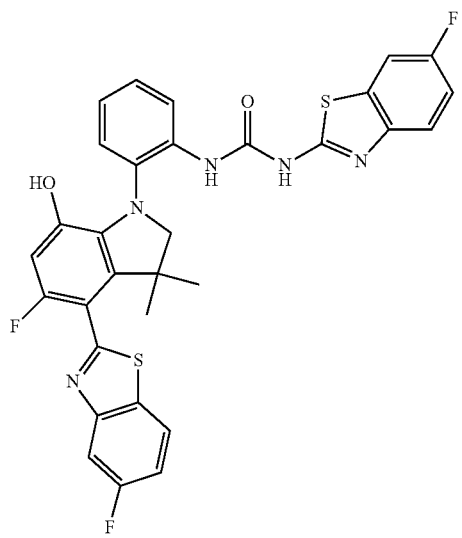 [SMILES: CC1(C)CN(c2ccccc2NC(=O)Nc2nc3ccc(F)cc3s2)c2c(O)cc(F)c(-c3nc4cc(F)ccc4s3)c21] | m/z 617.9 (M + H)+, RT = 4.20 min (Method C) |
| 153 | 1-(5-Chlorothiazolo[5,4-b]pyridin-2-yl)-3-(2-(5-fluoro-4-(5-fluorobenzo[d]thiazol-2-yl)-7-hydroxy-3,3-dimethylindolin-1-yl)phenyl)urea | 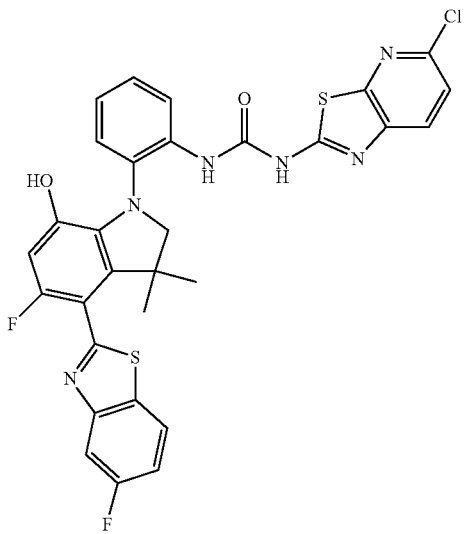 [SMILES: CC1(C)CN(c2ccccc2NC(=O)Nc2nc3ccc(Cl)nc3s2)c2c(O)cc(F)c(-c3nc4cc(F)ccc4s3)c21] | m/z 634.9 (M + H)+, RT = 4.20 min (Method C) |

-continued

| Example No. | Compound Name | Compound Structure | LC-MS |
|---|---|---|---|
| 154 | 1-(6-Chlorobenzo[d]thiazol-2-yl)-3-(2-(5-fluoro-4-(5-fluorobenzo[d]thiazol-2-yl)-7-hydroxy-3,3-dimethylindolin-1-yl)phenyl)urea | 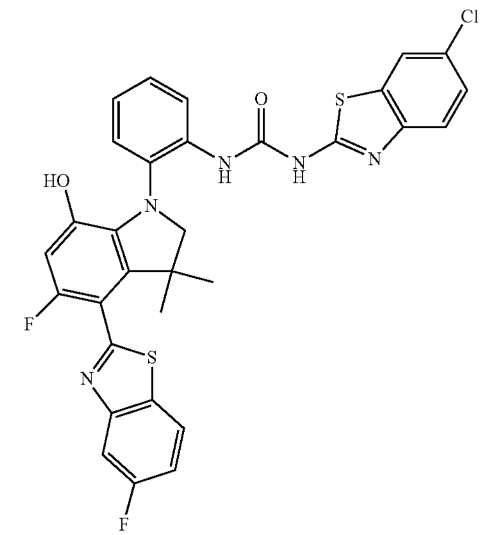 [SMILES: CC1(C)CN(c2ccccc2NC(=O)Nc2nc3ccc(Cl)cc3s2)c2c(O)cc(F)c(-c3nc4cc(F)ccc4s3)c21] | m/z 633.8 (M + H)+, RT = 4.39 min (Method C) |
| 155 | 1-(2-(4-(6-Chlorobenzo[d]thiazol-2-yl)-5-fluoro-7-hydroxy-3,3-dimethylindolin-1-yl)phenyl)-3-(6-fluorobenzo[d]thiazol-2-yl)urea | 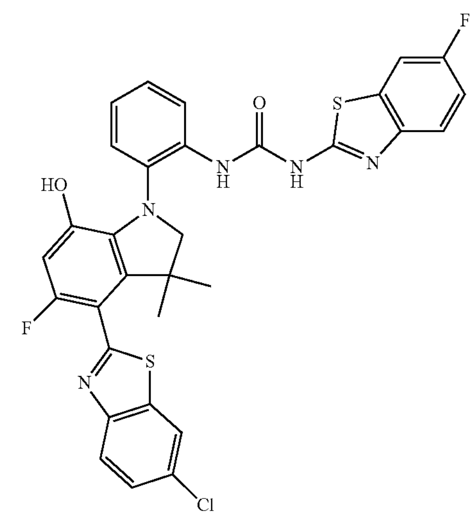 [SMILES: CC1(C)CN(c2ccccc2NC(=O)Nc2nc3ccc(F)cc3s2)c2c(O)cc(F)c(-c3nc4ccc(Cl)cc4s3)c21] | m/z 633.9 (M + H)+, RT = 2.30 min (Method D) |
| 156 | 1-(6-Chlorobenzo[d]thiazol-2-yl)-3-(2-(4-(5-chlorobenzo[d]thiazol-2-yl)-5-fluoro-7-hydroxy-3,3-dimethylindolin-1-yl)phenyl)urea | 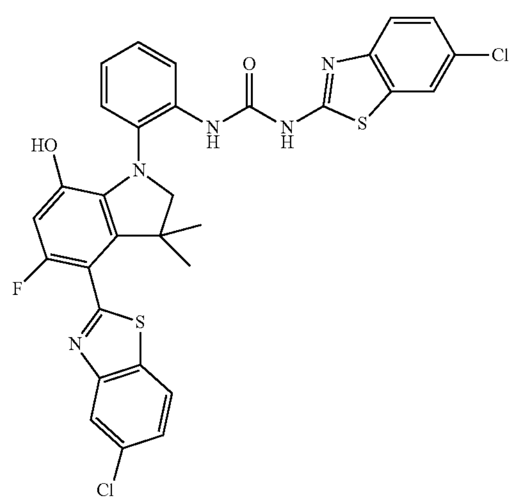 [SMILES: CC1(C)CN(c2ccccc2NC(=O)Nc2nc3ccc(Cl)cc3s2)c2c(O)cc(F)c(-c3nc4cc(Cl)ccc4s3)c21] | m/z 651.0 (M + H)+, RT = 2.36 min (Method D) |

-continued

| Example No. | Compound Name | Compound Structure | LC-MS |
|---|---|---|---|
| 157 | 1-(2-(4-(5-Chlorobenzo[d]thiazol-2-yl)-5-fluoro-7-hydroxy-3,3-dimethylindolin-1-yl)phenyl)-3-(5-fluorothiazolo[5,4-b]pyridin-2-yl)urea | 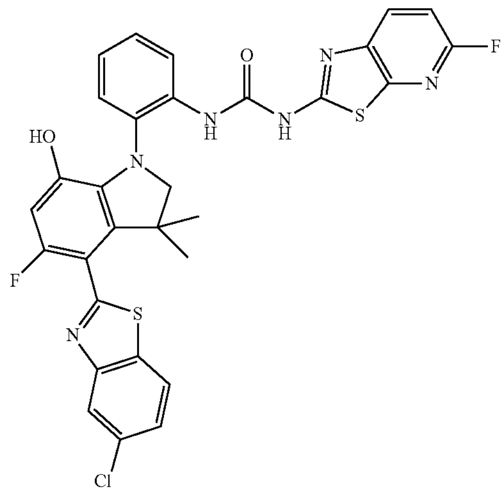 [SMILES: CC1(C)CN(c2ccccc2NC(=O)Nc2nc3ccc(F)nc3s2)c2c(O)cc(F)c(-c3nc4cc(Cl)ccc4s3)c21] | m/z 635.0 (M + H)+, RT = 2.23 min (Method D) |
| 158 | 1-(2-(5-Fluoro-7-hydroxy-3,3-dimethyl-4-(6-(trifluoromethyl)pyridin-3-yl)indolin-1-yl)phenyl)-3-(6-fluorobenzo[d]thiazol-2-yl)urea | 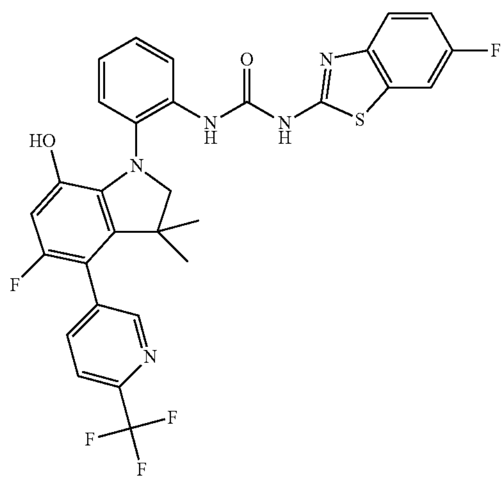 [SMILES: CC1(C)CN(c2ccccc2NC(=O)Nc2nc3ccc(F)cc3s2)c2c(O)cc(F)c(-c3ccc(C(F)(F)F)nc3)c21] | m/z 612.0 (M + H)+, RT = 2.10 min (Method D) |
| 159 | 1-(2-(5-Fluoro-4-(5-fluoropyridin-2-yl)-7-hydroxy-3,3-dimethylindolin-1-yl)phenyl)-3-(4-(trifluoromethoxy)phenyl)urea | 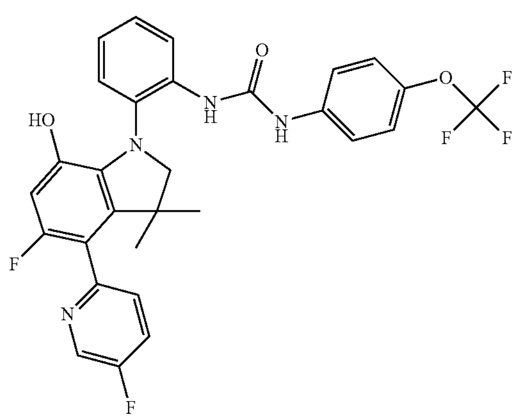 [SMILES: CC1(C)CN(c2ccccc2NC(=O)Nc2ccc(OC(F)(F)F)cc2)c2c(O)cc(F)c(-c3ccc(F)cn3)c21] | m/z 571.3 (M + H)+, RT = 3.91 min (Method C) |

-continued

| Example No. | Compound Name | Compound Structure | LC-MS |
|---|---|---|---|
| 160 | 1-(2-(4-(2-(tert-Butyl)pyrimidin-5-yl)-5-fluoro-7-hydroxy-3,3-dimethylindolin-1-yl)phenyl)-3-(4-(trifluoromethoxy)phenyl)urea | 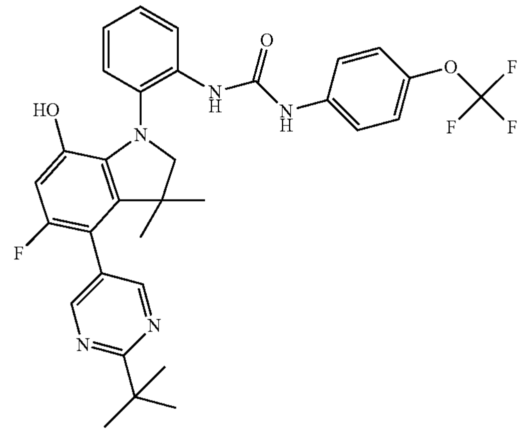 [SMILES: CC(C)(C)c1ncc(-c2c(F)cc(O)c3c2C(C)(C)CN3c2ccccc2NC(=O)Nc2ccc(OC(F)(F)F)cc2)cn1] | m/z 610.4 (M + H)+, RT = 4.19 min (Method C) |
| 161 | 1-(2-(4-(2,6-Difluoropyridin-4-yl)-5-fluoro-7-hydroxy-3,3-dimethylindolin-1-yl)phenyl)-3-(4-(trifluoromethoxy)phenyl)urea | 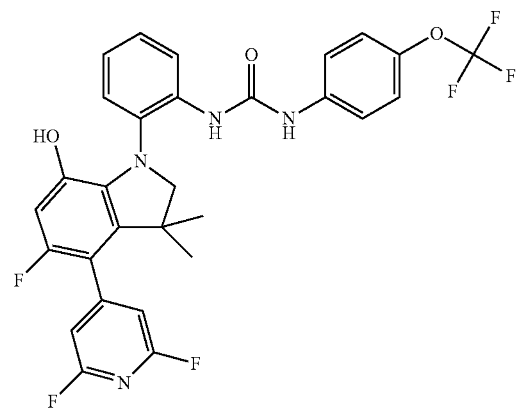 [SMILES: CC1(C)CN(c2ccccc2NC(=O)Nc2ccc(OC(F)(F)F)cc2)c2c(O)cc(F)c(-c3cc(F)nc(F)c3)c21] | m/z 589.0 (M + H)+, RT = 2.08 min (Method D) |
| 162 | 1-(2-(4-(5-Chloropyridin-2-yl)-5-fluoro-7-hydroxy-3,3-dimethylindolin-1-yl)phenyl)-3-(4-(trifluoromethoxy)phenyl)urea | 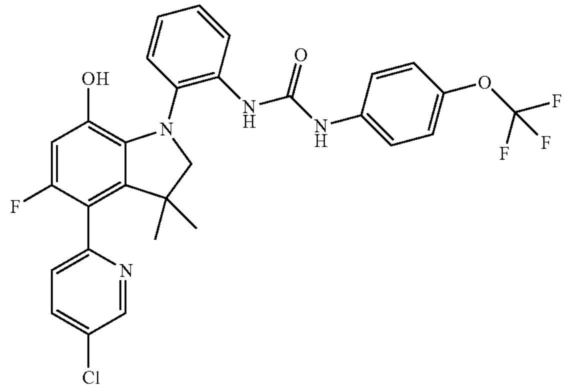 [SMILES: CC1(C)CN(c2ccccc2NC(=O)Nc2ccc(OC(F)(F)F)cc2)c2c(O)cc(F)c(-c3ccc(Cl)cn3)c21] | m/z 587.3 (M + H)+, RT = 3.62 min (Method C) |

-continued

| Example No. | Compound Name | Compound Structure | LC-MS |
|---|---|---|---|
| 163 | 1-(2-(4-(5-Chloropyrazin-2-yl)-5-fluoro-7-hydroxy-3,3-dimethylindolin-1-yl)phenyl)-3-(4-(trifluoromethoxy)phenyl)urea | 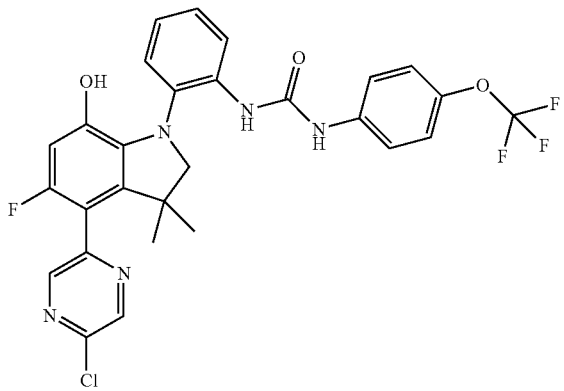 [SMILES: CC1(C)CN(c2ccccc2NC(=O)Nc2ccc(OC(F)(F)F)cc2)c2c(O)cc(F)c(-c3cnc(Cl)cn3)c21] | m/z 588.0 (M + H)+, RT = 3.57 min (Method C) |
| 164 | 1-(2-(5-Fluoro-4-(5-fluoropyrimidin-2-yl)-7-hydroxy-3,3-dimethylindolin-1-yl)phenyl)-3-(4-(trifluoromethoxy)phenyl)urea | 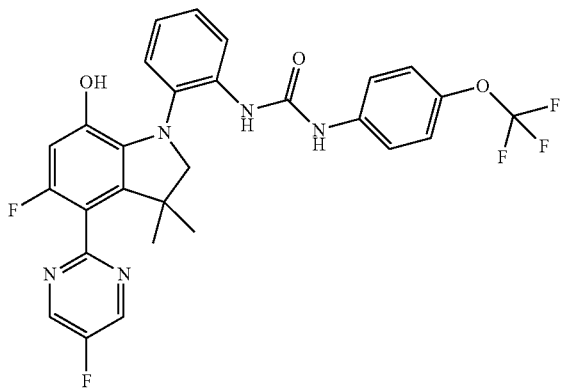 [SMILES: CC1(C)CN(c2ccccc2NC(=O)Nc2ccc(OC(F)(F)F)cc2)c2c(O)cc(F)c(-c3ncc(F)cn3)c21] | m/z 571.9 (M + H)+, RT = 1.99 min (Method D) |
| 165 | 1-(2-(4-(6-(tert-Butyl)pyridin-3-yl)-5-fluoro-7-hydroxy-3,3-dimethylindolin-1-yl)phenyl)-3-(4-(trifluoromethoxy)phenyl)urea | 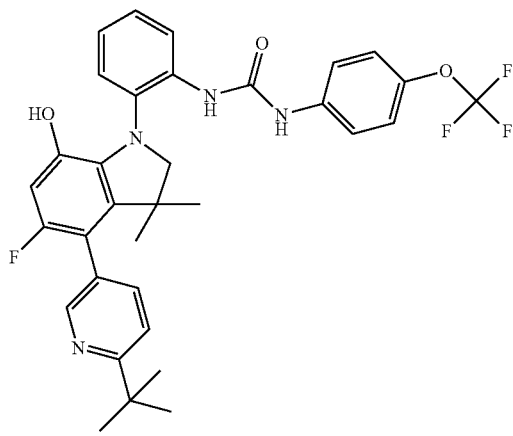 [SMILES: CC(C)(C)c1ccc(-c2c(F)cc(O)c3c2C(C)(C)CN3c2ccccc2NC(=O)Nc2ccc(OC(F)(F)F)cc2)cn1] | m/z 609.0 (M + H)+, RT = 1.95 min (Method D) |

-continued

| Example No. | Compound Name | Compound Structure | LC-MS |
|---|---|---|---|
| 166 | 1-(2-(4-(5-Bromopyrimidin-2-yl)-5-fluoro-7-hydroxy-3,3-dimethylindolin-1-yl)phenyl)-3-(4-(trifluoromethoxy)phenyl)urea | 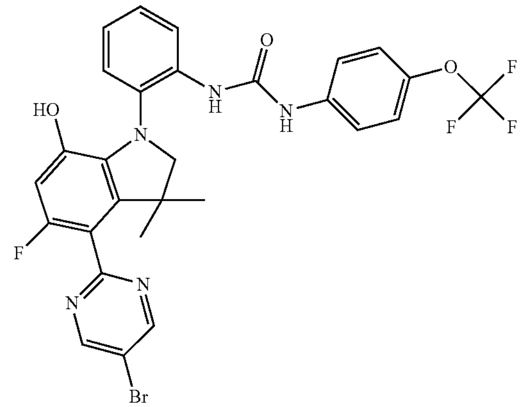 [SMILES: CC1(C)CN(c2ccccc2NC(=O)Nc2ccc(OC(F)(F)F)cc2)c2c(O)cc(F)c(-c3ncc(Br)cn3)c21] | m/z 633.8 (M + H)+, RT = 4.39 min (Method C) |
| 167 | 1-(2-(4-(5-Chlorobenzo[d]thiazol-2-yl)-5-fluoro-7-hydroxy-3,3-dimethylindolin-1-yl)phenyl)-3-(2-chlorothiazol-4-yl)urea | 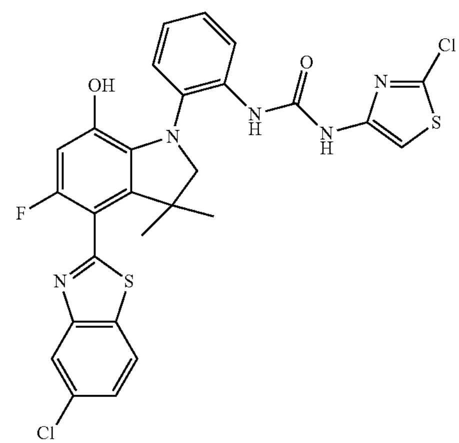 [SMILES: CC1(C)CN(c2ccccc2NC(=O)Nc2csc(Cl)n2)c2c(O)cc(F)c(-c3nc4cc(Cl)ccc4s3)c21] | m/z 601.0 (M + H)+, RT = 4.09 min (Method C) |
| 168 | 1-(2-(5-Fluoro-7-hydroxy-3,3-dimethyl-4-(5-(trifluoromethyl)pyridin-2-yl)indolin-1-yl)phenyl)-3-(6-fluorobenzo[d]thiazol-2-yl)urea | 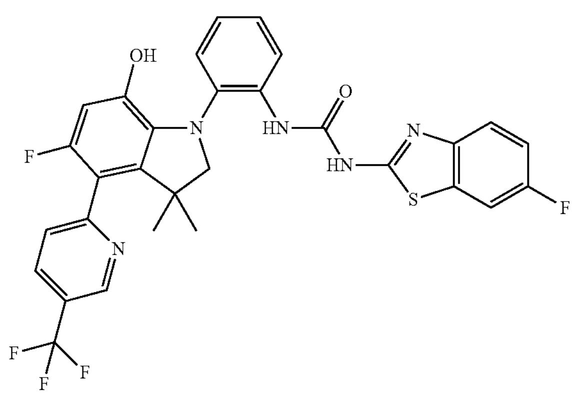 [SMILES: CC1(C)CN(c2ccccc2NC(=O)Nc2nc3ccc(F)cc3s2)c2c(O)cc(F)c(-c3ccc(C(F)(F)F)cn3)c21] | m/z 612.0 (M + H)+, RT = 4.13 min (Method C) |

| Example No. | Compound Name | Compound Structure | LC-MS |
|---|---|---|---|
| 169 | 1-(2-Chlorothiazol-4-yl)-3-(2-(5-fluoro-7-hydroxy-3,3-dimethyl-4-(5-(trifluoromethyl)pyridin-2-yl)indolin-1-yl)phenyl)urea | 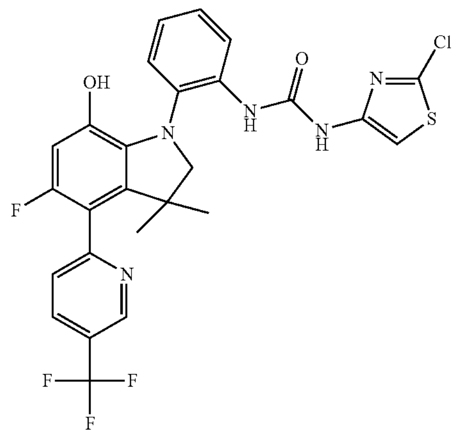 [SMILES: CC1(C)CN(c2ccccc2NC(=O)Nc2csc(Cl)n2)c2c(O)cc(F)c(-c3ccc(C(F)(F)F)cn3)c21] | m/z 578.0 (M + H)+, RT = 3.97 min (Method C) |
| 170 | 1-(2-(4-(5-Fluorobenzo[d]thiazol-2-yl)-7-hydroxy-3,3-dimethylindolin-1-yl)phenyl)-3-(4-(trifluoromethoxy)phenyl)urea | 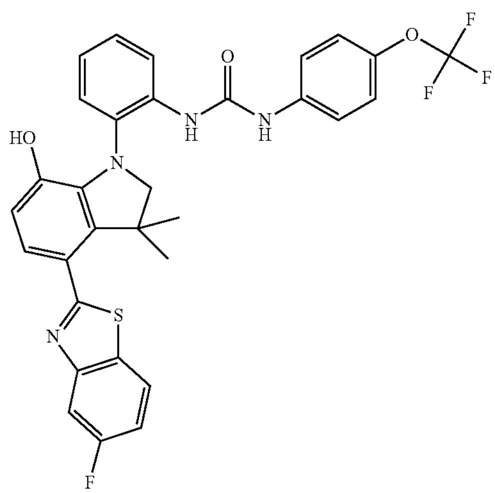 [SMILES: CC1(C)CN(c2ccccc2NC(=O)Nc2ccc(OC(F)(F)F)cc2)c2c(O)ccc(-c3nc4cc(F)ccc4s3)c21] | m/z 609.0 (M + H)+, RT = 2.71 min (Method D) |
| 171 | 1-(6-Fluorobenzo[d]thiazol-2-yl)-3-(2-(4-(5-fluorobenzo[d]thiazol-2-yl)-7-hydroxy-3,3-dimethylindolin-1-yl)phenyl)urea | 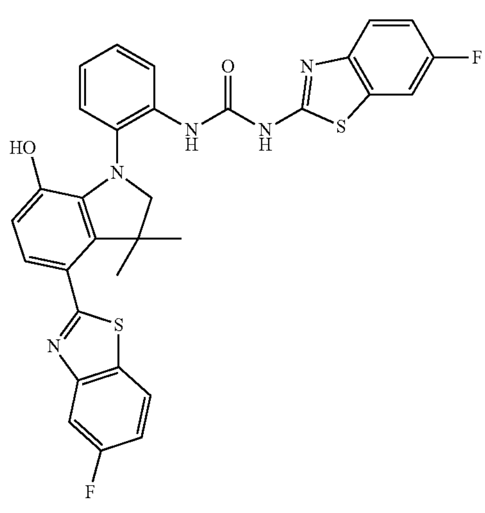 [SMILES: CC1(C)CN(c2ccccc2NC(=O)Nc2nc3ccc(F)cc3s2)c2c(O)ccc(-c3nc4cc(F)ccc4s3)c21] | m/z 600.0 (M + H)+, RT = 2.52 min (Method D) |

-continued

| Example No. | Compound Name | Compound Structure | LC-MS |
|---|---|---|---|
| 172 | 1-(6-Chlorobenzo[d]thiazol-2-yl)-3-(2-(4-(5-fluorobenzo[d]thiazol-2-yl)-7-hydroxy-3,3-dimethylindolin-1-yl)phenyl)urea, TFA | 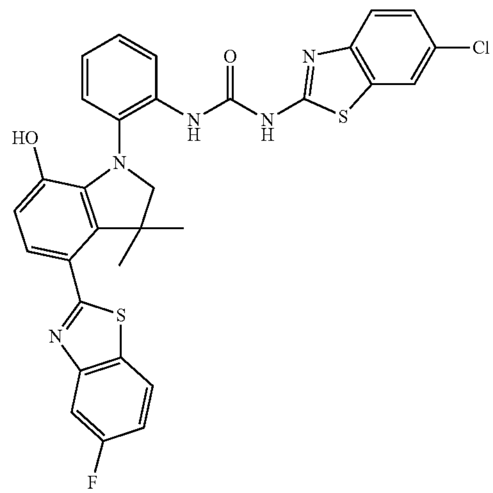 [SMILES: CC1(C)CN(c2ccccc2NC(=O)Nc2nc3ccc(Cl)cc3s2)c2c(O)ccc(-c3nc4cc(F)ccc4s3)c21] | m/z 617.0 (M + H)+, RT = 2.63 min (Method D) |
| 173 | 1-(5-Chlorothiazolo[5,4-b]pyridin-2-yl)-3-(2-(4-(5-fluorobenzo[d]thiazol-2-yl)-7-hydroxy-3,3-dimethylindolin-1-yl)phenyl)urea | 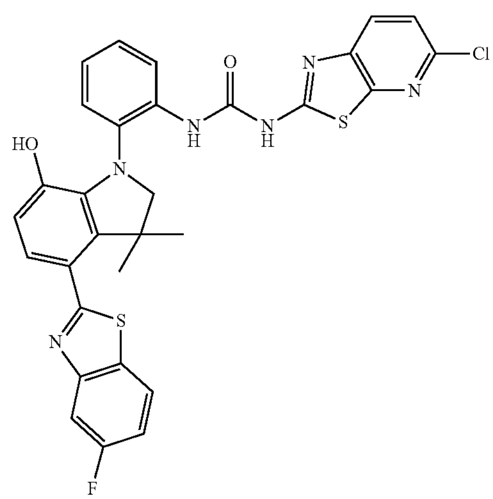 [SMILES: CC1(C)CN(c2ccccc2NC(=O)Nc2nc3ccc(Cl)nc3s2)c2c(O)ccc(-c3nc4cc(F)ccc4s3)c21] | m/z 617.6 (M + H)+, RT = 2.53 min (Method D) |
| 174 | 1-(2-(4-(6-Fluorobenzo[d]thiazol-2-yl)-7-hydroxy-3,3-dimethylindolin-1-yl)phenyl)-3-(4-(trifluoromethoxy)phenyl)urea | 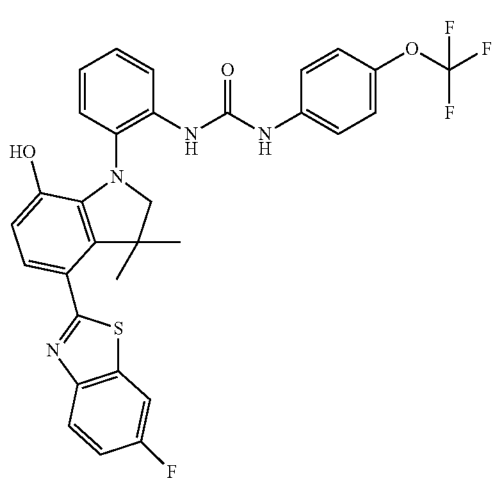 [SMILES: CC1(C)CN(c2ccccc2NC(=O)Nc2ccc(OC(F)(F)F)cc2)c2c(O)ccc(-c3nc4ccc(F)cc4s3)c21] | m/z 609.0 (M + H)+, RT = 2.47 min (Method D) |

-continued

| Example No. | Compound Name | Compound Structure | LC-MS |
|---|---|---|---|
| 175 | 1-(6-Fluorobenzo[d]thiazol-2-yl)-3-(2-(4-(6-fluorobenzo[d]thiazol-2-yl)-7-hydroxy-3,3-dimethylindolin-1-yl)phenyl)urea | 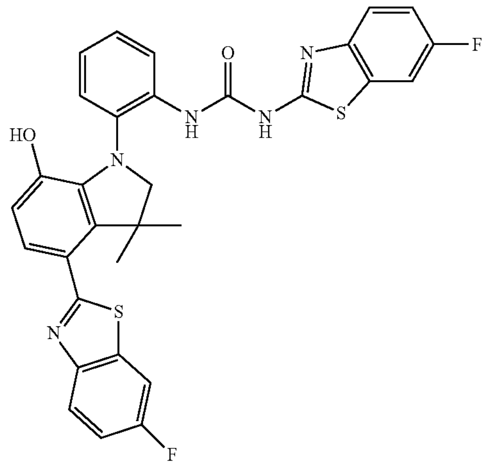 [SMILES: CC1(C)CN(c2ccccc2NC(=O)Nc2nc3ccc(F)cc3s2)c2c(O)ccc(-c3nc4ccc(F)cc4s3)c21] | m/z 600.0 (M + H)+, RT = 2.53 min (Method D) |
| 176 | 1-(5-Chlorothiazolo[5,4-b]pyridin-2-yl)-3-(2-(4-(6-fluorobenzo[d]thiazol-2-yl)-7-hydroxy-3,3-dimethylindolin-1-yl)phenyl)urea | 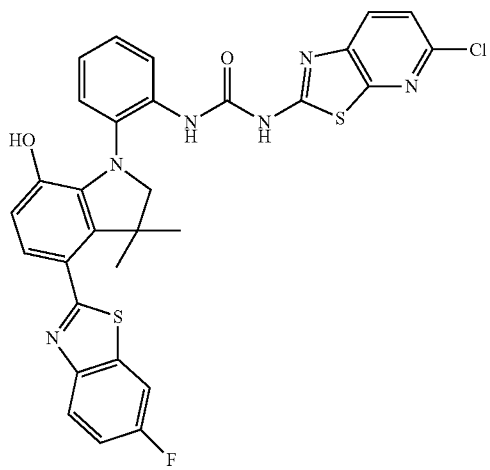 [SMILES: CC1(C)CN(c2ccccc2NC(=O)Nc2nc3ccc(Cl)nc3s2)c2c(O)ccc(-c3nc4ccc(F)cc4s3)c21] | m/z 617.0 (M + H)+, RT = 4.29 min (Method C) |
| 177 | 1-(2-(4-(5-Chlorobenzo[d]thiazol-2-yl)-6-fluoro-7-hydroxy-3,3-dimethylindolin-1-yl)phenyl)-3-(4-(trifluoromethoxy)phenyl)urea | 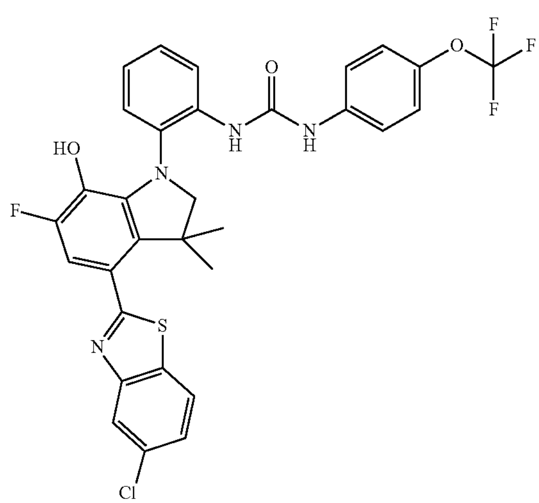 [SMILES: CC1(C)CN(c2ccccc2NC(=O)Nc2ccc(OC(F)(F)F)cc2)c2c(O)c(F)cc(-c3nc4cc(Cl)ccc4s3)c21] | m/z 644.0 (M + H)+, RT = 2.30 min (Method D) |

-continued

| Example No. | Compound Name | Compound Structure | LC-MS |
|---|---|---|---|
| 178 | 1-(2-(5-Fluoro-4-(6-fluorobenzo[d]thiazol-2-yl)-7-hydroxy-3,3-dimethylindolin-1-yl)phenyl)-3-(5-fluorothiazolo[5,4-b]pyridin-2-yl)urea | 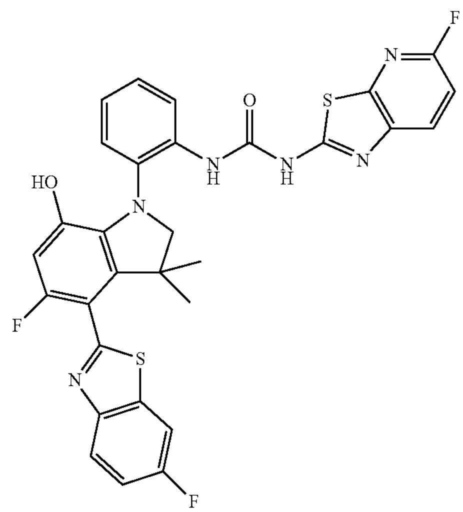 [SMILES: CC1(C)CN(c2ccccc2NC(=O)Nc2nc3ccc(F)nc3s2)c2c(O)cc(F)c(-c3nc4ccc(F)cc4s3)c21] | m/z 619.1 (M + H)+, RT = 1.20 min (Method B) |
| 179 | 1-(2-(5-Fluoro-4-(6-fluorobenzo[d]thiazol-2-yl)-7-hydroxy-3,3-dimethylindolin-1-yl)phenyl)-3-(6-methoxybenzo[d]thiazol-2-yl)urea | 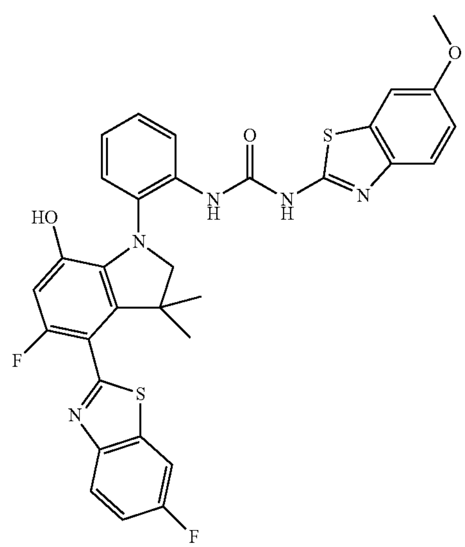 [SMILES: COc1ccc2nc(NC(=O)Nc3ccccc3N3CC(C)(C)c4c(-c5nc6ccc(F)cc6s5)c(F)cc(O)c43)sc2c1] | m/z 630.1 (M + H)+, RT = 1.20 min (Method B) |
| 180 | 1-(2-(4-(5-Chlorobenzo[d]thiazol-2-yl)-5-fluoro-7-hydroxy-3,3-dimethylindolin-1-yl)phenyl)-3-(2-(trifluoromethyl)thiazol-4-yl)urea | 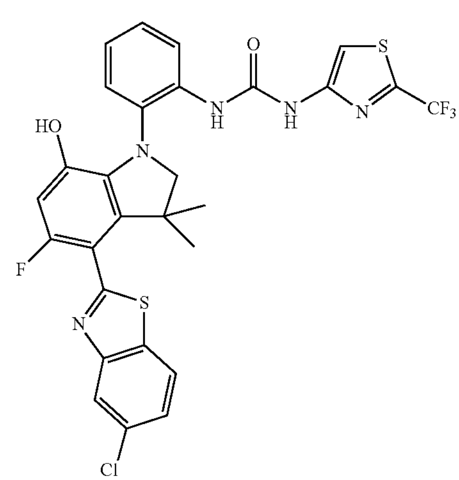 [SMILES: CC1(C)CN(c2ccccc2NC(=O)Nc2csc(C(F)(F)F)n2)c2c(O)cc(F)c(-c3nc4cc(Cl)ccc4s3)c21] | m/z 633.8 (M + H)+, RT = 2.30 min (Method D) |

-continued

| Example No. | Compound Name | Compound Structure | LC-MS |
|---|---|---|---|
| 181 | 1-(2-Chlorothiazol-4-yl)-3-(2-(5-fluoro-4-(5-fluorobenzo[d]thiazol-2-yl)-7-hydroxy-3,3-dimethylindolin-1-yl)phenyl)urea | 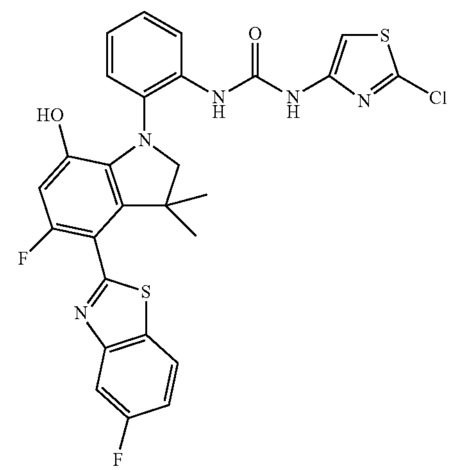 [SMILES: CC1(C)CN(c2ccccc2NC(=O)Nc2csc(Cl)n2)c2c(O)cc(F)c(-c3nc4cc(F)ccc4s3)c21] | m/z 584.0 (M + H)+, RT = 1.22 min (Method B) |
| 182 | 1-(2-(5-Fluoro-4-(5-fluorobenzo[d]thiazol-2-yl)-7-hydroxy-3,3-dimethylindolin-1-yl)phenyl)-3-(5-fluorothiazolo[5,4-b]pyridin-2-yl)urea | 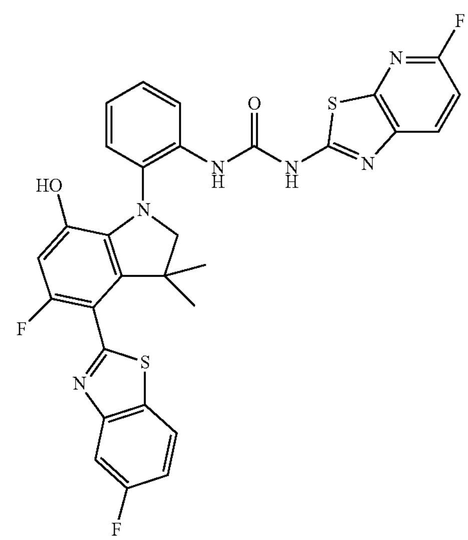 [SMILES: CC1(C)CN(c2ccccc2NC(=O)Nc2nc3ccc(F)nc3s2)c2c(O)cc(F)c(-c3nc4cc(F)ccc4s3)c21] | m/z 619.3 (M + H)+, RT = 1.20 min (Method B) |
| 183 | 1-(2-(5-Fluoro-7-hydroxy-3,3-dimethyl-4-(1-methyl-3-(trifluoromethyl)-1H-pyrazol-5-yl)indolin-1-yl)phenyl)-3-(4-(trifluoromethoxy)phenyl)urea | 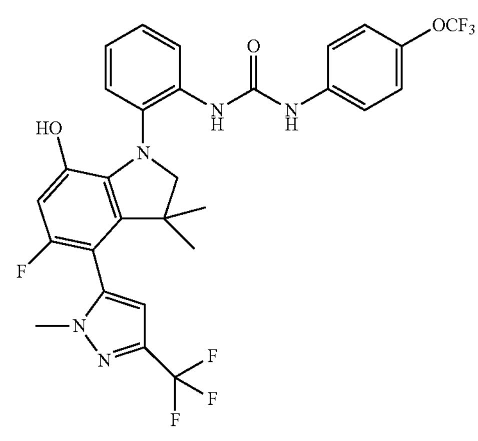 [SMILES: Cn1nc(C(F)(F)F)cc1-c1c(F)cc(O)c2c1C(C)(C)CN2c1ccccc1NC(=O)Nc1ccc(OC(F)(F)F)cc1] | m/z 624.3.0 (M + H)+, RT = 1.90 min (Method F) |

-continued

| Example No. | Compound Name | Compound Structure | LC-MS |
|---|---|---|---|
| 184 | 1-(2-(5-Fluoro-7-hydroxy-4-(1-isobutyl-1H-pyrazol-4-yl)-3,3-dimethylindolin-1-yl)phenyl)-3-(4-(trifluoromethoxy)phenyl)urea | 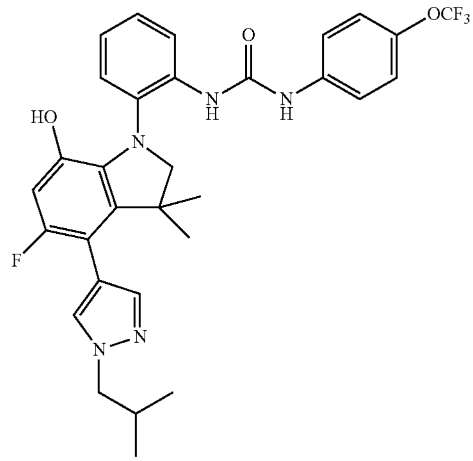 [SMILES: CC(C)Cn1cc(-c2c(F)cc(O)c3c2C(C)(C)CN3c2ccccc2NC(=O)Nc2ccc(OC(F)(F)F)cc2)cn1] | m/z 598.3 (M + H)+, RT = 1.83 min (Method F) |
| 185 | 1-(2-(5-Fluoro-7-hydroxy-4-(1-isopentyl-1H-pyrazol-4-yl)-3,3-dimethylindolin-1-yl)phenyl)-3-(4-(trifluoromethoxy)phenyl)urea | 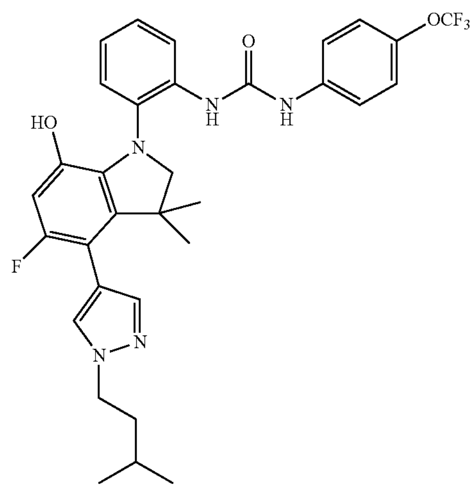 [SMILES: CC(C)CCn1cc(-c2c(F)cc(O)c3c2C(C)(C)CN3c2ccccc2NC(=O)Nc2ccc(OC(F)(F)F)cc2)cn1] | m/z 612.2 (M + H)+, RT = 2.06 min (Method F) |
| 186 | 1-(2-(5-Fluoro-7-hydroxy-3,3-dimethyl-4-(5-methyl-1-phenyl-1H-pyrazol-4-yl)indolin-1-yl)phenyl)-3-(4-(trifluoromethoxy)phenyl)urea | 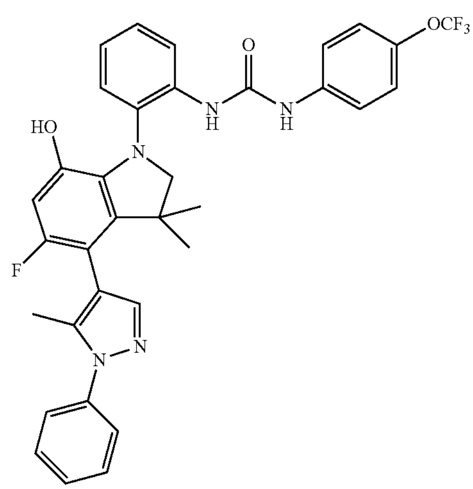 [SMILES: Cc1c(-c2c(F)cc(O)c3c2C(C)(C)CN3c2ccccc2NC(=O)Nc2ccc(OC(F)(F)F)cc2)cnn1-c1ccccc1] | m/z 632.3 (M + H)+, RT = 1.85 min (Method F) |

| Example No. | Compound Name | Compound Structure | LC-MS |
|---|---|---|---|
| 187 | 1-(2-(5-Fluoro-7-hydroxy-3,3-dimethyl-4-(1,3,5-trimethyl-1H-pyrazol-4-yl)indolin-1-yl)phenyl)-3-(4-(trifluoromethoxy)phenyl)urea | 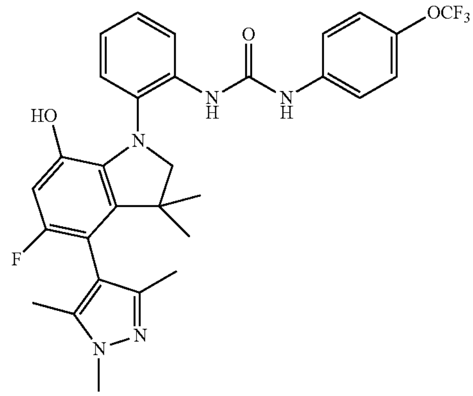 [SMILES: Cc1nn(C)c(C)c1-c1c(F)cc(O)c2c1C(C)(C)CN2c1ccccc1NC(=O)Nc1ccc(OC(F)(F)F)cc1] | m/z 584.2 (M + H)+, RT = 1.45 min (Method F) |
| 188 | 1-(2-(5-Fluoro-4-(6-fluoropyridin-3-yl)-7-hydroxy-3,3-dimethylindolin-1-yl)phenyl)-3-(4-(trifluoromethoxy)phenyl)urea | 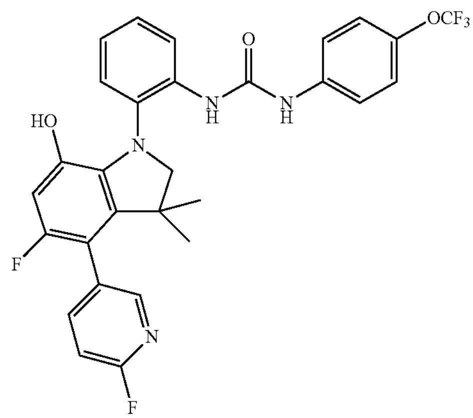 [SMILES: CC1(C)CN(c2ccccc2NC(=O)Nc2ccc(OC(F)(F)F)cc2)c2c(O)cc(F)c(-c3ccc(F)nc3)c21] | m/z 571.2 (M + H)+, RT = 1.75 min (Method F) |
| 189 | 1-(2-(5-Fluoro-7-hydroxy-3,3-dimethyl-4-(2-(methylthio)pyrimidin-5-yl)indolin-1-yl)phenyl)-3-(4-(trifluoromethoxy)phenyl)urea | 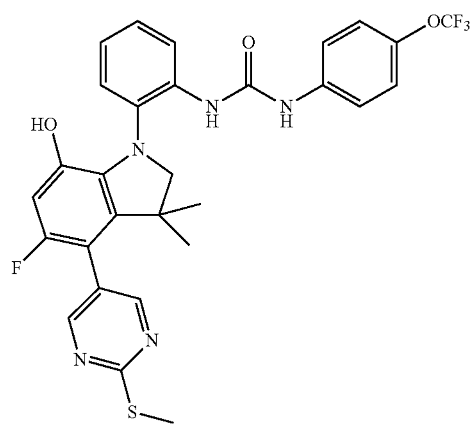 [SMILES: CSc1ncc(-c2c(F)cc(O)c3c2C(C)(C)CN3c2ccccc2NC(=O)Nc2ccc(OC(F)(F)F)cc2)cn1] | m/z 600.1 (M + H)+, RT = 1.82 min (Method F) |

| Example No. | Compound Name | Compound Structure | LC-MS |
|---|---|---|---|
| 190 | 1-(2-(5-Fluoro-4-(2-fluoropyridin-4-yl)-7-hydroxy-3,3-dimethylindolin-1-yl)phenyl)-3-(4-(trifluoromethoxy)phenyl)urea | 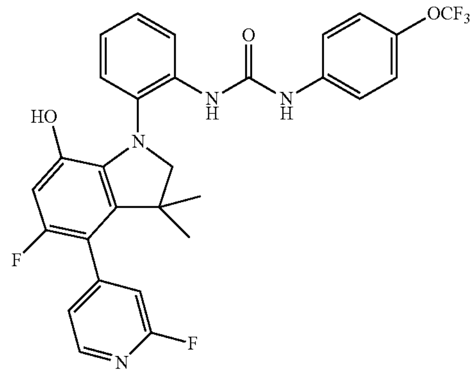 [SMILES: CC1(C)CN(c2ccccc2NC(=O)Nc2ccc(OC(F)(F)F)cc2)c2c(O)cc(F)c(-c3ccnc(F)c3)c21] | m/z 571.1 (M + H)+, RT = 1.69 min (Method F) |
| 191 | 1-(2-(5-Fluoro-7-hydroxy-3,3-dimethyl-4-(2-methylpyridin-4-yl)indolin-1-yl)phenyl)-3-(4-(trifluoromethoxy)phenyl)urea | 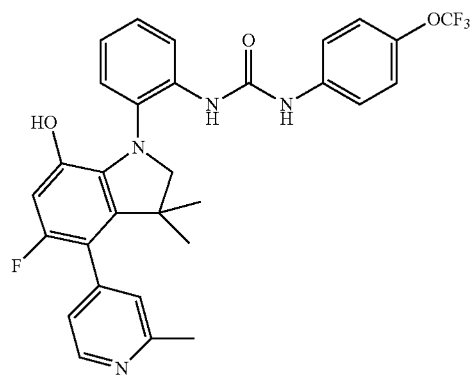 [SMILES: Cc1cc(-c2c(F)cc(O)c3c2C(C)(C)CN3c2ccccc2NC(=O)Nc2ccc(OC(F)(F)F)cc2)ccn1] | m/z 567.1 (M + H)+, RT = 1.14 min (Method F) |
| 192 | 1-(2-(5-Fluoro-4-(6-fluoro-5-methylpyridin-3-yl)-7-hydroxy-3,3-dimethylindolin-1-yl)phenyl)-3-(4-(trifluoromethoxy)phenyl)urea | 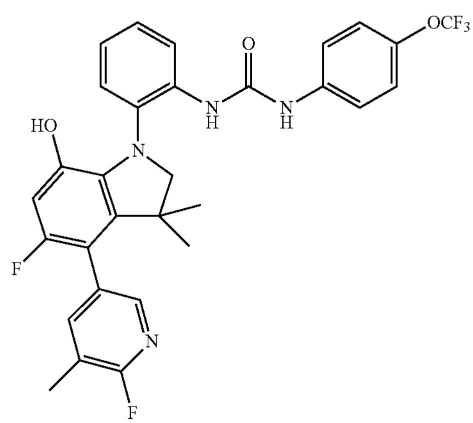 [SMILES: Cc1cc(-c2c(F)cc(O)c3c2C(C)(C)CN3c2ccccc2NC(=O)Nc2ccc(OC(F)(F)F)cc2)cnc1F] | m/z 585.1 (M + H)+, RT = 1.76 min (Method F) |

Example 193

1-(2-(4-(4-Fluorophenyl)-7-hydroxy-3,3-dimethylindolin-1-yl)phenyl)-3-(4-(trifluoromethoxy)phenyl)urea

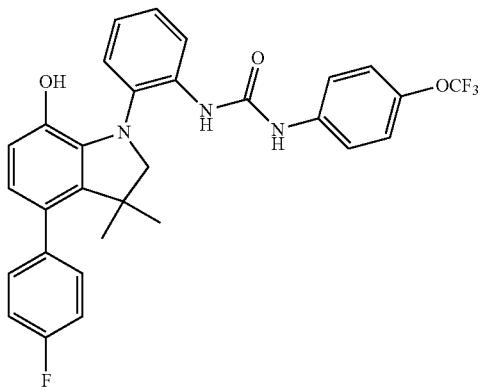 [SMILES: CC1(C)CN(c2ccccc2NC(=O)Nc2ccc(OC(F)(F)F)cc2)c2c(O)ccc(-c3ccc(F)cc3)c21]

Example 193A.

1-(2-(4-(4-Fluorophenyl)-7-methoxy-3,3-dimethylindolin-1-yl)phenyl)-3-(4-(trifluoromethoxy)phenyl)urea A mixture of 1-(2-(4-bromo-7-methoxy-3,3-dimethylindolin-1-yl)phenyl)-3-(4-(trifluoromethoxy)phenyl)urea (36 mg, 0.065 mmol), 4-fluorophenylboronic acid (11 mg, 0.079 mmol), Pd(PPh$_3$)$_4$ (8 mg, 7 μmol), and Na$_2$CO$_3$ (2.0 M solution, 90 μL, 0.18 mmol) in DME (2 mL) was bubbled with argon for 3 min, sealed and heated at 100° C. for 24 h. Another 4-fluorophenylboronic acid (10 mg, 0.072 mmol) was added, degassed with argon, sealed and heated at 100° C. for another 24 h. The reaction mixture was cooled down to room temperature, filtered off solid, concentrated and purified by flash chromatography to give a mixture of Example 193A and starting material, which was used in next step without further purification. LCMS (ESI) m/z 566.0 (M+H)$^+$, RT=4.38 min (Method C).

Example 193

To Example 193A (30 mg, 0.053 mmol) in DCM (2 mL) was added tetrabutylammonium iodide (98 mg, 0.27 mmol) under argon and cooled down to −78° C. BCl$_3$ (1 M in DCM, 265 μL, 0.265 mmol) was added dropwise. The reaction mixture was allowed to gradually warm up to room temperature and stirred at room temperature for 16 h. The reaction mixture was concentrated and purified by flash chromatography, eluting with EtOAc/hexanes to give Example 193 (10 mg, 34%) as an off-white solid. LCMS (ESI) m/z 552.1 (M+H)$^+$, RT=4.16 min (Method C). $^1$H NMR (400 MHz, MeOD) δ ppm 1.06 (s, 6 H), 3.10 (d, J=9.85 Hz, 1 H), 3.73 (d, J=9.85 Hz, 1 H), 6.52 (d, J=8.08 Hz, 1 H), 6.62 (d, J=8.08 Hz, 1 H), 6.99 (qd, J=7.87, 1.64 Hz, 2H), 7.04-7.12 (m, 3 H), 7.17 (d, J=8.34 Hz, 2 H), 7.25-7.32 (m, 2 H), 7.48-7.54 (m, 2 H), 7.83-7.89 (m, 1 H).

Example 194

1-(2-(5-Fluoro-4-(4-fluorophenyl)-7-hydroxy-3,3-dimethylindolin-1-yl)phenyl)-3-(4-(trifluoromethoxy)phenyl)urea

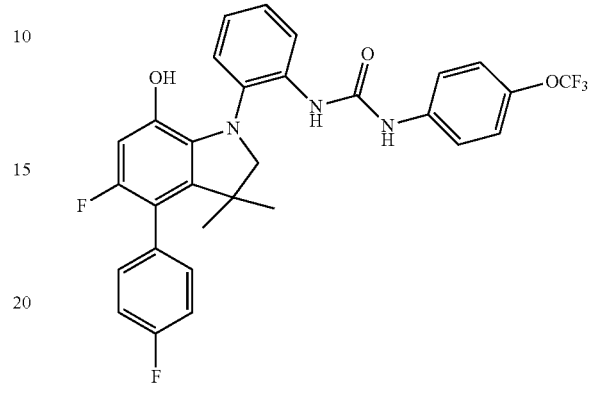

Example 194A.

5-Fluoro-4-(4-fluorophenyl)-7-methoxy-3,3-dimethyl-1-(2-nitrophenyl)indoline

To Intermediate 20 (187 mg, 0.435 mmol) in 5 mL of DME was added 4-fluorophenylboronic acid (74 mg, 0.53 mmol), Pd(PPh$_3$)$_4$ (52 mg, 0.045 mmol), and Na$_2$CO$_3$ (1 M solution, 1 mL, 1 mmol). The reaction mixture was bubbled with argon for 3 min, sealed and heated at 100° C. for 20 h before cooling down to room temperature. The reaction mixture was partitioned between water and EtOAc. The organic layer was dried over Na$_2$SO$_4$, concentrated to give Example 194A, which was used directly in the next step without further purification. LCMS (ESI) m/z 411.4 (M+H)$^+$, RT=3.63 min (Method C).

Example 194B.

2-(5-Fluoro-4-(4-fluorophenyl)-7-methoxy-3,3-dimethylindolin-1-yl)aniline

To Example 194A (176 mg, 0.430 mmol) in EtOAc (10 mL) and MeOH (10 mL) was added zinc (562 mg, 8.60 mmol) and NH$_4$Cl (460 mg, 8.60 mmol). The reaction mixture was stirred at room temperature for 30 min. The reaction mixture was filtered, concentrated and purified by flash chromatography to give Example 194B (125 mg, 76.0%) as a yellow solid. LCMS (ESI) m/z 381.5 (M+H)$^+$, RT=3.42 min (Method C).

Example 194C.

1-(2-Aminophenyl)-5-fluoro-4-(4-fluorophenyl)-3,3-dimethylindolin-7-ol

To Example 194B (125 mg, 0.329 mmol) in DCM (5 mL) was added tetrabutylammonium iodide (607 mg, 1.64 mmol) under argon and cooled down to −78° C. BCl$_3$ (1 M in DCM, 1.643 mL, 1.643 mmol) was added dropwise. The reaction mixture was allowed to gradually warm up to room temperature and stirred at room temperature for 16 h. The reaction mixture was quenched with MeOH, concentrated and purified by flash chromatography, eluting with EtOAc/hexanes to give Example 194C (34 mg, 28%) as a white solid. LCMS (ESI) m/z 367.0 (M+H)$^+$, RT=4.16 min (Method C).

Example 194

A solution of 1-isocyanato-4-(trifluoromethoxy)benzene (10 mg, 0.049 mmol) and Example 194C (15 mg, 0.041 mmol) in DCM (2 mL) was stirred at room temperature. The reaction mixture was concentrated and purified by Prep HPLC to give Example 194 (16 mg, 69%) as an off-white solid. LCMS (ESI) m/z 570.0 (M+H)$^+$, RT=4.13 min (Method C). $^1$H NMR (400 MHz, MeOD) δ ppm 1.02 (s, 3 H), 1.05 (s, 3H), 3.10 (d, J=9.85 Hz, 1 H), 3.76 (d, J=10.11 Hz, 1 H), 6.41-6.50 (m, 1 H), 6.91-7.00 (m, 2 H), 7.04-7.10 (m, 1 H), 7.11-7.19 (m, 4 H), 7.29 (s, 2 H), 7.52 (d, J=8.84 Hz, 2 H), 7.85-7.94 (m, 1 H).

Examples 195 to 252 were prepared according the procedures described in Example 193 or 194.

| Example No. | Compound Name | Compound Structure | LC-MS (ESI) m/z |
|---|---|---|---|
| 195 | 1-(2-(7-Hydroxy-3,3-dimethyl-4-phenylindolin-1-yl)phenyl)-3-(4-(trifluoromethoxy)phenyl)urea | 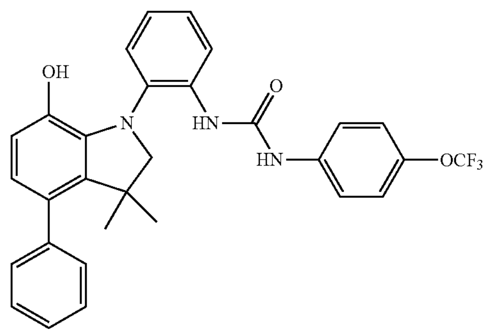 [SMILES: CC1(C)CN(c2ccccc2NC(=O)Nc2ccc(OC(F)(F)F)cc2)c2c(O)ccc(-c3ccccc3)c21] | m/z 534.1 (M + H)$^+$, RT = 4.20 min (Method C) |
| 196 | 1-(2-(7-Hydroxy-3,3-dimethyl 4-(4-(trifluoromethyl)phenyl) indolin-1-yl)phenyl)-3-(4-(trifluoromethoxy)phenyl)urea | 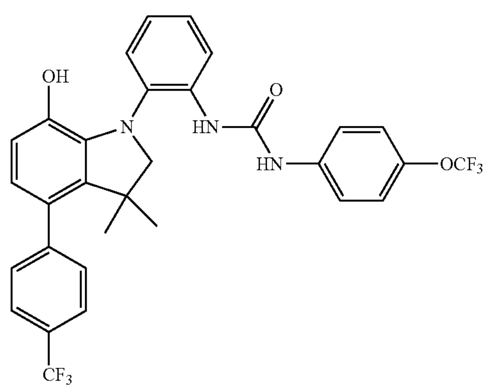 [SMILES: CC1(C)CN(c2ccccc2NC(=O)Nc2ccc(OC(F)(F)F)cc2)c2c(O)ccc(-c3ccc(C(F)(F)F)cc3)c21] | m/z 602.1 (M + H)$^+$, RT = 4.28 min (Method C) |
| 197 | 1-(2-(4-(3,5-Difluorophenyl)-7-hydroxy-3,3-dimethylindolin-1-yl)phenyl)-3-(4-(trifluoromethoxy)phenyl)urea | 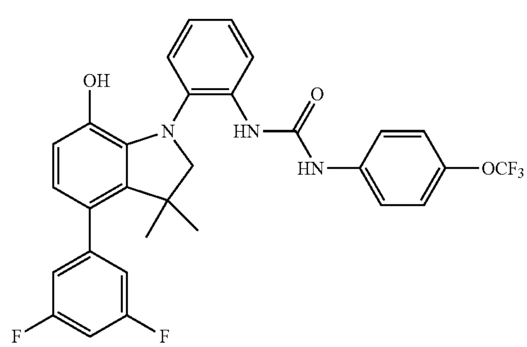 [SMILES: CC1(C)CN(c2ccccc2NC(=O)Nc2ccc(OC(F)(F)F)cc2)c2c(O)ccc(-c3cc(F)cc(F)c3)c21] | m/z 570.0 (M + H)$^+$, RT = 4.23 min (Method C) |

-continued

| Example No. | Compound Name | Compound Structure | LC-MS (ESI) m/z |
|---|---|---|---|
| 198 | 1-(2-Chlorothiazol-4-yl)-3-(2-(4-(4-fluorophenyl)-7-hydroxy-3,3-dimethylindolin-1-yl)phenyl)urea | 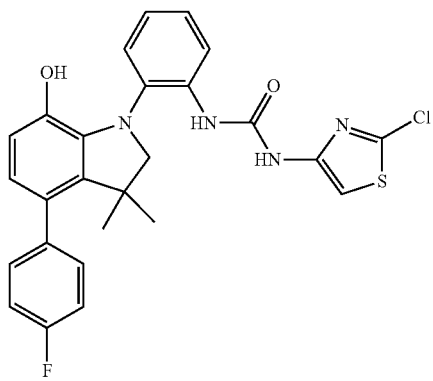 [SMILES: CC1(C)CN(c2ccccc2NC(=O)Nc2csc(Cl)n2)c2c(O)ccc(-c3ccc(F)cc3)c21] | m/z 509.0 (M + H)+, RT = 4.03 min (Method C) |
| 199 | 1-(6-Chlorobenzo[d]thiazol-2-yl)-3-(2-(4-(4-fluorophenyl)-7-hydroxy-3,3-dimethylindolin-1-yl)phenyl)urea | 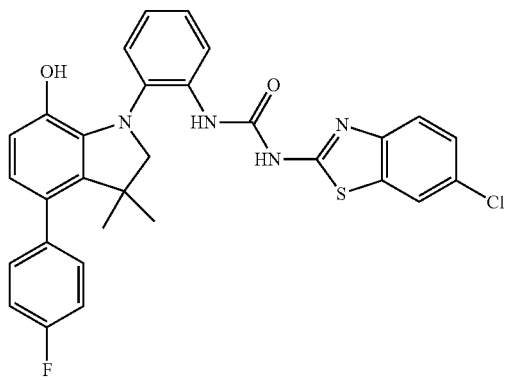 [SMILES: CC1(C)CN(c2ccccc2NC(=O)Nc2nc3ccc(Cl)cc3s2)c2c(O)ccc(-c3ccc(F)cc3)c21] | m/z 559.0 (M + H)+, RT = 4.36 min (Method C) |
| 200 | 1-(2-(4-(4-Fluorophenyl)-7-hydroxy-3,3-dimethylindolin-1-yl)phenyl)-3-(4-(1-isobutylpyrrolidin-2-yl)phenyl)urea | 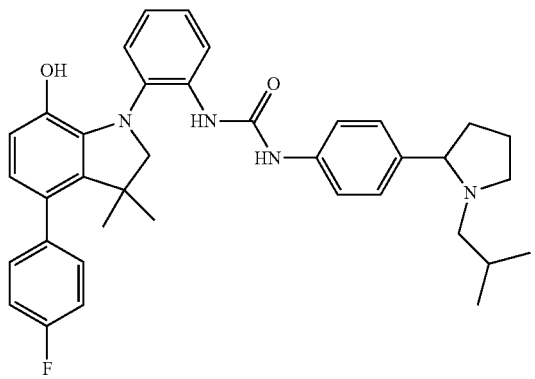 [SMILES: CC(C)CN1CCCC1c1ccc(NC(=O)Nc2ccccc2N2CC(C)(C)c3c(-c4ccc(F)cc4)ccc(O)c32)cc1] | m/z 593.2 (M + H)+, RT = 3.46 min (Method C) |
| 201 | 1-(2-(4-(4-Fluorophenyl)-7-hydroxy-3,3-dimethylindolin-1-yl)phenyl)-3-(2-methylthiazol-4-yl)urea | 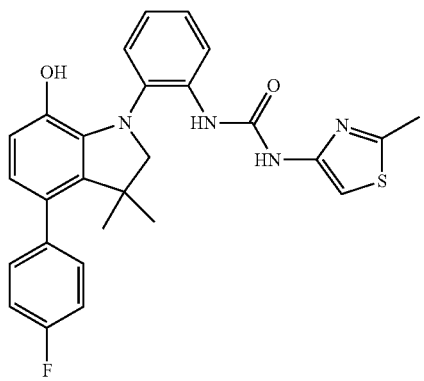 [SMILES: Cc1nc(NC(=O)Nc2ccccc2N2CC(C)(C)c3c(-c4ccc(F)cc4)ccc(O)c32)cs1] | m/z 489.0 (M + H)+, RT = 3.95 min (Method C) |

| Example No. | Compound Name | Compound Structure | LC-MS (ESI) m/z |
|---|---|---|---|
| 202 | 1-(2-(4-(4-Fluorophenyl)-7-hydroxy-3,3-dimethylindolin-1-yl)phenyl)-3-(4-(1-neopentylpyrrolidin-2-yl)phenyl)urea | 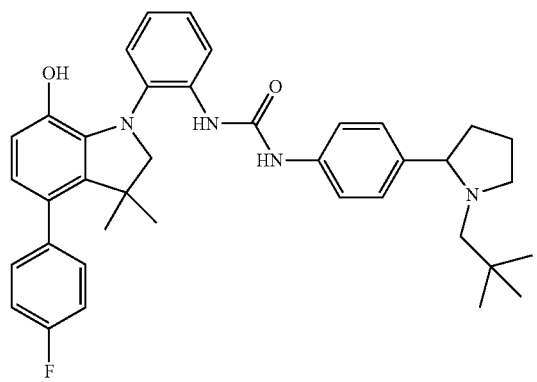 [SMILES: CC(C)(C)CN1CCCC1c1ccc(NC(=O)Nc2ccccc2N2CC(C)(C)c3c(-c4ccc(F)cc4)ccc(O)c32)cc1] | m/z 607.2 (M + H)+, RT = 3.50 min (Method C) |
| 203 | 1-(2-(4-(2,4-Difluorophenyl)-7-hydroxy-3,3-dimethylindolin-1-yl)phenyl)-3-(4-(trifluoromethoxy)phenyl)urea | 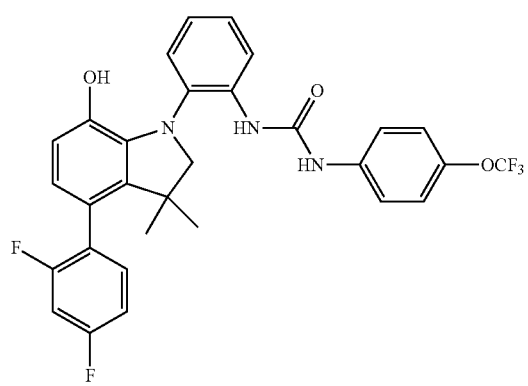 [SMILES: CC1(C)CN(c2ccccc2NC(=O)Nc2ccc(OC(F)(F)F)cc2)c2c(O)ccc(-c3ccc(F)cc3F)c21] | m/z 570.0 (M + H)+, RT = 4.17 min (Method C) |
| 204 | 1-(2-(4-(3,4-Difluorophenyl)-7-hydroxy-3,3-dimethylindolin-1-yl)phenyl)-3-(4-(trifluoromethoxy)phenyl)urea | 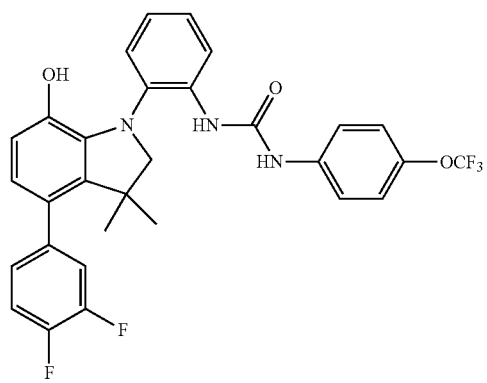 [SMILES: CC1(C)CN(c2ccccc2NC(=O)Nc2ccc(OC(F)(F)F)cc2)c2c(O)ccc(-c3ccc(F)c(F)c3)c21] | m/z 570.0 (M + H)+, RT = 4.24 min (Method C) |
| 205 | 1-(2-(4-(4-Chlorophenyl)-7-hydroxy-3,3-dimethylindolin-1-yl)phenyl)-3-(4-(trifluoromethoxy)phenyl)urea | 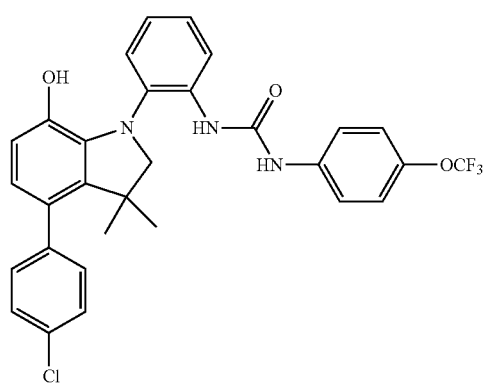 [SMILES: CC1(C)CN(c2ccccc2NC(=O)Nc2ccc(OC(F)(F)F)cc2)c2c(O)ccc(-c3ccc(Cl)cc3)c21] | m/z 568.0 (M + H)+, RT = 4.30 min (Method C) |

-continued

| Example No. | Compound Name | Compound Structure | LC-MS (ESI) m/z |
|---|---|---|---|
| 206 | 1-(2-(4-(3-Fluorophenyl)-7-hydroxy-3,3-dimethylindolin-1-yl)phenyl)-3-(4-(trifluoromethoxy)phenyl)urea | 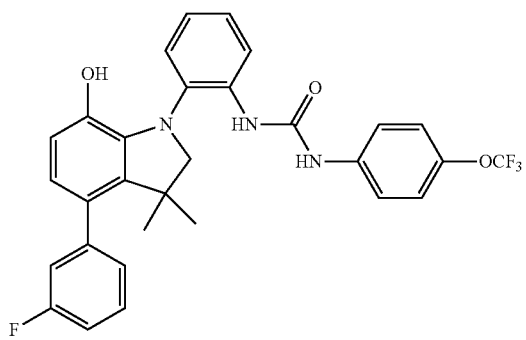 [SMILES: CC1(C)CN(c2ccccc2NC(=O)Nc2ccc(OC(F)(F)F)cc2)c2c(O)ccc(-c3cccc(F)c3)c21] | m/z 552.0 (M + H)+, RT = 4.18 min (Method C) |
| 207 | 1-(2-(4-(2-Fluorophenyl)-7-hydroxy-3,3-dimethylindolin-1-yl)phenyl)-3-(4-(trifluoromethoxy)phenyl)urea | 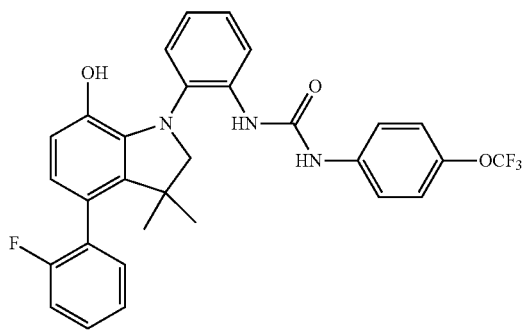 [SMILES: CC1(C)CN(c2ccccc2NC(=O)Nc2ccc(OC(F)(F)F)cc2)c2c(O)ccc(-c3ccccc3F)c21] | m/z 552.3 (M + H)+, RT = 2.18 min (Method D) |
| 208 | 1-(2-(4-(4-Fluorophenyl)-7-hydroxy-3,3-dimethylindolin-1-yl)phenyl)-3-(2-(trifluoromethyl)thiazol-4-yl)urea | 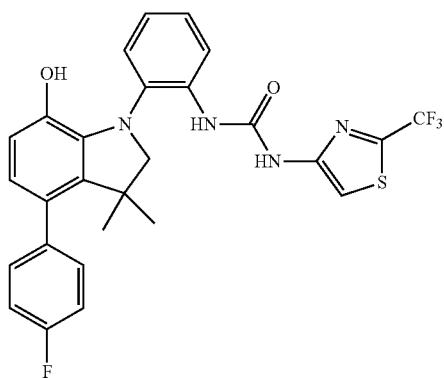 [SMILES: CC1(C)CN(c2ccccc2NC(=O)Nc2csc(C(F)(F)F)n2)c2c(O)ccc(-c3ccc(F)cc3)c21] | m/z 543.1 (M + H)+, RT = 4.10 min (Method C) |
| 209 | 1-(5-Chlorothiazolo[5,4-b]pyridin-2-yl)-3-(2-(4-(4-fluorophenyl)-7-hydroxy-3,3-dimethylindolin-1-yl)phenyl)urea | 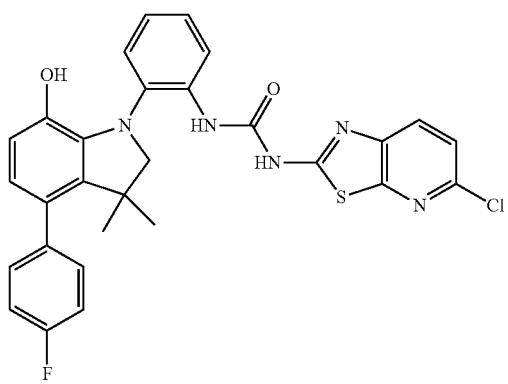 [SMILES: CC1(C)CN(c2ccccc2NC(=O)Nc2nc3ccc(Cl)nc3s2)c2c(O)ccc(-c3ccc(F)cc3)c21] | m/z 560.0 (M + H)+, RT = 4.23 min (Method C) |

-continued

| Example No. | Compound Name | Compound Structure | LC-MS (ESI) m/z |
|---|---|---|---|
| 210 | 1-(6-Fluorobenzo[d]thiazol-2-yl)-3-(2-(4-(4-fluorophenyl)-7-hydroxy-3,3-dimethylindolin-1-yl)phenyl)urea | 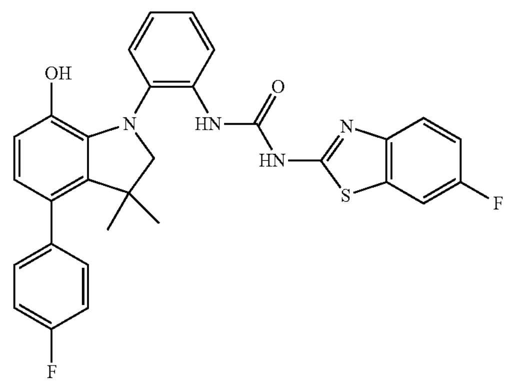 [SMILES: CC1(C)CN(c2ccccc2NC(=O)Nc2nc3ccc(F)cc3s2)c2c(O)ccc(-c3ccc(F)cc3)c21] | m/z 543.0 (M + H)+, RT = 4.24 min (Method C) |
| 211 | 1-(2-(4-(4-Fluorophenyl)-7-hydroxy-3,3-dimethylindolin-1-yl)phenyl)-3-(4-(1-isobutylpiperidin-4-yl)phenyl)urea | 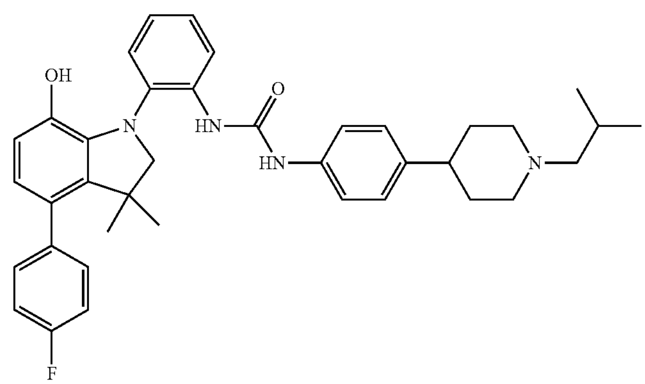 [SMILES: CC(C)CN1CCC(c2ccc(NC(=O)Nc3ccccc3N3CC(C)(C)c4c(-c5ccc(F)cc5)ccc(O)c43)cc2)CC1] | |
| 212 | 1-(2-Chlorothiazol-4-yl)-3-(2-(5-fluoro-4-(4-fluorophenyl)-7-hydroxy-3,3-dimethylindolin-1-yl)phenyl)urea | 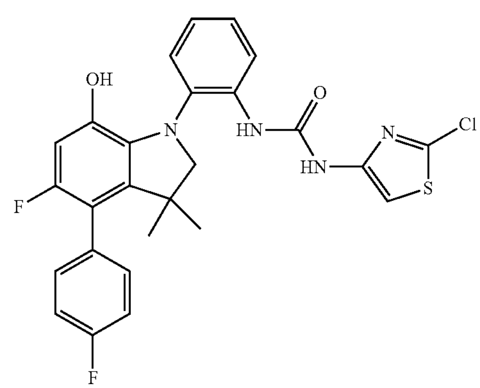 [SMILES: CC1(C)CN(c2ccccc2NC(=O)Nc2csc(Cl)n2)c2c(O)cc(F)c(-c3ccc(F)cc3)c21] | m/z 527.0 (M + H)+, RT = 4.07 min (Method C) |
| 213 | 1-(2-(5-Fluoro-4-(4-fluorophenyl)-7-hydroxy-3,3-dimethylindolin-1-yl)phenyl)-3-(6-fluorobenzo[d]thiazol-2-yl)urea | 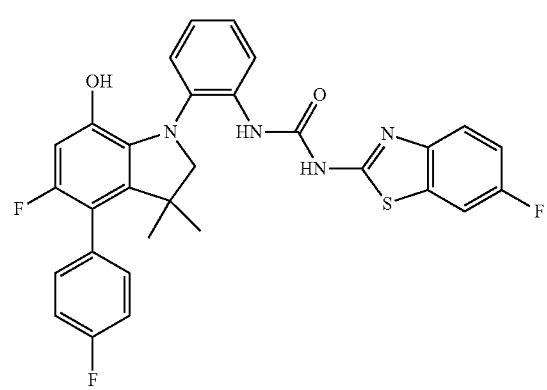 [SMILES: CC1(C)CN(c2ccccc2NC(=O)Nc2nc3ccc(F)cc3s2)c2c(O)cc(F)c(-c3ccc(F)cc3)c21] | m/z 561.1 (M + H)+, RT = 4.15 min (Method C) |

-continued

| Example No. | Compound Name | Compound Structure | LC-MS (ESI) m/z |
|---|---|---|---|
| 214 | 1-(2-(4-(4-Chlorophenyl)-5-fluoro-7-hydroxy-3,3-dimethylindolin-1-yl)phenyl)-3-(4-(trifluoromethoxy)phenyl)urea | 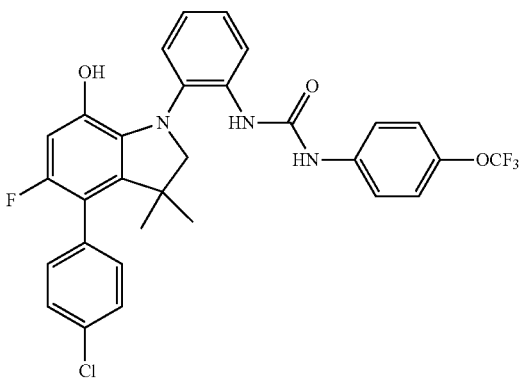 [SMILES: CC1(C)CN(c2ccccc2NC(=O)Nc2ccc(OC(F)(F)F)cc2)c2c(O)cc(F)c(-c3ccc(Cl)cc3)c21] | m/z 586.1 (M + H)+, RT = 4.30 min (Method C) |
| 215 | 1-(2-(4-(4-Chlorophenyl)-5-fluoro-7-hydroxy-3,3-dimethylindolin-1-yl)phenyl)-3-(2-chlorothiazol-4-yl)urea | 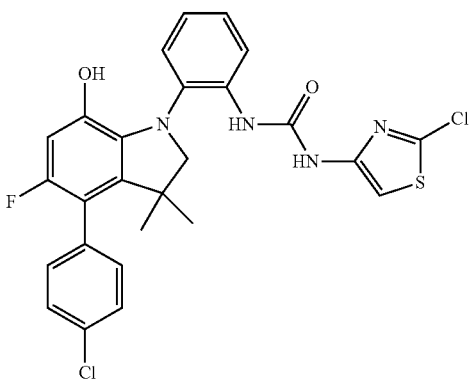 [SMILES: CC1(C)CN(c2ccccc2NC(=O)Nc2csc(Cl)n2)c2c(O)cc(F)c(-c3ccc(Cl)cc3)c21] | m/z 543.2 (M + H)+, RT = 4.22 min (Method C) |
| 216 | 1-(2-(5-Fluoro-7-hydroxy-3,3-dimethyl-4-(4-(trifluoromethyl)phenyl)indolin-1-yl)phenyl)-3-(4-(trifluoromethoxy)phenyl)urea | 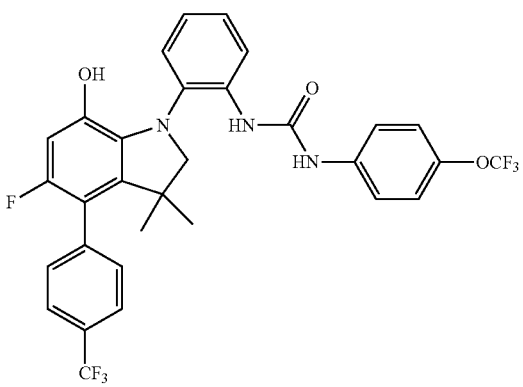 [SMILES: CC1(C)CN(c2ccccc2NC(=O)Nc2ccc(OC(F)(F)F)cc2)c2c(O)cc(F)c(-c3ccc(C(F)(F)F)cc3)c21] | m/z 620.5 (M + H)+, RT = 3.79 min (Method E) |
| 217 | 1-(2-(5-Fluoro-7-hydroxy-3,3-dimethyl-4-(4-(trifluoromethyl)phenyl)indolin-1-yl)phenyl)-3-(2-(trifluoromethyl)thiazol-4-yl)urea | 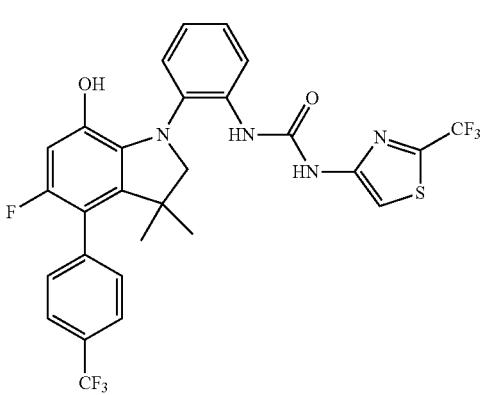 [SMILES: CC1(C)CN(c2ccccc2NC(=O)Nc2csc(C(F)(F)F)n2)c2c(O)cc(F)c(-c3ccc(C(F)(F)F)cc3)c21] | m/z 611.4 (M + H)+, RT = 3.71 min (Method E) |

-continued

| Example No. | Compound Name | Compound Structure | LC-MS (ESI) m/z |
|---|---|---|---|
| 218 | 1-(2-(4-(4-Chlorophenyl)-5-fluoro-7-hydroxy-3,3-dimethylindolin-1-yl)phenyl)-3-(2-(trifluoromethyl)thiazol-4-yl)urea | 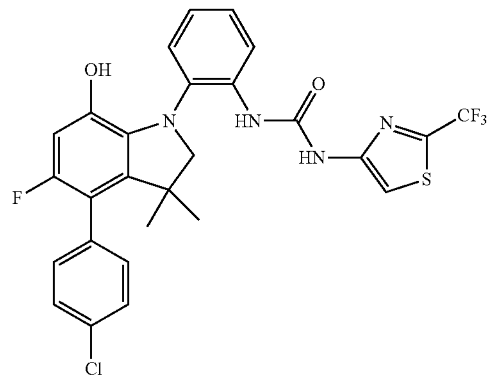 [SMILES: CC1(C)CN(c2ccccc2NC(=O)Nc2csc(C(F)(F)F)n2)c2c(O)cc(F)c(-c3ccc(Cl)cc3)c21] | m/z 577.2 (M + H)+, RT = 4.28 min (Method C) |
| 219 | 1-(2-(5-Fluoro-4-(4-fluorophenyl)-7-hydroxy-3,3-dimethylindolin-1-yl)phenyl)-3-(6-fluorobenzo[d]thiazol-2-yl)urea | 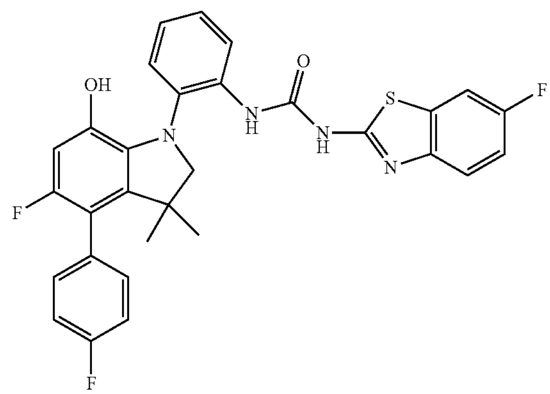 [SMILES: CC1(C)CN(c2ccccc2NC(=O)Nc2nc3ccc(F)cc3s2)c2c(O)cc(F)c(-c3ccc(F)cc3)c21] | m/z 561.1 (M + H)+, RT = 4.16 min (Method C) |
| 220 | 1-(2-(4-(4-Chlorophenyl)-5-fluoro-7-hydroxy-3,3-dimethylindolin-1-yl)phenyl)-3-(4-(trifluoromethoxy)phenyl)urea | 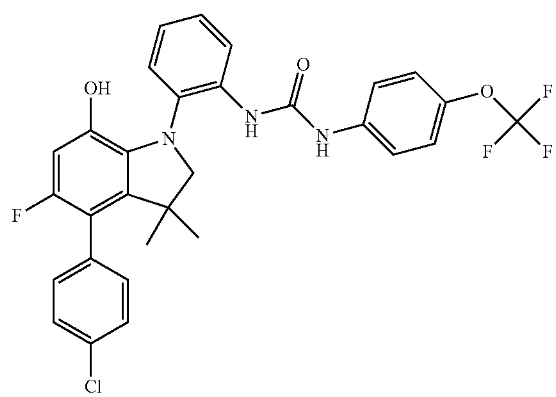 [SMILES: CC1(C)CN(c2ccccc2NC(=O)Nc2ccc(OC(F)(F)F)cc2)c2c(O)cc(F)c(-c3ccc(Cl)cc3)c21] | m/z 586.1 (M + H)+, RT = 4.27 min (Method C) |
| 221 | 1-(2-(4-(4-Chlorophenyl)-5-fluoro-7-hydroxy-3,3-dimethylindolin-1-yl)phenyl)-3-(2-chlorothiazol-4-yl)urea | 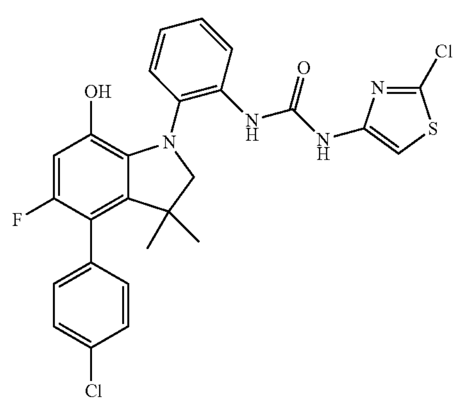 [SMILES: CC1(C)CN(c2ccccc2NC(=O)Nc2csc(Cl)n2)c2c(O)cc(F)c(-c3ccc(Cl)cc3)c21] | m/z 543.2 (M + H)+, RT = 4.20 min (Method C) |

-continued

| Example No. | Compound Name | Compound Structure | LC-MS (ESI) m/z |
|---|---|---|---|
| 222 | 1-(2-(5-Fluoro-7-hydroxy-3,3-dimethyl-4-(4-(trifluoromethyl)phenyl)indolin-1-yl)phenyl)-3-(4-(trifluoromethoxy)phenyl)urea | 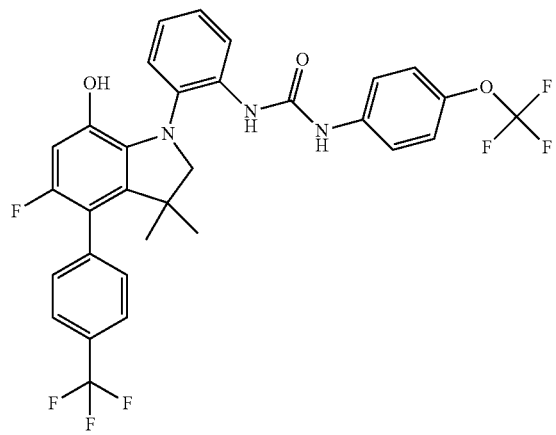 [SMILES: CC1(C)CN(c2ccccc2NC(=O)Nc2ccc(OC(F)(F)F)cc2)c2c(O)cc(F)c(-c3ccc(C(F)(F)F)cc3)c21] | m/z 620.5 (M + H)+, RT = 3.76 min (Method C) |
| 223 | 1-(2-(4-(4-Chlorophenyl)-5-fluoro-7-hydroxy-3,3-dimethylindolin-1-yl)phenyl)-3-(2-(trifluoromethyl)thiazol-4-yl)urea | 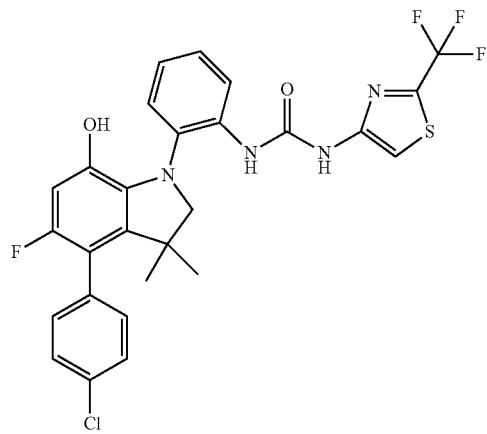 [SMILES: CC1(C)CN(c2ccccc2NC(=O)Nc2csc(C(F)(F)F)n2)c2c(O)cc(F)c(-c3ccc(Cl)cc3)c21] | m/z 577.2 (M + H)+, RT = 4.25 min (Method C) |
| 224 | 1-(2-(4-(4-Chlorophenyl)-5-fluoro-7-hydroxy-3,3-dimethylindolin-1-yl)phenyl)-3-(6-fluorobenzo[d]thiazol-2-yl)urea | 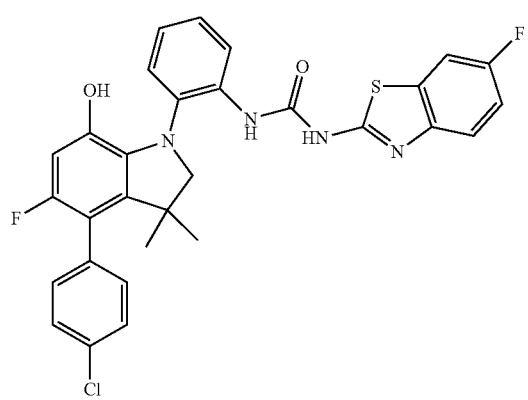 [SMILES: CC1(C)CN(c2ccccc2NC(=O)Nc2nc3ccc(F)cc3s2)c2c(O)cc(F)c(-c3ccc(Cl)cc3)c21] | m/z 577.4 (M + H)+, RT = 4.33 min (Method C) |

-continued

| Example No. | Compound Name | Compound Structure | LC-MS (ESI) m/z |
|---|---|---|---|
| 225 | 1-(6-Chlorobenzo[d]thiazol-2-yl)-3-(2-(4-(4-chlorophenyl)-5-fluoro-7-hydroxy-3,3-dimethylindolin-1-yl)phenyl)urea | 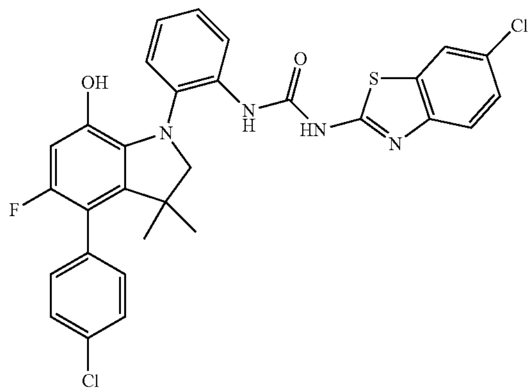 [SMILES: CC1(C)CN(c2ccccc2NC(=O)Nc2nc3ccc(Cl)cc3s2)c2c(O)cc(F)c(-c3ccc(Cl)cc3)c21] | m/z 593.3 (M + H)+, RT = 4.48 min (Method C) |
| 226 | 1-(2-(4-(4-Chlorophenyl)-5-fluoro-7-hydroxy-3,3-dimethylindolin-1-yl)phenyl)-3-(5-chlorothiazolo[5,4-b]pyridin-2-yl)urea | 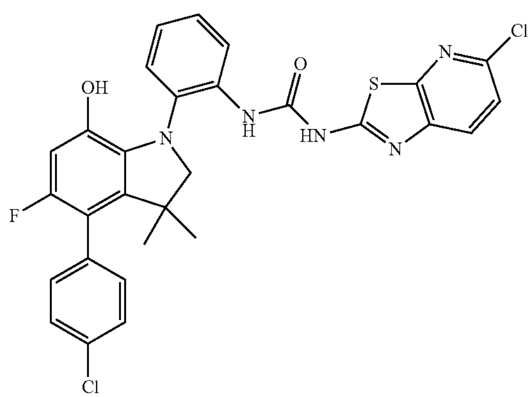 [SMILES: CC1(C)CN(c2ccccc2NC(=O)Nc2nc3ccc(Cl)nc3s2)c2c(O)cc(F)c(-c3ccc(Cl)cc3)c21] | m/z 594.3 (M + H)+, RT = 4.36 min (Method C) |
| 227 | 1-(2-(4-(4-Chlorophenyl)-5-fluoro-7-hydroxy-3,3-dimethylindolin-1-yl)phenyl)-3-(5-fluorothiazolo[5,4-b]pyridin-2-yl)urea | 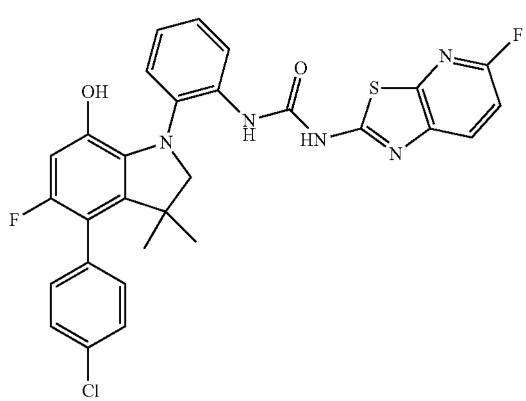 [SMILES: CC1(C)CN(c2ccccc2NC(=O)Nc2nc3ccc(F)nc3s2)c2c(O)cc(F)c(-c3ccc(Cl)cc3)c21] | m/z 578.3 (M + H)+, RT = 4.27 min (Method C) |

-continued

| Example No. | Compound Name | Compound Structure | LC-MS (ESI) m/z |
|---|---|---|---|
| 228 | 1-(2-(5-Fluoro-4-(4-fluorophenyl)-7-hydroxy-3,3-dimethylindolin-1-yl)phenyl)-3-(2-(trifluoromethyl)thiazol-4-yl)urea | 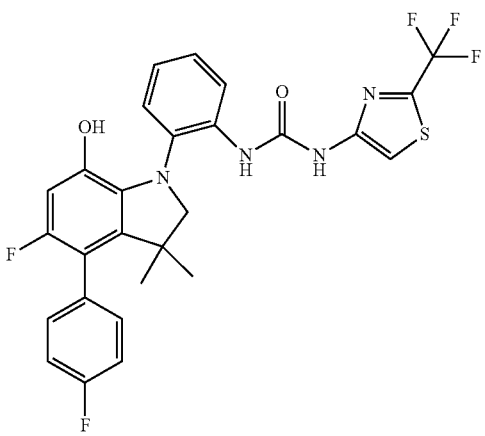 [SMILES: CC1(C)CN(c2ccccc2NC(=O)Nc2csc(C(F)(F)F)n2)c2c(O)cc(F)c(-c3ccc(F)cc3)c21] | m/z 561.3 (M + H)+, RT = 4.16 min (Method C) |
| 229 | 1-(2-(6-Fluoro-7-hydroxy-3,3-dimethyl-4-(4-(trifluoromethyl)phenyl)indolin-1-yl)phenyl)-3-(4-(trifluoromethoxy)phenyl)urea | 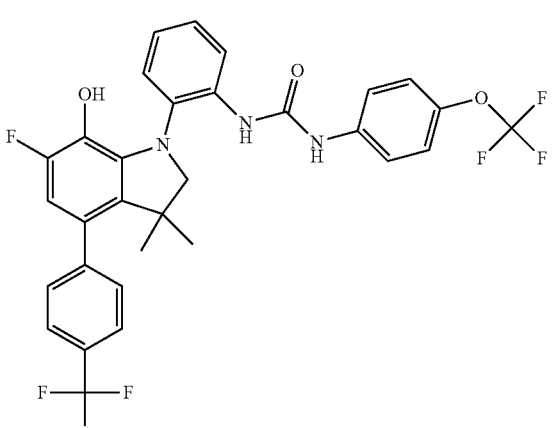 | m/z 620.4 (M + H)+, RT = 4.30 min (Method C) |
| 230 | 1-(2-(6-Fluoro-7-hydroxy-3,3-dimethyl-4-phenylindolin-1-yl)phenyl)-3-(4-(trifluoromethoxy)phenyl)urea | 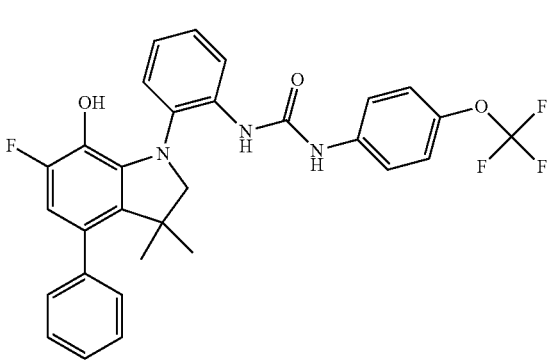 [SMILES: CC1(C)CN(c2ccccc2NC(=O)Nc2ccc(OC(F)(F)F)cc2)c2c(O)c(F)cc(-c3ccccc3)c21] | m/z 552.0 (M + H)+, RT = 2.20 min (Method D) |

-continued

| Example No. | Compound Name | Compound Structure | LC-MS (ESI) m/z |
|---|---|---|---|
| 231 | 1-(2-(4-(4-Chlorophenyl)-6-fluoro-7-hydroxy-3,3-dimethylindolin-1-yl)phenyl)-3-(4-(trifluoromethoxy)phenyl)urea | 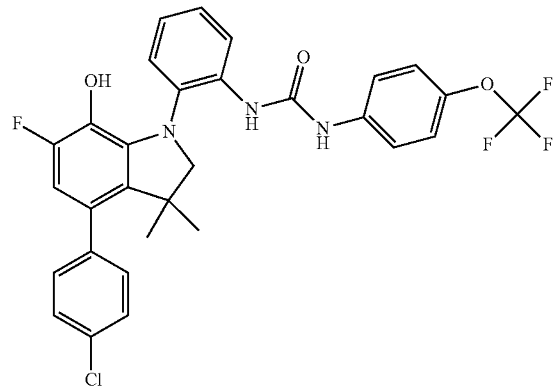 | m/z 586.0 (M + H)+, RT = 2.26 min (Method D) |
| 232 | 1-(2-(6-Fluoro-4-(4-fluorophenyl)-7-hydroxy-3,3-dimethylindolin-1-yl)phenyl)-3-(4-(trifluoromethoxy)phenyl)urea | 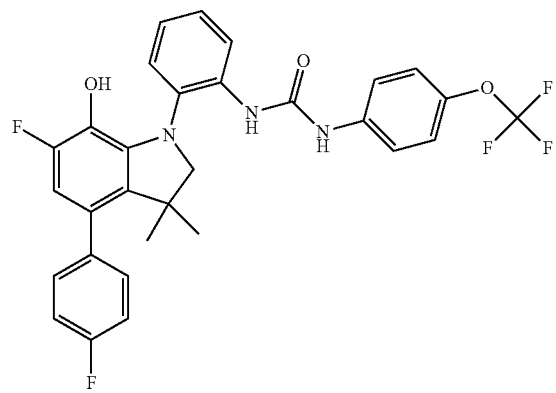 [SMILES: CC1(C)CN(c2ccccc2NC(=O)Nc2ccc(OC(F)(F)F)cc2)c2c(O)c(F)cc(-c3ccc(F)cc3)c21] | m/z 570.3 (M + H)+, RT = 4.21 min (Method C) |
| 233 | 1-(2-(5-Fluoro-4-(4-fluorophenyl)-7-hydroxy-3,3-dimethylindolin-1-yl)phenyl)-3-(5-fluorothiazolo[5,4-b]pyridin-2-yl)urea | 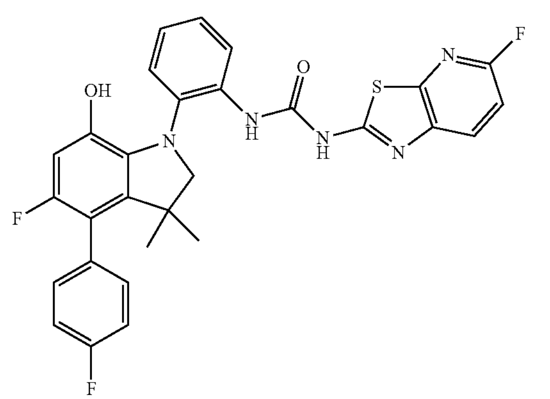 [SMILES: CC1(C)CN(c2ccccc2NC(=O)Nc2nc3ccc(F)nc3s2)c2c(O)cc(F)c(-c3ccc(F)cc3)c21] | m/z 562.3 (M + H)+, RT = 4.10 min (Method C) |
| 234 | 1-(2-(4-(4-Chloro-3-fluorophenyl)-5-fluoro-7-hydroxy-3,3-dimethylindolin-1-yl)phenyl)-3-(4-(trifluoromethoxy)phenyl)urea | 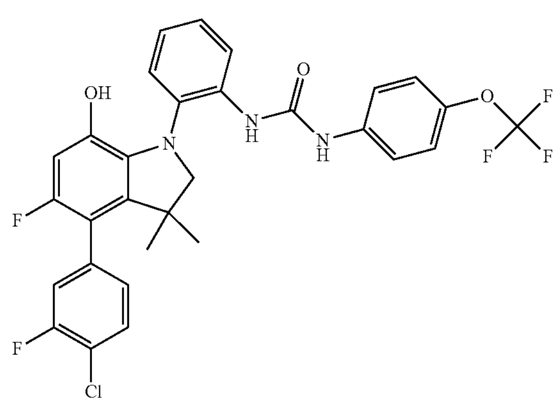 | m/z 604.3 (M + H)+, RT = 4.28 min (Method C) |

| Example No. | Compound Name | Compound Structure | LC-MS (ESI) m/z |
|---|---|---|---|
| 235 | 1-(2-(4-(3-Chlorophenyl)-5-fluoro-7-hydroxy-3,3-dimethylindolin-1-yl)phenyl)-3-(4-(trifluoromethoxy)phenyl)urea | 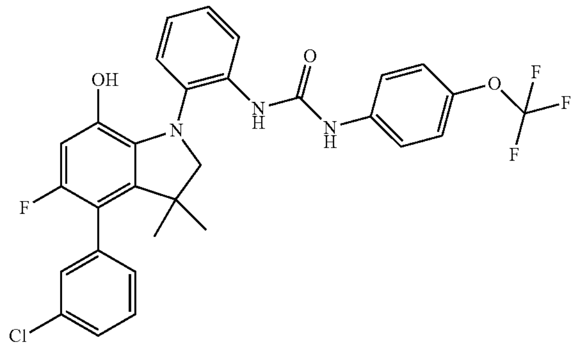 [SMILES: CC1(C)CN(c2ccccc2NC(=O)Nc2ccc(OC(F)(F)F)cc2)c2c(O)cc(F)c(-c3cccc(Cl)c3)c21] | m/z 586.3 (M + H)+, RT = 4.18 min (Method C) |
| 236 | 1-(2-(4-(4-Chloro-2-fluorophenyl)-5-fluoro-7-hydroxy-3,3-dimethylindolin-1-yl)phenyl)-3-(4-(trifluoromethoxy)phenyl)urea | 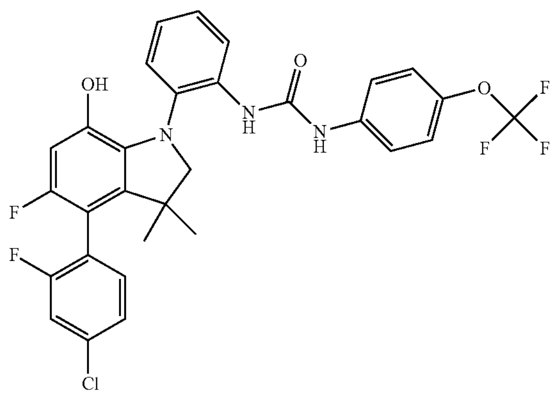 [SMILES: CC1(C)CN(c2ccccc2NC(=O)Nc2ccc(OC(F)(F)F)cc2)c2c(O)cc(F)c(-c3ccc(Cl)cc3F)c21] | m/z 604.3 (M + H)+, RT = 4.26 min (Method C) |
| 237 | 1-(2-(4-(3-Chloro-4-fluorophenyl)-5-fluoro-7-hydroxy-3,3-dimethylindolin-1-yl)phenyl)-3-(4-(trifluoromethoxy)phenyl)urea | 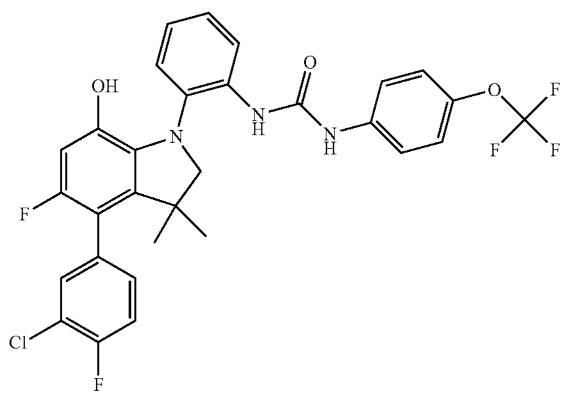 [SMILES: CC1(C)CN(c2ccccc2NC(=O)Nc2ccc(OC(F)(F)F)cc2)c2c(O)cc(F)c(-c3ccc(F)c(Cl)c3)c21] | m/z 604.3 (M + H)+, RT = 4.27 min (Method C) |
| 238 | 1-(2-(4-(4-Chlorophenyl)-5-fluoro-7-hydroxy-3,3-dimethylindolin-1-yl)phenyl)-3-(4-(1-isobutylpiperidin-4-yl)phenyl)urea | 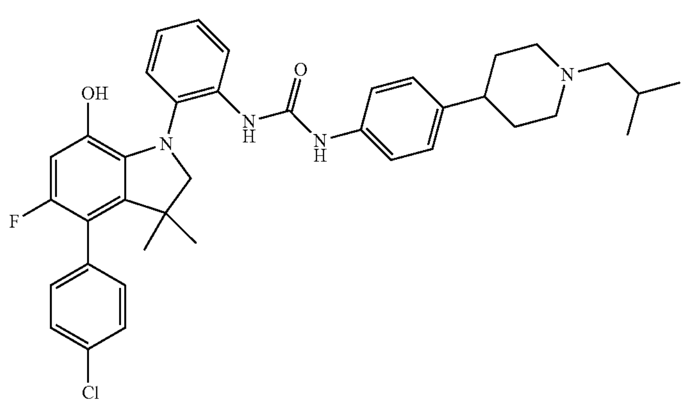 [SMILES: CC(C)CN1CCC(c2ccc(NC(=O)Nc3ccccc3N3CC(C)(C)c4c(-c5ccc(Cl)cc5)c(F)cc(O)c43)cc2)CC1] | m/z 641.5 (M + H)+, RT = 3.56 min (Method C) |

| Example No. | Compound Name | Compound Structure | LC-MS (ESI) m/z |
|---|---|---|---|
| 239 | 1-(2-Chlorothiazol-4-yl)-3-(2-(5-fluoro-7-hydroxy-3,3-dimethyl-4-(4-(trifluoromethyl)phenyl)indolin-1-yl)phenyl)urea | 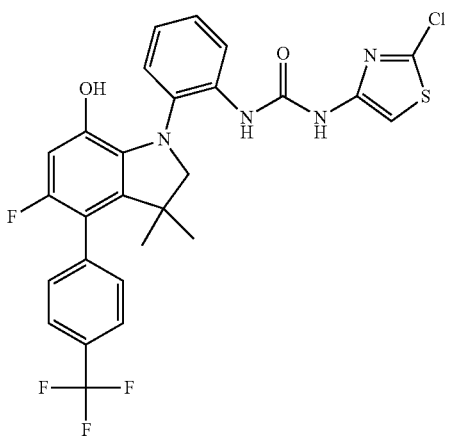 [SMILES: CC1(C)CN(c2ccccc2NC(=O)Nc2csc(Cl)n2)c2c(O)cc(F)c(-c3ccc(C(F)(F)F)cc3)c21] | m/z 577.3 (M + H)+, RT = 4.15 min (Method C) |
| 240 | 1-(2-(4-(4-Chlorophenyl)-5-fluoro-7-hydroxy-3,3-dimethylindolin-1-yl)phenyl)-3-(4-(1-neopentylpiperidin-4-yl)phenyl)urea | 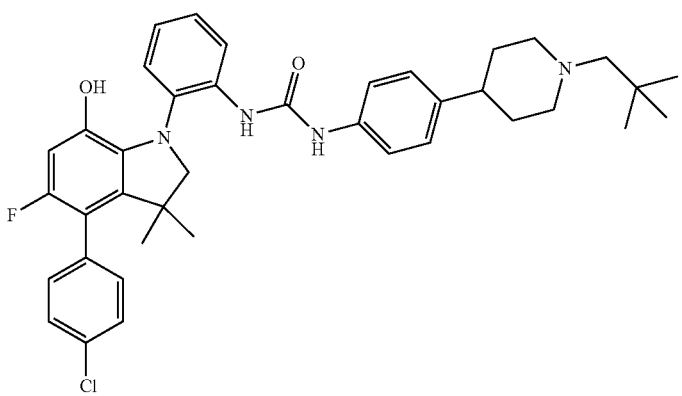 [SMILES: CC(C)(C)CN1CCC(c2ccc(NC(=O)Nc3ccccc3N3CC(C)(C)c4c(-c5ccc(Cl)cc5)c(F)cc(O)c43)cc2)CC1] | m/z 655.5 (M + H)+, RT = 3.61 min (Method C) |
| 241 | 1-(2-(4-(4-(tert-Butyl)phenyl)-5-fluoro-7-hydroxy-3,3-dimethylindolin-1-yl)phenyl)-3-(4-(trifluoromethoxy)phenyl)urea | 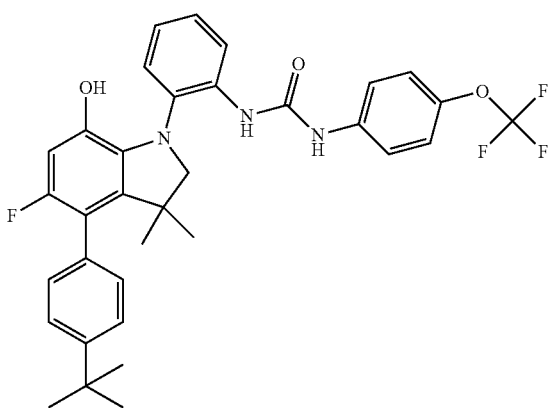 [SMILES: CC(C)(C)c1ccc(-c2c(F)cc(O)c3c2C(C)(C)CN3c2ccccc2NC(=O)Nc2ccc(OC(F)(F)F)cc2)cc1] | m/z 608.5 (M + H)+, RT = 4.41 min (Method C) |

| Example No. | Compound Name | Compound Structure | LC-MS (ESI) m/z |
|---|---|---|---|
| 242 | 1-(2-(4-(4-(tert-Butyl)phenyl)-5-fluoro-7-hydroxy-3,3-dimethylindolin-1-yl)phenyl)-3-(2-chlorothiazol-4-yl)urea | 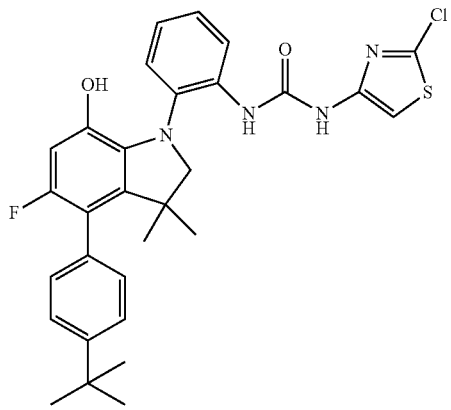 [SMILES: CC(C)(C)c1ccc(-c2c(F)cc(O)c3c2C(C)(C)CN3c2ccccc2NC(=O)Nc2csc(Cl)n2)cc1] | m/z 565.4 (M + H)+, RT = 4.37 min (Method C) |
| 243 | 1-(2-(4-(4-(tert-Butyl)phenyl)-5-fluoro-7-hydroxy-3,3-dimethylindolin-1-yl)phenyl)-3-(2-(trifluoromethyl)thiazol-4-yl)urea | 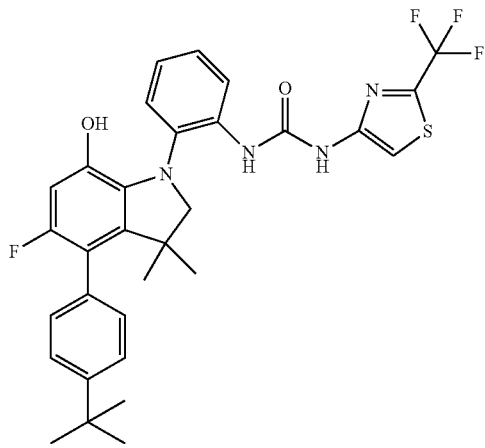 [SMILES: CC(C)(C)c1ccc(-c2c(F)cc(O)c3c2C(C)(C)CN3c2ccccc2NC(=O)Nc2csc(C(F)(F)F)n2)cc1] | m/z 599.4 (M + H)+, RT = 4.42 min (Method C) |
| 244 | Methyl 4-(5-fluoro-7-hydroxy-3,3-dimethyl-1-(2-(3-(4-(trifluoromethoxy)phenyl)ureido)phenyl)indolin-4-yl)benzoate | 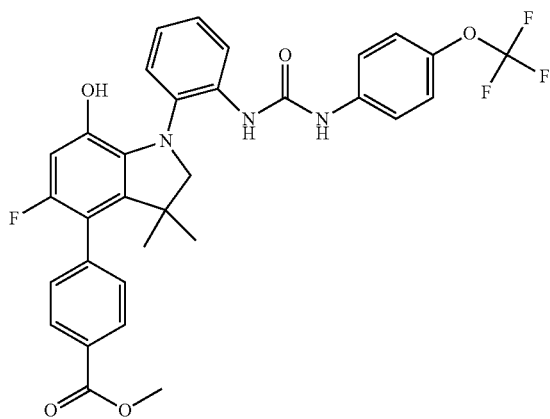 [SMILES: COC(=O)c1ccc(-c2c(F)cc(O)c3c2C(C)(C)CN3c2ccccc2NC(=O)Nc2ccc(OC(F)(F)F)cc2)cc1] | m/z 610.4 (M + H)+, RT = 4.09 min (Method C) |

-continued

| Example No. | Compound Name | Compound Structure | LC-MS (ESI) m/z |
|---|---|---|---|
| 245 | 1-(2-(5-Fluoro-4-(4-fluoro-3-methylphenyl)-7-hydroxy-3,3-dimethylindolin-1-yl)phenyl)-3-(4-(trifluoromethoxy)phenyl)urea | 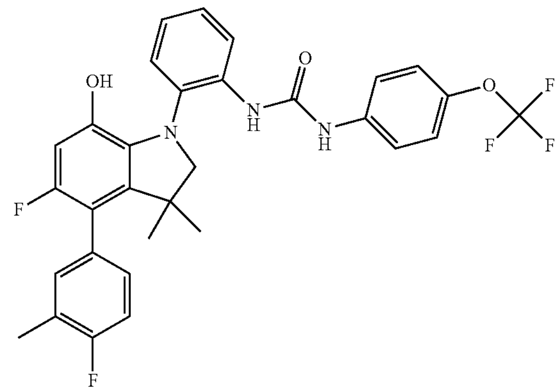 [SMILES: Cc1cc(-c2c(F)cc(O)c3c2C(C)(C)CN3c2ccccc2NC(=O)Nc2ccc(OC(F)(F)F)cc2)ccc1F] | m/z 584.4 (M + H)+, RT = 4.27 min (Method C) |
| 246 | 1-(2-(5-Fluoro-7-hydroxy-3,3-dimethyl-4-(4-(trifluoromethyl)phenyl)indolin-1-yl)phenyl)-3-(1-neopentylpiperidin-4-yl)urea | 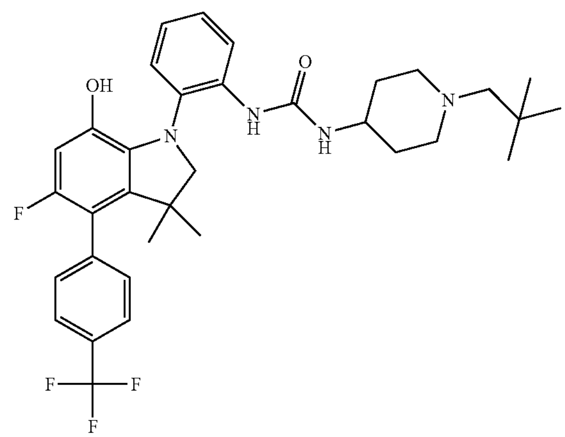 [SMILES: CC(C)(C)CN1CCC(NC(=O)Nc2ccccc2N2CC(C)(C)c3c(-c4ccc(C(F)(F)F)cc4)c(F)cc(O)c32)CC1] | m/z 613.6 (M + H)+, RT = 3.56 min (Method C) |
| 247 | 1-(2-(4-(3-Cyanophenyl)-5-fluoro-7-hydroxy-3,3-dimethylindolin-1-yl)phenyl)-3-(4-(trifluoromethoxy)phenyl)urea | 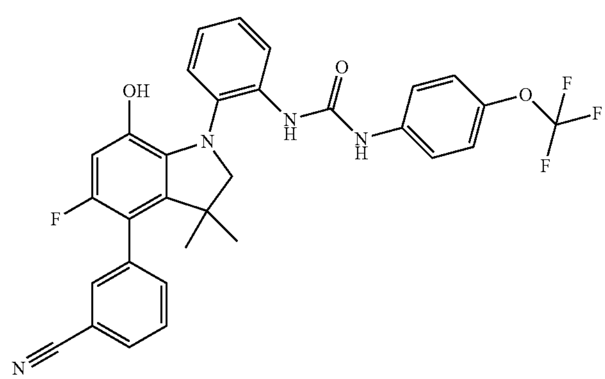 [SMILES: CC1(C)CN(c2ccccc2NC(=O)Nc2ccc(OC(F)(F)F)cc2)c2c(O)cc(F)c(-c3cccc(C#N)c3)c21] | m/z 577.4 (M + H)+, RT = 3.97 min (Method C) |

-continued

| Example No. | Compound Name | Compound Structure | LC-MS (ESI) m/z |
|---|---|---|---|
| 248 | 1-(2-(4-(4-Cyanophenyl)-5-fluoro-7-hydroxy-3,3-dimethylindolin-1-yl)phenyl)-3-(4-(trifluoromethoxy)phenyl)urea | 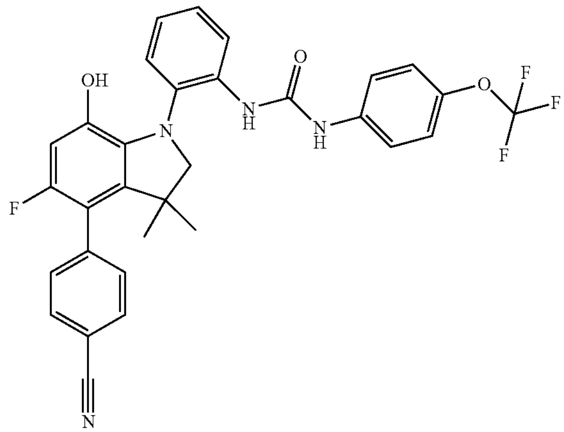 [SMILES: CC1(C)CN(c2ccccc2NC(=O)Nc2ccc(OC(F)(F)F)cc2)c2c(O)cc(F)c(-c3ccc(C#N)cc3)c21] | m/z 577.4 (M + H)+, RT = 3.96 min (Method C) |
| 249 | 1-(2-(4-(3-((Dimethylamino)methyl)phenyl)-5-fluoro-7-hydroxy-3,3-dimethylindolin-1-yl)phenyl)-3-(4-(trifluoromethoxy)phenyl)urea | 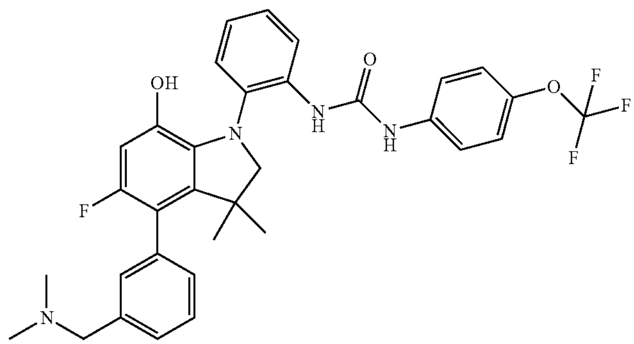 [SMILES: CN(C)Cc1cccc(-c2c(F)cc(O)c3c2C(C)(C)CN3c2ccccc2NC(=O)Nc2ccc(OC(F)(F)F)cc2)c1] | m/z 609.0 (M + H)+, RT = 3.30 min (Method C) |
| 250 | 1-(2-(5-Fluoro-7-hydroxy-3,3-dimethyl-4-(4-(prop-1-en-2-yl)phenyl)indolin-1-yl)phenyl)-3-(4-(trifluoromethoxy)phenyl)urea | 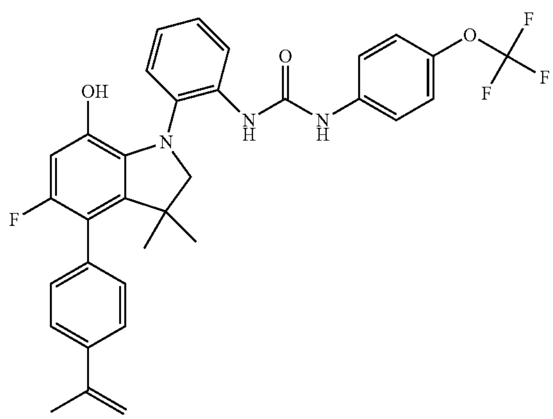 [SMILES: C=C(C)c1ccc(-c2c(F)cc(O)c3c2C(C)(C)CN3c2ccccc2NC(=O)Nc2ccc(OC(F)(F)F)cc2)cc1] | m/z 592.5 (M + H)+, RT = 3.89 min (Method E) |
| 251 | 1-(2-(5-Fluoro-7-hydroxy-3,3-dimethyl-4-(3-(morpholinomethyl)phenyl)indolin-1-yl)phenyl)-3-(4-(trifluoromethoxy)phenyl)urea | 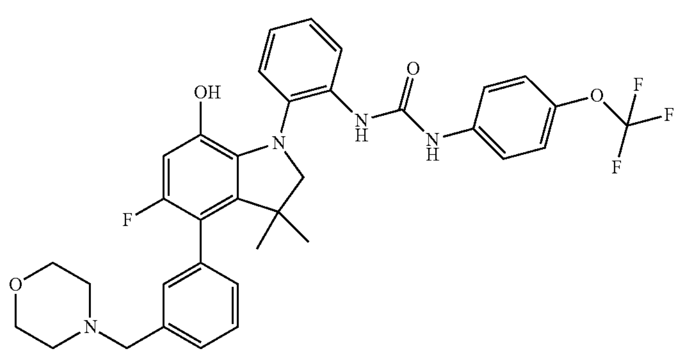 [SMILES: CC1(C)CN(c2ccccc2NC(=O)Nc2ccc(OC(F)(F)F)cc2)c2c(O)cc(F)c(-c3cccc(CN4CCOCC4)c3)c21] | m/z 651.3 (M + H)+, RT = 3.26 min (Method C) |

| Example No. | Compound Name | Compound Structure | LC-MS (ESI) m/z |
|---|---|---|---|
| 252 | 1-(2-(4-Cyclopropyl-5-fluoro-7-hydroxy-3,3-dimethylindolin-1-yl)phenyl)-3-(4-(trifluoromethoxy)phenyl)urea | 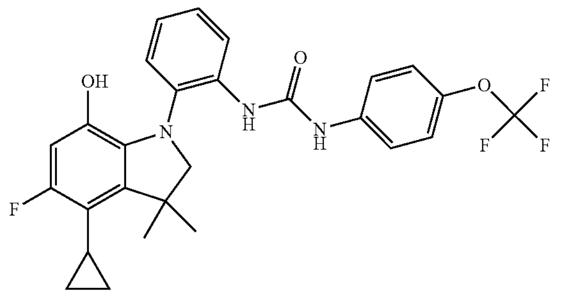 [SMILES: CC1(C)CN(c2ccccc2NC(=O)Nc2ccc(OC(F)(F)F)cc2)c2c(O)cc(F)c(C3CC3)c21] | m/z 516.2 (M + H)+, RT = 4.14 min (Method C) |

Example 253

1-(2-(5-Fluoro-7-hydroxy-4-(1-isopropyl-5-(trifluoromethyl)-1H-pyrazol-3-yl)-3,3-dimethylindolin-1-yl)phenyl)-3-(6-fluorobenzo[d]thiazol-2-yl)urea

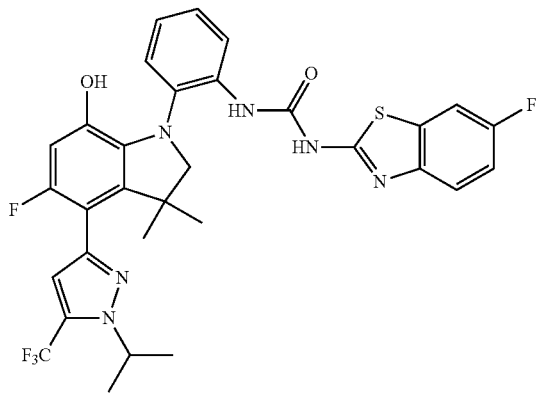 [SMILES: CC(C)n1nc(-c2c(F)cc(O)c3c2C(C)(C)CN3c2ccccc2NC(=O)Nc2nc3ccc(F)cc3s2)cc1C(F)(F)F]

Example 253A.

4-(1-Ethoxyvinyl)-5-fluoro-7-methoxy-3,3-dimethyl-1-(2-nitrophenyl)indoline

A mixture of 4-bromo-5-fluoro-7-methoxy-3,3-dimethyl-1-(2-nitrophenyl)indoline (0.50 g, 1.3 mmol), tributyl(1-ethoxyvinyl)stannane (0.90 mL, 2.7 mmol), and bis(triphenylphosphine)palladium(II) chloride [Pd(PPh$_3$)$_2$Cl$_2$] (91 mg, 0.13 mmol) in toluene (10 mL) was heated at 110° C. for 16 h. The reaction mixture was filtered, and the filtrate was loaded on a 40 g silica gel column which was eluted with a 30 min gradient from 0-100% EtOAc/hexane to give Example 253A (442 mg, 1.14 mmol, 90% yield) as a red solid. $^1$H NMR (400 MHz, CDCl$_3$) δ ppm 8.03 (1 H, dd, J=8.28, 1.76 Hz), 7.40 (1 H, td, J=7.72, 1.63 Hz), 7.06 (1 H, dd, J=8.41, 1.13 Hz), 6.94-7.01 (1 H, m), 6.50 (1 H, d, J=11.04 Hz), 4.48 (1 H, d, J=2.01 Hz), 4.24 (1 H, d, J=2.01 Hz), 3.90 (2 H, q, J=6.94 Hz), 3.83 (1 H, d, J=9.54 Hz), 3.58 (3 H, s), 3.52 (1 H, d, J=9.54 Hz), 1.35-1.42 (6 H, m), 1.32 (3 H, s).

Example 253B.

1-(5-Fluoro-7-methoxy-3,3-dimethyl-1-(2-nitrophenyl)indolin-4-yl)ethanone

A mixture of Example 253A (347 mg, 0.898 mmol) and 1 N HCl (1.0 mL, 1.0 mmol) in THF (5 mL) was stirred at rt for 2 h. The reaction was extracted with EtOAC, and the organic layer was washed with brine, dried over MgSO$_4$, filtered and concentrated. The crude product was dissolved in a small amount of DCM/hexane and was charged to a 40 g silica gel cartridge which was eluted with a 30 min gradient from 0-100% EtOAc/hexane to give Example 253B (296 mg, 0.826 mmol, 92.0% yield) as a red solid. LCMS m/z 359.2 (M+H)+, RT=1.64 min (Method F). $^1$H NMR (400 MHz, CDCl$_3$) δ ppm 8.03 (1 H, dd, J=8.28, 1.76 Hz), 7.42 (1 H, ddd, J=8.41, 7.03, 1.63 Hz), 6.98-7.08 (2 H, m), 6.50 (1 H, d, J=12.05 Hz), 3.84 (1 H, d, J=9.54 Hz), 3.62 (3 H, s), 3.56 (1 H, d, J=9.54 Hz), 2.59 (3 H, d, J=3.26 Hz), 1.38 (3 H, s), 1.32 (3 H, s).

Example 253C.

4,4,4-Trifluoro-1-(5-fluoro-7-methoxy-3,3-dimethyl-1-(2-nitrophenyl)indolin-4-yl)butane-1,3-dione Dimethoxy ethane was added to NaH (77 mg, 1.9 mmol) in a 0.2-0.3 ml microwave vial purged with nitrogen. Ethyl trifluoroacetate (0.230 ml, 1.93 mmol) was added followed by the addition of Example 253B (230 mg, 0.642 mmol). The mixture was purged with nitrogen, and then heated in a microwave reactor for 15 min. The reaction was cooled to rt, diluted with EtOAc (30 mL) and quenched with 1 N HCl (10 mL). The organic layer was separated, washed with brine, dried over MgSO$_4$, filtered and concentrated. The crude product was dissolved in a small amount of DCM/hexane and charged to a 40 g silica gel cartridge which was eluted with a 30 min gradient from 0-100% EtOAc/hexane to give Example 253C (244 mg, 0.537 mmol, 84% yield) as a red foam. $^1$H NMR (400 MHz, CDCl$_3$) δ ppm 8.04 (1H, dd, J=8.28, 1.51 Hz), 7.41-7.49 (1 H, m), 7.00-7.11 (2 H, m), 6.54 (1 H, d, J=12.05 Hz), 6.35 (1 H, d, J=3.51 Hz), 3.84 (1 H, d, J=9.29 Hz), 3.69 (1 H, d, J=9.29 Hz), 3.62 (3 H, s), 1.45 (3 H, s), 1.35-1.40 (3 H, m).

Example 253D

5-Fluoro-7-methoxy-3,3-dimethyl-1-(2-nitrophenyl)-4-(5-(trifluoromethyl)-1H-pyrazol-3-yl)indoline To a solution of Example 253C (300 mg, 0.660 mmol) in AcOH (1 mL) was added hydrazine (0.104 mL, 3.30 mmol).

The mixture was heated at 90° C. for 1.5 h. The solvent was evaporated by coevaporating with toluene. The residue was diluted with DCM, washed with water, dried over MgSO$_4$, filtered and concentrated. The crude product was dissolved in a small amount of DCM and charged to a 40 g silica gel cartridge which was eluted with a 30 min gradient from 0-100% EtOAc/hexane to give Example 253D (257 mg, 0.571 mmol, 86.0% yield) as a red solid. LCMS m/z 451.1 (M+H)$^+$, RT=1.9 min (Method F).

Example 253E.

(5-Fluoro-4-(1-isopropyl-3-(trifluoromethyl)-1H-pyrazol-5-yl)-7-methoxy-3,3-dimethyl-1-(2-nitrophenyl)indoline) and 253F (5-Fluoro-4-(1-isopropyl-3-(trifluoromethyl)-1H-pyrazol-5-yl)-7-methoxy-3,3-dimethyl-1-(2-nitrophenyl)indoline)

To a solution of Example 253D (251 mg, 0.557 mmol) in DMF (1.0 mL) was added 2-iodopropane (0.111 mL, 1.12 mmol). The mixture was heated at 90° C. for 1 h. The reaction mixture was diluted with EtOAc, washed with water, dried over anhydrous sodium sulfate, filtered and evaporated to give the crude product as a red solid. The crude product was dissolved in a small amount of DCM and charged to a 24 g silica gel cartridge which was eluted with a 25 min gradient from 0-50% EtOAc/hexane to give Example 253E (124 mg, 0.252 mmol, 45.2% yield) and Example 253F (135 mg, 0.274 mmol, 49.2% yield), respectively. Example 257E: LCMS m/z 493 (M+H)$^+$ RT=2.2 min (Method F). $^1$H NMR (400 MHz, CDCl$_3$) δ ppm 8.03 (1 H, dd, J=8.34, 1.52 Hz), 7.41 (1 H, ddd, J=8.46, 7.07, 1.64 Hz), 7.07 (1 H, dd, J=8.34, 1.26 Hz), 6.99 (1H, ddd, J=8.34, 7.07, 1.26 Hz), 6.66 (1 H, d, J=1.52 Hz), 6.57 (1 H, d, J=11.37 Hz), 4.68 (1 H, dt, J=12.95, 6.54 Hz), 3.84 (1 H, d, J=9.60 Hz), 3.62 (3 H, s), 3.49 (1 H, d, J=9.60 Hz), 1.56 (6 H, dd, J=6.44, 2.65 Hz), 1.22 (3 H, s), 1.19 (3 H, s). Example 257F: LCMS m/z=493 (M+H)$^+$, RT=2.1 min (Method F).

Example 253G.

2-(5-Fluoro-4-(1-isopropyl-5-(trifluoromethyl)-1H-pyrazol-3-yl)-7-methoxy-3,3-dimethylindolin-1-yl)aniline To a solution of Example 253E (136 mg, 0.276 mmol) in 1:1 MeOH/THF (6 mL) at rt was added 10% Pd/C (14 mg, 0.28 mmol). An atmosphere of H$_2$ balloon was then introduced, and the mixture was stirred at ambient temperature for 1 h during which the mixture turned to a light yellow solution. The reaction was filtered and the filtrate was concentrated to give Example 253G as a light yellow solid which was used without purification. LCMS m/z 463.1 (M+H)$^+$, RT=1.7 min (Method F).

Example 253H.

1-(2-(5-Fluoro-7-hydroxy-4-(1-isopropyl-5-(trifluoromethyl)-1H-pyrazol-3-yl)-3,3-dimethylindolin-1-yl)phenyl)-3-(6-fluorobenzo[d]thiazol-2-yl)urea To a suspension of Example 253G (58 mg, 0.13 mmol), DMAP (3.1 mg, 0.025 mmol) and potassium carbonate (34.7 mg, 0.251 mmol) in DCE (3 mL) was added 4-nitrophenyl chloroformate (26.1 mg, 0.125 mmol). The mixture was stirred at rt for 16 h. Then 6-fluorobenzo[d]thiazol-2-amine (25.3 mg, 0.150 mmol) was added, and the mixture was heated at 90° C. for 30 min in a microwave reactor and then at 55° C. for 3 days. The reaction was diluted with CHCl$_3$ (50 mL), washed with NaHCO$_3$ solution. The organic layer was dried over sodium sulfate and concentrated. The crude product was dissolved in a small amount of DCM and charged to a 12 g silica gel cartridge which was eluted with a 25 min gradient of 0-100% EtOAc/hexane to give Example 253H (60 mg, 0.091 mmol, 73% yield) as a yellow solid. LCMS m/z 657.1 (M+H)$^+$, RT=2.3 min, (Method F).

Example 253

To a suspension of Example 253H (60 mg, 0.091 mmol) in DCM (3 mL) in a 20-ml vial was added tetrabutylammonium iodide (326 mg, 0.883 mmol) and boron trichloride (1.0 M in DCM) (0.883 mL, 0.883 mmol). The mixture was stirred at rt for 16 h. The reaction was then heated at 55° C. for 5 h and stirred at rt for another 16 h. The reaction was quenched with MeOH (2 mL) and water (10 drops) and stirred at rt for 30 min. The mixture was concentrated, and the residue was dissolved in MeOH, filtered and purified by reverse phase preparative HPLC (YMC Sunfire, 5μ, C18 column, 30×100 mm, 10 min gradient from 30-100% B. A=H$_2$O/ACN/TFA 90/10/0.1. B=ACN/H$_2$O/TFA 90/10/0.1) to give Example 253 (29 mg, 0.045 mmol, 51% yield) as a light yellow solid. LCMS m/z 643.1 (M+H)$^+$, RT=2.1 min (Method F). $^1$H NMR (400 MHz, MeOD) δ ppm 8.03-8.09 (1 H, m), 7.61 (1 H, dd, J=8.41, 2.64 Hz), 7.50 (1H, dd, J=8.66, 4.39 Hz), 7.10-7.18 (2 H, m), 7.01-7.06 (2 H, m), 6.74 (1 H, s), 6.50 (1H, d, J=11.04 Hz), 4.68-4.80 (1 H, m), 3.82 (1 H, d, J=9.79 Hz), 3.16 (1 H, d, J=9.79 Hz), 1.57 (6 H, d, J=6.53 Hz), 1.24 (3 H, s), 1.17 (3 H, s).

Example 254

1-(2-(4-(2-tert-Butyloxazol-4-yl)-5-fluoro-7-hydroxy-3,3-dimethylindolin-1-yl)phenyl)-3-(6-fluorobenzo[d]thiazol-2-yl)urea

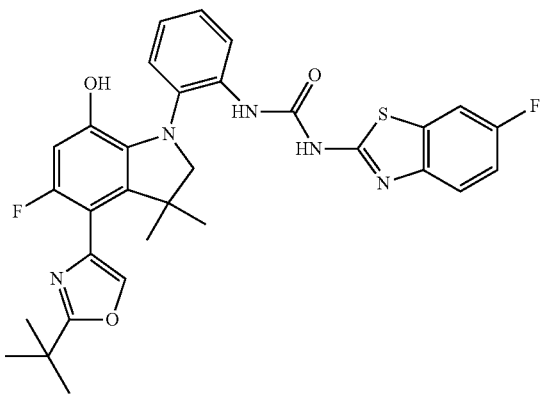 [SMILES: CC(C)(C)c1nc(-c2c(F)cc(O)c3c2C(C)(C)CN3c2ccccc2NC(=O)Nc2nc3ccc(F)cc3s2)co1]

Example 254A.

2-Bromo-1-(5-fluoro-7-methoxy-3,3-dimethyl-1-(2-nitrophenyl)indolin-4-yl)ethanone To a solution of 4-(1-ethoxyvinyl)-5-fluoro-7-methoxy-3,3-dimethyl-1-(2-nitrophenyl)indoline (0.95 g, 2.50 mmol) in THF (20 mL) at −78° C. was added dropwise a solution of NBS (recrystallized) (0.438 g, 2.46 mmol) in THF (10 mL).

The mixture was stirred at rt −78° C. for 30 min. The reaction was quenched with addition of hydrochloric acid (20 mL, 20 mmol) and stirred at rt for 30 min. The mixture was extracted with EtOAc, washed with brine, dried over MgSO$_4$, filtered and concentrated. The crude product was dissolved in a small amount of DCM and charged to a 80 g silica gel cartridge which was eluted with a 45 min gradient from 0-50% EtOAc/hexane to give Example 254A (0.77 g, 1.7 mmol, 72% yield) as a red solid. $^1$H NMR (400 MHz, CDCl$_3$) δ ppm 8.03 (1 H, dd, J=8.28, 1.51 Hz), 7.38-7.48 (1 H, m), 6.99-7.09 (2 H, m), 6.51 (1 H, d, J=12.55 Hz), 4.43 (2 H, dd, J=9.54, 2.01 Hz), 3.84 (1 H, d, J=9.54 Hz), 3.67 (1 H, d, J=9.29 Hz), 3.62 (3 H, s), 1.42 (3 H, s), 1.33 (3 H, s).

Example 254B.

2-tert-Butyl-4-(5-fluoro-7-methoxy-3,3-dimethyl-1-(2-nitrophenyl)indolin-4-yl)oxazole A mixture of Example 254A and pivalamide (251 mg, 2.48 mmol) was heated at 140° C. 5 h. The crude reaction mixture was dissolved in DCM, washed with water, dried over MgSO$_4$, filtered and concentrated. The crude product was dissolved in a small amount of DCM and charged to a 24 g silica gel cartridge which was eluted with a 30 min gradient from 0-100% EtOAc/hexane to give Example 254B (136 mg, 0.309 mmol, 42.3% yield). LCMS m/z 440.2 (M+H)$^+$, RT=2.0 min (Method F).

Example 254

Example 254 was prepared as a light yellow solid from Example 254B following similar procedures as Example 253. LCMS m/z 590 (M+H)$^+$, RT=2.0 min, (Method F). $^1$H NMR (400 MHz, MeOD) δ ppm 8.06 (1 H, d, J=7.78 Hz), 7.83 (1 H, s), 7.61 (1 H, dd, J=8.28, 2.51 Hz), 7.52 (1 H, dd, J=8.66, 4.89 Hz), 7.10-7.20 (2 H, m), 6.98-7.08 (2 H, m), 6.49 (1 H, d, J=10.79 Hz), 3.85 (1 H, d, J=10.04 Hz), 3.15 (1 H, d, J=10.04 Hz), 1.44 (9 H, s), 1.24-1.27 (3 H, m), 1.22 (3 H, s).

Example 255

1-(2-(5-Fluoro-7-hydroxy-4-(isoxazol-5-yl)-3,3-dimethylindolin-1-yl)phenyl)-3-(4-(trifluoromethoxy)phenyl)urea Example 255A.

7-chloro-2-(5-fluoro-7-methoxy-3,3-dimethyl-1-(2-nitrophenyl)indolin-4-yl)imidazo[1,2-c]pyridine A mixture of 2-bromo-1-(5-fluoro-7-methoxy-3,3-dimethyl-1-(2-nitrophenyl)indolin-4-yl)ethanone (81 mg, 0.19 mmol) and 4-chloropyridin-2-amine (51 mg, 0.40 mmol) in ethanol (1.5 mL) was heated at 160° C. in a microwave reactor for 30 min during which the mixture became a dark red solution. The reaction was concentrated and the residue was dissolved in a small amount of DCM and charged to a 12 g silica gel cartridge which was eluted with a 30 min gradient from 0-80% EtOAc/hexane to give Example 255A (48 mg, 0.10 mmol, 56% yield) as a red solid. $^1$H NMR (400 MHz, CDCl$_3$) δ ppm 8.09 (1 H, d, J=7.28 Hz), 8.04 (1 H, dd, J=8.28, 1.51 Hz), 7.62-7.68 (2 H, m), 7.42 (1 H, td, J=7.78, 1.51 Hz), 7.08 (1 H, dd, J=8.41, 1.13 Hz), 6.95-7.03 (1 H, m), 6.83 (1 H, dd, J=7.03, 2.01 Hz), 6.59 (1 H, d, J=11.29 Hz), 3.85 (1 H, d, J=9.79 Hz), 3.64 (3 H, s), 3.50 (1 H, d, J=9.54 Hz), 1.22 (6 H, d, J=7.03 Hz).

Example 255

Example 255 was prepared as a light brown solid from Example 255A following similar procedures as Example 253. LCMS m/z 543.2 (M+H)$^+$, RT=2.0 min (Method F). $^1$H NMR (400 MHz, MeOD) δ ppm 8.40 (1 H, d, J=1.76 Hz), 7.83 (1 H, d, J=8.03 Hz), 7.32-7.46 (2 H, m), 7.06-7.17 (2 H, m), 7.00 (1 H, d, J=3.76 Hz), 6.88 (2 H, d, J=3.76 Hz), 6.34-6.47 (2 H, m), 3.71 (1 H, d, J=9.79 Hz), 3.08 (1 H, d, J=10.04 Hz), 1.12 (6 H, d, J=5.77 Hz).

Example 256

1-(2-(5-Fluoro-7-hydroxy-4-(3-isopropyl-1,2,4-oxadiazol-5-yl)-3,3-dimethylindolin-1-yl)phenyl)-3-(4-(trifluoromethoxy)phenyl)urea

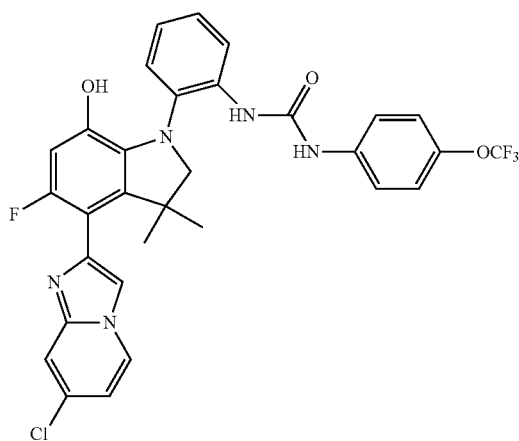 [SMILES: CC1(C)CN(c2ccccc2NC(=O)Nc2ccc(OC(F)(F)F)cc2)c2c(O)cc(F)c(-c3cn4ccc(Cl)cc4n3)c21]

Example 256A.

5-Fluoro-7-methoxy-3,3-dimethyl-1-(2-nitrophenyl)indoline-4-carboxylic acid

Bromine (0.148 mL, 2.88 mmol) was added to sodium hydroxide (9.60 mL, 9.60 mmol) and the mixture was stirred at 0° C. for 20 min. 1-(5-Fluoro-7-methoxy-3,3-dimethyl- 1-(2-nitrophenyl)indolin-4-yl)ethanone (344 mg, 0.960 mmol) was dissolved in dioxane (22 mL) and added dropwise over 1 h at 0° C. After 20 h, bromine (0.049 mL, 0.960 mmol) was added and the mixture was maintained at 0-5° C. for 5 days. The reaction was diluted with water, acidified with hydrochloric acid (1.0 M, aq.) then extracted with ethyl acetate. The extracts were dried over magnesium sulfate, filtered and the solvents were removed to provide Example 256A (346 mg, 11.0 mmol, 100% yield) as a brown solid. LCMS m/z 361 (M+H)$^+$, RT=1.55 min (Method F).

Example 256B.

1-(2-Aminophenyl)-5-fluoro-7-methoxy-3,3-dimethylindoline-4-carboxylic acid

Following similar procedure as Example 253G, Example 256B was obtained (183 mg, 100% yield) as a brown solid. LCMS m/z 331 (M+H)$^+$, RT=1.05 min (Method F).

Example 256C.

5-Fluoro-7-methoxy-3,3-dimethyl-1-(2-(3-(4-(trifluoromethoxy)phenyl)ureido)phenyl)indoline-4-carboxylic acid Following similar procedure as Example 253H, Example 256C was obtained (206 mg, 69.4% yield) as a white solid. LCMS m/z 534 (M+H)$^+$, RT=1.93 min (Method F).

Example 256D.

N-(5-Fluoro-7-methoxy-3,3-dimethyl-1-(2-(3-(4-(trifluoromethoxy)phenyl)ureido)phenyl)indoline-4-carbonyloxy)isobutyrimidamide:

Example 256C (50 mg, 0.094 mmol) and N'-hydroxy-2-methylpropanimidamide (14.4 mg, 0.141 mmol) were dissolved in dichloromethane (5 mL). Triethylamine (0.039 mL, 0.28 mmol) and PyBOP (98 mg, 0.19 mmol) were added and the mixture was stirred at room temperature for 48 h. The reaction mixture was loaded onto CELITE® and purified by flash chromatography (40 g silica gel cartridge; 0-100% ethyl acetate/hexane over 14 min, 40 mL/min) to provide Example 256D (42 mg, 73% yield) as a yellow solid. LCMS m/z 534 (M+H)$^+$, RT=1.93 min (Method F).

Example 256E 1-(2-(5-Fluoro-4-(3-isopropyl-1,2,4-oxadiazol-5-yl)-7-methoxy-3,3-dimethylindolin-1-yl)phenyl)-3-(4-(trifluoromethoxy)phenyl)urea Example 256D (39 mg, 0.064 mmol) was dissolved in acetonitrile (4 mL). TBAF (0.4 mL, 0.4 mmol) was added and the mixture was stirred at 50° C. for 23 h. The reaction mixture was loaded onto CELITE® and purified by flash chromatography (12 g silica gel cartridge; 0-60% ethyl acetate/hexane over 11 min, 30 mL/min) to provide Example 256E (19.8 mg, 51.8% yield) as a tan solid. LCMS m/z 600 (M+H)$^+$, RT=2.32 min (Method F).

Example 256

Example 256E (19 mg, 0.032 mmol) and tetrabutylammonium iodide (117 mg, 0.317 mmol) were dissolved in dichloromethane (1 mL). Boron trichloride (0.317 mL, 0.317 mmol) (1.0 M in dichloromethane) was added and the mixture was stirred at room temperature for 21 h. The reaction was quenched with methanol and water and stirred at room temperature for 2 h. Dichloromethane and water were added. The pH of the aqueous layer was 1. The reaction was extracted with dichloromethane. The organic extracts were dried over magnesium sulfate, filtered and the solvent removed to provide 98 mg of the crude product as a brown oil. The crude product was dissolved in methanol/acetonitrile and purified by prep HPLC (PHENOMENEX® Axia Luna 5u C18 30×100 column; 10-90% acetonitrile, water with 0.1% TFA over 10 min.; 40 mL/min; UV detection at 220 nm) to yield Example 256 (3.76 mg, 20.3% yield) as a white powder. LCMS m/z 586.2 (M+H)$^+$, RT=2.15 min (Method F). $^1$H NMR (400 MHz, MeOD) δ ppm 7.96 (dd, J=8.0, 2.5 Hz, 1H), 7.61-7.46 (m, 2H), 7.20 (d, J=8.3 Hz, 2H), 7.14 (d, J=4.5 Hz, 1H), 7.00 (d, J=4.0 Hz, 2H), 6.57 (d, J=11.5 Hz, 1H), 3.85 (d, J=10.0 Hz, 1H), 3.27-3.14 (m, 2H), 1.41 (d, J=6.8 Hz, 6H), 1.27 (s, 6H).

Example 257

1-(5-Chlorothiazolo[5,4-b]pyridin-2-yl)-3-(2-(5-fluoro-7-hydroxy-3,3-dimethyl-4-(5-(trifluoromethyl)-1,2,4-oxadiazol-3-yl)indolin-1-yl)phenyl)urea

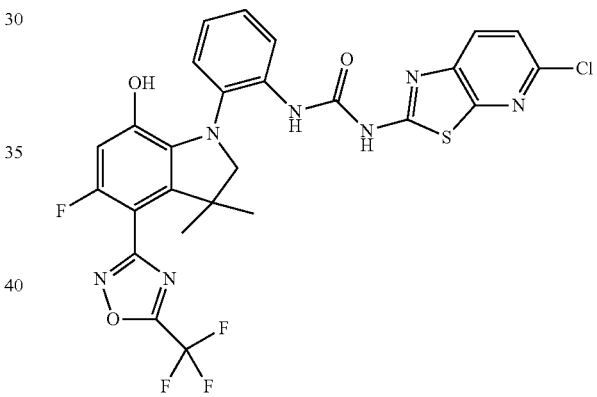

Example 257A.

5-Fluoro-7-methoxy-3,3-dimethyl-1-(2-nitrophenyl)indoline-4-carbonitrile

4-Bromo-5-fluoro-7-methoxy-3,3-dimethyl-1-(2-nitrophenyl)indoline (1.48 g, 3.74 mmol), zinc (0.070 g, 1.1 mmol), zinc cyanide (0.90 g, 7.5 mmol) and bis-(tri-t-butylphosphine)palladium(0) (0.10 g, 0.19 mmol) were combined with dimethylformamide (20 mL) in a microwave tube and sealed. The reaction was heated under microwave irradiation at 120° C. for 30 min. After cooling to room temperature, the reaction was combined with water/ice and extracted with ethyl acetate (2×). The organics were pooled together and washed with brine (2×), dried over sodium sulfate, filtered and concentrated. The crude product was purified by flash chromatography (40 g cartridge, 0 to 40% ethyl acetate/hexanes) to afford Example 257A (980 mg, 77%) as a white solid. LC/MS m/z 342.1 (M+H)$^+$, RT=1.61 min (Method F).

Example 257B.

(Z)-5-Fluoro-N'-hydroxy-7-methoxy-3,3-dimethyl-1-(2-nitrophenyl)indoline-4-carboximidamide Example 257A (900 mg, 2.64 mmol) was dissolved in 1-butanol (25 mL) and treated with hydroxylamine hydrochloride (916 mg, 13.2 mmol) and triethylamine (1.80 mL, 13.2 mmol). The reaction was heated at reflux for 16 hours. After cooling to room temperature, the reaction was concentrated and purified by flash chromatography (12 g Cartridge, 0 to 100% ethyl acetate/hexanes) to afford a mixture of the desired product and the undesired amide that could not be separated. This mixture was dissolved in methanol and purified by reverse phase preparative HPLC (YMC Sunfire, 5μ, C18 column, 30×100 mm, 10 min gradient from 30-100% B. A=$H_2O$/MeOH/$NH_4OAc$ 90/10/10 mM B=MeOH/$H_2O$/$NH_4OAc$ 90/10/10 mM) to afford Example 257B (500 mg, 51%) as a white solid. LC/MS m/z 375.1 $(M+H)^+$, RT=0.87 min (Method F).

Example 257C.

3-(5-Fluoro-7-methoxy-3,3-dimethyl-1-(2-nitrophenyl)indolin-4-yl)-5-(trifluoromethyl)-1,2,4-oxadiazole Example 257B (0.50 g, 1.3 mmol) was stirred with dry pyridine (10 mL) in a round bottomed flask and heated to reflux. To this solution was added trifluoroacetic anhydride (0.38 mL, 2.7 mmol) at a rate to maintain a gentle reflux. Heating was removed and the reaction allowed to cool to room temperature. Pyridine was concentrated in vacuo, and the resulting crude product was dissolved in ethyl acetate and washed with water (2×), brine (2×), dried over sodium sulfate, filtered and concentrated. The crude product was purified by flash chromatography (40 g cartridge, 0 to 30% ethyl acetate/hexanes) to afford Example 257C (180 mg, 30%). $^1$H NMR (400 MHz, $CDCl_3$) δ 8.10-8.02 (m, 1H), 7.50-7.43 (m, 1H), 7.14-7.03 (m, 2H), 6.63 (d, J=11.3 Hz, 1H), 3.89-3.70 (m, 2H), 3.64 (s, 3H), 1.34 (s, 3H), 1.19 (s, 3H). MS 353.1 $(M+H)^+$.

Example 257

Following similar procedures as those of Example 253, Example 257 was obtained from Example 257C (8.0 mg, 22%) as a white solid. $^1$H NMR (400 MHz, $CDCl_3$) δ 7.98-7.87 (m, 1H), 7.73 (d, J=8.3 Hz, 1H), 7.38 (d, J=8.6 Hz, 1H), 7.24-7.09 (m, 3H), 6.63 (m, 1H), 3.84-3.73 (m, 1H), 3.28-3.15 (m, 1H), 1.29-1.24 (s, 3H), 1.12 (s, 3H). LCMS m/z 620.2 $(M+H)^+$, RT=1.92 min (Method F).

Examples 258 to 278 were prepared according to the procedures described in Examples 253 to 257.

| Example No. | Compound Name | Compound Structure | LC-MS (ESI) m/z |
|---|---|---|---|
| 258 | 1-(2-(5-Fluoro-7-hydroxy-4-(2-isopropyloxazol-4-yl)-3,3-dimethylindolin-1-yl)phenyl)-3-(4-(trifluoromethoxy)phenyl)urea | 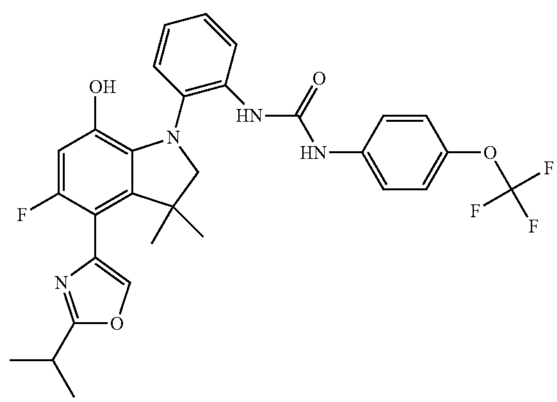 [SMILES: CC(C)c1nc(-c2c(F)cc(O)c3c2C(C)(C)CN3c2ccccc2NC(=O)Nc2ccc(OC(F)(F)F)cc2)co1] | m/z 585.3 $(M + H)^+$, RT = 1.94 min (Method F) |
| 259 | 1-(2-(4-(2-(tert-Butyl)oxazol-4-yl)-5-fluoro-7-hydroxy-3,3-dimethylindolin-1-yl)phenyl)-3-(4-(trifluoromethoxy)phenyl)urea | 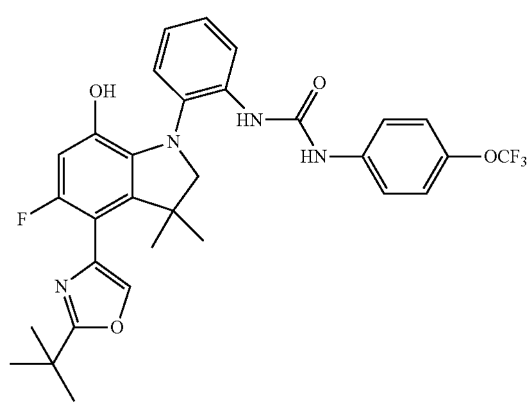 [SMILES: CC(C)(C)c1nc(-c2c(F)cc(O)c3c2C(C)(C)CN3c2ccccc2NC(=O)Nc2ccc(OC(F)(F)F)cc2)co1] | m/z 599.2 $(M + H)^+$, RT = 2.0 min (Method F) |

-continued

| Example No. | Compound Name | Compound Structure | LC-MS (ESI) m/z |
|---|---|---|---|
| 260 | 1-(2-(5-Fluoro-7-hydroxy-4-(2-isobutyloxazol-4-yl)-3,3-dimethylindolin-1-yl)phenyl)-3-(4-(trifluoromethoxy)phenyl)urea | 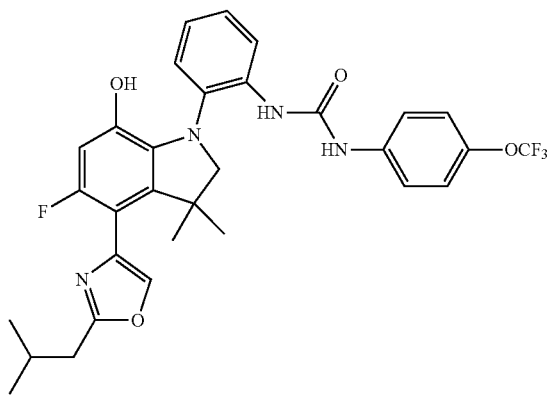 [SMILES: CC(C)Cc1nc(-c2c(F)cc(O)c3c2C(C)(C)CN3c2ccccc2NC(=O)Nc2ccc(OC(F)(F)F)cc2)co1] | m/z 599.2 (M + H)⁺, RT = 2.0 min (Method F) |
| 261 | 1-(2-(5-Fluoro-7-hydroxy-4-(isoxazol-5-yl)-3,3-dimethylindolin-1-yl)phenyl)-3-(4-(trifluoromethoxy)phenyl)urea | 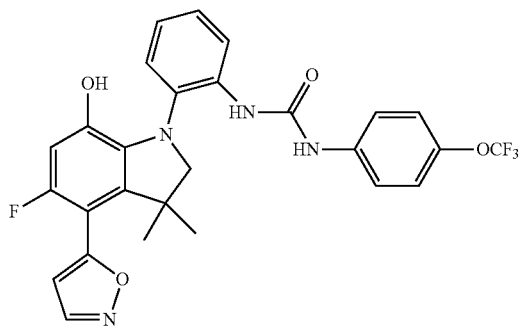 [SMILES: CC1(C)CN(c2ccccc2NC(=O)Nc2ccc(OC(F)(F)F)cc2)c2c(O)cc(F)c(-c3ccno3)c21] | m/z 543.2 (M + H)⁺, RT = 2.0 min (Method F) |
| 262 | 1-(2-(5-Fluoro-7-hydroxy-3,3-dimethyl-4-(3-(trifluoromethyl)isoxazol-5-yl)indolin-1-yl)phenyl)-3-(4-(trifluoromethoxy)phenyl)urea | 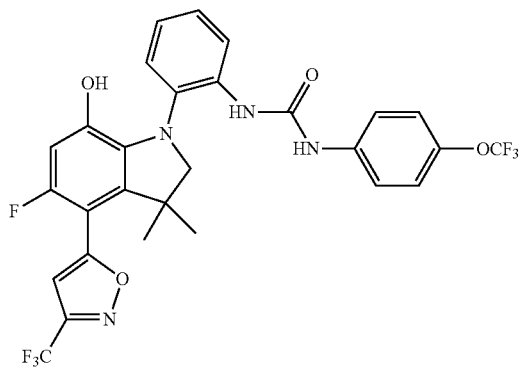 [SMILES: CC1(C)CN(c2ccccc2NC(=O)Nc2ccc(OC(F)(F)F)cc2)c2c(O)cc(F)c(-c3cc(C(F)(F)F)no3)c21] | m/z 611.2 (M + H)⁺, RT = 2.2 min (Method F) |
| 263 | 1-(5-Chlorothiazolo[5,4-b]pyridin-2-yl)-3-(2-(5-fluoro-7-hydroxy-3,3-dimethyl-4-(3-(trifluoromethyl)isoxazol-5-yl)indolin-1-yl)phenyl)urea | 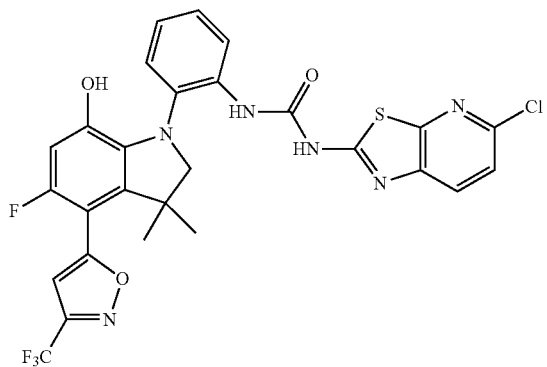 [SMILES: CC1(C)CN(c2ccccc2NC(=O)Nc2nc3ccc(Cl)nc3s2)c2c(O)cc(F)c(-c3cc(C(F)(F)F)no3)c21] | m/z 619.1 (M + H)⁺, RT = 2.1 min (Method F) |

-continued

| Example No. | Compound Name | Compound Structure | LC-MS (ESI) m/z |
|---|---|---|---|
| 264 | 1-(2-(5-Fluoro-7-hydroxy-3,3-dimethyl-4-(3-(trifluoromethyl)isoxazol-5-yl)indolin-1-yl)phenyl)-3-(6-fluorobenzo[d]thiazol-2-yl)urea | 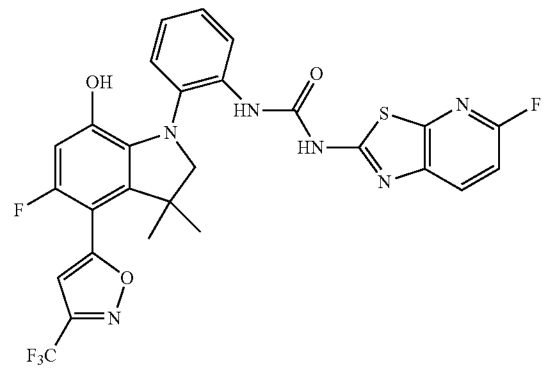 [SMILES: CC1(C)CN(c2ccccc2NC(=O)Nc2nc3ccc(F)nc3s2)c2c(O)cc(F)c(-c3cc(C(F)(F)F)no3)c21] | m/z 602.1 (M + H)+, RT = 2.1 min (Method F) |
| 265 | 1-(6-Chlorobenzo[d]thiazol-2-yl)-3-(2-(5-fluoro-7-hydroxy-3,3-dimethyl-4-(3-(trifluoromethyl)isoxazol-5-yl)indolin-1-yl)phenyl)urea | 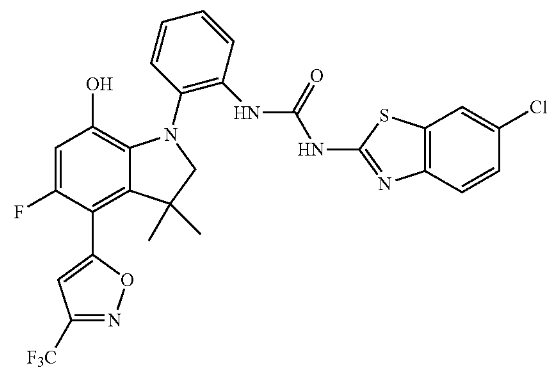 | m/z 18.1 (M + H)+, RT = 2.24 min (Method F) |
| 266 | 1-(6-Chlorobenzo[d]thiazol-2-yl)-3-(2-(5-fluoro-7-hydroxy-4-(1-isopropyl-5-(trifluoromethyl)-1H-pyrazol-3-yl)-3,3-dimethylindolin-1-yl)phenyl)urea | 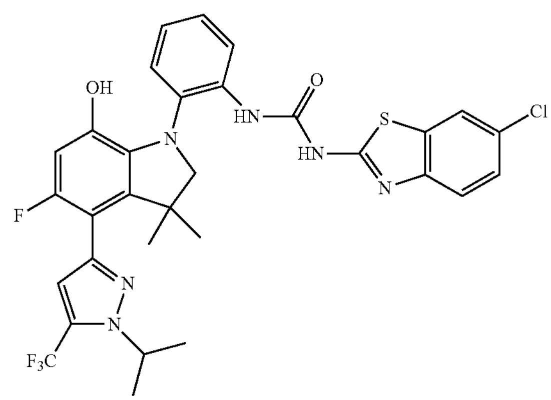 [SMILES: CC(C)n1nc(-c2c(F)cc(O)c3c2C(C)(C)CN3c2ccccc2NC(=O)Nc2nc3ccc(Cl)cc3s2)cc1C(F)(F)F] | m/z 659.7 (M + H)+, RT = 2.2 min (Method F) |
| 267 | 1-(2-(5-Fluoro-7-hydroxy-4-(1-isopropyl-3-(trifluoromethyl)-1H-pyrazol-5-yl)-3,3-dimethylindolin-1-yl)phenyl)-3-(6-fluorobenzo[d]thiazol-2-yl)urea | 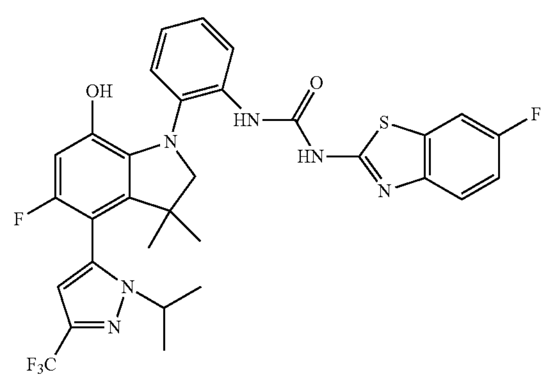 [SMILES: CC(C)n1nc(C(F)(F)F)cc1-c1c(F)cc(O)c2c1C(C)(C)CN2c1ccccc1NC(=O)Nc1nc2ccc(F)cc2s1] | m/z 643.1 (M + H)+, RT = 2.0 min (Method F) |

-continued

| Example No. | Compound Name | Compound Structure | LC-MS (ESI) m/z |
|---|---|---|---|
| 268 | 1-(6-Chlorobenzo[d]thiazol-2-yl)-3-(2-(5-fluoro-7-hydroxy-4-(1-isopropyl-3-(trifluoromethyl)-1H-pyrazol-5-yl)-3,3-dimethylindolin-1-yl)phenyl)urea | 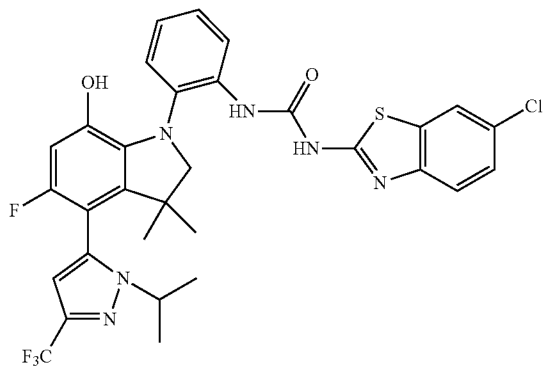 [SMILES: CC(C)n1nc(C(F)(F)F)cc1-c1c(F)cc(O)c2c1C(C)(C)CN2c1ccccc1NC(=O)Nc1nc2ccc(Cl)cc2s1] | m/z 659.1 (M + H)+, RT = 2.1 min (Method F) |
| 269 | 1-(2-Chlorothiazol-4-yl)-3-(2-(5-fluoro-7-hydroxy-3,3-dimethyl 4-(3-(trifluoromethyl)isoxazol-5-yl)indolin-1-yl)phenyl)urea | 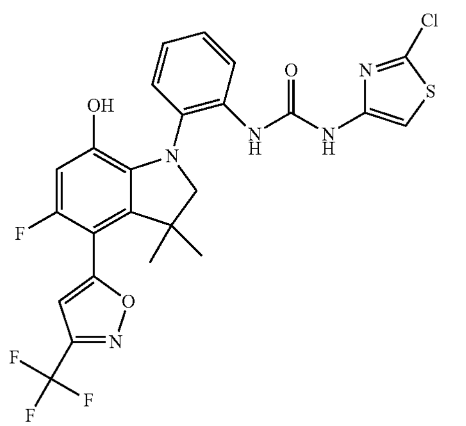 [SMILES: CC1(C)CN(c2ccccc2NC(=O)Nc2csc(Cl)n2)c2c(O)cc(F)c(-c3cc(C(F)(F)F)no3)c21] | m/z 567.9 (M + H)+, RT = 2.0 min (Method F) |
| 270 | 1-(2-(4-(2-(tert-Butyl)oxazol-4-yl)-5-fluoro-7-hydroxy-3,3-dimethylindolin-1-yl)phenyl)-3-(6-chlorobenzo[d]thiazol-2-yl)urea | 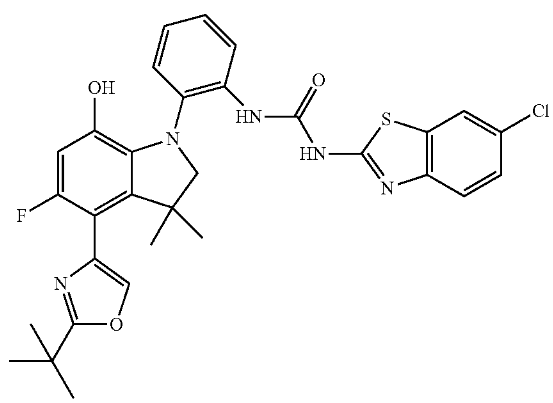 [SMILES: CC(C)(C)c1nc(-c2c(F)cc(O)c3c2C(C)(C)CN3c2ccccc2NC(=O)Nc2nc3ccc(Cl)cc3s2)co1] | m/z 606.1 (M + H)+, RT = 2.2 min (Method F) |
| 271 | 1-(2-(5-Fluoro-7-hydroxy-4-(1-isopropyl-5-(trifluoromethyl)-1H-pyrazol-3-yl)-3,3-dimethylindolin-1-yl)phenyl)-3-(4-(trifluoromethoxy)phenyl)urea | 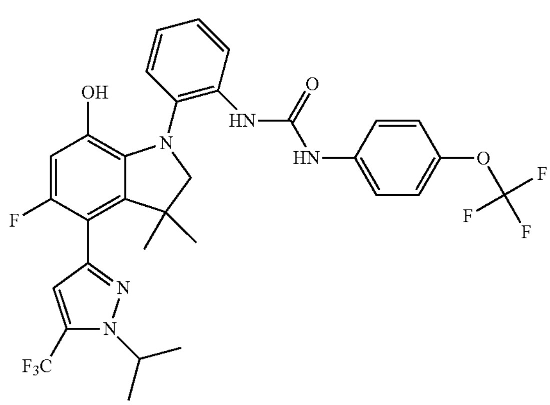 [SMILES: CC(C)n1nc(-c2c(F)cc(O)c3c2C(C)(C)CN3c2ccccc2NC(=O)Nc2ccc(OC(F)(F)F)cc2)cc1C(F)(F)F] | m/z 652.1 (M + H)+, RT = 2.2 min (Method F) |

-continued

| Example No. | Compound Name | Compound Structure | LC-MS (ESI) m/z |
|---|---|---|---|
| 272 | 1-(2-(5-Fluoro-7-hydroxy-4-(1-isopropyl-5-(trifluoromethyl)-1H-pyrazol-3-yl)-3,3-dimethylindolin-1-yl)phenyl)-3-(2-(trifluoromethyl)thiazol-4-yl)urea | 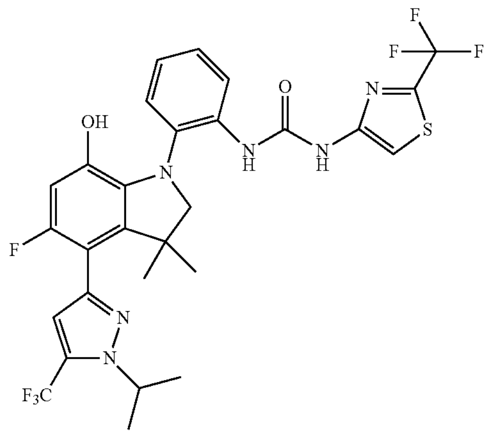 [SMILES: CC(C)n1nc(-c2c(F)cc(O)c3c2C(C)(C)CN3c2ccccc2NC(=O)Nc2csc(C(F)(F)F)n2)cc1C(F)(F)F] | m/z 643.0 (M + H)+, RT = 2.4 min (Method F) |
| 273 | 1-(2-Chlorothiazol-4-yl)-3-(2-(5-fluoro-7-hydroxy-4-(1-isopropyl-5-(trifluoromethyl)-1H-pyrazol-3-yl)-3,3-dimethylindolin-1-yl)phenyl)urea | 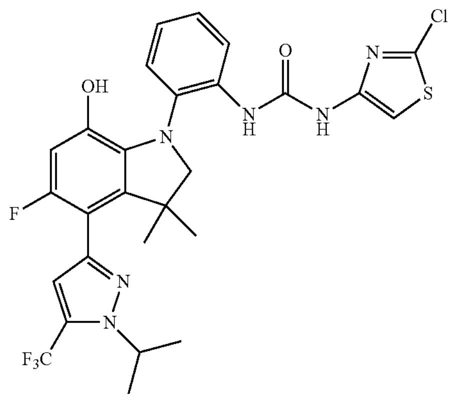 [SMILES: CC(C)n1nc(-c2c(F)cc(O)c3c2C(C)(C)CN3c2ccccc2NC(=O)Nc2csc(Cl)n2)cc1C(F)(F)F] | m/z 609.0 (M + H)+, RT = 2.4 min (Method F) |
| 274 | 1-(2-(5-Fluoro-7-hydroxy-3,3-dimethyl-4-(2-methyloxazol-4-yl)indolin-1-yl)phenyl)-3-(4-(trifluoromethoxy)phenyl)urea | 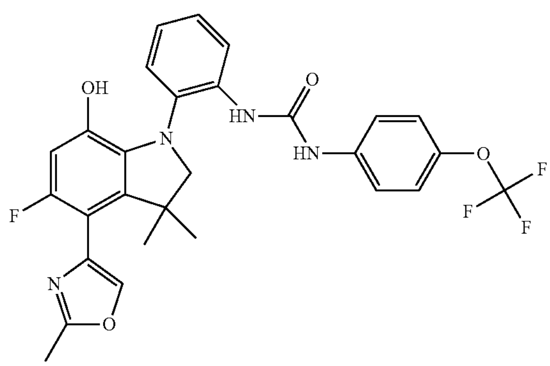 [SMILES: Cc1nc(-c2c(F)cc(O)c3c2C(C)(C)CN3c2ccccc2NC(=O)Nc2ccc(OC(F)(F)F)cc2)co1] | m/z 557.2 (M + H)+, RT = 1.7 min (Method F) |
| 275 | 1-(2-(5-Fluoro-7-hydroxy-3,3-dimethyl 4-(3-(trifluoromethyl)-1H-pyrazol-5-yl)indolin-1-yl)phenyl)-3-(4-(trifluoromethoxy)phenyl)urea | 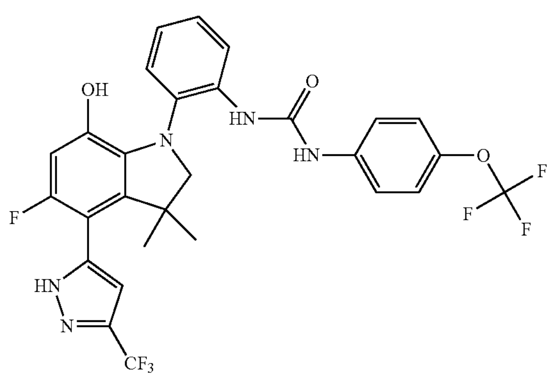 [SMILES: CC1(C)CN(c2ccccc2NC(=O)Nc2ccc(OC(F)(F)F)cc2)c2c(O)cc(F)c(-c3cc(C(F)(F)F)n[nH]3)c21] | m/z 610.3 (M + H)+, RT = 2.0 min (Method F) |

| Example No. | Compound Name | Compound Structure | LC-MS (ESI) m/z |
|---|---|---|---|
| 276 | 1-(2-(5-Fluoro-7-hydroxy-3,3-dimethyl-4-(5-(trifluoromethyl)-1,2,4-oxadiazol-3-yl)indolin-1-yl)phenyl)-3-(4-(trifluoromethoxy)phenyl)urea | 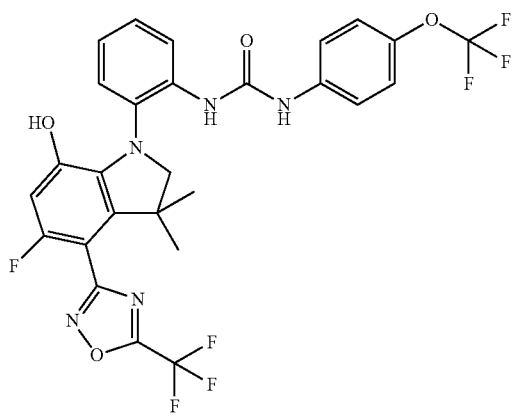 [SMILES: CC1(C)CN(c2ccccc2NC(=O)Nc2ccc(OC(F)(F)F)cc2)c2c(O)cc(F)c(-c3noc(C(F)(F)F)n3)c21] | m/z 612.2 (M + H)+, RT = 1.96 min (Method F) |
| 277 | 1-(2-(5-Fluoro-7-hydroxy-3,3-dimethyl-4-(5-(trifluoromethyl)-1,2,4-oxadiazol-3-yl)indolin-1-yl)phenyl)-3-(6-fluorobenzo[d]thiazol-2-yl)urea | 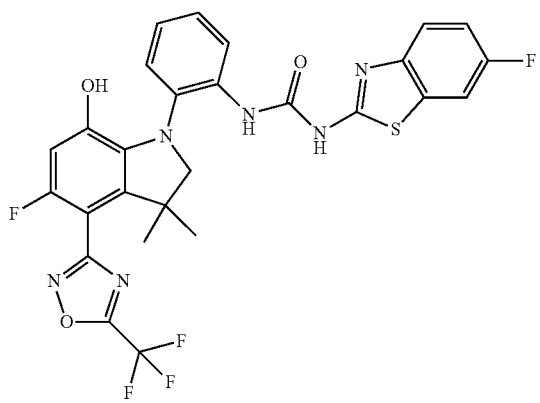 [SMILES: CC1(C)CN(c2ccccc2NC(=O)Nc2nc3ccc(F)cc3s2)c2c(O)cc(F)c(-c3noc(C(F)(F)F)n3)c21] | m/z 603.1 (M + H)+, RT = 1.89 min (Method F) |
| 278 | 1-(2-(4-(5-(tert-Butyl)-1,2,4-oxadiazol-3-yl)-5-fluoro-7-hydroxy-3,3-dimethylindolin-1-yl)phenyl)-3-(4-(trifluoromethoxy)phenyl)urea | 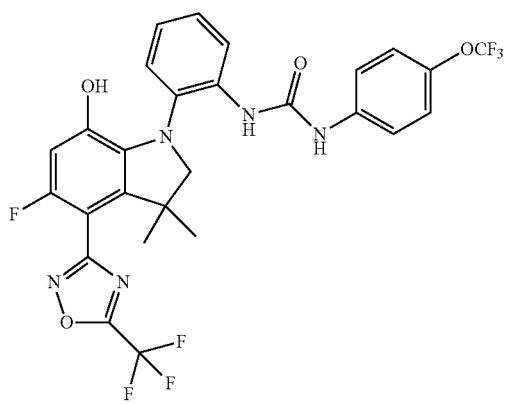 | m/z 600.1 (M + H)+, RT = 2.13 min (Method F) |

What is claimed is:

1. A compound of Formula (I):

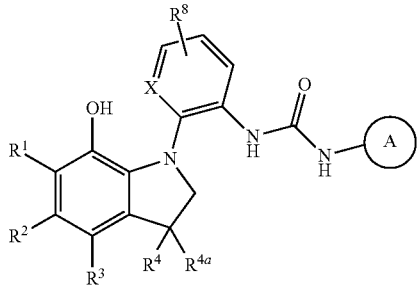

(I)

or a stereoisomer, a tautomer or a pharmaceutically acceptable salt thereof, wherein:

X is independently CH or N;

ring A is independently selected from $C_{3-6}$ carbocycle substituted with 0-3 $R^5$ and a heterocycle substituted with 0-2 $R^5$; wherein said heterocycle is selected from thienyl, thiazolyl, thiadiazolyl, pyridyl,

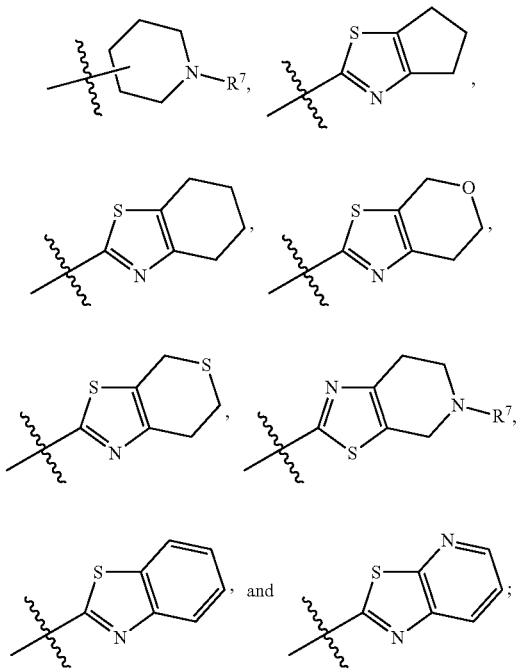

$R^1$ is independently selected from H, halogen and OH;

$R^2$ is independently H or halogen;

$R^3$ is independently selected from a ring moiety substituted with 0-3 $R^6$ and selected from the group consisting of $C_{3-6}$ cycloalkyl, phenyl;

$R^4$ and $R^{4a}$ are, independently at each occurrence, selected from $C_{1-6}$ alkyl, $CO_2(C_{1-4}$ alkyl) and $C_{1-6}$ haloalkyl;

$R^5$ is, independently at each occurrence, selected from halogen, $C_{1-6}$ alkyl, $C_{1-6}$ alkoxy, $C_{1-6}$ alkylthio, $C_{1-6}$ haloalkyl, $C_{1-6}$ haloalkoxy, $CO_2(C_{1-4}$ alkyl), $NO_2$, and

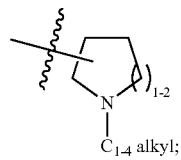

$R^6$ is, independently at each occurrence, selected from halogen, $C_{1-6}$ alkyl, $C_{2-6}$ alkenyl, $C_{1-6}$ haloalkyl, $C_{1-4}$ alkoxy, $C_{1-4}$ haloalkoxy, $C_{1-4}$ alkylthio, $CH_2OH$, CN, $CO_2(C_{1-4}$ alkyl), $NH(C_{1-4}$ alkyl), $CH_2N(C_{1-4}$ alkyl)$_2$, and morpholinylmethyl;

$R^7$ is independently selected from $C_{1-6}$ alkyl, $C_{1-6}$ haloalkyl, $CO(C_{1-4}$ alkyl), $-(CH_2)_{1-2}-C_{3-6}$ cycloalkyl, and $COCF_3$; and $R^8$ is independently selected from H, halogen and CN.

2. A compound according to claim 1, wherein:

ring A is independently selected from

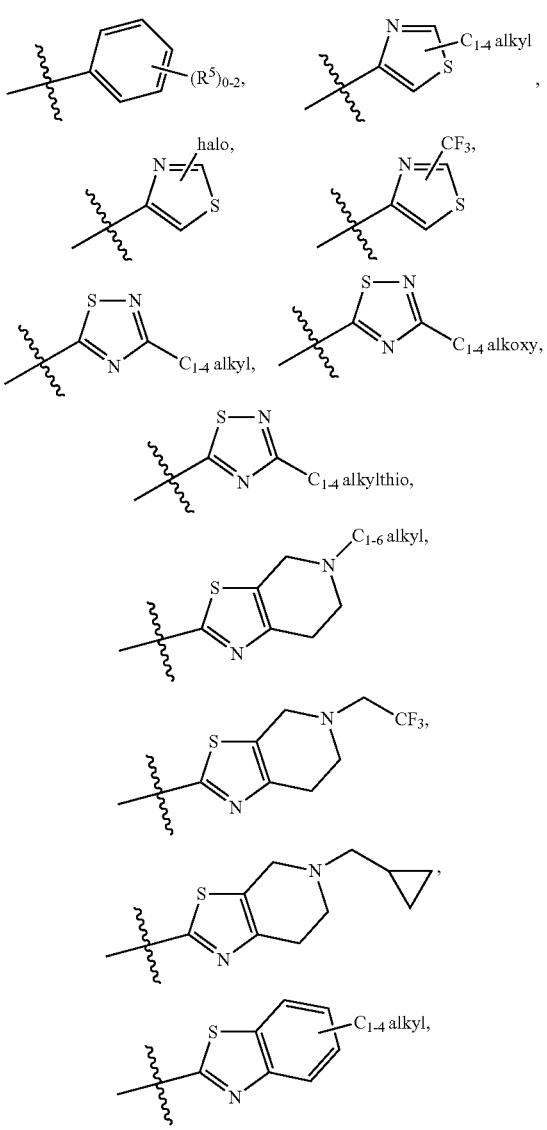

-continued

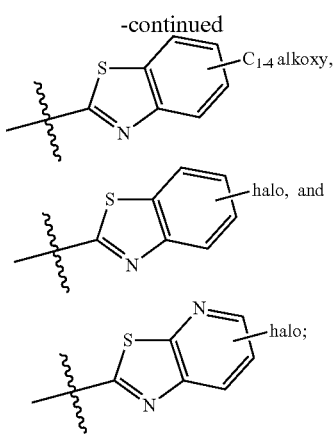

R$^1$ is independently H or halogen;
R$^2$ is independently H or halogen;
R$^3$ is independently selected from a ring moiety substituted with 0-2 R$^6$ and selected from the group consisting of phenyl;
R$^4$ is independently C$_{1-6}$ alkyl;
R$^{4a}$ is independently selected from C$_{1-6}$ alkyl, CO$_2$(C$_{1-4}$ alkyl) and C$_{1-6}$ haloalkyl;
R$^5$ is, independently at each occurrence, selected from halogen, C$_{1-6}$ alkyl, C$_{1-6}$ alkoxy, C$_{1-6}$ haloalkyl, C$_{1-6}$ haloalkoxy, and

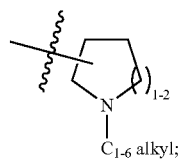

and
R$^8$ is independently selected from H or halogen.
3. A compound according to claim 1, wherein:
ring A is independently selected from

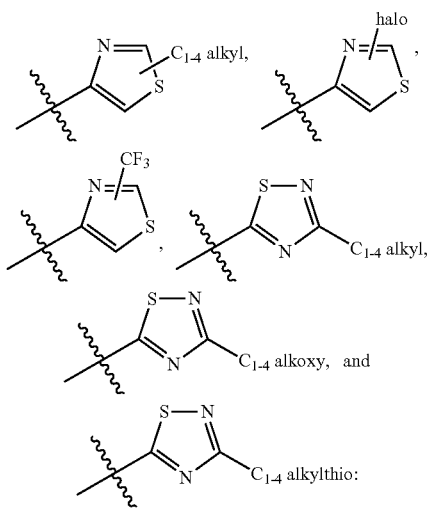

R$^1$ is independently H or halogen;
R$^2$ is independently H or halogen;
R$^3$ is independently selected from a ring moiety substituted with 0-2 R$^6$ and selected from the group consisting of phenyl;
R$^4$ is independently C$_{1-6}$ alkyl;
R$^{4a}$ a is independently C$_{1-6}$ alkyl or CO$_2$(C$_{1-4}$ alkyl);
R$^6$ is, independently at each occurrence, selected from H, halogen, C$_{1-6}$ alkyl, C$_{1-6}$ haloalkyl, C$_{1-4}$ alkoxy, and C$_{1-4}$ haloalkoxy; and
R$^8$ is independently H or halogen.
4. A compound according to claim 1, wherein:
ring A is independently selected from

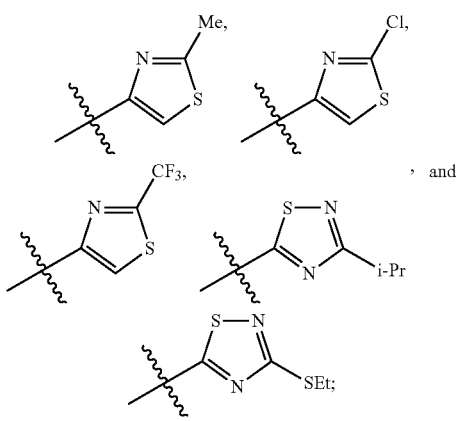

R$^1$ is independently H or F;
R$^2$ is independently H or F;
R$^3$ is independently selected from 4-(t-Bu)-Ph, 4-F-Ph, 4-Cl-Ph, 4-CF$_3$-Ph;
R$^4$ is independently Me or Et;
R$^{4a}$ is independently selected from Me, Et and CO$_2$Et; and
R$^8$ is H.
5. A compound according to claim 1, wherein:
ring A is independently selected from

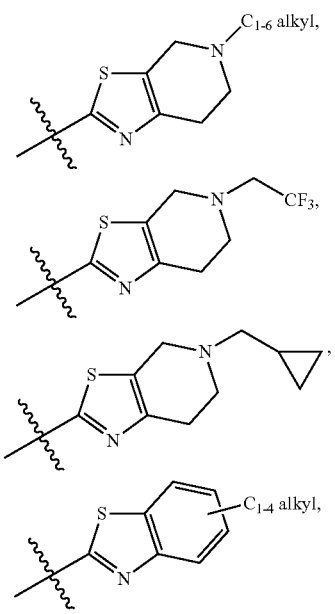

-continued

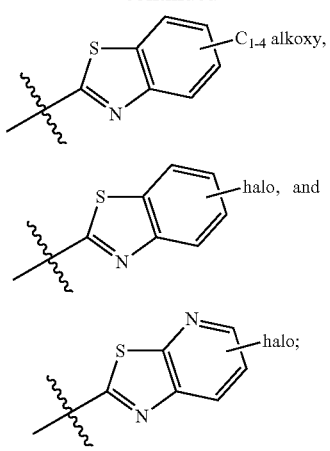

R¹ is independently H or halogen;
R² is independently H or halogen;
R³ is independently selected from a ring moiety substituted with 0-2 R⁶ and phenyl;
R⁴ is independently $C_{1-6}$ alkyl;
$R^{4a}$ is independently $C_{1-6}$ alkyl or $CO_2(C_{1-4}$ alkyl);
R⁶ is, independently at each occurrence, selected from H, halogen, $C_{1-6}$ alkyl, $C_{1-6}$ haloalkyl, $C_{1-4}$ alkoxy, and $C_{1-4}$ haloalkoxy; and
R⁸ is independently H or halogen.

6. A compound according to claim 1, wherein:
ring A is independently selected from

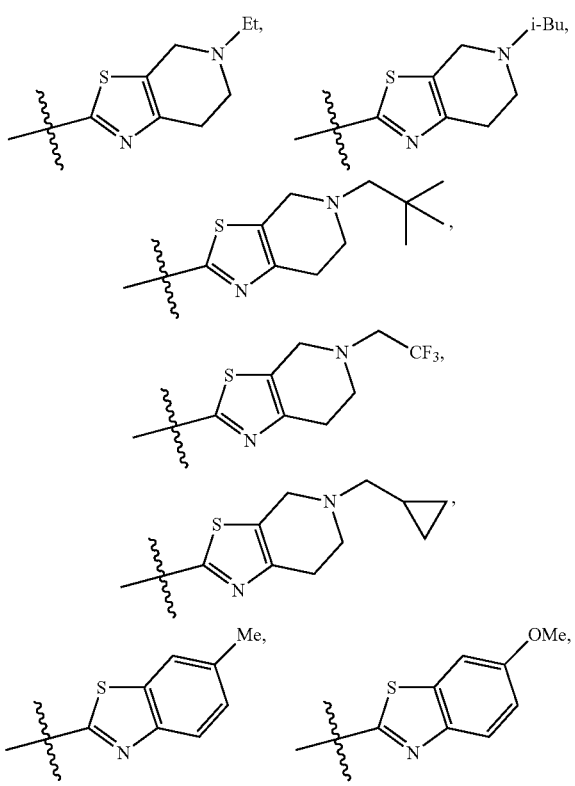

-continued

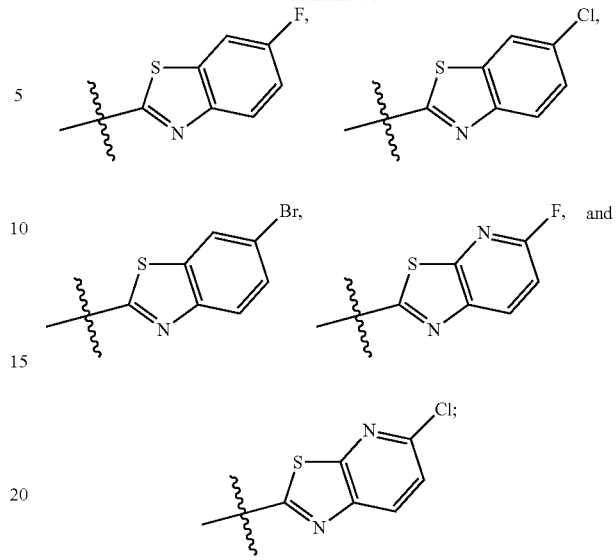

R¹ is independently H or F;
R² is independently H or F;
R³ is independently selected from 4-F-Ph, 4-Cl-Ph;
R⁴ is independently Me or Et;
$R^{4a}$ a is independently selected from Me, Et and $CO_2Et$; and
R⁸ is independently H or F.

7. A compound according to claim 1, wherein the compound is of Formula (II):

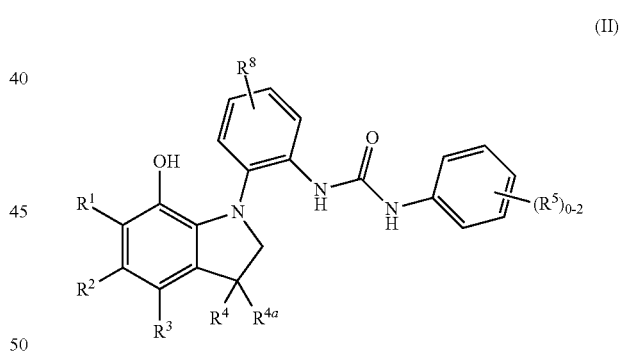

(II)

or a stereoisomer, a tautomer or a pharmaceutically acceptable salt thereof, wherein:
R¹ is independently H or halogen;
R² is independently H or halogen;
R³ is independently selected from a ring moiety substituted with 0-2 R⁶ and selected from the group consisting of phenyl;
R⁴ is independently $C_{1-6}$ alkyl;
$R^{4a}$ a is independently selected from $C_{1-6}$ alkyl, $CO_2(C_{1-4}$ alkyl) and $C_{1-6}$ haloalkyl;
R⁵ is, independently at each occurrence, selected from halogen, $C_{1-6}$ alkyl, $C_{1-6}$ alkoxy, $C_{1-6}$ haloalkyl, $C_{1-6}$ haloalkoxy, and

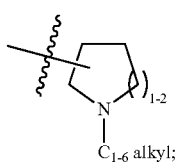

$R^6$ is, independently at each occurrence, selected from halogen, $C_{1-6}$ alkyl, $C_{2-6}$ alkenyl, $C_{1-6}$ haloalkyl, $C_{1-4}$ alkoxy, $C_{1-4}$ haloalkoxy, $C_{1-4}$ alkylthio, $CH_2OH$, CN, $CO_2(C_{1-4}$ alkyl), $NH(C_{1-4}$ alkyl), $CH_2N(C_{1-4}$ alkyl)$_2$, and morpholinylmethyl; and $R^8$ is independently H or halogen.

8. A compound according to claim 1, wherein:

$R^1$ is independently H or F;

$R^2$ is independently H or F;

$R^3$ is independently selected from Ph, 4-(t-Bu)-Ph, 2-F-Ph, 3-F-Ph, 4-F-Ph, 3-Cl-Ph, 4-Cl-Ph, 4-$CF_3$-Ph, 4-$CO_2$Me-Ph, 3-CN-Ph, 4-CN-Ph, 3-$CH_2N(Me)_2$-Ph, 3-Me-4-F-Ph, 2,4-diF-Ph, 3,4-diF-Ph, 3,5-diF-Ph, 2-F-4-Cl-Ph, 3-F-4-Cl-Ph, 3-Cl-4-F-Ph, $R^4$ is independently Me or Et;

$R^{4a}$ a is independently selected from Me, Et, $CO_2Et$, and $CH_2CF_3$;

$R^5$ is, independently at each occurrence, selected from Me, Et, t-Bu, F, $CF_3$, $OCF_3$,

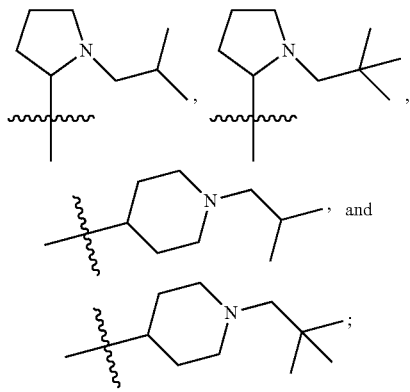

and $R^8$ is independently H or F.

9. A pharmaceutical composition, comprising: a pharmaceutically acceptable carrier and a compound of claim 1.

* * * * *

UNITED STATES PATENT AND TRADEMARK OFFICE
CERTIFICATE OF CORRECTION

PATENT NO. : 9,540,323 B2  
APPLICATION NO. : 14/418023  
DATED : January 10, 2017  
INVENTOR(S) : Alexandre L'Heureux et al.

It is certified that error appears in the above-identified patent and that said Letters Patent is hereby corrected as shown below:

In the Specification

Column 1, Line 3 (approx.), Below "Title" insert -- CROSS-REFERENCES TO RELATED APPLICATION --.

In the Claims

Column 257, Line 63 (Approx.), In Claim 3, delete "alkylthio:" and insert -- alkylthio; --, therefor.

Column 258, Line 5 (Approx.), In Claim 3, after "$R^{4a}$" delete "a".

Column 260, Line 30 (Approx.), In Claim 6, after "$R^{4a}$" delete "a".

Column 260, Line 61 (Approx.), In Claim 7, after "$R^{4a}$" delete "a".

Column 261, Line 24 (Approx.), In Claim 8, after "$R^{4a}$" delete "a".

Signed and Sealed this  
Second Day of January, 2018

Joseph Matal  
*Performing the Functions and Duties of the*  
*Under Secretary of Commerce for Intellectual Property and*  
*Director of the United States Patent and Trademark Office*